(12) United States Patent
Bretschneider et al.

(10) Patent No.: US 8,487,118 B2
(45) Date of Patent: Jul. 16, 2013

(54) CYCLIC DIONES AND THEIR USE AS INSECTICIDES, ACARICIDES AND/OR FUNGICIDES

(75) Inventors: Thomas Bretschneider, Lohmar (DE); Reiner Fischer, Monheim (DE); Stefan Lehr, Liederbach (DE); Jürgen Benting, Leichlingen (DE); Arnd Voerste, Köln (DE)

(73) Assignee: Bayer CropScience AG (DE)

( * ) Notice: Subject to any disclaimer, the term of this patent is extended or adjusted under 35 U.S.C. 154(b) by 45 days.

(21) Appl. No.: 13/145,195

(22) PCT Filed: Jan. 14, 2010

(86) PCT No.: PCT/EP2010/000154
§ 371 (c)(1),
(2), (4) Date: Sep. 13, 2011

(87) PCT Pub. No.: WO2010/081689
PCT Pub. Date: Jul. 22, 2010

(65) Prior Publication Data
US 2012/0046464 A1 Feb. 23, 2012

(30) Foreign Application Priority Data
Jan. 19, 2009 (EP) .................................... 09150834

(51) Int. Cl.
C07D 311/00 (2006.01)
C07C 39/00 (2006.01)
A01N 25/34 (2006.01)
A01M 1/24 (2006.01)

(52) U.S. Cl.
USPC ............... 549/28; 549/331; 568/43; 424/404; 424/405; 43/132.1

(58) Field of Classification Search
USPC ................. 568/43; 549/28, 331; 546/15, 340
See application file for complete search history.

(56) References Cited

U.S. PATENT DOCUMENTS

| | | |
|---|---|---|
| 4,245,432 A | 1/1981 | Dannelly |
| 4,272,417 A | 6/1981 | Barke et al. |
| 4,761,373 A | 8/1988 | Anderson et al. |
| 4,808,430 A | 2/1989 | Kouno |
| 5,013,659 A | 5/1991 | Bedbrook et al. |
| 5,084,082 A | 1/1992 | Sebastian |
| 5,141,870 A | 8/1992 | Bedbrook et al. |
| 5,198,599 A | 3/1993 | Thill |
| 5,273,894 A | 12/1993 | Strauch et al. |
| 5,276,268 A | 1/1994 | Strauch et al. |
| 5,304,732 A | 4/1994 | Anderson et al. |
| 5,331,107 A | 7/1994 | Anderson et al. |
| 5,378,824 A | 1/1995 | Bedbrook et al. |
| 5,434,283 A | 7/1995 | Wong et al. |
| 5,463,175 A | 10/1995 | Barry et al. |
| 5,561,236 A | 10/1996 | Leemans et al. |
| 5,605,011 A | 2/1997 | Bedbrook et al. |
| 5,637,489 A | 6/1997 | Strauch et al. |
| 5,646,024 A | 7/1997 | Leemans et al. |
| 5,648,477 A | 7/1997 | Leemans et al. |
| 5,712,107 A | 1/1998 | Nichols |
| 5,731,180 A | 3/1998 | Dietrich |
| 5,739,082 A | 4/1998 | Donn |
| 5,767,361 A | 6/1998 | Dietrich |
| 5,773,702 A | 6/1998 | Penner et al. |
| 5,776,760 A | 7/1998 | Barry et al. |
| 5,789,566 A | 8/1998 | Bonhomme et al. |
| 5,824,790 A | 10/1998 | Keeling et al. |
| 5,840,946 A | 11/1998 | Wong et al. |
| 5,866,782 A | 2/1999 | Iwabuchi et al. |
| 5,876,739 A | 3/1999 | Turnblad et al. |
| 5,908,810 A | 6/1999 | Donn |
| 5,908,975 A | 6/1999 | Caimi et al. |
| 5,928,937 A | 7/1999 | Kakefuda et al. |

(Continued)

FOREIGN PATENT DOCUMENTS

| | | |
|---|---|---|
| EP | 0 663 956 B1 | 6/2005 |
| JP | 2006-304779 A | 11/2006 |
| WO | WO 89/10396 A1 | 11/1989 |
| WO | WO 91/02069 A1 | 2/1991 |
| WO | WO 92/14827 A1 | 9/1992 |
| WO | WO 94/04693 A2 | 3/1994 |
| WO | WO 94/09144 A1 | 4/1994 |
| WO | WO 94/11520 A2 | 5/1994 |
| WO | WO 94/21795 A1 | 9/1994 |
| WO | WO 95/04826 A1 | 2/1995 |

(Continued)

OTHER PUBLICATIONS

Barry, G., et al., "Inhibitors of Amino Acid Biosynthesis: Strategies for Imparting Glyphosate Tolerance to Crop Plants," *Current Topics in Plant Pathology* 7:139-145, American Society of Plant Physiologists, United States (1992).

(Continued)

*Primary Examiner* — Sikarl Witherspoon
(74) *Attorney, Agent, or Firm* — Sterne, Kessler, Goldstein & Fox P.L.L.C.

(57) ABSTRACT

The present invention relates to the use of compounds of Formula (I)

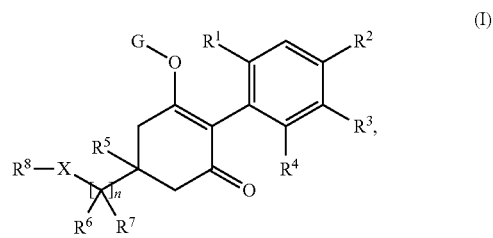

wherein
$R^1$, $R^2$, $R^3$, $R^4$, $R^5$, $R^6$, $R^7$, $R^8$, X, n and G have the meanings given above
as insecticides and/or acaricides and/or fungicides.

10 Claims, No Drawings

U.S. PATENT DOCUMENTS

| | | | |
|---|---|---|---|
| 5,965,755 | A | 10/1999 | Sernyk et al. |
| 5,969,169 | A | 10/1999 | Fan |
| 6,013,861 | A | 1/2000 | Bird et al. |
| 6,063,947 | A | 5/2000 | DeBonte et al. |
| 6,130,367 | A | 10/2000 | Kossmann et al. |
| 6,162,966 | A | 12/2000 | Kossmann et al. |
| 6,169,190 | B1 | 1/2001 | Lanuza et al. |
| 6,207,880 | B1 | 3/2001 | Kossmann et al. |
| 6,211,436 | B1 | 4/2001 | Kossmann et al. |
| 6,229,072 | B1 | 5/2001 | Burns et al. |
| 6,245,968 | B1 | 6/2001 | Boudec et al. |
| 6,255,561 | B1 | 7/2001 | Kossman et al. |
| 6,255,563 | B1 | 7/2001 | Emmermann et al. |
| 6,268,549 | B1 | 7/2001 | Sailland et al. |
| 6,270,828 | B1 | 8/2001 | DeBonte et al. |
| 6,284,479 | B1 | 9/2001 | Nichols |
| 6,307,124 | B1 | 10/2001 | Kossmann et al. |
| 6,323,392 | B1 | 11/2001 | Charne |
| 6,417,370 | B1 * | 7/2002 | Lieb et al. ............ 548/408 |
| 6,566,585 | B1 | 5/2003 | Quanz |
| 6,566,587 | B1 | 5/2003 | Lebrun et al. |
| 6,590,141 | B1 | 7/2003 | Frohberg |
| 6,596,928 | B1 | 7/2003 | Landschutze |
| 6,699,694 | B1 | 3/2004 | Buttcher et al. |
| 6,734,341 | B2 | 5/2004 | Singletary et al. |
| 6,791,010 | B1 | 9/2004 | Frohberg |
| 6,812,010 | B1 | 11/2004 | Derose et al. |
| 6,890,732 | B1 | 5/2005 | Loerz et al. |
| 6,891,088 | B1 | 5/2005 | Neuhaus et al. |
| 6,951,969 | B1 | 10/2005 | Loerz et al. |
| 7,112,665 | B1 | 9/2006 | Leemans et al. |
| 7,304,209 | B2 | 12/2007 | Zink et al. |
| 8,058,210 | B2 | 11/2011 | Lieb et al. |
| 2002/0031826 | A1 | 3/2002 | Nichols |
| 2003/0176428 | A1 | 9/2003 | Schneidersmann et al. |
| 2003/0216260 | A1 | 11/2003 | Ruther et al. |
| 2005/0257283 | A1 | 11/2005 | Matringe et al. |
| 2006/0015966 | A1 | 1/2006 | Landschutse |
| 2006/0168690 | A1 | 7/2006 | Shibatani et al. |
| 2008/0250533 | A1 | 10/2008 | Frohberg |

FOREIGN PATENT DOCUMENTS

| | | |
|---|---|---|
| WO | WO 95/07355 | 3/1995 |
| WO | WO 95/13389 | 5/1995 |
| WO | WO 95/26407 A1 | 10/1995 |
| WO | WO 95/31553 A1 | 11/1995 |
| WO | WO 95/35026 A1 | 12/1995 |
| WO | WO 96/01904 A1 | 1/1996 |
| WO | WO 96/19581 A1 | 6/1996 |
| WO | WO 96/33270 A1 | 10/1996 |
| WO | WO 96/34968 A2 | 11/1996 |
| WO | WO 97/20936 A1 | 6/1997 |
| WO | WO 97/41213 A1 | 11/1997 |
| WO | WO 97/45545 A1 | 12/1997 |
| WO | WO 97/47806 A1 | 12/1997 |
| WO | WO 97/47807 A1 | 12/1997 |
| WO | WO 97/47808 A1 | 12/1997 |
| WO | WO 98/00549 A1 | 1/1998 |
| WO | WO 98/20145 A2 | 5/1998 |
| WO | WO 98/22604 A1 | 5/1998 |
| WO | WO 98/27212 A1 | 6/1998 |
| WO | WO 98/27806 A1 | 7/1998 |
| WO | WO 98/32326 A2 | 7/1998 |
| WO | WO 98/39460 A1 | 9/1998 |
| WO | WO 98/40503 A1 | 9/1998 |
| WO | WO 99/24593 AI | 9/1998 |
| WO | WO 99/12950 A2 | 3/1999 |
| WO | WO 99/43649 A1 | 9/1999 |
| WO | WO 99/53072 A1 | 10/1999 |
| WO | WO 99/57965 | 11/1999 |
| WO | WO 99/66050 A1 | 12/1999 |
| WO | WO 00/04173 A1 | 1/2000 |
| WO | WO 00/11192 A2 | 3/2000 |
| WO | WO 00/14249 A1 | 3/2000 |
| WO | WO 00/28052 A2 | 5/2000 |
| WO | WO 00/47727 A2 | 8/2000 |
| WO | WO 00/66746 A1 | 11/2000 |
| WO | WO 00/66747 A1 | 11/2000 |
| WO | WO 00/73422 A1 | 12/2000 |
| WO | WO 00/77229 A2 | 12/2000 |
| WO | WO 01/14569 A2 | 3/2001 |
| WO | WO 01/17333 A1 | 3/2001 |
| WO | WO 01/19975 A2 | 3/2001 |
| WO | WO 01/24615 A1 | 4/2001 |
| WO | WO 01/65922 A2 | 9/2001 |
| WO | WO 01/66704 A2 | 9/2001 |
| WO | WO 01/74770 A1 | 10/2001 |
| WO | WO 01/98509 A2 | 12/2001 |
| WO | WO 02/26995 A1 | 4/2002 |
| WO | WO 02/28186 A2 | 4/2002 |
| WO | WO 02/34923 A2 | 5/2002 |
| WO | WO 02/36782 A2 | 5/2002 |
| WO | WO 02/45485 A1 | 6/2002 |
| WO | WO 02/79410 A2 | 10/2002 |
| WO | WO 02/080675 A1 | 10/2002 |
| WO | WO 02/101059 A2 | 12/2002 |
| WO | WO 03/013226 A2 | 2/2003 |
| WO | WO 03/033540 A2 | 4/2003 |
| WO | WO 03/071860 A2 | 9/2003 |
| WO | WO 03/092360 A2 | 11/2003 |
| WO | WO 2004/040012 A2 | 5/2004 |
| WO | WO 2004/053219 A2 | 6/2004 |
| WO | WO 2004/056999 A1 | 7/2004 |
| WO | WO 2004/078983 A2 | 9/2004 |
| WO | WO 2004/090140 A2 | 10/2004 |
| WO | WO 2004/106529 A2 | 12/2004 |
| WO | WO 2005/002324 A2 | 1/2005 |
| WO | WO 2005/002359 A2 | 1/2005 |
| WO | WO 2005/012515 A2 | 2/2005 |
| WO | WO 2005/017157 A1 | 2/2005 |
| WO | WO 2005/020673 A1 | 2/2005 |
| WO | WO 2005/030941 A1 | 4/2005 |
| WO | WO 2005/030942 A1 | 4/2005 |
| WO | WO 2005/093093 A2 | 10/2005 |
| WO | WO 2005/095617 A2 | 10/2005 |
| WO | WO 2005/095618 A2 | 10/2005 |
| WO | WO 2005/095619 A1 | 10/2005 |
| WO | WO 2005/095632 A2 | 10/2005 |
| WO | WO 2005/123927 A1 | 12/2005 |
| WO | WO 2006/007373 A2 | 1/2006 |
| WO | WO 2006/015376 A2 | 2/2006 |
| WO | WO 2006/018319 A1 | 2/2006 |
| WO | WO 2006/021972 A2 | 3/2006 |
| WO | WO 2006/024351 A1 | 3/2006 |
| WO | WO 2006/032469 A2 | 3/2006 |
| WO | WO 2006/032538 A1 | 3/2006 |
| WO | WO 2006/045633 A1 | 5/2006 |
| WO | WO 2006/060634 A2 | 6/2006 |
| WO | WO 2006/063862 A1 | 6/2006 |
| WO | WO 2006/072603 A2 | 7/2006 |
| WO | WO 2006/103107 A1 | 10/2006 |
| WO | WO 2006/108702 A1 | 10/2006 |
| WO | WO 2006/133827 A2 | 12/2006 |
| WO | WO 2006/136351 A2 | 12/2006 |
| WO | WO 2007/009823 A1 | 1/2007 |
| WO | WO 2007/024782 A2 | 3/2007 |
| WO | WO 2007/027777 A2 | 3/2007 |
| WO | WO 2007/039314 A2 | 4/2007 |
| WO | WO 2007/039316 A1 | 4/2007 |
| WO | WO 2007/107326 A1 | 9/2007 |
| WO | WO 2007/131699 A2 | 11/2007 |
| WO | WO 2008/017518 A1 | 2/2008 |
| WO | Wo 2008/080630 A1 | 7/2008 |
| WO | WO 2008/080631 A1 | 7/2008 |
| WO | WO 2008/090008 A1 | 7/2008 |
| WO | WO 2008/110308 A2 | 9/2008 |
| WO | WO 96/21023 A1 | 7/2011 |

OTHER PUBLICATIONS

Comai, L., et al., "An Altered aroA Gene Product Confers Resistance to the Herbicide Glyphosate," *Science* 221:370-371, American Association for the Advancement of Science, United States (1983).

Crickmore, N., et al., "Revision of the Nomenclature for the *Bacillus thuringiensis* Pesticidal Crystal Proteins," *Microbiology and Molecular Biology Reviews* 62(3):807-813, American Association for Microbiology, United States (1998).

Gasser, C.S., et al., "Structure, Expression, and Evolution of the 5-Enolpyruvylshikimate-3-phosphate Synthase Genes of Petunia and Tomato," The Journal of Biological Chemistry 263(9):4280-4289, American Association for Biochemistry and Molecular Biology, Inc., United States (1988).

Moellenbeck, D.J., et al., "Insecticidal proteins from *Bacillus thuringiensis* protect corn from corn rootworms," *Nature Biotechnology* 19:668-672, Nature Publishing Group, United States (2001).

Schnepf, E.E., et al., "Characterization of Cry34/Cry35 Binary Insecticidal Proteins from Diverse *Bacillus thuringiensis* Strain Collections," *Applied and Environmental Microbiology* 71(4):1765-1774, American Society for Microbiology, United States (2005).

Shah, D.M., et al., "Engineering Herbicide Tolerance in Transgenic Plants," *Science* 233:478-481, American Association for the Advancement of Science, United States (1986).

Tranel, P.J., et al., "Resistance of weeds to ALS-inhibiting herbicides: what have we learned?," *Weed Science* 50:700-712, Weed Science Society of America, United States (2002).

Wegler, R., "Chemie der Pflanzenschutz-und Schadlingsbekampfungsmittel [Chemistry of Plant Protection and Pest Control Agents]," *R. Wegler ed.* 2:401-412, Springer-Verlag, Berlin (1970).

English language Abstract of WIPO Patent Publication No. WO 99/57965 A1, European Patent Office, espacenet database—Worldwide (1999).

English language Abstract of WIPO Patent Publication No. WO 01/14569 A2, European Patent Office, espacenet database—Worldwide (2001).

English language Abstract of Japanese Patent Publication No. 2006-304779 A, Japanese Patent Office, Patent & Utility Model Gazette D3, Patent Abstracts of Japan, (2006).

International Search Report for International Application No. PCT/EP2010/000154, European Patent Office, The Hague, Netherlands, mailed on Apr. 19, 2011.

\* cited by examiner

CYCLIC DIONES AND THEIR USE AS INSECTICIDES, ACARICIDES AND/OR FUNGICIDES

The present invention relates to the use of cyclic diones and derivatives thereof as insecticides and/or acaricides and/or fungicides.

Cyclic diones having herbicidal action are described, for example, in WO 01/74770. WO 2008/110308.

Novel cyclohexanedione compounds, and derivatives thereof, having insecticidal and/or acaricidal and/or fungicidal properties have now been found.

The present invention accordingly relates to the use of compounds of formula (I)

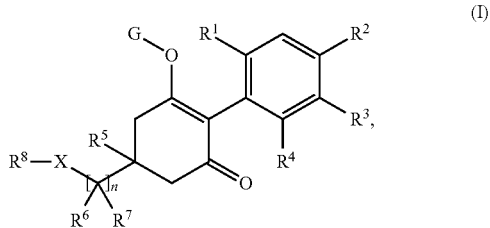

wherein
$R^1$ is methyl, ethyl, n-propyl, iso-propyl, cyclopropyl, halomethyl, haloethyl, halogen, vinyl, ethynyl, methoxy, ethoxy, halomethoxy or haloethoxy,
$R^2$ and $R^3$ are, independently of each other hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkylsulfonyloxy, $C_1$-$C_6$haloalkylsulfonyloxy, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio $C_1$-$C_3$alkylsulfinyl or $C_1$-$C_3$alkylsulfonyl, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl,
$R^4$ is hydrogen, methyl, ethyl, n-propyl, iso-propyl, halomethyl, haloethyl, halogen, vinyl, ethynyl, methoxy, ethoxy, halomethoxy or haloethoxy,
n is 0, 1, 2 or 3,
X is O, S, S(O) or S(0)$_2$.
$R^5$ is hydrogen or methyl,
$R^6$ and $R^7$ are independently of each other hydrogen, methyl or ethyl, where, when n is 2 or 3, the meanings of the 4 or 6 substituents $R^6$ and $R^7$ do not have to be the same,
$R^8$ is $C_1$-$C_{18}$alkyl, $C_1$-$C_{18}$haloalkyl, $C_3$-$C_7$cycloalkyl, $C_3$-$C_7$cycloalkyl substituted by methyl or ethyl, $C_1$-$C_6$alkoxy$C_1$-$C_{12}$alkyl, $C_3$-$C_{18}$ alkenyl or $C_3$-$C_{18}$ alkenyl substituted by halogen, $C_3$-$C_{18}$alkynyl or $C_3$-$C_{18}$alkynyl substituted by halogen, or
$R^5$ when n denotes 1 or 2, and $R^8$ together form a $C_2$-$C_5$ alkylene chain, which is unsubstituted or substituted by methyl or ethyl, or an $C_2$-$C_5$alkenylene chain, which is unsubstituted or substituted by methyl or ethyl, where, when n is 2, the meanings of the 4 substituents $R^6$ and $R^7$ do not have to be the same, or
$R^6$ when n denotes 1, and one of $R^5$, $R^7$ and $R^8$ together form a $C_2$-$C_5$alkylene chain, which is unsubstituted or substituted by methyl or ethyl, or an $C_2$-$C_5$alkenylene chain, which is unsubstituted or substituted by methyl or ethyl, and
G represents hydrogen (a) or represents one of the groups

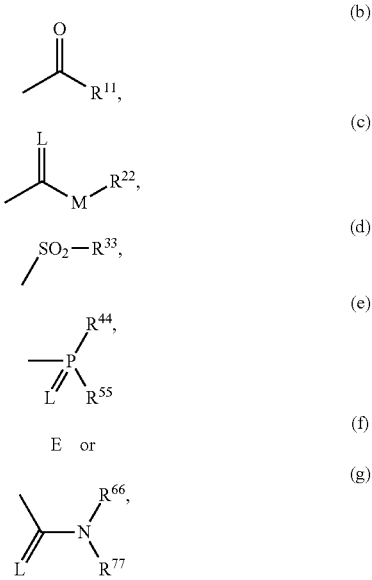

in which
E represents a metal ion or an ammonium ion,
L represents oxygen or sulphur and
M represents oxygen or sulphur,
$R^{11}$ represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulphur,
represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl,
represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl,
represents optionally halogen- or $C_1$-$C_6$-alkyl-substituted 5- or 6-membered hetaryl having one or two heteroatoms from the group consisting of oxygen, sulphur and nitrogen,
represents optionally halogen- or $C_1$-$C_6$-alkyl-substituted phenoxy-$C_1$-$C_6$-alkyl or
represents optionally halogen-, amino- or $C_1$-$C_6$-alkyl-substituted 5- or 6-membered hetaryloxy-$C_1$-$C_6$-alkyl having one or two heteroatoms from the group consisting of oxygen, sulphur and nitrogen,
$R^{22}$ represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl,
represents optionally halogen-, $C_1$-$C_6$-alkyl- or $C_1$-$C_6$-alkoxy-substituted $C_3$-$C_8$-cycloalkyl or
represents in each case optionally halogen-, cyano-, nitro-, $C_1$-$C_6$-alkyl-, $C_1$-$C_6$-alkoxy-$C_1$-$C_6$-haloalkyl- or $C_1$-$C_6$-haloalkoxy-substituted phenyl or benzyl,
$R^{33}$ represents optionally halogen-substituted $C_1$-$C_8$-alkyl or in each case optionally halogen-, $C_1$-$C_6$-alkyl-, $C_1$-$C_6$- alkoxy-, $C_1$-$C_4$-haloalkyl-, $C_1$-$C_4$-haloalkoxy-, cyano- or nitro-substituted phenyl or benzyl, $R^{44}$ and $R^{55}$ independently of one another represent in each case optionally halogen-substituted $C_1$-$C_8$-alkyl, $C_1$-$C_8$-alkoxy, $C_1$-$C_8$-alkylamino, di($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^{66}$ and $R^{77}$ independently of one another represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulphur as insecticides and/or acaricides and/or fungicides.

In the substituent definitions of the compounds of the formula (I), the alkyl substituents and alkyl moieties of alkoxy, alkylamino etc. having 1 to 6 carbon atoms are preferably methyl, ethyl, propyl, butyl, pentyl and hexyl as well as straight and branched isomers thereof. Higher alkyl groups of up to 18 carbon atoms comprise preferably octyl, nonyl, decyl, undecyl and dodecyl. The alkenyl and alkynyl radicals having 2 to 6 carbon atoms as well as up to 18 carbon atoms can be straight or branched and can contain more than 1 double or triple bond, respectively. Examples are vinyl, allyl, propargyl, butenyl, butynyl, pentenyl and pentynyl suitable cycloalkyl groups contain 3 to 6 carbon atoms and are for example cyclopropyl, cyclobutyl, cyclopentyl, cyclohexyl and cycloheptyl. Cyclopropyl, cyclobutyl, cyclopentyl and cyclohexyl are preferred. Preferred examples of heteroaryls are thienyl, furyl, pyrrolyl, oxazolyl, thiazolyl, pyrazolyl, imidazolyl, triazolyl, tetrazolyl, pyridyl, pyrimidinyl, pyrazinyl, triazinyl, benzofuryl, benzothienyl, benzothiazolyl, benzoxazolyl, indolyl, quinolinyl and quinoxalinyl groups, and, where appropriate, N-oxides and salts thereof. The group G is hydrogen or an alkali metal, alkaline earth metal, sulfonium (—S($C_1$-$C_6$alkyl$_3$)$^+$), ammonium (—NH$_4^+$ or —N($C_1$-$C_6$alkyl)$_4^+$), a C(O)—$C_1$-$C_4$-alkyl group or a leaving group. This latentiating group G is selected to allow its removal by one or a combination of biochemical, chemical or physical processes to afford compounds of Formula (I) where G is H before, during or following application to the treated area or plants. Examples of these processes include enzymatic cleavage, chemical hydrolysis and photolysis. Compounds bearing latentiating groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils. A large number of latentiating groups, which are known in the art, can be used in the new compounds.

In a preferred group of compounds of the formula I, $R^1$ is methyl, ethyl, vinyl, ethynyl, methoxy or halogen. More preferably, $R^1$ is methyl, ethyl, methoxy or halogen. Most preferably, $R^1$ is methyl or ethyl.

In a preferred group of compounds of the formula I, $R^2$ is hydrogen, halogen, methyl, ethyl, phenyl or phenyl substituted by $C_1$-$C_3$alkyl, $C_1$-$C_3$haloalkyl, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl.

Preferably. $R^2$ is methyl.

In a preferred group of compounds of the formula I, $R^3$ is hydrogen, halogen, methyl, ethyl, phenyl or phenyl substituted by $C_1$-$C_3$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl.

Preferably, $R^2$ and $R^3$ are independently hydrogen, methyl, ethyl, halogen, optionally substituted phenyl or optionally substituted heteroaryl.

Preferably, $R^4$ is hydrogen, methyl, ethyl, vinyl or ethynyl and, more preferably, $R^4$ is hydrogen, methyl or ethyl.

Preferably, $R^5$ denotes hydrogen.

Another suitable group of compounds of the formula (I) is characterized by $R^6$ and $R^7$ each being hydrogen.

Preferably, $R^6$ and $R^7$ are methyl or ethyl, or $R^6$ is hydrogen and $R^7$ is methyl or ethyl.

In a preferred group of compounds of the formula (I), $R^8$, when X denotes S(O) or S(O)$_2$, is $C_7$-$C_{18}$alkyl, $C_3$-$C_7$cycloalkyl, $C_3$-$C_7$cycloalkyl substituted by methyl or ethyl, $C_1$-$C_6$alkoxy $C_1$-$C_{12}$alkyl. $C_1$-$C_6$alkylthio$C_1$-$C_{12}$alkyl, $C_3$-$C_{18}$alkenyl, $C_3$-$C_{18}$alkynyl or $C_3$-$C_{18}$alkynyl substituted by halogen.

More preferably, $R^8$ is $C_1$-$C_6$alkyl or $C_3$-$C_7$cycloalkyl, and, in particular, $R^8$ is methyl, ethyl or propyl.

In another preferred group of compounds of the formula (I), $R^8$, when X denotes O or S, is methyl, ethyl, propyl, butyl, pentyl or hexyl, $C_7$-$C_{18}$alkyl, $C_3$-$C_7$cycloalkyl, $C_3$-$C_7$cycloalkyl substituted by methyl or ethyl. $C_1$-$C_6$alkoxyd $C_1$-$C_{12}$alkyl, $C_1$-$C_6$alkylthio $C_1$-$C_{12}$ alkyl, $C_3$-$C_{18}$ alkenyl, $C_3$-$C_{18}$alkynyl or $C_3$-$C_{18}$alkynyl substituted by halogen.

It is particularly preferred, that in the compounds of the formula (I), $R^8$, when X denotes O or S, is methyl, ethyl or propyl, and in particular ethyl or propyl.

Another group of preferred compounds of the formula (I) $R^8$, when X denotes S(O) or S(0)$_2$, is $C_1$-$C_{18}$alkyl, $C_3$-$C_7$cycloalkyl, $C_3$-$C_7$cycloalkyl substituted by methyl or ethyl, $C_1$-$C_6$alkoxy$C_1$-$C_{12}$alkyl, $C_1$-$C_6$alkylthio$C_1$-$C_{12}$alkyl, $C_3$-$C_{18}$alkenyl, $C_3$-$C_{18}$alkynyl or $C_3$-$C_{18}$alkynyl substituted by halogen, and $R^6$ and $R^7$ are methyl or ethyl, or $R^6$ is hydrogen and $R^7$ is methyl or ethyl.

Preferably, in the compounds of formula (I), the substituent $R^8$—X—$[CR^6R^7]_n$ is different from $CH_3OCH_2$— and $CH_3SCH_2$—.

It is preferred that G is hydrogen, an alkali metal or alkaline earth metal, where hydrogen is especially preferred.

Preferably in the compounds of the formula (I), n is 1 or 2.

In the case that in the compounds of the formula (I) n denotes 2 or 3, the meanings of the 4 or 6 substituents $R^6$ and $R^7$ do not have to be the same. For example, the partial structure $[CR^6R^7]_2$ comprises also groups such as CH(CH$_3$)CH$_2$, C(CH$_3$)$_2$CH$_2$, CH$_2$CH(CH$_3$) and CH$_2$C(CH$_3$)$_2$.

In another preferred group of compounds of the formula (I) $R^5$, when n denotes 1 or 2, and $R^8$ together form a $C_2$-$C_5$ alkylene chain.

In another preferred group of compounds of the formula (I), $R^5$, when n denotes 1, and $R^8$ together form a propylene chain and $R^6$ and $R^7$ are each hydrogen.

Preferably, $R^5$, when n denotes 1 or 2 and in particular 2, and $R^8$ together form an ethylene chain and $R^6$ and $R^7$ are each hydrogen. These meanings of $R^5$ apply especially when X is O or when X is S(O) or S(0)$_2$.

In another preferred group of compounds of the formula (I) $R^1$, $R^2$ and $R^4$ are independently of each other methyl or ethyl and $R^3$ is hydrogen.

In another preferred group of compounds of the formula (I) $R^1$ is methyl or ethyl, $R^2$ is hydrogen, $R^3$ is phenyl or phenyl substituted by $C_1$-$C_4$alkyl, $C_1$-$C_3$haloalkyl, $C_1$-$C_3$alkoxy, $C_1$-$C_3$haloalkoxy, cyano, nitro or halogen, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro or halogen.

In another preferred group of compounds of the formula (I) $R^1$ is methyl or ethyl, $R^2$ is phenyl or phenyl substituted by $C_1$-$C_4$alkyl, $C_1$-$C_3$haloalkyl, $C_1$-$C_3$alkoxy, $C_1$-$C_3$haloalkoxy, cyano, nitro or halogen, or heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro or halogen. $R^3$ is hydrogen and $R^4$ is hydrogen, methyl or ethyl.

The invention relates also to the salts which the compounds of formula I are able to form with amines, alkali metal and alkaline earth metal bases or quaternary ammonium bases. Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_8$alkylamines, $C_1$-$C_4$hydroalkylamines and $C_2$-$C_4$-alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylainine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isbpropylamine and diisopropylamine.

Preferred quaternary ammonium bases suitable for salt formation correspond, for example, to the formula $[N(R_a R_b R_c R_d)]OH$ wherein $R_a$, $R_b$, $R_c$ and $R_d$ are each independently of the others $C_1$-$C_4$alkyl. Further suitable tetraalkylammonium bases with other anions can be obtained, for example, by anion exchange reactions.

Depending on the nature of the substituents G, $R^2$, $R^3$, $R^6$, $R^7$ and $R^8$, compounds of Formula (I) may exist in different isomeric forms. When G is hydrogen, for example, compounds of Formula (I) may exist in different tautomeric forms. This invention covers all such isomers and tautomers and mixtures thereof in all proportions. Also, when substituents contain double bonds, cis- and trans-isomers can exist. These isomers, too, are within the scope of the claimed compounds of the Formula (I).

The compounds of the formula (I) are known compounds (WO 2008/110308).

The following compounds are preferred compounds:

TABLE T1

| Compound Number | Structure | $^1$H NMR-CDCl$_3$ unless stated |
|---|---|---|
| T1 | 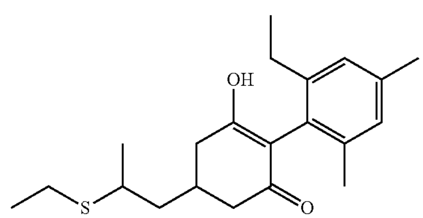 [SMILES: CCSC(C)CC1CC(=O)C(c2c(C)cc(C)cc2CC)=C(O)C1] | δ 6.96 (d, 2H), 5.54 (br s, 1H), 2.88 (m, 1H), 2.19-2.76 (m, 9H), 2.30 (s, 3H), 2.06, 2.02 (2 × S, 3H), 1.58-1.78 (m, 2H), 1.34 (d, 3H), 1.27 (t, 3H), 1.08 (q, 3H) |
| T2 | 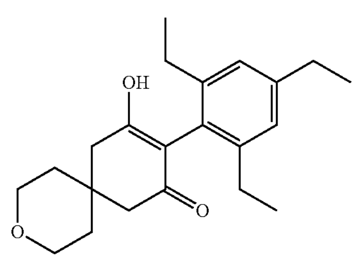 [SMILES: CCc1cc(CC)c(C2=C(O)CC3(CCOCC3)CC2=O)c(CC)c1] | δ 7.00 (s, 2H), 5.55 (s, 1H), 3.75 (t, 4H), 2.56-2.69 (m, 6H), 2.34 (m, 4H), 1.71 (t, 4H), 1.25 (t, 3H), 1.07 (t, 6H) |
| T3 | 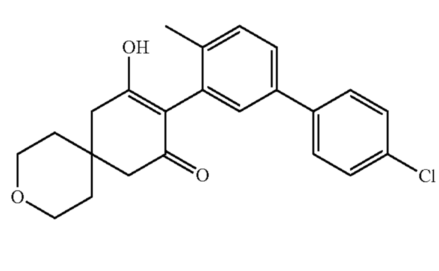 [SMILES: Cc1ccc(-c2ccc(Cl)cc2)cc1C1=C(O)CC2(CCOCC2)CC1=O] | δ 7.51-7.44 (m, 3H), 7.40-7.35 (m, 3H), 7.22 (d, 1H), 5.83 (s, 1H), 3.74 (m, 4H), 2.65 (s, 2H), 2.58 (q, 2H), 2.15 (s, 3H), 1.72 (m, 4H) |

TABLE T1-continued
| | | |
|---|---|---|
| T4 | 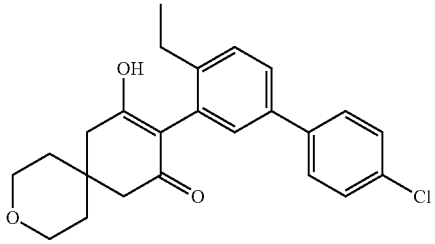 [SMILES: CCc1ccc(-c2ccc(Cl)cc2)cc1C1=C(O)CC2(CCOCC2)CC1=O] | δ 7.53 (dd, 1H), 7.50-7.45 (m, 2H), 7.43-7.36 (m, 3H), 7.20 (d, 1H), 5.79 (s, 1H), 3.75 (m, 4H), 2.65 (s, 2H), 2.59 (q, 2H), 2.45 (m, 2H), 1.72 (t, 4H) 1.13 (t, 3H) |
| T5 | 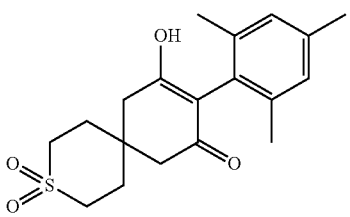 [SMILES: Cc1cc(C)c(C2=C(O)CC3(CCS(=O)(=O)CC3)CC2=O)c(C)c1] | δ 6.95 (s, 2H), 5.59 (br s, 1H), 3.07 (m, 4H), 2.67 (d, 4H), 2.29 (s, 3H), 2.24 (m, 4H), 2.04 (s, 6H), |
| T6 | 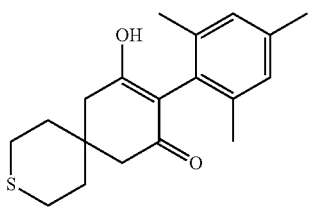 [SMILES: Cc1cc(C)c(C2=C(O)CC3(CCSCC3)CC2=O)c(C)c1] | δ 6.94 (s, 2H), 5.56 (br s, 1H), 2.70 (m, 4H), 2.56 (s, 2H), 2.42 (s, 2H), 2.28 (s, 3H), 2.04 (s, 6H), 1.95 (m, 4H) |
| T7 | 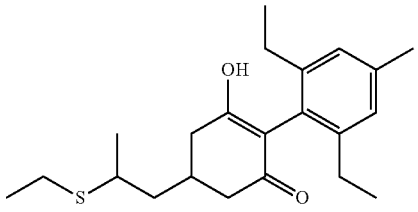 [SMILES: CCSC(C)CC1CC(=O)C(c2c(CC)cc(C)cc2CC)=C(O)C1] | δ 6.98 (d, 2H), 5.52 (d, 1H), 2.93-2.83 (m, 1H), 2.21-2.76 (m, 11H), 2.33 (s, 3H), 1.78-1.59 (m, 2H), 1.34 (dd, 3H), 1.27 (m, 3H), 1.08 (m, 6H) |
| T8 | 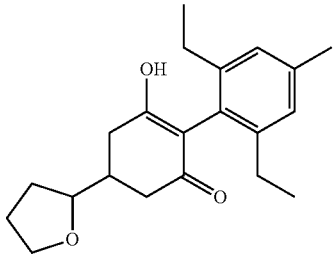 [SMILES: CCc1cc(C)cc(CC)c1C1=C(O)CC(C2CCCO2)CC1=O] | δ 6.98 (s, 2H), 5.54 (br s, 1H), 3.89-3.77 (br m, 3H), 2.8-2.70 (m, 1H), 2.62-2.55 (m, 2H), 2.38-2.30 (m, 9H), 2.07-1.90 (m, 3H), 1.7-1.55 (m, 1H), 1.09-1.05 (m, 6H) |
| T9 | 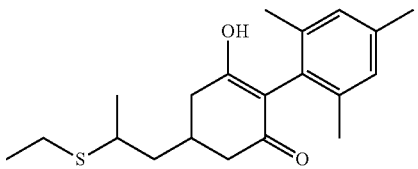 [SMILES: CCSC(C)CC1CC(=O)C(c2c(C)cc(C)cc2C)=C(O)C1] | δ 6.94 (d, 2H), 5.56 (br d, 1H), 2.88 (m, 1H), 2.75-2.19- (m, 7H), 2.28 (s, 3H), 2.07 (s, 3H), 2.03 (s, 3H), 1.77-1.57 (m, 2H), 1.34 (dd, 3H), 1.27 (m, 3H) |
| T10 | 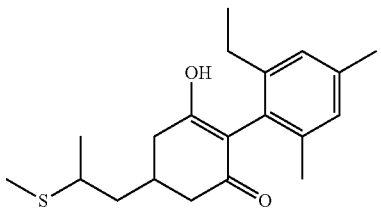 | δ 6.96 (m, 2H), 5.53 (d, 1H), 2.82-2.19 (m, 8H), 2.30 (s, 3H), 2.09 (dd, 3H), 2.06, 2.02 (2 × S, 3H), 1.78-1.57 (m, 2H), 1.34 (dd, 3H), 1.07 (m, 3H) |

TABLE T1-continued
| T11 | 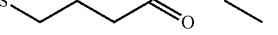 | δ 6.98 (s, 2H), 5.26 (bs, 1H), 2.71 (s, 4H), 2.54 (br s, 4H), 2.33 (m, 7H), 1.92 (br s, 4H), 1.06 (t, 6H) |
| --- | --- | --- |
| T12 |  | δ 6.94 (s, 2H), 5.60 (br s, 1H), 2.68 (m, 2H), 2.60 (t, 2H), 2.50-2.25 (m, 3H), 2.28 (s, 3H), 2.13 (s, 3H), 2.06 (s, 3H), 2.03 (s, 3H), 1.79 (q, 2H) |
| T13 |  | δ 6.96 (s, 1H), 6.95 (s, 1H), 5.60 (br s, 1H), 2.68 (m, 2H), 2.60 (t, 2H), 2.50-2.25 (m, 5H), 2.30 (s, 3H), 2.13 (s, 3H), 2.06, 2.02 (2 × s, 3H), 1.79 (q, 2H), 1.08 (m, 3H) |
| T14 |  | δ 7.00 (s, 2H), 5.61 (br s, 1H), 3.12 (m, 2H), 2.96 (s, 3H), 2.72 (m, 2H), 2.53-2.41 (m, 2H), 2.40-2.25 (m, 5H), 2.33 (s, 3H), 2.16-2.01 (m, 2H), 1.08 (t, 6H) |
| T15 |  | δ 6.98 (s, 2H), 2.78 (t, 2H), 2.72 (m, 2H), 2.61 (s, 3H), 2.48-2.27 (m, 10H), 2.03-1.95 (m, 2H), 1.08 (m, 6H) |
| T16 |  | δ 6.99 (s, 2H), 5.62 (br s, 1H), 2.69 (m, 2H), 2.60 (m, 2H), 2.46-2.46 (m, 7H), 2.33 (s, 3H), 2.14 (s, 3H), 1.80 (q, 2H), 1.08 (m, 6H) |
| T17 |  | δ 7.00 (d, 2H), 5.58 (d, 1H), 2.85-2.22 (m, 10H), 2.33 (s, 3H), 2.10 (d, 3H), 1.78-1.57 (m, 2H), 1.34 (d, 3H), 1.08 (q, 6H) |

TABLE T1-continued
| | | |
|---|---|---|
| T18 | 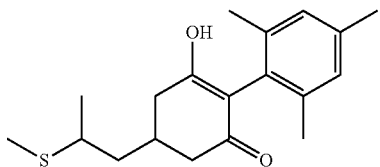 | δ 6.95 (s, 2H), 5.61 (s, 1H), 2.83-2.17 (m, 6H), 2.28 (s, 3H), 2.10 (d, 3H), 2.07 (s, 3H), 2.03 (s, 3H), 1.78-1.59 (m, 2H), 1.34 (d, 3H) |
| T19 | 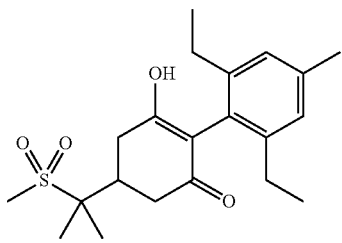 | δ 6.99 (s, 2H), 5.59 (br s, 1H), 3.09-3.00 (m, 1H), 2.90 (s, 3H), 2.87-2.76 (m, 3H), 2.55-2.25 (m, 5H), 2.33 (s, 3H), 1.51 (s, 6H), 1.16-1.02 (m, 6H) |
| T20 | 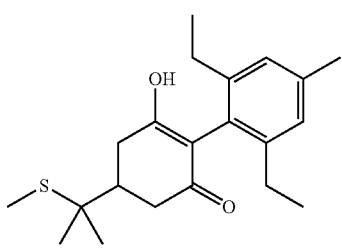 | δ 6.98 (s, 2H), 5.66 (s, 1H), 2.83-2.59 (m, 3H), 2.49-2.22 (m, 6H), 2.33 (s, 3H), 2.07 (s, 3H), 1.37 (s, 3H), 1.35 (s, 3H), 1.15-1.02 (m, 6H) |
| T21 | 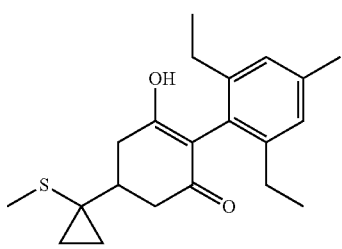 | δ 6.98 (s, 2H), 5.70 (s, 1H), 2.99-2.87 (dd, 1H), 2.75-2.50 (m, 3H), 2.42-2.25 (m, 4H), 2.32 (s, 3H), 2.16 (s, 3H), 1.80-1.67 (m, 1H), 1.15-1.01 (m, 6H), 0.99 (m, 2H), 0.82 (m, 2H) |
| T22 | 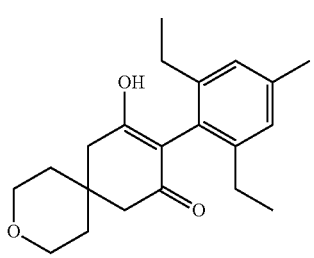 [SMILES: CCc1cc(C)cc(CC)c1C1=C(O)CC2(CCOCC2)CC1=O] | δ 6.97 (s, 2H), 5.83 (br s, 1H), 3.72 (t, 4H), 2.59 (br s, 4H), 2.39-2.27 (m, 4H), 2.32 (s, 3H), 1.69 (t, 4H), 1.06 (t, 6H) |
| T23 | 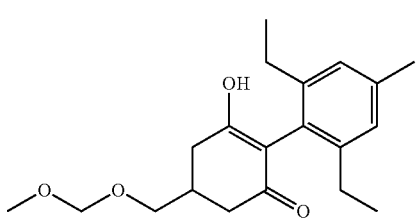 | δ 6.98 (s, 2H), 5.61 (br s, 1H), 4.67 (s, 2H), 3.63-3.53 (m, 2H), 3.39 (s, 3H), 2.75-2.52 (m, 4H), 2.49-2.24 (m, 5H), 2.32 (s, 3H), 1.08 (t, 6H) |
| T24 | 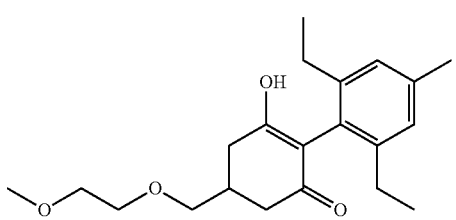 | δ 6.98 (s, 2H), 5.62 (br s, 1H), 3.69-3.45 (m, 6H), 3.39 (s, 3H), 2.80-2.48 (m, 4H), 2.48-2.22 (m, 5H), 2.32 (s, 3H), 1.08 (t, 6H) |

TABLE T1-continued
| T25 | 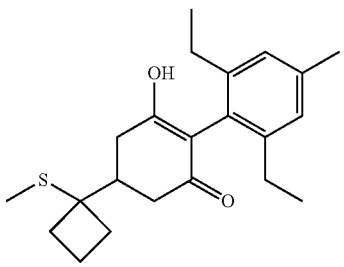 | δ 6.98 (s, 2H), 5.60 (br s, 1H), 2.75-2.27 (m, 10H), 2.32 (s, 3H), 2.27-2.10 (m, 4H), 2.12 (s, 3H), 1.98-1.85 (m, 1H), 1.18-1.02 (m, 6H) |
|---|---|---|
| T26 | 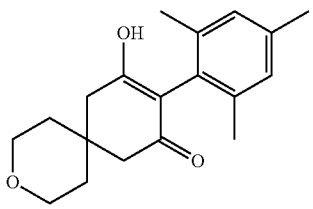 [SMILES: Cc1cc(C)c(C2=C(O)CC3(CCOCC3)CC2=O)c(C)c1] | δ 6.94 (s, 2H), 5.50 (br s, 1H), 3.75 (t, 4H), 2.61 (d, 4H), 2.28 (s, 3H), 2.05 (s, 6H), 1.72 (t, 4H) |
| T27 | 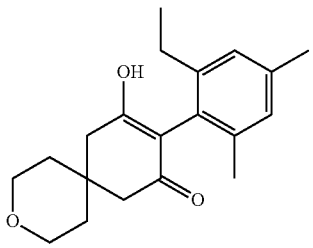 [SMILES: CCc1cc(C)cc(C)c1C1=C(O)CC2(CCOCC2)CC1=O] | δ 6.96 (s, 2H), 5.55 (br s, 1H), 3.75 (t, 4H), 2.63 (br s, 2H), 2.58 (br s, 2H), 2.30 (s, 3H), 2.41-2.24 (m, 2H), 2.04 (s, 3H), 1.71 (t, 4H), 1.06 (t, 3H) |
| T28 | 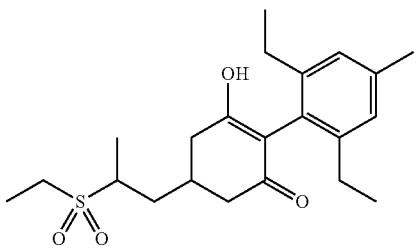 [SMILES: CCc1cc(C)cc(CC)c1C1=C(O)CC(CC(C)S(=O)(=O)CC)CC1=O] | δ 6.99 (s, 2H), 5.67 (d, 1H), 3.16-3.05 (m, 1H), 3.01 (q, 2H), 2.80-2.61 (m, 2H), 2.55-2.13 (m, 7H), 2.33 (s, 3H), 1.82-1.60 (m, 2H), 1.48-1.38 (m, 6H), 1.08 (q, 6H) |
| T29 | 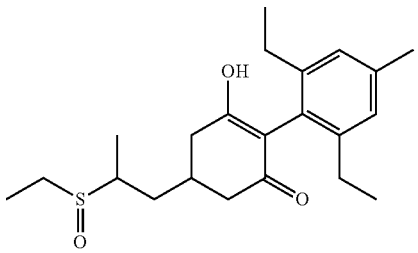 [SMILES: CCc1cc(C)cc(CC)c1C1=C(O)CC(CC(C)S(=O)CC)CC1=O] | δ 6.98 (s, 2H), 6.00 (br s, 1H), 2.87-2.18 (m, 12H), 2.33 (s, 3H), 1.81-1.52 (m, 2H), 1.44-1.23 (m, 6H), 1.08 (q, 6H) |
| T30 | 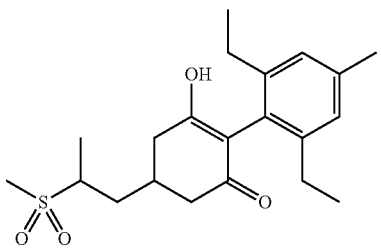 | δ 6.99 (s, 2H), 5.59 (d, 1H), 3.12-3.02 (m, 1H), 2.88 (d, 3H), 2.81-2.62 (m, 2H), 2.55-2.16 (m, 10H), 1.80-1.53 (m, 2H), 1.47 (dd, 3H), 1.08 (m 6H) |

TABLE T1-continued

| | | |
|---|---|---|
| T31 | | δ 6.97 (d, 2H), 5.59 (s, 1H), 3.11 (m, 2H), 2.95 (s, 3H), 2.71 (m, 2H), 2.52-2.24 (m, 5H), 2.30 (s, 3H), 2.16-1.97 (m, 2H), 2.03 (d, 3H), 1.07 (t, 3H) |
| T32 | | δ 6.98 (s, 2H), 5.52 (s, 1H), 2.84 (m, 1H), 2.68 (m, 2H), 2.53 (m, 3H), 2.43-2.20 (m, 6H), 2.32 (s, 3H), 1.78-1.56 (m, 4H), 1.34 (dd, 3H), 1.08 (q, 6H), 1.01 (t, 3H) |
| T33 | | δ 7.18 (d, 1H), 7.09 (d, 1H), 6.85 (s, 1H), 5.70 (br s, 1H), 3.74 (t, 4H), 2.63 (s, 2H), 2.57 (s, 1H), 2.55 (s, 1H), 2.30 (s, 3H), 2.07 (s, 3H), 1.75-1.68 (m, 4H) |
| T34 | | δ 7.17 (d, 1H), 7.08 (d, 1H), 6.86 (s, 1H), 5.81 (br s, 1H), 3.35 (s, 3H), 3.26 (m, 1H), 2.58 (s, 1H), 2.51 (br s, 2H), 2.42 (s, 1H), 2.30 (s, 3H), 2.07 (s, 3H), 1.91-1.73 (m, 4H), 1.65-1.50 (m, 2H), 1.50-1.34 (m, 2H |
| T35 | | δ 6.94 (s, 2H), 5.53 (br d, 1H), 2.84 (m, 1H), 2.75-2.60 (m, 2H), 2.59-2.46 (m, 3H), 2.37 (dd, 1H), 2.28 (s, 3H), 2.24 (dd, 1H), 2.07 (s, 3H), 2.03 (s, 3H), 1.77-1.55 (m, 4H), 1.33 (dd, 3H), 1.00 (t, 3H) |
| T36 | | δ 6.99 (s, 2H), 5.57 (d, 1H), 3.11-3.01 (m, 1H), 2.94 (m, 2H), 2.78-2.61 (m, 2H), 2.55-2.13 (m, 7H), 2.33 (s, 3H), 1.99-1.84 (m, 2H), 1.81-1.52 (m, 2H), 1.44 (t, 3H), 1.16-1.03 (m, 9H) |
| T37 | | δ 6.98 (s, 2H), 5.86-5.72 (m, 1H), 2.85-1.52 (m, 16H), 2.33 (s, 3H), 1.30 (t, 3H), 1.16-1.04 (m, 9H) |

TABLE T1-continued
| | | |
|---|---|---|
| T38 | 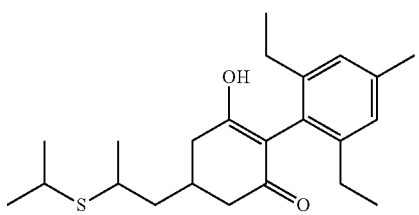 [SMILES: CCc1cc(C)cc(CC)c1C1=C(O)CC(CC(C)SC(C)C)CC1=O] | δ 6.98 (s, 2H), 5.51 (br d, 1H), 3.02 (m, 1H), 2.93 (m, 1H), 2.69 (m, 2H), 2.53 (m, 1H), 2.44-2.21 (m, 6H), 2.33 (s, 3H), 1.78-1.59 (m, 2H), 1.34 (dd, 3H), 1.29 (dd, 6H), 1.08 (q, 6H) |
| T39 | 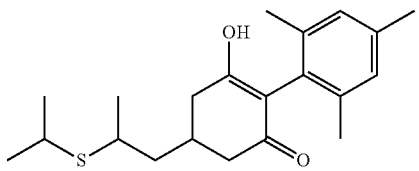 [SMILES: Cc1cc(C)c(C2=C(O)CC(CC(C)SC(C)C)CC2=O)c(C)c1] | δ 6.93 (s, 2H), 5.62 (br s, 1H), 3.02 (m, 1H), 2.92 (m, 1H), 2.74-2.60 (m, 2H), 2.59-2.45 (m, 1H), 2.37 (m, 1H), 2.28 (s, 3H), 2.23 (m, 1H), 2.07 (s, 3H), 2.03 (s, 3H), 1.77-1.58 (m, 2H), 1.33 (dd, 3H), 1.28 (dd, 6H) |
| T40 | 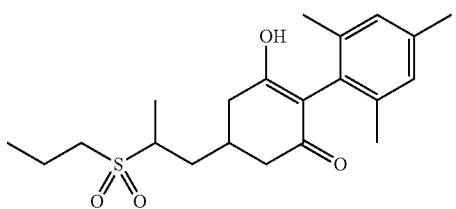 [SMILES: CCCS(=O)(=O)C(C)CC1CC(=O)C(c2c(C)cc(C)cc2C)=C(O)C1] | δ 6.94 (s, 2H), 5.61 (d, 1H), 3.11-3.01 (m, 1H), 2.94 (m, 2H), 2.78-2.59 (m, 2H), 2.54-2.11 (m, 3H), 2.28 (s, 3H), 2.06 (s, 3H), 2.03 (s, 3H), 1.91 (m, 2H), 1.80-1.54 (m, 2H), 1.44 (dd, 3H), 1.12 (m, 3H) |
| T41 | 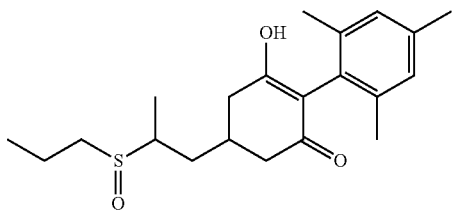 [SMILES: CCCS(=O)C(C)CC1CC(=O)C(c2c(C)cc(C)cc2C)=C(O)C1] | δ 6.94 (s, 2H), 6.19-5.86 (m, 1H), 2.84-1.41 (m, 12H), 2.28 (s, 3H), 2.06 (s, 3H), 2.03 (s, 3H), 1.30 (t, 3H), 1.10 (m, 3H) |
| T42 | 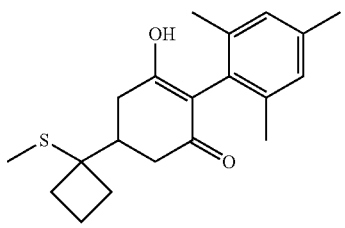 | MS (electrospray ES+): 331 (M + H)+<br>HPLC retention time 1.64 min |
| T43 | 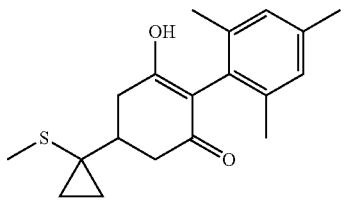 | MS (electrospray ES+): 317 (M + H)+<br>HPLC retention time 1.57 min |
| T44 | 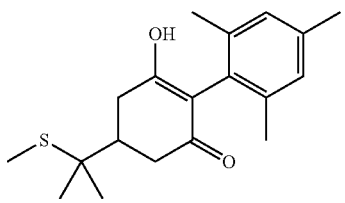 | MS (electrospray ES+): 319 (M + H)+<br>HPLC retention time 1.50 min |

TABLE T1-continued

| | | |
|---|---|---|
| T45 | [structure] | MS (electrospray ES+): 303 (M + H)+ <br> HPLC retention time 1.30 min |
| T46 | [structure] | MS (electrospray ES+): 317 (M + H)+ <br> HPLC retention time 1.55 min |
| T47 | [structure] | MS (electrospray ES+): 317 (M + H)+ <br> HPLC retention time 1.60 min |
| T48 | [structure] | MS (electrospray ES+): 317 (M + H)+ <br> HPLC retention time 1.64 min |
| T49 | [structure] | MS (electrospray ES+): 305 (M + H)+ <br> HPLC retention time 1.40 min |
| T50 | [structure] | MS (electrospray ES+): 331 (M + H)+ <br> HPLC retention time 1.80 min |
| T51 | [structure] | MS (electrospray ES+): 345 (M + H)+ <br> HPLC retention time 1.84 min |

TABLE T1-continued
| T52 | 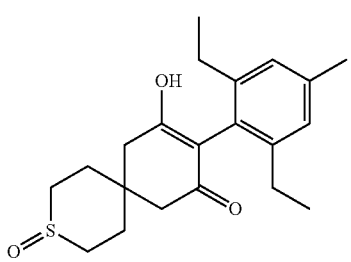 [SMILES: CCc1cc(C)cc(CC)c1C1=C(O)CC2(CCS(=O)CC2)CC1=O] | δ 6.99 (s, 2H), 5.84 (s, 1H), 2.93 (m, 2H), 2.77 (m, 2), 2.64 (s, 2H); 2.58 (s, 2H); 2.45 (m, 2H), 2.33 (m, 7H), 1.85 (m, 2H), 1.07 (t, 6H) |
| --- | --- | --- |
| T53 | 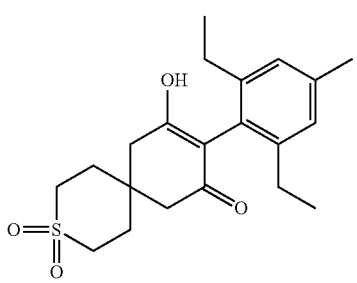 [SMILES: CCc1cc(C)cc(CC)c1C1=C(O)CC2(CCS(=O)(=O)CC2)CC1=O] | δ 6.99 (s, 2H), 5.84 (bs, 1H), 3.06 (m, 4H) 2.66 (s, 2H), 2.60 (s, 2H), 2.37-2.28 (m, 7H), 2.25-2.22 (m, 4H), 1.06 (2 x t, 6H) |
| T54 | 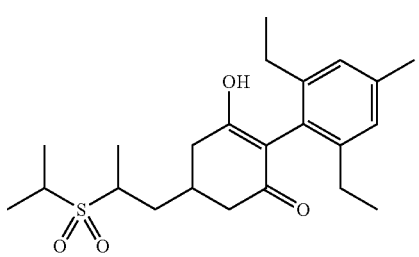 [SMILES: CCc1cc(C)cc(CC)c1C1=C(O)CC(CC(C)S(=O)(=O)C(C)C)CC1=O] | δ 6.99 (s, 2H), 5.64, 5.60 (2xs, 1H), 3.15-3.36 (m, 2H), 2.70 (m, 2H), 2.08-2.56 (m, 7H), 2.33 (s, 3H), 1.65-1.84 (m, 2H), 1.35-1.46 (m, 9H), 1.08 (q, 4H) |
| T55 | 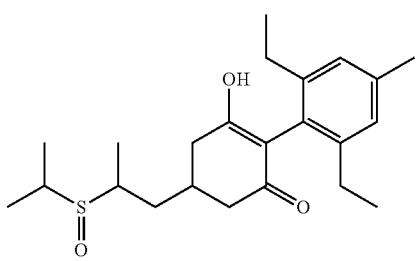 [SMILES: CCc1cc(C)cc(CC)c1C1=C(O)CC(CC(C)S(=O)C(C)C)CC1=O] | δ 6.98 (s, 2H), 6.11, 6.04, 6.00, 5.88 (4xS, 1H), 1.57-2.92 (m, 13H), 2.33 (s, 3H), 1.17-1.42 (m, 9H), 1.08 (q, 6H) |
| T56 | 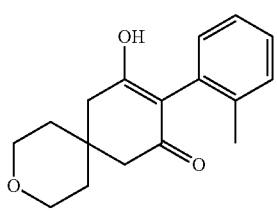 [SMILES: Cc1ccccc1C1=C(O)CC2(CCOCC2)CC1=O] | d$_3$-MeCN δ 7.26 (m, 1H), 7.22 (m, 2H), 7.00 (d, 1H), 3.69 (m, 4H), 2.65 (m, 2H), 2.48 (m, 2H), 2.10 (s, 3H), 1.67 (m, 4H) |
| T57 | 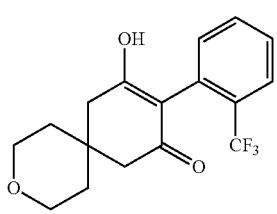 [SMILES: O=C1CC2(CCOCC2)CC(O)=C1c1ccccc1C(F)(F)F] | d$_3$-MeCN δ 7.78 (d, 1H), 7.65 (t, 1H), 7.54 (t, 1H), 7.20 (d, 1H), 3.69 (m, 4H), 2.56 (m, 4H), 1.66 (m, 4H) |

TABLE T1-continued
| T58 | 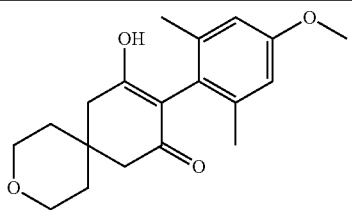 | d₃-MeCN δ 6.69 (s, 2H), 3.79 (s, 3H), 3.69 (m, 4H), 2.65 (m, 2H), 2.49 (m, 2H), 2.02 (s, 6H), 1.68 (m, 4H) |
| --- | --- | --- |
| T59 | 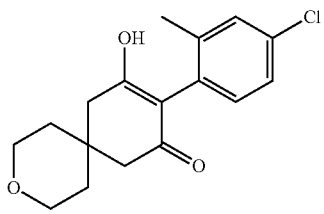 [SMILES: Cc1cc(Cl)ccc1C1=C(O)CC2(CCOCC2)CC1=O] | δ 7.29 (d, 1H), 7.22 (dd, 1H), 6.97 (d, 1H), 5.97 (br. s, 1H), 3.72 (t, 4H), 2.62 (s, 2H), 2.54 (q, 2H), 2.09 (s, 3H), 1.69 (q, 4H) |
| T60 | 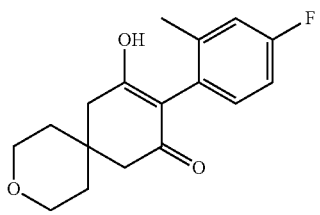 [SMILES: Cc1cc(F)ccc1C1=C(O)CC2(CCOCC2)CC1=O] | d₃-MeCN δ 7.06-6.93 (m, 3H), 3.69 (m, 4H), 2.7-2.4 (br, 4H), 2.10 (s, 3H), 1.67 (m, 4H) |
| T61 | 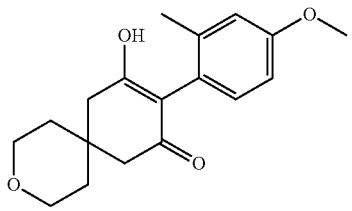 [SMILES: COc1ccc(C2=C(O)CC3(CCOCC3)CC2=O)c(C)c1] | d₃-MeCN δ 6.90 (d, 1H), 6.86, (d, 1H), 6.78 (dd, 1H), 3.81 (s, 3H), 3.49 (m, 4H), 2.7-2.4 (br, 4H), 2.06 (s, 3H), 1.67 (m, 4H) |
| T62 | 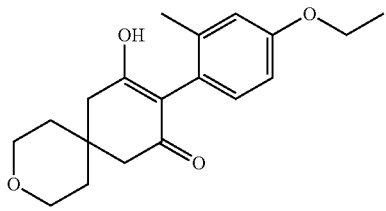 [SMILES: CCOc1ccc(C2=C(O)CC3(CCOCC3)CC2=O)c(C)c1] | δ 6.93 (s, 1H), 6.84 (d, 1H), 6.77 (dd, 1H), 5.81 (br. s, 1H), 4.03 (q, 2H), 3.73 (m, 4H), 2.62 (s, 2H), 2.55 (q, 2H), 2.08 (s, 3H), 1.70 (q, 4H), 1.41 (t, 3H) |
| T63 | 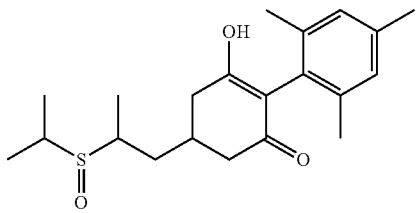 [SMILES: Cc1cc(C)c(C2=C(O)CC(CC(C)S(=O)C(C)C)CC2=O)c(C)c1] | δ 6.93 (s, 2H), 5.92-6.38 (m, 1H), 2.19-2.91 (m, 7H), 2.28 (s, 3H), 2.07 (s, 3H), 2.03 (s, 3H), 1.57-1.94 (m, 2H), 1.16-1.41 (m, 9H) |

TABLE T1-continued
| | | |
|---|---|---|
| T64 | 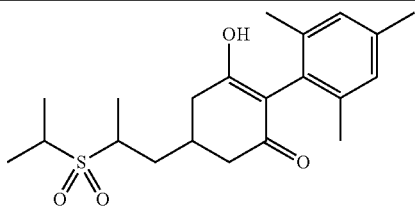 | δ 6.94 (s, 2H), 5.68 (d, 1H), 3.16-3.34 (m, 2H), 2.69 (m, 2H), 2.12-2.53 (m, 3H), 2.28 (s, 3H), 2.06 (s, 3H), 2.03 (s, 3H), 1.62-1.84 (m, 2H), 1.40 (m, 9H) |
| T65 | 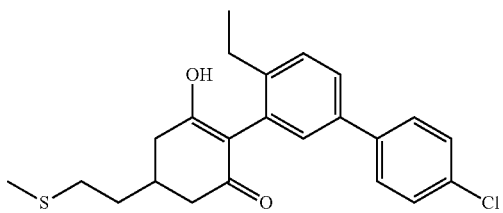 [SMILES: CCc1ccc(-c2ccc(Cl)cc2)cc1C1=C(O)CC(CCSC)CC1=O] | δ 7.20-7.55 (m, 7H), 5.77 (d, 1H), 2.56-2.78 (m, 4H), 2.36-2.53 (m, 4H), 2.27 (m, 1H), 2.14 (d, 3H), 1.79 (q, 2H), 1.15 (m, 3H) |
| T66 | 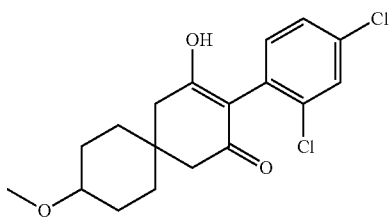 [SMILES: COC1CCC2(CC1)CC(=O)C(c1ccc(Cl)cc1Cl)=C(O)C2] | MS (electrospray ES+): 355 (M + H)+<br>HPLC retention time 1.32 min |
| T67 | 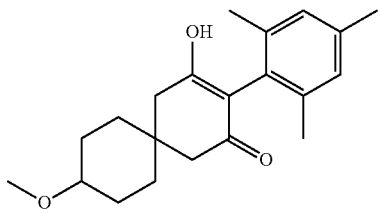 | δ 6.94 (s, 2H), 5.46 (bs, 1H), 3.37 (s, 3H), 3.10 (m, 1H), 2.64-2.61 (m, 2H), 2.48 (m, 1H), 2.28 (s, 3H), 2.25 (m, 1H), 2.13 (m, 2H), 2.06 (m, 7H), 1.91 (m, 2H), 1.33 (m, 1H), 1.19 (m, 2H), 1.07 (m, 2H) |
| T68 | 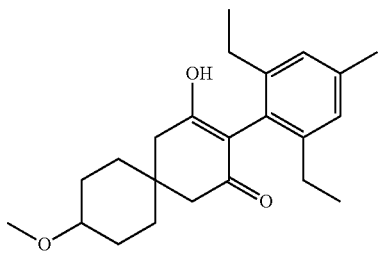 | δ 6.97 (s, 2H), 5.60 (bs, 1H), 3.35 (s, 3H), 3.27 (m, 1H), 2.60 (m, 4H), 2.32 (m, 7H), 1.84 (m, 4H), 1.58 (bs, 2H), 1.44 (m, 2H), 1.06 (t, 6H) |
| T69 | 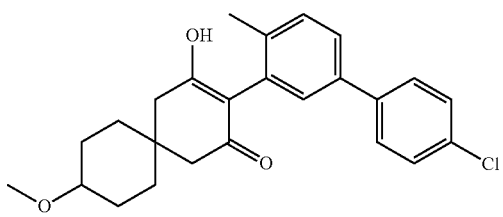 [SMILES: COC1CCC2(CC1)CC(=O)C(c1cc(-c3ccc(Cl)cc3)ccc1C)=C(O)C2] | δ 6.97 7.49 (m, 3H), 7.39 (m, 3H), 7.24 (m, 1H), 5.68 (bs, 1H), 3.35 (s, 3H), 3.30 (m, 1H), 2.55 (m, 4H), 2.16 (s, 3H), 1.84 (m, 4H), 1.58 (m, 1H), 1.44, m, 2H), 1.25 (m, 1H) |

TABLE T1-continued

| | | |
|---|---|---|
| T70 | 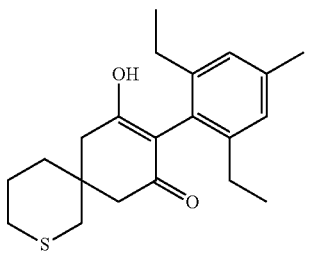 [SMILES: CCc1cc(C)cc(CC)c1C1=C(O)CC2(CCCSC2)CC1=O] | δ 6.98 (s, 2H), 5.52 (s, 1H), 3.03 (d, 1H), 2.72 (m, 2H), 2.57 (m, 4H) 2.32 (m, 7H), 1.91 (m, 2H), 1.73 (m, 1H), 1.55 (m, 2H), 1.06 (2 x t, 6H) |
| T71 | 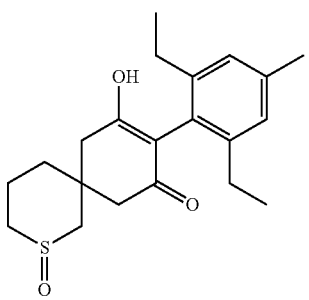 [SMILES: CCc1cc(C)cc(CC)c1C1=C(O)CC2(CCCS(=O)C2)CC1=O] | δ 6.99 (s, 2H), 5.63 (s, 1H), 3.20 (m, 2H), 3.10 (m, 1H), 3.00 (m, 2H), 2.86 (m, 1H), 2.63 (q, 2H), 2.33 (m, 8H), 2.33 (m, 1H), 1.99 (m, 1H), 1.67 (m, 1H), 1.09 (2 x t, 6H), |
| T72 | 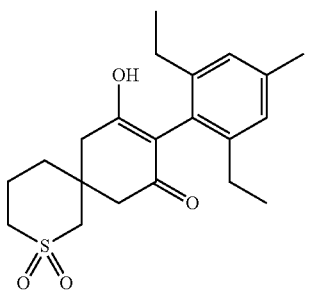 [SMILES: CCc1cc(C)cc(CC)c1C1=C(O)CC2(CCCS(=O)(=O)C2)CC1=O] | δ 6.99 (s, 2H), 5.92 (2s, 1H), 3.39 (m, 1H), 3.12 (m, 1H), 2.94 (m, 2H), 2.79 (m, 2H), 2.62 (m, 2H), 2.33 (m, 8H), 2.17 (m, 1H), 1.67 (m, 2H), 1.09 (m, 6H) |
| T73 | 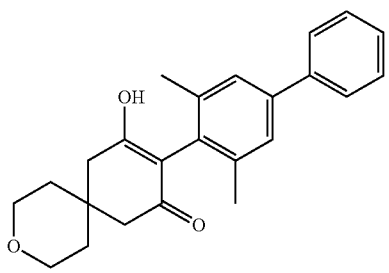 [SMILES: Cc1cc(-c2ccccc2)cc(C)c1C1=C(O)CC2(CCOCC2)CC1=O] | δ 7.57 (d, 2H), 7.42 (dd, 2H), 7.35 (d, 1H), 7.33 (s, 2H), 5.91 (bs, 1H), 3.73 (dd, 4H), 2.64 (s, 2H), 2.58 (s, 2H), 2.14 (s, 6H), 1.72 (dd, 4H) |

Note:
Compounds characterised by HPLC-MS were analysed using an Agilent 1100 Series HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using a three minute run time, according to the following gradient table:

| Time (mins) | Solvent A (%) | Solvent B (%) | Flow (ml/mn) | Pressure (bar) |
|---|---|---|---|---|
| 0.00 | 90.0 | 10.0 | 1.700 | 400 |
| 2.50 | 0.0 | 100 | 1.700 | 400 |
| 2.80 | 0.00 | 100 | 1.700 | 400 |
| 2.90 | 90.0 | 10.0 | 1.700 | 400 |

Solvent A: $H_2O/CH_3CN$ 90/10 with 0.1% HCOOH
Solvent B: 0.1% HCOOH in $CH_3CN$ The characteristic values obtained for each compound were the retention time (recorded in minutes) and the molecular ion, typically the cation M+H⁺ as listed in Table T1.

T 74

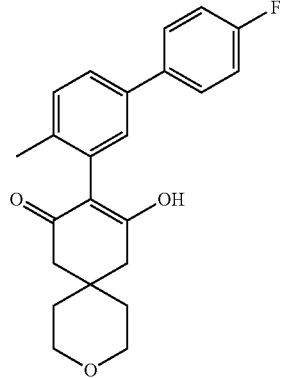

¹H-NMR (400 MHz in d₆DMSO) δ=1.58-1.61 (m, 4H), 2.04 (s, 3H), 3.60-3.62 (m 4H), 5.69 (s), 7.11-7.12 (d, 1H), 7.18-7.23 (m, 3H), 7.37-7.40 (dd, 1H), 7.57-7.61 (m, 2H) ppm

T 75

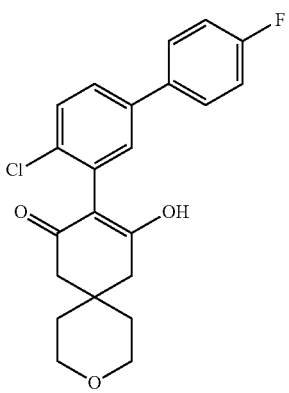

¹H-NMR (400 MHz in d₆DMSO): δ=1.57-1.59, 1.63-1.65 (2m, 4H), 3.59-3.61 (m 4H), 5.75 (s), 7.25-7.32 (m, 3H), 7.46-7.48 (d, 1H), 7.52-7.54 (m, 1H), 7.64-7.68 (m, 2H) ppm

T 76

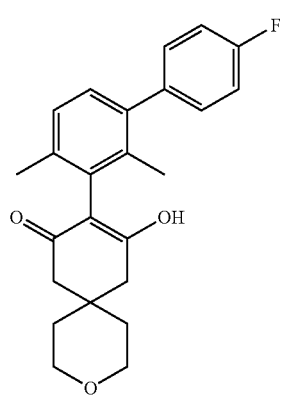

¹H-NMR (400 MHz in d₆DMSO): δ=1.57-1.61 (m, 4H), 1.86 (s, 3H), 2.00 (s 3H), 3.59-3.62 (m, 4H), 6.96-6.98 (d, 1H), 7.03-7.05 (d, 1H), 7.20-7.30 (m, 4H) ppm The spelling C.C used in the following tables indicates the presence of a triple bond between these 2 carbon atoms. For example, CH₂C.CH denotes a propargyl group.

TABLE 1

This Table contains 646 compounds of the following type,

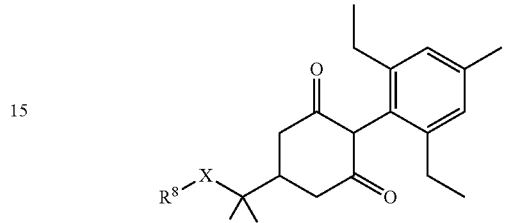

where X, R², R³ and R⁴ are as defined below:

| Compound number | R⁶ | R⁷ | X | R⁸ |
|---|---|---|---|---|
| 1.1 | H | H | O | CH₂CH₃ |
| 1.2 | H | H | O | CH₂CH₂CH₃ |
| 1.3 | H | H | O | CH(CH₃)₂ |
| 1.4 | H | H | O | CH₂CH₂CH₂CH₃ |
| 1.5 | H | H | O | CH₂CH(CH₃)₂ |
| 1.6 | H | H | O | CH(CH₃)CH₂CH₃ |
| 1.7 | H | H | O | C(CH₃)₃ |
| 1.8 | H | H | O | CH₂CH₂CH₂CH₂CH₃ |
| 1.9 | H | H | O | CH₂CH₂CH(CH₃)₂ |
| 1.10 | H | H | O | CH₂C(CH₃)₃ |
| 1.11 | H | H | O | CH₂CH(CH₃)CH₂CH₃ |
| 1.12 | H | H | O | CH(CH₃)CH₂CH₂CH₃ |
| 1.13 | H | H | O | C(CH₃)₂CH₂CH₃ |
| 1.14 | H | H | O | CH₂CH=CH₂ |
| 1.15 | H | H | O | CH₂CH=CHCH₃ |
| 1.16 | H | H | O | CH₂CH=C(CH₃)₂ |
| 1.17 | H | H | O | CH₂C(CH₃)=CH₂ |
| 1.18 | H | H | O | CH₂C(CH₃)=CHCH₃ |
| 1.19 | H | H | O | CH₂C(CH₃)=C(CH₃)₂ |
| 1.20 | H | H | O | CH(CH₃)CH=CH₂ |
| 1.21 | H | H | O | CH(CH₃)CH=CHCH₃ |
| 1.22 | H | H | O | CH(CH₃)CH=C(CH₃)₂ |
| 1.23 | H | H | O | C(CH₃)₂CH=CH₂ |
| 1.24 | H | H | O | C(CH₃)₂CH=CHCH₃ |
| 1.25 | H | H | O | C(CH₃)₂CH=C(CH₃)₂ |
| 1.26 | H | H | O | CH₂CH=CHCl |
| 1.27 | H | H | O | CH₂CH=CCl₂ |
| 1.28 | H | H | O | CH₂CCl=CHCl |
| 1.29 | H | H | O | CH₂CCl=CCl₂ |
| 1.30 | H | H | O | CH₂CH=CF₂ |
| 1.31 | H | H | O | CH₂CF=CF₂ |
| 1.32 | H | H | O | CH₂C•CH |
| 1.33 | H | H | O | CH₂C•CCH₃ |
| 1.34 | H | H | O | CH₂C•CCH₂CH₃ |
| 1.35 | H | H | O | CH(CH₃)C•CH |
| 1.36 | H | H | O | CH(CH₃)C•CCH₃ |
| 1.37 | H | H | O | CH(CH₃)C•CCH₂CH₃ |
| 1.38 | H | H | O | C(CH₃)₂C•CH |
| 1.39 | H | H | O | C(CH₃)₂C•CCH₃ |
| 1.40 | H | H | O | C(CH₃)₂C•CCH₂CH₃ |
| 1.41 | H | H | O | Cyclopropyl |
| 1.42 | H | H | O | Cyclobutyl |
| 1.43 | H | H | O | Cyclopentyl |
| 1.44 | H | H | O | Cyclohexyl |
| 1.45 | H | H | O | CH₂CF₃ |
| 1.46 | H | H | O | CH₂CH₂CF₃ |
| 1.47 | H | H | O | CH₂-cyclopropyl |
| 1.48 | H | H | O | CH₂-cyclobutyl |
| 1.49 | H | H | O | CH₂-cyclopentyl |
| 1.50 | H | H | O | CH₂-cyclohexyl |
| 1.51 | H | H | O | CH₂OCH₃ |
| 1.52 | H | H | O | CH₂OCH₂CH₃ |
| 1.53 | H | H | O | CH₂CH₂OCH₃ |

TABLE 1-continued

This Table contains 646 compounds of the following type,

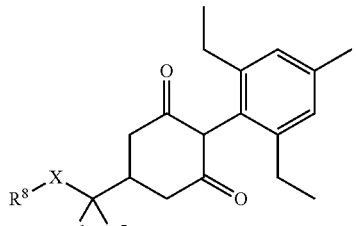

where X, $R^2$, $R^3$ and $R^4$ are as defined below:

| Compound number | $R^6$ | $R^7$ | X | $R^8$ |
|---|---|---|---|---|
| 1.54 | H | H | O | $CH_2CH_2OCH_2CH_3$ |
| 1.55 | $CH_3$ | H | O | $CH_3$ |
| 1.56 | $CH_3$ | H | O | $CH_2CH_3$ |
| 1.57 | $CH_3$ | H | O | $CH_2CH_2CH_3$ |
| 1.58 | $CH_3$ | H | O | $CH(CH_3)_2$ |
| 1.59 | $CH_3$ | H | O | $CH_2CH_2CH_2CH_3$ |
| 1.60 | $CH_3$ | H | O | $CH_2CH(CH_3)_2$ |
| 1.61 | $CH_3$ | H | O | $CH(CH_3)CH_2CH_3$ |
| 1.62 | $CH_3$ | H | O | $C(CH_3)_3$ |
| 1.63 | $CH_3$ | H | O | $CH_2CH_2CH_2CH_2CH_3$ |
| 1.64 | $CH_3$ | H | O | $CH_2CH_2CH(CH_3)_2$ |
| 1.65 | $CH_3$ | H | O | $CH_2C(CH_3)_3$ |
| 1.66 | $CH_3$ | H | O | $CH_2CH(CH_3)CH_2CH_3$ |
| 1.67 | $CH_3$ | H | O | $CH(CH_3)CH_2CH_2CH_3$ |
| 1.68 | $CH_3$ | H | O | $C(CH_3)_2CH_2CH_3$ |
| 1.69 | $CH_3$ | H | O | $CH_2CH=CH_2$ |
| 1.70 | $CH_3$ | H | O | $CH_2CH=CHCH_3$ |
| 1.71 | $CH_3$ | H | O | $CH_2CH=C(CH_3)_2$ |
| 1.72 | $CH_3$ | H | O | $CH_2C(CH_3)=CH_2$ |
| 1.73 | $CH_3$ | H | O | $CH_2C(CH_3)=CHCH_3$ |
| 1.74 | $CH_3$ | H | O | $CH_2C(CH_3)=C(CH_3)_2$ |
| 1.75 | $CH_3$ | H | O | $CH(CH_3)CH=CH_2$ |
| 1.76 | $CH_3$ | H | O | $CH(CH_3)CH=CHCH_3$ |
| 1.77 | $CH_3$ | H | O | $CH(CH_3)CH=C(CH_3)_2$ |
| 1.78 | $CH_3$ | H | O | $C(CH_3)_2CH=CH_2$ |
| 1.79 | $CH_3$ | H | O | $C(CH_3)_2CH=CHCH_3$ |
| 1.80 | $CH_3$ | H | O | $C(CH_3)_2CH=C(CH_3)_2$ |
| 1.81 | $CH_3$ | H | O | $CH_2CH=CHCl$ |
| 1.82 | $CH_3$ | H | O | $CH_2CH=CCl_2$ |
| 1.83 | $CH_3$ | H | O | $CH_2CCl=CHCl$ |
| 1.84 | $CH_3$ | H | O | $CH_2CCl=CCl_2$ |
| 1.85 | $CH_3$ | H | O | $CH_2CH=CF_2$ |
| 1.86 | $CH_3$ | H | O | $CH_2CF=CF_2$ |
| 1.87 | $CH_3$ | H | O | $CH_2C•CH$ |
| 1.88 | $CH_3$ | H | O | $CH_2C•CCH_3$ |
| 1.89 | $CH_3$ | H | O | $CH_2C•CCH_2CH_3$ |
| 1.90 | $CH_3$ | H | O | $CH(CH_3)C•CH$ |
| 1.91 | $CH_3$ | H | O | $CH(CH_3)C•CCH_3$ |
| 1.92 | $CH_3$ | H | O | $CH(CH_3)C•CCH_2CH_3$ |
| 1.93 | $CH_3$ | H | O | $C(CH_3)_2C•CH$ |
| 1.94 | $CH_3$ | H | O | $C(CH_3)_2C•CCH_3$ |
| 1.95 | $CH_3$ | H | O | $C(CH_3)_2C•CCH_2CH_3$ |
| 1.96 | $CH_3$ | H | O | Cyclopropyl |
| 1.97 | $CH_3$ | H | O | Cyclobutyl |
| 1.98 | $CH_3$ | H | O | Cyclopentyl |
| 1.99 | $CH_3$ | H | O | Cyclohexyl |
| 1.100 | $CH_3$ | H | O | $CH_2CF_3$ |
| 1.101 | $CH_3$ | H | O | $CH_2CH_2CF_3$ |
| 1.102 | $CH_3$ | H | O | $CH_2$-cyclopropyl |
| 1.103 | $CH_3$ | H | O | $CH_2$-cyclobutyl |
| 1.104 | $CH_3$ | H | O | $CH_2$-cyclopentyl |
| 1.105 | $CH_3$ | H | O | $CH_2$-cyclohexyl |
| 1.106 | $CH_3$ | H | O | $CH_2OCH_3$ |
| 1.107 | $CH_3$ | H | O | $CH_2OCH_2CH_3$ |
| 1.108 | $CH_3$ | H | O | $CH_2CH_2OCH_3$ |
| 1.109 | $CH_3$ | H | O | $CH_2CH_2OCH_2CH_3$ |
| 1.110 | $CH_3$ | $CH_3$ | O | $CH_3$ |
| 1.111 | $CH_3$ | $CH_3$ | O | $CH_2CH_3$ |
| 1.112 | $CH_3$ | $CH_3$ | O | $CH_2CH_2CH_3$ |
| 1.113 | $CH_3$ | $CH_3$ | O | $CH(CH_3)_2$ |
| 1.114 | $CH_3$ | $CH_3$ | O | $CH_2CH_2CH_2CH_3$ |

TABLE 1-continued

This Table contains 646 compounds of the following type,

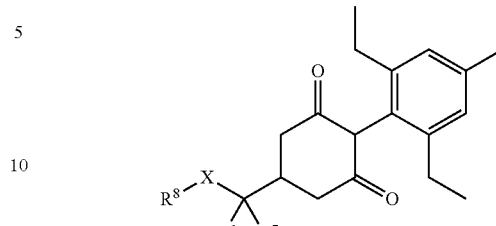

where X, $R^2$, $R^3$ and $R^4$ are as defined below:

| Compound number | $R^6$ | $R^7$ | X | $R^8$ |
|---|---|---|---|---|
| 1.115 | $CH_3$ | $CH_3$ | O | $CH_2CH(CH_3)_2$ |
| 1.116 | $CH_3$ | $CH_3$ | O | $CH(CH_3)CH_2CH_3$ |
| 1.117 | $CH_3$ | $CH_3$ | O | $C(CH_3)_3$ |
| 1.118 | $CH_3$ | $CH_3$ | O | $CH_2CH_2CH_2CH_2CH_3$ |
| 1.119 | $CH_3$ | $CH_3$ | O | $CH_2CH_2CH(CH_3)_2$ |
| 1.120 | $CH_3$ | $CH_3$ | O | $CH_2C(CH_3)_3$ |
| 1.121 | $CH_3$ | $CH_3$ | O | $CH_2CH(CH_3)CH_2CH_3$ |
| 1.122 | $CH_3$ | $CH_3$ | O | $CH(CH_3)CH_2CH_2CH_3$ |
| 1.123 | $CH_3$ | $CH_3$ | O | $C(CH_3)_2CH_2CH_3$ |
| 1.124 | $CH_3$ | $CH_3$ | O | $CH_2CH=CH_2$ |
| 1.125 | $CH_3$ | $CH_3$ | O | $CH_2CH=CHCH_3$ |
| 1.126 | $CH_3$ | $CH_3$ | O | $CH_2CH=C(CH_3)_2$ |
| 1.127 | $CH_3$ | $CH_3$ | O | $CH_2C(CH_3)=CH_2$ |
| 1.128 | $CH_3$ | $CH_3$ | O | $CH_2C(CH_3)=CHCH_3$ |
| 1.129 | $CH_3$ | $CH_3$ | O | $CH_2C(CH_3)=C(CH_3)_2$ |
| 1.130 | $CH_3$ | $CH_3$ | O | $CH(CH_3)CH=CH_2$ |
| 1.131 | $CH_3$ | $CH_3$ | O | $CH(CH_3)CH=CHCH_3$ |
| 1.132 | $CH_3$ | $CH_3$ | O | $CH(CH_3)CH=C(CH_3)_2$ |
| 1.133 | $CH_3$ | $CH_3$ | O | $C(CH_3)_2CH=CH_2$ |
| 1.134 | $CH_3$ | $CH_3$ | O | $C(CH_3)_2CH=CHCH_3$ |
| 1.135 | $CH_3$ | $CH_3$ | O | $C(CH_3)_2CH=C(CH_3)_2$ |
| 1.136 | $CH_3$ | $CH_3$ | O | $CH_2CH=CHCl$ |
| 1.137 | $CH_3$ | $CH_3$ | O | $CH_2CH=CCl_2$ |
| 1.138 | $CH_3$ | $CH_3$ | O | $CH_2CCl=CHCl$ |
| 1.139 | $CH_3$ | $CH_3$ | O | $CH_2CCl=CCl_2$ |
| 1.140 | $CH_3$ | $CH_3$ | O | $CH_2CH=CF_2$ |
| 1.141 | $CH_3$ | $CH_3$ | O | $CH_2CF=CF_2$ |
| 1.142 | $CH_3$ | $CH_3$ | O | $CH_2C•CH$ |
| 1.143 | $CH_3$ | $CH_3$ | O | $CH_2C•CCH_3$ |
| 1.144 | $CH_3$ | $CH_3$ | O | $CH_2C•CCH_2CH_3$ |
| 1.145 | $CH_3$ | $CH_3$ | O | $CH(CH_3)C•CH$ |
| 1.146 | $CH_3$ | $CH_3$ | O | $CH(CH_3)C•CCH_3$ |
| 1.147 | $CH_3$ | $CH_3$ | O | $CH(CH_3)C•CCH_2CH_3$ |
| 1.148 | $CH_3$ | $CH_3$ | O | $C(CH_3)_2C•CH$ |
| 1.149 | $CH_3$ | $CH_3$ | O | $C(CH_3)_2C•CCH_3$ |
| 1.150 | $CH_3$ | $CH_3$ | O | $C(CH_3)_2C•CCH_2CH_3$ |
| 1.151 | $CH_3$ | $CH_3$ | O | Cyclopropyl |
| 1.152 | $CH_3$ | $CH_3$ | O | Cyclobutyl |
| 1.153 | $CH_3$ | $CH_3$ | O | Cyclopentyl |
| 1.154 | $CH_3$ | $CH_3$ | O | Cyclohexyl |
| 1.155 | $CH_3$ | $CH_3$ | O | $CH_2CF_3$ |
| 1.156 | $CH_3$ | $CH_3$ | O | $CH_2CH_2CF_3$ |
| 1.157 | $CH_3$ | $CH_3$ | O | $CH_2$-cyclopropyl |
| 1.158 | $CH_3$ | $CH_3$ | O | $CH_2$-cyclobutyl |
| 1.159 | $CH_3$ | $CH_3$ | O | $CH_2$-cyclopentyl |
| 1.160 | $CH_3$ | $CH_3$ | O | $CH_2$-cyclohexyl |
| 1.161 | $CH_3$ | $CH_3$ | O | $CH_2OCH_3$ |
| 1.162 | $CH_3$ | $CH_3$ | O | $CH_2OCH_2CH_3$ |
| 1.163 | $CH_3$ | $CH_3$ | O | $CH_2CH_2OCH_3$ |
| 1.164 | $CH_3$ | $CH_3$ | O | $CH_2CH_2OCH_2CH_3$ |
| 1.165 | H | H | S | $CH_2CH_3$ |
| 1.166 | H | H | S | $CH_2CH_2CH_3$ |
| 1.167 | H | H | S | $CH(CH_3)_2$ |
| 1.168 | H | H | S | $CH_2CH_2CH_2CH_3$ |
| 1.169 | H | H | S | $CH_2CH(CH_3)_2$ |
| 1.170 | H | H | S | $CH(CH_3)CH_2CH_3$ |
| 1.171 | H | H | S | $C(CH_3)_3$ |
| 1.172 | H | H | S | $CH_2CH_2CH_2CH_2CH_3$ |
| 1.173 | H | H | S | $CH_2CH_2CH(CH_3)_2$ |
| 1.174 | H | H | S | $CH_2C(CH_3)_3$ |
| 1.175 | H | H | S | $CH_2CH(CH_3)CH_2CH_3$ |

TABLE 1-continued

This Table contains 646 compounds of the following type,

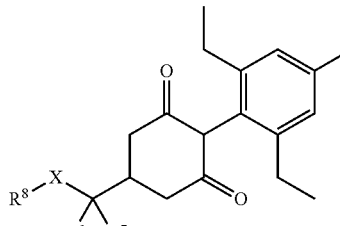

where X, $R^2$, $R^3$ and $R^4$ are as defined below:

| Compound number | $R^6$ | $R^7$ | X | $R^8$ |
|---|---|---|---|---|
| 1.176 | H | H | S | $CH(CH_3)CH_2CH_2CH_3$ |
| 1.177 | H | H | S | $C(CH_3)_2CH_2CH_3$ |
| 1.178 | H | H | S | $CH_2CH=CH_2$ |
| 1.179 | H | H | S | $CH_2CH=CHCH_3$ |
| 1.180 | H | H | S | $CH_2CH=C(CH_3)_2$ |
| 1.181 | H | H | S | $CH_2C(CH_3)=CH_2$ |
| 1.182 | H | H | S | $CH_2C(CH_3)=CHCH_3$ |
| 1.183 | H | H | S | $CH_2C(CH_3)=C(CH_3)_2$ |
| 1.184 | H | H | S | $CH(CH_3)CH=CH_2$ |
| 1.185 | H | H | S | $CH(CH_3)CH=CHCH_3$ |
| 1.186 | H | H | S | $CH(CH_3)CH=C(CH_3)_2$ |
| 1.187 | H | H | S | $C(CH_3)_2CH=CH_2$ |
| 1.188 | H | H | S | $C(CH_3)_2CH=CHCH_3$ |
| 1.189 | H | H | S | $C(CH_3)_2CH=C(CH_3)_2$ |
| 1.190 | H | H | S | $CH_2CH=CHCl$ |
| 1.191 | H | H | S | $CH_2CH=CCl_2$ |
| 1.192 | H | H | S | $CH_2CCl=CHCl$ |
| 1.193 | H | H | S | $CH_2CCl=CCl_2$ |
| 1.194 | H | H | S | $CH_2CH=CF_2$ |
| 1.195 | H | H | S | $CH_2CF=CF_2$ |
| 1.196 | H | H | S | $CH_2C \bullet CH$ |
| 1.197 | H | H | S | $CH_2C \bullet CCH_3$ |
| 1.198 | H | H | S | $CH_2C \bullet CCH_2CH_3$ |
| 1.199 | H | H | S | $CH(CH_3)C \bullet CH$ |
| 1.200 | H | H | S | $CH(CH_3)C \bullet CCH_3$ |
| 1.201 | H | H | S | $CH(CH_3)C \bullet CCH_2CH_3$ |
| 1.202 | H | H | S | $C(CH_3)_2C \bullet CH$ |
| 1.203 | H | H | S | $C(CH_3)_2C \bullet CCH_3$ |
| 1.204 | H | H | S | $C(CH_3)_2C \bullet CCH_2CH_3$ |
| 1.205 | H | H | S | Cyclopropyl |
| 1.206 | H | H | S | Cyclobutyl |
| 1.207 | H | H | S | Cyclopentyl |
| 1.208 | H | H | S | Cyclohexyl |
| 1.209 | H | H | S | $CH_2CF_3$ |
| 1.210 | H | H | S | $CH_2CH_2CF_3$ |
| 1.211 | H | H | S | $CH_2$-cyclopropyl |
| 1.212 | H | H | S | $CH_2$-cyclobutyl |
| 1.213 | H | H | S | $CH_2$-cyclopentyl |
| 1.214 | H | H | S | $CH_2$-cyclohexyl |
| 1.215 | $CH_3$ | H | S | $CH_3$ |
| 1.216 | $CH_3$ | H | S | $CH_2CH_3$ |
| 1.217 | $CH_3$ | H | S | $CH_2CH_2CH_3$ |
| 1.218 | $CH_3$ | H | S | $CH(CH_3)_2$ |
| 1.219 | $CH_3$ | H | S | $CH_2CH_2CH_2CH_3$ |
| 1.220 | $CH_3$ | H | S | $CH_2CH(CH_3)_2$ |
| 1.221 | $CH_3$ | H | S | $CH(CH_3)CH_2CH_3$ |
| 1.222 | $CH_3$ | H | S | $C(CH_3)_3$ |
| 1.223 | $CH_3$ | H | S | $CH_2CH_2CH_2CH_2CH_3$ |
| 1.224 | $CH_3$ | H | S | $CH_2CH_2CH(CH_3)_2$ |
| 1.225 | $CH_3$ | H | S | $CH_2C(CH_3)_3$ |
| 1.226 | $CH_3$ | H | S | $CH_2CH(CH_3)CH_2CH_3$ |
| 1.227 | $CH_3$ | H | S | $CH(CH_3)CH_2CH_2CH_3$ |
| 1.228 | $CH_3$ | H | S | $C(CH_3)_2CH_2CH_3$ |
| 1.229 | $CH_3$ | H | S | $CH_2CH=CH_2$ |
| 1.230 | $CH_3$ | H | S | $CH_2CH=CHCH_3$ |
| 1.231 | $CH_3$ | H | S | $CH_2CH=C(CH_3)_2$ |
| 1.232 | $CH_3$ | H | S | $CH_2C(CH_3)=CH_2$ |
| 1.233 | $CH_3$ | H | S | $CH_2C(CH_3)=CHCH_3$ |
| 1.234 | $CH_3$ | H | S | $CH_2C(CH_3)=C(CH_3)_2$ |
| 1.235 | $CH_3$ | H | S | $CH(CH_3)CH=CH_2$ |
| 1.236 | $CH_3$ | H | S | $CH(CH_3)CH=CHCH_3$ |

TABLE 1-continued

This Table contains 646 compounds of the following type,

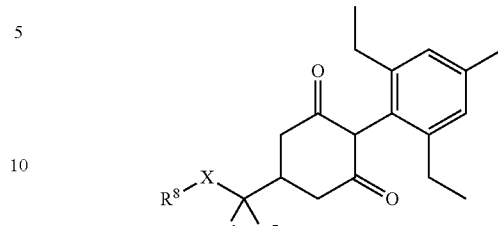

where X, $R^2$, $R^3$ and $R^4$ are as defined below:

| Compound number | $R^6$ | $R^7$ | X | $R^8$ |
|---|---|---|---|---|
| 1.237 | $CH_3$ | H | S | $CH(CH_3)CH=C(CH_3)_2$ |
| 1.238 | $CH_3$ | H | S | $C(CH_3)_2CH=CH_2$ |
| 1.239 | $CH_3$ | H | S | $C(CH_3)_2CH=CHCH_3$ |
| 1.240 | $CH_3$ | H | S | $C(CH_3)_2CH=C(CH_3)_2$ |
| 1.241 | $CH_3$ | H | S | $CH_2CH=CHCl$ |
| 1.242 | $CH_3$ | H | S | $CH_2CH=CCl_2$ |
| 1.243 | $CH_3$ | H | S | $CH_2CCl=CHCl$ |
| 1.244 | $CH_3$ | H | S | $CH_2CCl=CCl_2$ |
| 1.245 | $CH_3$ | H | S | $CH_2CH=CF_2$ |
| 1.246 | $CH_3$ | H | S | $CH_2CF=CF_2$ |
| 1.247 | $CH_3$ | H | S | $CH_2C \bullet CH$ |
| 1.248 | $CH_3$ | H | S | $CH_2C \bullet CCH_3$ |
| 1.249 | $CH_3$ | H | S | $CH_2C \bullet CCH_2CH_3$ |
| 1.250 | $CH_3$ | H | S | $CH(CH_3)C \bullet CH$ |
| 1.251 | $CH_3$ | H | S | $CH(CH_3)C \bullet CCH_3$ |
| 1.252 | $CH_3$ | H | S | $CH(CH_3)C \bullet CCH_2CH_3$ |
| 1.253 | $CH_3$ | H | S | $C(CH_3)_2C \bullet CH$ |
| 1.254 | $CH_3$ | H | S | $C(CH_3)_2C \bullet CCH_3$ |
| 1.255 | $CH_3$ | H | S | $C(CH_3)_2C \bullet CCH_2CH_3$ |
| 1.256 | $CH_3$ | H | S | Cyclopropyl |
| 1.257 | $CH_3$ | H | S | Cyclobutyl |
| 1.258 | $CH_3$ | H | S | Cyclopentyl |
| 1.259 | $CH_3$ | H | S | Cyclohexyl |
| 1.260 | $CH_3$ | H | S | $CH_2CF_3$ |
| 1.261 | $CH_3$ | H | S | $CH_2CH_2CF_3$ |
| 1.262 | $CH_3$ | H | S | $CH_2$-cyclopropyl |
| 1.263 | $CH_3$ | H | S | $CH_2$-cyclobutyl |
| 1.264 | $CH_3$ | H | S | $CH_2$-cyclopentyl |
| 1.265 | $CH_3$ | H | S | $CH_2$-cyclohexyl |
| 1.266 | $CH_3$ | $CH_3$ | S | $CH_3$ |
| 1.267 | $CH_3$ | $CH_3$ | S | $CH_2CH_3$ |
| 1.268 | $CH_3$ | $CH_3$ | S | $CH_2CH_2CH_3$ |
| 1.269 | $CH_3$ | $CH_3$ | S | $CH(CH_3)_2$ |
| 1.270 | $CH_3$ | $CH_3$ | S | $CH_2CH_2CH_2CH_3$ |
| 1.271 | $CH_3$ | $CH_3$ | S | $CH_2CH(CH_3)_2$ |
| 1.272 | $CH_3$ | $CH_3$ | S | $CH(CH_3)CH_2CH_3$ |
| 1.273 | $CH_3$ | $CH_3$ | S | $C(CH_3)_3$ |
| 1.274 | $CH_3$ | $CH_3$ | S | $CH_2CH_2CH_2CH_2CH_3$ |
| 1.275 | $CH_3$ | $CH_3$ | S | $CH_2CH_2CH(CH_3)_2$ |
| 1.276 | $CH_3$ | $CH_3$ | S | $CH_2C(CH_3)_3$ |
| 1.277 | $CH_3$ | $CH_3$ | S | $CH_2CH(CH_3)CH_2CH_3$ |
| 1.278 | $CH_3$ | $CH_3$ | S | $CH(CH_3)CH_2CH_2CH_3$ |
| 1.279 | $CH_3$ | $CH_3$ | S | $C(CH_3)_2CH_2CH_3$ |
| 1.280 | $CH_3$ | $CH_3$ | S | $CH_2CH=CH_2$ |
| 1.281 | $CH_3$ | $CH_3$ | S | $CH_2CH=CHCH_3$ |
| 1.282 | $CH_3$ | $CH_3$ | S | $CH_2CH=C(CH_3)_2$ |
| 1.283 | $CH_3$ | $CH_3$ | S | $CH_2C(CH_3)=CH_2$ |
| 1.284 | $CH_3$ | $CH_3$ | S | $CH_2C(CH_3)=CHCH_3$ |
| 1.285 | $CH_3$ | $CH_3$ | S | $CH_2C(CH_3)=C(CH_3)_2$ |
| 1.286 | $CH_3$ | $CH_3$ | S | $CH(CH_3)CH=CH_2$ |
| 1.287 | $CH_3$ | $CH_3$ | S | $CH(CH_3)CH=CHCH_3$ |
| 1.288 | $CH_3$ | $CH_3$ | S | $CH(CH_3)CH=C(CH_3)_2$ |
| 1.289 | $CH_3$ | $CH_3$ | S | $C(CH_3)_2CH=CH_2$ |
| 1.290 | $CH_3$ | $CH_3$ | S | $C(CH_3)_2CH=CHCH_3$ |
| 1.291 | $CH_3$ | $CH_3$ | S | $C(CH_3)_2CH=C(CH_3)_2$ |
| 1.292 | $CH_3$ | $CH_3$ | S | $CH_2CH=CHCl$ |
| 1.293 | $CH_3$ | $CH_3$ | S | $CH_2CH=CCl_2$ |
| 1.294 | $CH_3$ | $CH_3$ | S | $CH_2CCl=CHCl$ |
| 1.295 | $CH_3$ | $CH_3$ | S | $CH_2CCl=CCl_2$ |
| 1.296 | $CH_3$ | $CH_3$ | S | $CH_2CH=CF_2$ |
| 1.297 | $CH_3$ | $CH_3$ | S | $CH_2CF=CF_2$ |

TABLE 1-continued

This Table contains 646 compounds of the following type,

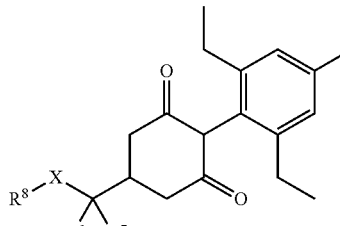

where X, R², R³ and R⁴ are as defined below:

| Compound number | R⁶ | R⁷ | X | R⁸ |
| --- | --- | --- | --- | --- |
| 1.298 | CH₃ | CH₃ | S | CH₂C•CH |
| 1.299 | CH₃ | CH₃ | S | CH₂C•CCH₃ |
| 1.300 | CH₃ | CH₃ | S | CH₂C•CCH₂CH₃ |
| 1.301 | CH₃ | CH₃ | S | CH(CH₃)C•CH |
| 1.302 | CH₃ | CH₃ | S | CH(CH₃)C•CCH₃ |
| 1.303 | CH₃ | CH₃ | S | CH(CH₃)C•CCH₂CH₃ |
| 1.304 | CH₃ | CH₃ | S | C(CH₃)₂C•CH |
| 1.305 | CH₃ | CH₃ | S | C(CH₃)₂C•CCH₃ |
| 1.306 | CH₃ | CH₃ | S | C(CH₃)₂C•CCH₂CH₃ |
| 1.307 | CH₃ | CH₃ | S | Cyclopropyl |
| 1.308 | CH₃ | CH₃ | S | Cyclobutyl |
| 1.309 | CH₃ | CH₃ | S | Cyclopentyl |
| 1.310 | CH₃ | CH₃ | S | Cyclohexyl |
| 1.311 | CH₃ | CH₃ | S | CH₂CF₃ |
| 1.312 | CH₃ | CH₃ | S | CH₂CH₂CF₃ |
| 1.313 | CH₃ | CH₃ | S | CH₂-cyclopropyl |
| 1.314 | CH₃ | CH₃ | S | CH₂-cyclobutyl |
| 1.315 | CH₃ | CH₃ | S | CH₂-cyclopentyl |
| 1.316 | CH₃ | CH₃ | S | CH₂-cyclohexyl |
| 1.317 | H | H | S(O) | CH₃ |
| 1.318 | H | H | S(O) | CH₂CH₃ |
| 1.319 | H | H | S(O) | CH₂CH₂CH₃ |
| 1.320 | H | H | S(O) | CH(CH₃)₂ |
| 1.321 | H | H | S(O) | CH₂CH₂CH₂CH₃ |
| 1.322 | H | H | S(O) | CH₂CH(CH₃)₂ |
| 1.323 | H | H | S(O) | CH(CH₃)CH₂CH₃ |
| 1.324 | H | H | S(O) | C(CH₃)₃ |
| 1.325 | H | H | S(O) | CH₂CH₂CH₂CH₂CH₃ |
| 1.326 | H | H | S(O) | CH₂CH₂CH(CH₃)₂ |
| 1.327 | H | H | S(O) | CH₂C(CH₃)₃ |
| 1.328 | H | H | S(O) | CH₂CH(CH₃)CH₂CH₃ |
| 1.329 | H | H | S(O) | CH(CH₃)CH₂CH₂CH₃ |
| 1.330 | H | H | S(O) | C(CH₃)₂CH₂CH₃ |
| 1.331 | H | H | S(O) | CH₂CH=CH₂ |
| 1.332 | H | H | S(O) | CH₂CH=CHCH₃ |
| 1.333 | H | H | S(O) | CH₂CH=C(CH₃)₂ |
| 1.334 | H | H | S(O) | CH₂C(CH₃)=CH₂ |
| 1.335 | H | H | S(O) | CH₂C(CH₃)=CHCH₃ |
| 1.336 | H | H | S(O) | CH₂C(CH₃)=C(CH₃)₂ |
| 1.337 | H | H | S(O) | CH(CH₃)CH=CH₂ |
| 1.338 | H | H | S(O) | CH(CH₃)CH=CHCH₃ |
| 1.339 | H | H | S(O) | CH(CH₃)CH=C(CH₃)₂ |
| 1.340 | H | H | S(O) | C(CH₃)₂CH=CH₂ |
| 1.341 | H | H | S(O) | C(CH₃)₂CH=CHCH₃ |
| 1.342 | H | H | S(O) | C(CH₃)₂CH=C(CH₃)₂ |
| 1.343 | H | H | S(O) | CH₂CH=CHCl |
| 1.344 | H | H | S(O) | CH₂CH=CCl₂ |
| 1.345 | H | H | S(O) | CH₂CCl=CHCl |
| 1.346 | H | H | S(O) | CH₂CCl=CCl₂ |
| 1.347 | H | H | S(O) | CH₂CH=CF₂ |
| 1.348 | H | H | S(O) | CH₂CF=CF₂ |
| 1.349 | H | H | S(O) | CH₂C•CH |
| 1.350 | H | H | S(O) | CH₂C•CCH₃ |
| 1.351 | H | H | S(O) | CH₂C•CCH₂CH₃ |
| 1.352 | H | H | S(O) | CH(CH₃)C•CH |
| 1.353 | H | H | S(O) | CH(CH₃)C•CCH₃ |
| 1.354 | H | H | S(O) | CH(CH₃)C•CCH₂CH₃ |
| 1.355 | H | H | S(O) | C(CH₃)₂C•CH |
| 1.356 | H | H | S(O) | C(CH₃)₂C•CCH₃ |
| 1.357 | H | H | S(O) | C(CH₃)₂C•CCH₂CH₃ |
| 1.358 | H | H | S(O) | Cyclopropyl |
| 1.359 | H | H | S(O) | Cyclobutyl |
| 1.360 | H | H | S(O) | Cyclopentyl |
| 1.361 | H | H | S(O) | Cyclohexyl |
| 1.362 | H | H | S(O) | CH₂CF₃ |
| 1.363 | H | H | S(O) | CH₂CH₂CF₃ |
| 1.364 | H | H | S(O) | CH₂-cyclopropyl |
| 1.365 | H | H | S(O) | CH₂-cyclobutyl |
| 1.366 | H | H | S(O) | CH₂-cyclopentyl |
| 1.367 | H | H | S(O) | CH₂-cyclohexyl |
| 1.368 | H | H | S(O) | CH₂OCH₃ |
| 1.369 | H | H | S(O) | CH₂OCH₂CH₃ |
| 1.370 | H | H | S(O) | CH₂CH₂OCH₃ |
| 1.371 | H | H | S(O) | CH₂CH₂OCH₂CH₃ |
| 1.372 | CH₃ | H | S(O) | CH₃ |
| 1.373 | CH₃ | H | S(O) | CH₂CH₃ |
| 1.374 | CH₃ | H | S(O) | CH₂CH₂CH₃ |
| 1.375 | CH₃ | H | S(O) | CH(CH₃)₂ |
| 1.376 | CH₃ | H | S(O) | CH₂CH₂CH₂CH₃ |
| 1.377 | CH₃ | H | S(O) | CH₂CH(CH₃)₂ |
| 1.378 | CH₃ | H | S(O) | CH(CH₃)CH₂CH₃ |
| 1.379 | CH₃ | H | S(O) | C(CH₃)₃ |
| 1.380 | CH₃ | H | S(O) | CH₂CH₂CH₂CH₂CH₃ |
| 1.381 | CH₃ | H | S(O) | CH₂CH₂CH(CH₃)₂ |
| 1.382 | CH₃ | H | S(O) | CH₂C(CH₃)₃ |
| 1.383 | CH₃ | H | S(O) | CH₂CH(CH₃)CH₂CH₃ |
| 1.384 | CH₃ | H | S(O) | CH(CH₃)CH₂CH₂CH₃ |
| 1.385 | CH₃ | H | S(O) | C(CH₃)₂CH₂CH₃ |
| 1.386 | CH₃ | H | S(O) | CH₂CH=CH₂ |
| 1.387 | CH₃ | H | S(O) | CH₂CH=CHCH₃ |
| 1.388 | CH₃ | H | S(O) | CH₂CH=C(CH₃)₂ |
| 1.389 | CH₃ | H | S(O) | CH₂C(CH₃)=CH₂ |
| 1.390 | CH₃ | H | S(O) | CH₂C(CH₃)=CHCH₃ |
| 1.391 | CH₃ | H | S(O) | CH₂C(CH₃)=C(CH₃)₂ |
| 1.392 | CH₃ | H | S(O) | CH(CH₃)CH=CH₂ |
| 1.393 | CH₃ | H | S(O) | CH(CH₃)CH=CHCH₃ |
| 1.394 | CH₃ | H | S(O) | CH(CH₃)CH=C(CH₃)₂ |
| 1.395 | CH₃ | H | S(O) | C(CH₃)₂CH=CH₂ |
| 1.396 | CH₃ | H | S(O) | C(CH₃)₂CH=CHCH₃ |
| 1.397 | CH₃ | H | S(O) | C(CH₃)₂CH=C(CH₃)₂ |
| 1.398 | CH₃ | H | S(O) | CH₂CH=CHCl |
| 1.399 | CH₃ | H | S(O) | CH₂CH=CCl₂ |
| 1.400 | CH₃ | H | S(O) | CH₂CCl=CHCl |
| 1.401 | CH₃ | H | S(O) | CH₂CCl=CCl₂ |
| 1.402 | CH₃ | H | S(O) | CH₂CH=CF₂ |
| 1.403 | CH₃ | H | S(O) | CH₂CF=CF₂ |
| 1.404 | CH₃ | H | S(O) | CH₂C•CH |
| 1.405 | CH₃ | H | S(O) | CH₂C•CCH₃ |
| 1.406 | CH₃ | H | S(O) | CH₂C•CCH₂CH₃ |
| 1.407 | CH₃ | H | S(O) | CH(CH₃)C•CH |
| 1.408 | CH₃ | H | S(O) | CH(CH₃)C•CCH₃ |
| 1.409 | CH₃ | H | S(O) | CH(CH₃)C•CCH₂CH₃ |
| 1.410 | CH₃ | H | S(O) | C(CH₃)₂C•CH |
| 1.411 | CH₃ | H | S(O) | C(CH₃)₂C•CCH₃ |
| 1.412 | CH₃ | H | S(O) | C(CH₃)₂C•CCH₂CH₃ |
| 1.413 | CH₃ | H | S(O) | Cyclopropyl |
| 1.414 | CH₃ | H | S(O) | Cyclobutyl |
| 1.415 | CH₃ | H | S(O) | Cyclopentyl |
| 1.416 | CH₃ | H | S(O) | Cyclohexyl |
| 1.417 | CH₃ | H | S(O) | CH₂CF₃ |
| 1.418 | CH₃ | H | S(O) | CH₂CH₂CF₃ |
| 1.419 | CH₃ | H | S(O) | CH₂-cyclopropyl |

TABLE 1-continued

This Table contains 646 compounds of the following type,

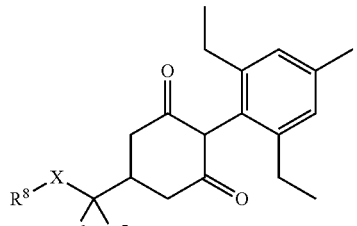

where X, R², R³ and R⁴ are as defined below:

| Compound number | R⁶ | R⁷ | X | R⁸ |
|---|---|---|---|---|
| 1.420 | CH₃ | H | S(O) | CH₂-cyclobutyl |
| 1.421 | CH₃ | H | S(O) | CH₂-cyclopentyl |
| 1.422 | CH₃ | H | S(O) | CH₂-cyclohexyl |
| 1.423 | CH₃ | H | S(O) | CH₂OCH₃ |
| 1.424 | CH₃ | H | S(O) | CH₂OCH₂CH₃ |
| 1.425 | CH₃ | H | S(O) | CH₂CH₂OCH₃ |
| 1.426 | CH₃ | H | S(O) | CH₂CH₂OCH₂CH₃ |
| 1.427 | CH₃ | CH₃ | S(O) | CH₃ |
| 1.428 | CH₃ | CH₃ | S(O) | CH₂CH₃ |
| 1.429 | CH₃ | CH₃ | S(O) | CH₂CH₂CH₃ |
| 1.430 | CH₃ | CH₃ | S(O) | CH(CH₃)₂ |
| 1.431 | CH₃ | CH₃ | S(O) | CH₂CH₂CH₂CH₃ |
| 1.432 | CH₃ | CH₃ | S(O) | CH₂CH(CH₃)₂ |
| 1.433 | CH₃ | CH₃ | S(O) | CH(CH₃)CH₂CH₃ |
| 1.434 | CH₃ | CH₃ | S(O) | C(CH₃)₃ |
| 1.435 | CH₃ | CH₃ | S(O) | CH₂CH₂CH₂CH₂CH₃ |
| 1.436 | CH₃ | CH₃ | S(O) | CH₂CH₂CH(CH₃)₂ |
| 1.437 | CH₃ | CH₃ | S(O) | CH₂C(CH₃)₃ |
| 1.438 | CH₃ | CH₃ | S(O) | CH₂CH(CH₃)CH₂CH₃ |
| 1.439 | CH₃ | CH₃ | S(O) | CH(CH₃)CH₂CH₂CH₃ |
| 1.440 | CH₃ | CH₃ | S(O) | C(CH₃)₂CH₂CH₃ |
| 1.441 | CH₃ | CH₃ | S(O) | CH₂CH=CH₂ |
| 1.442 | CH₃ | CH₃ | S(O) | CH₂CH=CHCH₃ |
| 1.443 | CH₃ | CH₃ | S(O) | CH₂CH=C(CH₃)₂ |
| 1.444 | CH₃ | CH₃ | S(O) | CH₂C(CH₃)=CH₂ |
| 1.445 | CH₃ | CH₃ | S(O) | CH₂C(CH₃)=CHCH₃ |
| 1.446 | CH₃ | CH₃ | S(O) | CH₂C(CH₃)=C(CH₃)₂ |
| 1.447 | CH₃ | CH₃ | S(O) | CH(CH₃)CH=CH₂ |
| 1.448 | CH₃ | CH₃ | S(O) | CH(CH₃)CH=CHCH₃ |
| 1.449 | CH₃ | CH₃ | S(O) | CH(CH₃)CH=C(CH₃)₂ |
| 1.450 | CH₃ | CH₃ | S(O) | C(CH₃)₂CH=CH₂ |
| 1.451 | CH₃ | CH₃ | S(O) | C(CH₃)₂CH=CHCH₃ |
| 1.452 | CH₃ | CH₃ | S(O) | C(CH₃)₂CH=C(CH₃)₂ |
| 1.453 | CH₃ | CH₃ | S(O) | CH₂CH=CHCl |
| 1.454 | CH₃ | CH₃ | S(O) | CH₂CH=CCl₂ |
| 1.455 | CH₃ | CH₃ | S(O) | CH₂CCl=CHCl |
| 1.456 | CH₃ | CH₃ | S(O) | CH₂CCl=CCl₂ |
| 1.457 | CH₃ | CH₃ | S(O) | CH₂CH=CF₂ |
| 1.458 | CH₃ | CH₃ | S(O) | CH₂CF=CF₂ |
| 1.459 | CH₃ | CH₃ | S(O) | CH₂C•CH |
| 1.460 | CH₃ | CH₃ | S(O) | CH₂C•CCH₃ |
| 1.461 | CH₃ | CH₃ | S(O) | CH₂C•CCH₂CH₃ |
| 1.462 | CH₃ | CH₃ | S(O) | CH(CH₃)C•CH |
| 1.463 | CH₃ | CH₃ | S(O) | CH(CH₃)C•CCH₃ |
| 1.464 | CH₃ | CH₃ | S(O) | CH(CH₃)C•CCH₂CH₃ |
| 1.465 | CH₃ | CH₃ | S(O) | C(CH₃)₂C•CH |
| 1.466 | CH₃ | CH₃ | S(O) | C(CH₃)₂C•CCH₃ |
| 1.467 | CH₃ | CH₃ | S(O) | C(CH₃)₂C•CCH₂CH₃ |
| 1.468 | CH₃ | CH₃ | S(O) | Cyclopropyl |
| 1.469 | CH₃ | CH₃ | S(O) | Cyclobutyl |
| 1.470 | CH₃ | CH₃ | S(O) | Cyclopentyl |
| 1.471 | CH₃ | CH₃ | S(O) | Cyclohexyl |
| 1.472 | CH₃ | CH₃ | S(O) | CH₂CF₃ |
| 1.473 | CH₃ | CH₃ | S(O) | CH₂CH₂CF₃ |
| 1.474 | CH₃ | CH₃ | S(O) | CH₂-cyclopropyl |
| 1.475 | CH₃ | CH₃ | S(O) | CH₂-cyclobutyl |
| 1.476 | CH₃ | CH₃ | S(O) | CH₂-cyclopentyl |
| 1.477 | CH₃ | CH₃ | S(O) | CH₂-cyclohexyl |
| 1.478 | CH₃ | CH₃ | S(O) | CH₂OCH₃ |
| 1.479 | CH₃ | CH₃ | S(O) | CH₂OCH₂CH₃ |
| 1.480 | CH₃ | CH₃ | S(O) | CH₂CH₂OCH₃ |

TABLE 1-continued

This Table contains 646 compounds of the following type,

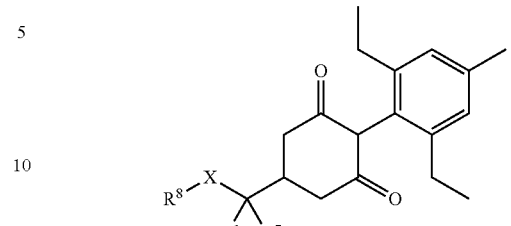

where X, R², R³ and R⁴ are as defined below:

| Compound number | R⁶ | R⁷ | X | R⁸ |
|---|---|---|---|---|
| 1.481 | CH₃ | CH₃ | S(O) | CH₂CH₂OCH₂CH₃ |
| 1.482 | H | H | SO₂ | CH₃ |
| 1.483 | H | H | SO₂ | CH₂CH₃ |
| 1.484 | H | H | SO₂ | CH₂CH₂CH₃ |
| 1.485 | H | H | SO₂ | CH(CH₃)₂ |
| 1.486 | H | H | SO₂ | CH₂CH₂CH₂CH₃ |
| 1.487 | H | H | SO₂ | CH₂CH(CH₃)₂ |
| 1.488 | H | H | SO₂ | CH(CH₃)CH₂CH₃ |
| 1.489 | H | H | SO₂ | C(CH₃)₃ |
| 1.490 | H | H | SO₂ | CH₂CH₂CH₂CH₂CH₃ |
| 1.491 | H | H | SO₂ | CH₂CH₂CH(CH₃)₂ |
| 1.492 | H | H | SO₂ | CH₂C(CH₃)₃ |
| 1.493 | H | H | SO₂ | CH₂CH(CH₃)CH₂CH₃ |
| 1.494 | H | H | SO₂ | CH(CH₃)CH₂CH₂CH₃ |
| 1.495 | H | H | SO₂ | C(CH₃)₂CH₂CH₃ |
| 1.496 | H | H | SO₂ | CH₂CH=CH₂ |
| 1.497 | H | H | SO₂ | CH₂CH=CHCH₃ |
| 1.498 | H | H | SO₂ | CH₂CH=C(CH₃)₂ |
| 1.499 | H | H | SO₂ | CH₂C(CH₃)=CH₂ |
| 1.500 | H | H | SO₂ | CH₂C(CH₃)=CHCH₃ |
| 1.501 | H | H | SO₂ | CH₂C(CH₃)=C(CH₃)₂ |
| 1.502 | H | H | SO₂ | CH(CH₃)CH=CH₂ |
| 1.503 | H | H | SO₂ | CH(CH₃)CH=CHCH₃ |
| 1.504 | H | H | SO₂ | CH(CH₃)CH=C(CH₃)₂ |
| 1.505 | H | H | SO₂ | C(CH₃)₂CH=CH₂ |
| 1.506 | H | H | SO₂ | C(CH₃)₂CH=CHCH₃ |
| 1.507 | H | H | SO₂ | C(CH₃)₂CH=C(CH₃)₂ |
| 1.508 | H | H | SO₂ | CH₂CH=CHCl |
| 1.509 | H | H | SO₂ | CH₂CH=CCl₂ |
| 1.510 | H | H | SO₂ | CH₂CCl=CHCl |
| 1.511 | H | H | SO₂ | CH₂CCl=CCl₂ |
| 1.512 | H | H | SO₂ | CH₂CH=CF₂ |
| 1.513 | H | H | SO₂ | CH₂CF=CF₂ |
| 1.514 | H | H | SO₂ | CH₂C•CH |
| 1.515 | H | H | SO₂ | CH₂C•CCH₃ |
| 1.516 | H | H | SO₂ | CH₂C•CCH₂CH₃ |
| 1.517 | H | H | SO₂ | CH(CH₃)C•CH |
| 1.518 | H | H | SO₂ | CH(CH₃)C•CCH₃ |
| 1.519 | H | H | SO₂ | CH(CH₃)C•CCH₂CH₃ |
| 1.520 | H | H | SO₂ | C(CH₃)₂C•CH |
| 1.521 | H | H | SO₂ | C(CH₃)₂C•CCH₃ |
| 1.522 | H | H | SO₂ | C(CH₃)₂C•CCH₂CH₃ |
| 1.523 | H | H | SO₂ | Cyclopropyl |
| 1.524 | H | H | SO₂ | Cyclobutyl |
| 1.525 | H | H | SO₂ | Cyclopentyl |
| 1.526 | H | H | SO₂ | Cyclohexyl |
| 1.527 | H | H | SO₂ | CH₂CF₃ |
| 1.528 | H | H | SO₂ | CH₂CH₂CF₃ |
| 1.529 | H | H | SO₂ | CH₂-cyclopropyl |
| 1.530 | H | H | SO₂ | CH₂-cyclobutyl |
| 1.531 | H | H | SO₂ | CH₂-cyclopentyl |
| 1.532 | H | H | SO₂ | CH₂-cyclohexyl |
| 1.533 | H | H | SO₂ | CH₂OCH₃ |
| 1.534 | H | H | SO₂ | CH₂OCH₂CH₃ |
| 1.535 | H | H | SO₂ | CH₂CH₂OCH₃ |
| 1.536 | H | H | SO₂ | CH₂CH₂OCH₂CH₃ |
| 1.537 | CH₃ | H | SO₂ | CH₃ |
| 1.538 | CH₃ | H | SO₂ | CH₂CH₃ |
| 1.539 | CH₃ | H | SO₂ | CH₂CH₂CH₃ |
| 1.540 | CH₃ | H | SO₂ | CH(CH₃)₂ |
| 1.541 | CH₃ | H | SO₂ | CH₂CH₂CH₂CH₃ |

TABLE 1-continued

This Table contains 646 compounds of the following type,

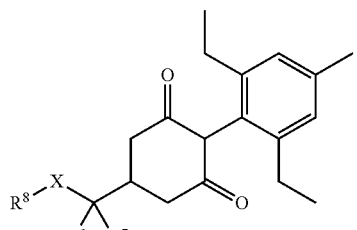

where X, $R^2$, $R^3$ and $R^4$ are as defined below:

| Compound number | $R^6$ | $R^7$ | X | $R^8$ |
|---|---|---|---|---|
| 1.542 | $CH_3$ | H | $SO_2$ | $CH_2CH(CH_3)_2$ |
| 1.543 | $CH_3$ | H | $SO_2$ | $CH(CH_3)CH_2CH_3$ |
| 1.544 | $CH_3$ | H | $SO_2$ | $C(CH_3)_3$ |
| 1.545 | $CH_3$ | H | $SO_2$ | $CH_2CH_2CH_2CH_2CH_3$ |
| 1.546 | $CH_3$ | H | $SO_2$ | $CH_2CH_2CH(CH_3)_2$ |
| 1.547 | $CH_3$ | H | $SO_2$ | $CH_2C(CH_3)_3$ |
| 1.548 | $CH_3$ | H | $SO_2$ | $CH_2CH(CH_3)CH_2CH_3$ |
| 1.549 | $CH_3$ | H | $SO_2$ | $CH(CH_3)CH_2CH_2CH_3$ |
| 1.550 | $CH_3$ | H | $SO_2$ | $C(CH_3)_2CH_2CH_3$ |
| 1.551 | $CH_3$ | H | $SO_2$ | $CH_2CH=CH_2$ |
| 1.552 | $CH_3$ | H | $SO_2$ | $CH_2CH=CHCH_3$ |
| 1.553 | $CH_3$ | H | $SO_2$ | $CH_2CH=C(CH_3)_2$ |
| 1.554 | $CH_3$ | H | $SO_2$ | $CH_2C(CH_3)=CH_2$ |
| 1.555 | $CH_3$ | H | $SO_2$ | $CH_2C(CH_3)=CHCH_3$ |
| 1.556 | $CH_3$ | H | $SO_2$ | $CH_2C(CH_3)=C(CH_3)_2$ |
| 1.557 | $CH_3$ | H | $SO_2$ | $CH(CH_3)CH=CH_2$ |
| 1.558 | $CH_3$ | H | $SO_2$ | $CH(CH_3)CH=CHCH_3$ |
| 1.559 | $CH_3$ | H | $SO_2$ | $CH(CH_3)CH=C(CH_3)_2$ |
| 1.560 | $CH_3$ | H | $SO_2$ | $C(CH_3)_2CH=CH_2$ |
| 1.561 | $CH_3$ | H | $SO_2$ | $C(CH_3)_2CH=CHCH_3$ |
| 1.562 | $CH_3$ | H | $SO_2$ | $C(CH_3)_2CH=C(CH_3)_2$ |
| 1.563 | $CH_3$ | H | $SO_2$ | $CH_2CH=CHCl$ |
| 1.564 | $CH_3$ | H | $SO_2$ | $CH_2CH=CCl_2$ |
| 1.565 | $CH_3$ | H | $SO_2$ | $CH_2CCl=CHCl$ |
| 1.566 | $CH_3$ | H | $SO_2$ | $CH_2CCl=CCl_2$ |
| 1.567 | $CH_3$ | H | $SO_2$ | $CH_2CH=CF_2$ |
| 1.568 | $CH_3$ | H | $SO_2$ | $CH_2CF=CF_2$ |
| 1.569 | $CH_3$ | H | $SO_2$ | $CH_2C\bullet CH$ |
| 1.570 | $CH_3$ | H | $SO_2$ | $CH_2C\bullet CCH_3$ |
| 1.571 | $CH_3$ | H | $SO_2$ | $CH_2C\bullet CCH_2CH_3$ |
| 1.572 | $CH_3$ | H | $SO_2$ | $CH(CH_3)C\bullet CH$ |
| 1.573 | $CH_3$ | H | $SO_2$ | $CH(CH_3)C\bullet CCH_3$ |
| 1.574 | $CH_3$ | H | $SO_2$ | $CH(CH_3)C\bullet CCH_2CH_3$ |
| 1.575 | $CH_3$ | H | $SO_2$ | $C(CH_3)_2C\bullet CH$ |
| 1.576 | $CH_3$ | H | $SO_2$ | $C(CH_3)_2C\bullet CCH_3$ |
| 1.577 | $CH_3$ | H | $SO_2$ | $C(CH_3)_2C\bullet CCH_2CH_3$ |
| 1.578 | $CH_3$ | H | $SO_2$ | Cyclopropyl |
| 1.579 | $CH_3$ | H | $SO_2$ | Cyclobutyl |
| 1.580 | $CH_3$ | H | $SO_2$ | Cyclopentyl |
| 1.581 | $CH_3$ | H | $SO_2$ | Cyclohexyl |
| 1.582 | $CH_3$ | H | $SO_2$ | $CH_2CF_3$ |
| 1.583 | $CH_3$ | H | $SO_2$ | $CH_2CH_2CF_3$ |
| 1.584 | $CH_3$ | H | $SO_2$ | $CH_2$-cyclopropyl |
| 1.585 | $CH_3$ | H | $SO_2$ | $CH_2$-cyclobutyl |
| 1.586 | $CH_3$ | H | $SO_2$ | $CH_2$-cyclopentyl |
| 1.587 | $CH_3$ | H | $SO_2$ | $CH_2$-cyclohexyl |
| 1.588 | $CH_3$ | H | $SO_2$ | $CH_2OCH_3$ |
| 1.589 | $CH_3$ | H | $SO_2$ | $CH_2OCH_2CH_3$ |
| 1.590 | $CH_3$ | H | $SO_2$ | $CH_2CH_2OCH_3$ |
| 1.591 | $CH_3$ | H | $SO_2$ | $CH_2CH_2OCH_2CH_3$ |
| 1.592 | $CH_3$ | $CH_3$ | $SO_2$ | $CH_3$ |
| 1.593 | $CH_3$ | $CH_3$ | $SO_2$ | $CH_2CH_3$ |
| 1.594 | $CH_3$ | $CH_3$ | $SO_2$ | $CH_2CH_2CH_3$ |
| 1.595 | $CH_3$ | $CH_3$ | $SO_2$ | $CH(CH_3)_2$ |
| 1.596 | $CH_3$ | $CH_3$ | $SO_2$ | $CH_2CH_2CH_2CH_3$ |
| 1.597 | $CH_3$ | $CH_3$ | $SO_2$ | $CH_2CH(CH_3)_2$ |
| 1.598 | $CH_3$ | $CH_3$ | $SO_2$ | $CH(CH_3)CH_2CH_3$ |
| 1.599 | $CH_3$ | $CH_3$ | $SO_2$ | $C(CH_3)_3$ |
| 1.600 | $CH_3$ | $CH_3$ | $SO_2$ | $CH_2CH_2CH_2CH_2CH_3$ |
| 1.601 | $CH_3$ | $CH_3$ | $SO_2$ | $CH_2CH_2CH(CH_3)_2$ |
| 1.602 | $CH_3$ | $CH_3$ | $SO_2$ | $CH_2C(CH_3)_3$ |

TABLE 1-continued

This Table contains 646 compounds of the following type,

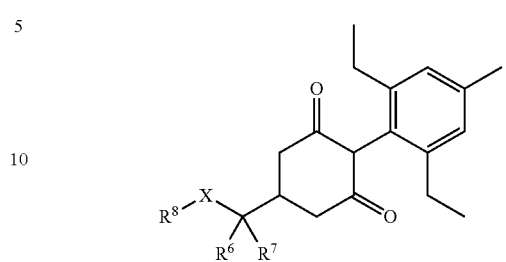

where X, $R^2$, $R^3$ and $R^4$ are as defined below:

| Compound number | $R^6$ | $R^7$ | X | $R^8$ |
|---|---|---|---|---|
| 1.603 | $CH_3$ | $CH_3$ | $SO_2$ | $CH_2CH(CH_3)CH_2CH_3$ |
| 1.604 | $CH_3$ | $CH_3$ | $SO_2$ | $CH(CH_3)CH_2CH_2CH_3$ |
| 1.605 | $CH_3$ | $CH_3$ | $SO_2$ | $C(CH_3)_2CH_2CH_3$ |
| 1.606 | $CH_3$ | $CH_3$ | $SO_2$ | $CH_2CH=CH_2$ |
| 1.607 | $CH_3$ | $CH_3$ | $SO_2$ | $CH_2CH=CHCH_3$ |
| 1.608 | $CH_3$ | $CH_3$ | $SO_2$ | $CH_2CH=C(CH_3)_2$ |
| 1.609 | $CH_3$ | $CH_3$ | $SO_2$ | $CH_2C(CH_3)=CH_2$ |
| 1.610 | $CH_3$ | $CH_3$ | $SO_2$ | $CH_2C(CH_3)=CHCH_3$ |
| 1.611 | $CH_3$ | $CH_3$ | $SO_2$ | $CH_2C(CH_3)=C(CH_3)_2$ |
| 1.612 | $CH_3$ | $CH_3$ | $SO_2$ | $CH(CH_3)CH=CH_2$ |
| 1.613 | $CH_3$ | $CH_3$ | $SO_2$ | $CH(CH_3)CH=CHCH_3$ |
| 1.614 | $CH_3$ | $CH_3$ | $SO_2$ | $CH(CH_3)CH=C(CH_3)_2$ |
| 1.615 | $CH_3$ | $CH_3$ | $SO_2$ | $C(CH_3)_2CH=CH_2$ |
| 1.616 | $CH_3$ | $CH_3$ | $SO_2$ | $C(CH_3)_2CH=CHCH_3$ |
| 1.617 | $CH_3$ | $CH_3$ | $SO_2$ | $C(CH_3)_2CH=C(CH_3)_2$ |
| 1.618 | $CH_3$ | $CH_3$ | $SO_2$ | $CH_2CH=CHCl$ |
| 1.619 | $CH_3$ | $CH_3$ | $SO_2$ | $CH_2CH=CCl_2$ |
| 1.620 | $CH_3$ | $CH_3$ | $SO_2$ | $CH_2CCl=CHCl$ |
| 1.621 | $CH_3$ | $CH_3$ | $SO_2$ | $CH_2CCl=CCl_2$ |
| 1.622 | $CH_3$ | $CH_3$ | $SO_2$ | $CH_2CH=CF_2$ |
| 1.623 | $CH_3$ | $CH_3$ | $SO_2$ | $CH_2CF=CF_2$ |
| 1.624 | $CH_3$ | $CH_3$ | $SO_2$ | $CH_2C\bullet CH$ |
| 1.625 | $CH_3$ | $CH_3$ | $SO_2$ | $CH_2C\bullet CCH_3$ |
| 1.626 | $CH_3$ | $CH_3$ | $SO_2$ | $CH_2C\bullet CCH_2CH_3$ |
| 1.627 | $CH_3$ | $CH_3$ | $SO_2$ | $CH(CH_3)C\bullet CH$ |
| 1.628 | $CH_3$ | $CH_3$ | $SO_2$ | $CH(CH_3)C\bullet CCH_3$ |
| 1.629 | $CH_3$ | $CH_3$ | $SO_2$ | $CH(CH_3)C\bullet CCH_2CH_3$ |
| 1.630 | $CH_3$ | $CH_3$ | $SO_2$ | $C(CH_3)_2C\bullet CH$ |
| 1.631 | $CH_3$ | $CH_3$ | $SO_2$ | $C(CH_3)_2C\bullet CCH_3$ |
| 1.632 | $CH_3$ | $CH_3$ | $SO_2$ | $C(CH_3)_2C\bullet CCH_2CH_3$ |
| 1.633 | $CH_3$ | $CH_3$ | $SO_2$ | Cyclopropyl |
| 1.634 | $CH_3$ | $CH_3$ | $SO_2$ | Cyclobutyl |
| 1.635 | $CH_3$ | $CH_3$ | $SO_2$ | Cyclopentyl |
| 1.636 | $CH_3$ | $CH_3$ | $SO_2$ | Cyclohexyl |
| 1.637 | $CH_3$ | $CH_3$ | $SO_2$ | $CH_2CF_3$ |
| 1.638 | $CH_3$ | $CH_3$ | $SO_2$ | $CH_2CH_2CF_3$ |
| 1.639 | $CH_3$ | $CH_3$ | $SO_2$ | $CH_2$-cyclopropyl |
| 1.640 | $CH_3$ | $CH_3$ | $SO_2$ | $CH_2$-cyclobutyl |
| 1.641 | $CH_3$ | $CH_3$ | $SO_2$ | $CH_2$-cyclopentyl |
| 1.642 | $CH_3$ | $CH_3$ | $SO_2$ | $CH_2$-cyclohexyl |
| 1.643 | $CH_3$ | $CH_3$ | $SO_2$ | $CH_2OCH_3$ |
| 1.644 | $CH_3$ | $CH_3$ | $SO_2$ | $CH_2OCH_2CH_3$ |
| 1.645 | $CH_3$ | $CH_3$ | $SO_2$ | $CH_2CH_2OCH_3$ |
| 1.646 | $CH_3$ | $CH_3$ | $SO_2$ | $CH_2CH_2OCH_2CH_3$ |

TABLE 2

This table contains 646 compounds of the following type,

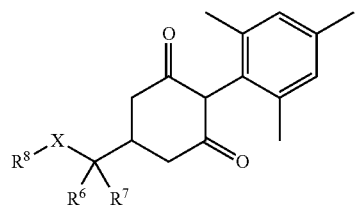

where X, $R^6$, $R^7$ and $R^8$ are as defined in Table 1

TABLE 3

This table contains 646 compounds of the following type,

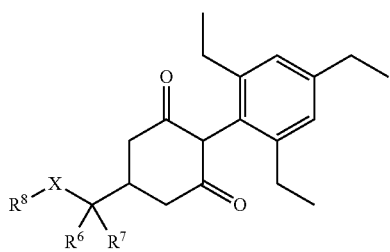

where X, $R^6$, $R^7$ and $R^8$ are as defined in Table 1

TABLE 4

Table 4 contains 646 compounds of the following type,

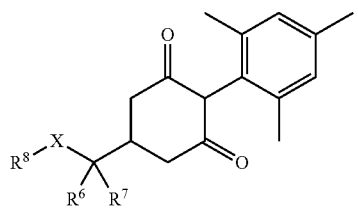

where X, $R^6$, $R^7$ and $R^8$ are as defined in Table 1.

TABLE 5

This table contains 646 compounds of the following type,

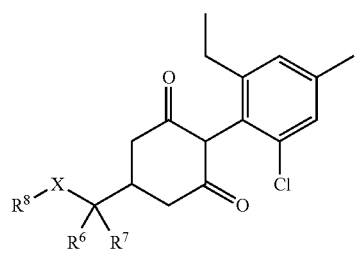

where X, $R^6$, $R^7$ and $R^8$ are as defined in Table 1.

TABLE 6

This table contains 646 compounds of the following type,

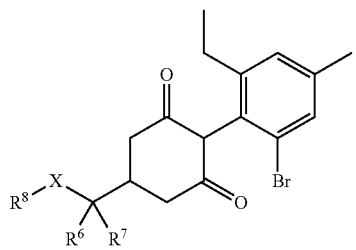

where X, $R^6$, $R^7$ and $R^8$ are as defined in Table 1.

TABLE 7

This table contains 646 compounds of the following type,

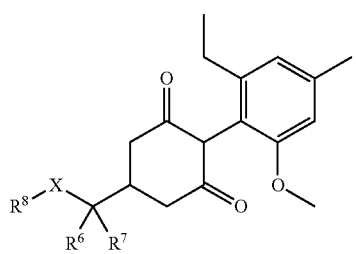

where X, $R^6$, $R^7$ and $R^8$ are as defined in Table 1.

TABLE 8

This table contains 646 compounds of the following type,

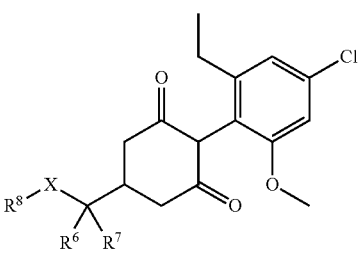

where X, $R^6$, $R^7$ and $R^8$ are as defined in Table 1.

TABLE 9

This table contains 646 compounds of the following type,

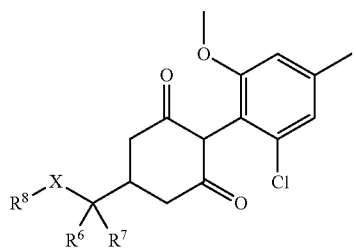

where X, $R^6$, $R^7$ and $R^8$ are as defined in Table 1.

TABLE 10

This table contains 646 compounds of the following type,

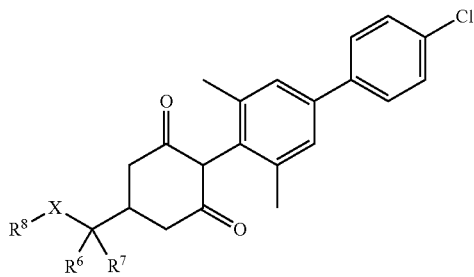

where X, $R^6$, $R^7$ and $R^8$ are as defined in Table 1.

TABLE 11

This table contains 646 compounds of the following type,

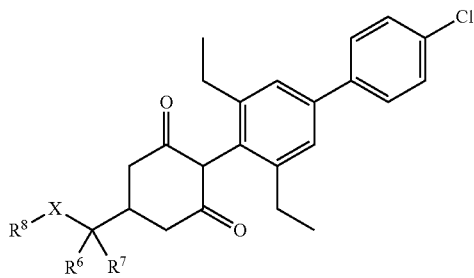

where X, $R^6$, $R^7$ and $R^8$ are as defined in Table 1.

TABLE 12

This table contains 646 compounds of the following type,

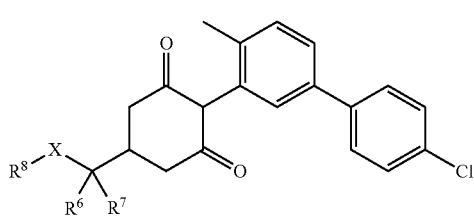

where X, $R^6$, $R^7$ and $R^8$ are as defined in Table 1.

TABLE 13

This table contains 646 compounds of the following type,

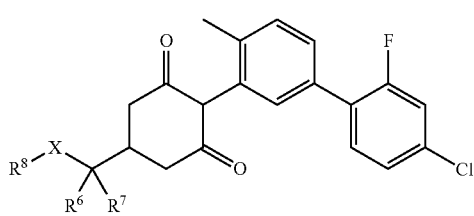

where X, $R^6$, $R^7$ and $R^8$ are as defined in Table 1.

TABLE 14

This table contains 646 compounds of the following type,

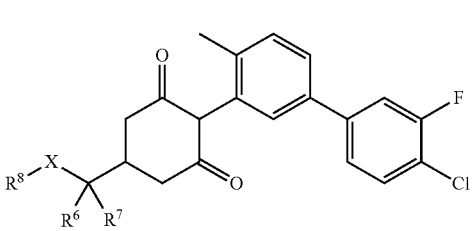

where X, $R^6$, $R^7$ and $R^8$ are as defined in Table 1.

TABLE 15

This table contains 646 compounds of the following type,

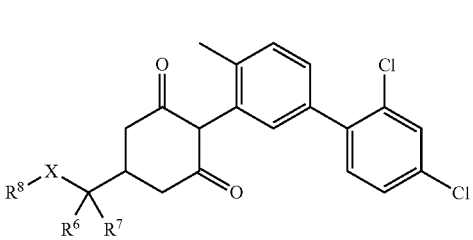

where X, $R^6$, $R^7$ and $R^8$ are as defined in Table 1.

TABLE 16

This table 12 contains 646 compounds of the following type,

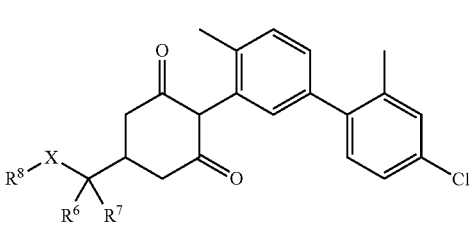

where X, $R^6$, $R^7$ and $R^8$ are as defined in Table 1.

TABLE 17

This table contains 646 compounds of the following type,

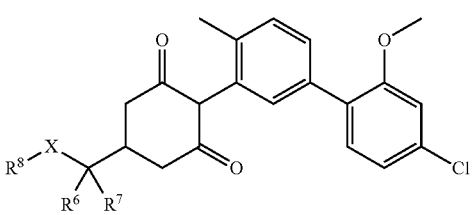

where X, $R^6$, $R^7$ and $R^8$ are as defined in Table 1.

TABLE 18

This table contains 646 compounds of the following type,

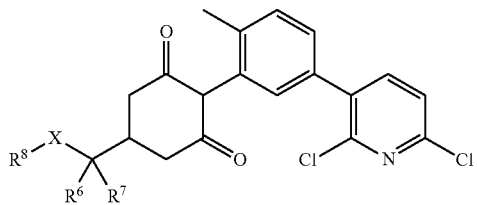

where X, R$^6$, R$^7$ and R$^8$ are as defined in Table 1.

TABLE 19

This table contains 646 compounds of the following type,

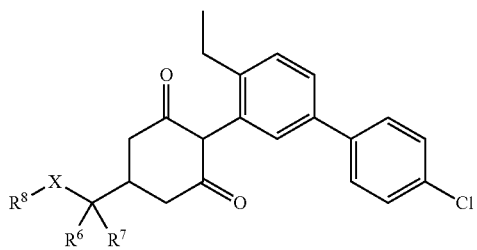

where X, R$^6$, R$^7$ and R$^8$ are as defined in Table 1.

TABLE 20

This table contains 646 compounds of the following type,

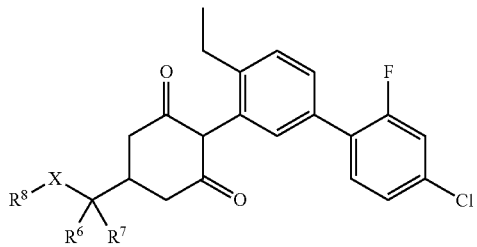

where X, R$^6$, R$^7$ and R$^8$ are as defined in Table 1.

TABLE 21

This table contains 646 compounds of the following type,

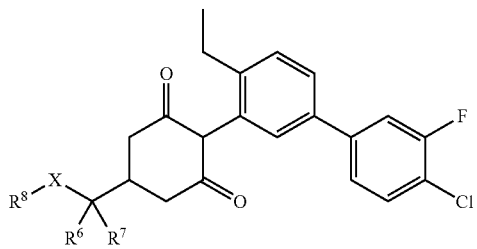

where X, R$^6$, R$^7$ and R$^8$ are as defined in Table 1.

TABLE 22

This table contains 646 compounds of the following type,

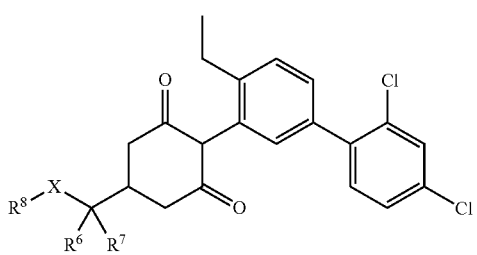

where X, R$^6$, R$^7$ and R$^8$ are as defined in Table 1.

TABLE 23

This table 12 contains 646 compounds of the following type,

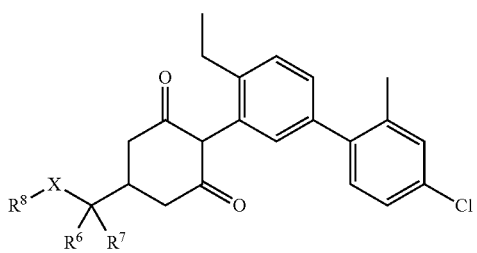

where X, R$^6$, R$^7$ and R$^8$ are as defined in Table 1.

TABLE 24

This table contains 646 compounds of the following type,

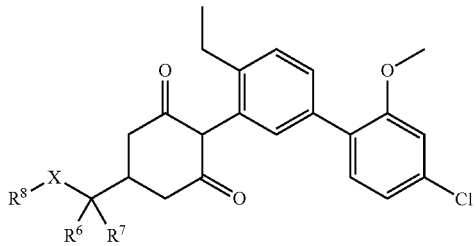

where X, R$^6$, R$^7$ and R$^8$ are as defined in Table 1.

TABLE 25

This table contains 646 compounds of the following type,

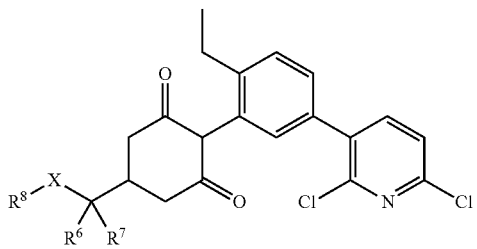

where X, R$^6$, R$^7$ and R$^8$ are as defined in Table 1.

TABLE 26

This table contains 618 compounds of the following type,

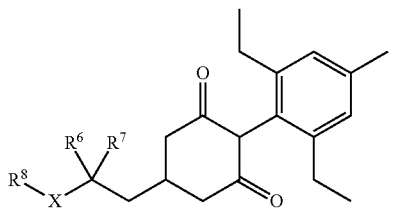

where X, $R^6$, $R^7$ and $R^8$ are as defined below:

| Compound number | $R^6$ | $R^7$ | X | $R^8$ |
|---|---|---|---|---|
| 26.1 | H | H | O | $CH_3$ |
| 26.2 | H | H | O | $CH_2CH_3$ |
| 26.3 | H | H | O | $CH_2CH_2CH_3$ |
| 26.4 | H | H | O | $CH(CH_3)_2$ |
| 26.5 | H | H | O | $CH_2CH_2CH_2CH_3$ |
| 26.6 | H | H | O | $CH_2CH(CH_3)_2$ |
| 26.7 | H | H | O | $CH(CH_3)CH_2CH_3$ |
| 26.8 | H | H | O | $C(CH_3)_3$ |
| 26.9 | H | H | O | $CH_2CH_2CH_2CH_2CH_3$ |
| 26.10 | H | H | O | $CH_2CH_2CH(CH_3)_2$ |
| 26.11 | H | H | O | $CH_2C(CH_3)_3$ |
| 26.12 | H | H | O | $CH_2CH(CH_3)CH_2CH_3$ |
| 26.13 | H | H | O | $CH(CH_3)CH_2CH_2CH_3$ |
| 26.14 | H | H | O | $C(CH_3)_2CH_2CH_3$ |
| 26.15 | H | H | O | $CH_2CH=CH_2$ |
| 26.16 | H | H | O | $CH_2CH=CHCH_3$ |
| 26.17 | H | H | O | $CH_2CH=C(CH_3)_2$ |
| 26.18 | H | H | O | $CH_2C(CH_3)=CH_2$ |
| 26.19 | H | H | O | $CH_2C(CH_3)=CHCH_3$ |
| 26.20 | H | H | O | $CH_2C(CH_3)=C(CH_3)_2$ |
| 26.21 | H | H | O | $CH(CH_3)CH=CH_2$ |
| 26.22 | H | H | O | $CH(CH_3)CH=CHCH_3$ |
| 26.23 | H | H | O | $CH(CH_3)CH=C(CH_3)_2$ |
| 26.24 | H | H | O | $C(CH_3)_2CH=CH_2$ |
| 26.25 | H | H | O | $C(CH_3)_2CH=CHCH_3$ |
| 26.26 | H | H | O | $C(CH_3)_2CH=C(CH_3)_2$ |
| 26.27 | H | H | O | $CH_2CH=CHCl$ |
| 26.28 | H | H | O | $CH_2CH=CCl_2$ |
| 26.29 | H | H | O | $CH_2CCl=CHCl$ |
| 26.30 | H | H | O | $CH_2CCl=CCl_2$ |
| 26.31 | H | H | O | $CH_2CH=CF_2$ |
| 26.32 | H | H | O | $CH_2CF=CF_2$ |
| 26.33 | H | H | O | $CH_2C•CH$ |
| 26.34 | H | H | O | $CH_2C•CCH_3$ |
| 26.35 | H | H | O | $CH_2C•CCH_2CH_3$ |
| 26.36 | H | H | O | $CH(CH_3)C•CH$ |
| 26.37 | H | H | O | $CH(CH_3)C•CCH_3$ |
| 26.38 | H | H | O | $CH(CH_3)C•CCH_2CH_3$ |
| 26.39 | H | H | O | $C(CH_3)_2C•CH$ |
| 26.40 | H | H | O | $C(CH_3)_2C•CCH_3$ |
| 26.41 | H | H | O | $C(CH_3)_2C•CCH_2CH_3$ |
| 26.42 | H | H | O | Cyclopropyl |
| 26.43 | H | H | O | Cyclobutyl |
| 26.44 | H | H | O | Cyclopentyl |
| 26.45 | H | H | O | Cyclohexyl |
| 26.46 | H | H | O | $CH_2CF_3$ |
| 26.47 | H | H | O | $CH_2CH_2CF_3$ |
| 26.48 | H | H | O | $CH_2$-cyclopropyl |
| 26.49 | H | H | O | $CH_2$-cyclobutyl |
| 26.50 | H | H | O | $CH_2$-cyclopentyl |
| 26.51 | H | H | O | $CH_2$-cyclohexyl |
| 26.52 | H | H | O | $CH_2OCH_3$ |
| 26.53 | H | H | O | $CH_2OCH_2CH_3$ |
| 26.54 | H | H | O | $CH_2CH_2OCH_3$ |
| 26.55 | H | H | O | $CH_2CH_2OCH_2CH_3$ |
| 26.56 | $CH_3$ | H | O | $CH_3$ |
| 26.57 | $CH_3$ | H | O | $CH_2CH_3$ |
| 26.58 | $CH_3$ | H | O | $CH_2CH_2CH_3$ |
| 26.59 | $CH_3$ | H | O | $CH(CH_3)_2$ |
| 26.60 | $CH_3$ | H | O | $CH_2CH_2CH_2CH_3$ |
| 26.61 | $CH_3$ | H | O | $CH_2CH(CH_3)_2$ |
| 26.62 | $CH_3$ | H | O | $CH(CH_3)CH_2CH_3$ |
| 26.63 | $CH_3$ | H | O | $C(CH_3)_3$ |
| 26.64 | $CH_3$ | H | O | $CH_2CH_2CH_2CH_2CH_3$ |
| 26.65 | $CH_3$ | H | O | $CH_2CH_2CH(CH_3)_2$ |
| 26.66 | $CH_3$ | H | O | $CH_2C(CH_3)_3$ |
| 26.67 | $CH_3$ | H | O | $CH_2CH(CH_3)CH_2CH_3$ |
| 26.68 | $CH_3$ | H | O | $CH(CH_3)CH_2CH_2CH_3$ |
| 26.69 | $CH_3$ | H | O | $C(CH_3)_2CH_2CH_3$ |
| 26.70 | $CH_3$ | H | O | $CH_2CH=CH_2$ |
| 26.71 | $CH_3$ | H | O | $CH_2CH=CHCH_3$ |
| 26.72 | $CH_3$ | H | O | $CH_2CH=C(CH_3)_2$ |
| 26.73 | $CH_3$ | H | O | $CH_2C(CH_3)=CH_2$ |
| 26.74 | $CH_3$ | H | O | $CH_2C(CH_3)=CHCH_3$ |
| 26.75 | $CH_3$ | H | O | $CH_2C(CH_3)=C(CH_3)_2$ |
| 26.76 | $CH_3$ | H | O | $CH(CH_3)CH=CH_2$ |
| 26.77 | $CH_3$ | H | O | $CH(CH_3)CH=CHCH_3$ |
| 26.78 | $CH_3$ | H | O | $CH(CH_3)CH=C(CH_3)_2$ |
| 26.79 | $CH_3$ | H | O | $C(CH_3)_2CH=CH_2$ |
| 26.80 | $CH_3$ | H | O | $C(CH_3)_2CH=CHCH_3$ |
| 26.81 | $CH_3$ | H | O | $C(CH_3)_2CH=C(CH_3)_2$ |
| 26.82 | $CH_3$ | H | O | $CH_2CH=CHCl$ |
| 26.83 | $CH_3$ | H | O | $CH_2CH=CCl_2$ |
| 26.84 | $CH_3$ | H | O | $CH_2CCl=CHCl$ |
| 26.85 | $CH_3$ | H | O | $CH_2CCl=CCl_2$ |
| 26.86 | $CH_3$ | H | O | $CH_2CH=CF_2$ |
| 26.87 | $CH_3$ | H | O | $CH_2CF=CF_2$ |
| 26.88 | $CH_3$ | H | O | $CH_2C•CH$ |
| 26.89 | $CH_3$ | H | O | $CH_2C•CCH_3$ |
| 26.90 | $CH_3$ | H | O | $CH_2C•CCH_2CH_3$ |
| 26.91 | $CH_3$ | H | O | $CH(CH_3)C•CH$ |
| 26.92 | $CH_3$ | H | O | $CH(CH_3)C•CCH_3$ |
| 26.93 | $CH_3$ | H | O | $CH(CH_3)C•CCH_2CH_3$ |
| 26.94 | $CH_3$ | H | O | $C(CH_3)_2C•CH$ |
| 26.95 | $CH_3$ | H | O | $C(CH_3)_2C•CCH_3$ |
| 26.96 | $CH_3$ | H | O | $C(CH_3)_2C•CCH_2CH_3$ |
| 26.97 | $CH_3$ | H | O | Cyclopropyl |
| 26.98 | $CH_3$ | H | O | Cyclobutyl |
| 26.99 | $CH_3$ | H | O | Cyclopentyl |
| 26.100 | $CH_3$ | H | O | Cyclohexyl |
| 26.101 | $CH_3$ | H | O | $CH_2CF_3$ |
| 26.102 | $CH_3$ | H | O | $CH_2CH_2CF_3$ |
| 26.103 | $CH_3$ | H | O | $CH_2$-cyclopropyl |
| 26.104 | $CH_3$ | H | O | $CH_2$-cyclobutyl |
| 26.105 | $CH_3$ | H | O | $CH_2$-cyclopentyl |
| 26.106 | $CH_3$ | H | O | $CH_2$-cyclohexyl |
| 26.107 | $CH_3$ | H | O | $CH_2OCH_3$ |
| 26.108 | $CH_3$ | H | O | $CH_2OCH_2CH_3$ |
| 26.109 | $CH_3$ | H | O | $CH_2CH_2OCH_3$ |
| 26.110 | $CH_3$ | H | O | $CH_2CH_2OCH_2CH_3$ |
| 26.111 | $CH_3$ | $CH_3$ | O | $CH_3$ |
| 26.112 | $CH_3$ | $CH_3$ | O | $CH_2CH_3$ |
| 26.113 | $CH_3$ | $CH_3$ | O | $CH_2CH_2CH_3$ |
| 26.114 | $CH_3$ | $CH_3$ | O | $CH(CH_3)_2$ |
| 26.115 | $CH_3$ | $CH_3$ | O | $CH_2CH_2CH_2CH_3$ |
| 26.116 | $CH_3$ | $CH_3$ | O | $CH_2CH(CH_3)_2$ |
| 26.117 | $CH_3$ | $CH_3$ | O | $CH(CH_3)CH_2CH_3$ |
| 26.118 | $CH_3$ | $CH_3$ | O | $C(CH_3)_3$ |
| 26.119 | $CH_3$ | $CH_3$ | O | $CH_2CH_2CH_2CH_2CH_3$ |
| 26.120 | $CH_3$ | $CH_3$ | O | $CH_2CH_2CH(CH_3)_2$ |
| 26.121 | $CH_3$ | $CH_3$ | O | $CH_2C(CH_3)_3$ |
| 26.122 | $CH_3$ | $CH_3$ | O | $CH_2CH(CH_3)CH_2CH_3$ |
| 26.123 | $CH_3$ | $CH_3$ | O | $CH(CH_3)CH_2CH_2CH_3$ |
| 26.124 | $CH_3$ | $CH_3$ | O | $C(CH_3)_2CH_2CH_3$ |
| 26.125 | $CH_3$ | $CH_3$ | O | $CH_2CH=CH_2$ |
| 26.126 | $CH_3$ | $CH_3$ | O | $CH_2CH=CHCH_3$ |

TABLE 26-continued

This table contains 618 compounds of the following type,

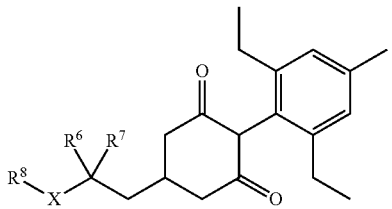

where X, $R^6$, $R^7$ and $R^8$ are as defined below:

| Compound number | $R^6$ | $R^7$ | X | $R^8$ |
|---|---|---|---|---|
| 26.127 | $CH_3$ | $CH_3$ | O | $CH_2CH=C(CH_3)_2$ |
| 26.128 | $CH_3$ | $CH_3$ | O | $CH_2C(CH_3)=CH_2$ |
| 26.129 | $CH_3$ | $CH_3$ | O | $CH_2C(CH_3)=CHCH_3$ |
| 26.130 | $CH_3$ | $CH_3$ | O | $CH_2C(CH_3)=C(CH_3)_2$ |
| 26.131 | $CH_3$ | $CH_3$ | O | $CH(CH_3)CH=CH_2$ |
| 26.132 | $CH_3$ | $CH_3$ | O | $CH(CH_3)CH=CHCH_3$ |
| 26.133 | $CH_3$ | $CH_3$ | O | $CH(CH_3)CH=C(CH_3)_2$ |
| 26.134 | $CH_3$ | $CH_3$ | O | $C(CH_3)_2CH=CH_2$ |
| 26.135 | $CH_3$ | $CH_3$ | O | $C(CH_3)_2CH=CHCH_3$ |
| 26.136 | $CH_3$ | $CH_3$ | O | $C(CH_3)_2CH=C(CH_3)_2$ |
| 26.137 | $CH_3$ | $CH_3$ | O | $CH_2CH=CHCl$ |
| 26.138 | $CH_3$ | $CH_3$ | O | $CH_2CH=CCl_2$ |
| 26.139 | $CH_3$ | $CH_3$ | O | $CH_2CCl=CHCl$ |
| 26.140 | $CH_3$ | $CH_3$ | O | $CH_2CCl=CCl_2$ |
| 26.141 | $CH_3$ | $CH_3$ | O | $CH_2CH=CF_2$ |
| 26.142 | $CH_3$ | $CH_3$ | O | $CH_2CF=CF_2$ |
| 26.143 | $CH_3$ | $CH_3$ | O | $CH_2C\bullet CH$ |
| 26.144 | $CH_3$ | $CH_3$ | O | $CH_2C\bullet CCH_3$ |
| 26.145 | $CH_3$ | $CH_3$ | O | $CH_2C\bullet CCH_2CH_3$ |
| 26.146 | $CH_3$ | $CH_3$ | O | $CH(CH_3)C\bullet CH$ |
| 26.147 | $CH_3$ | $CH_3$ | O | $CH(CH_3)C\bullet CCH_3$ |
| 26.148 | $CH_3$ | $CH_3$ | O | $CH(CH_3)C\bullet CCH_2CH_3$ |
| 26.149 | $CH_3$ | $CH_3$ | O | $C(CH_3)_2C\bullet CH$ |
| 26.150 | $CH_3$ | $CH_3$ | O | $C(CH_3)_2C\bullet CCH_3$ |
| 26.151 | $CH_3$ | $CH_3$ | O | $C(CH_3)_2C\bullet CCH_2CH_3$ |
| 26.152 | $CH_3$ | $CH_3$ | O | Cyclopropyl |
| 26.153 | $CH_3$ | $CH_3$ | O | Cyclobutyl |
| 26.154 | $CH_3$ | $CH_3$ | O | Cyclopentyl |
| 26.155 | $CH_3$ | $CH_3$ | O | Cyclohexyl |
| 26.156 | $CH_3$ | $CH_3$ | O | $CH_2CF_3$ |
| 26.157 | $CH_3$ | $CH_3$ | O | $CH_2CH_2CF_3$ |
| 26.158 | $CH_3$ | $CH_3$ | O | $CH_2$-cyclopropyl |
| 26.159 | $CH_3$ | $CH_3$ | O | $CH_2$-cyclobutyl |
| 26.160 | $CH_3$ | $CH_3$ | O | $CH_2$-cyclopentyl |
| 26.161 | $CH_3$ | $CH_3$ | O | $CH_2$-cyclohexyl |
| 26.162 | $CH_3$ | $CH_3$ | O | $CH_2OCH_3$ |
| 26.163 | $CH_3$ | $CH_3$ | O | $CH_2OCH_2CH_3$ |
| 26.164 | $CH_3$ | $CH_3$ | O | $CH_2CH_2OCH_3$ |
| 26.165 | $CH_3$ | $CH_3$ | O | $CH_2CH_2OCH_2CH_3$ |
| 26.166 | H | H | S | $CH_3$ |
| 26.167 | H | H | S | $CH_2CH_3$ |
| 26.168 | H | H | S | $CH_2CH_2CH_3$ |
| 26.169 | H | H | S | $CH(CH_3)_2$ |
| 26.170 | H | H | S | $CH_2CH_2CH_2CH_3$ |
| 26.171 | H | H | S | $CH_2CH(CH_3)_2$ |
| 26.172 | H | H | S | $CH(CH_3)CH_2CH_3$ |
| 26.173 | H | H | S | $C(CH_3)_3$ |
| 26.174 | H | H | S | $CH_2CH_2CH_2CH_2CH_3$ |
| 26.175 | H | H | S | $CH_2CH_2CH(CH_3)_2$ |
| 26.176 | H | H | S | $CH_2C(CH_3)_3$ |
| 26.177 | H | H | S | $CH_2CH(CH_3)CH_2CH_3$ |
| 26.178 | H | H | S | $CH(CH_3)CH_2CH_2CH_3$ |
| 26.179 | H | H | S | $C(CH_3)_2CH_2CH_3$ |
| 26.180 | H | H | S | $CH_2CH=CH_2$ |
| 26.181 | H | H | S | $CH_2CH=CHCH_3$ |
| 26.182 | H | H | S | $CH_2CH=C(CH_3)_2$ |
| 26.183 | H | H | S | $CH_2C(CH_3)=CH_2$ |
| 26.184 | H | H | S | $CH_2C(CH_3)=CHCH_3$ |
| 26.185 | H | H | S | $CH_2C(CH_3)=C(CH_3)_2$ |
| 26.186 | H | H | S | $CH(CH_3)CH=CH_2$ |
| 26.187 | H | H | S | $CH(CH_3)CH=CHCH_3$ |
| 26.188 | H | H | S | $CH(CH_3)CH=C(CH_3)_2$ |
| 26.189 | H | H | S | $C(CH_3)_2CH=CH_2$ |

TABLE 26-continued

This table contains 618 compounds of the following type,

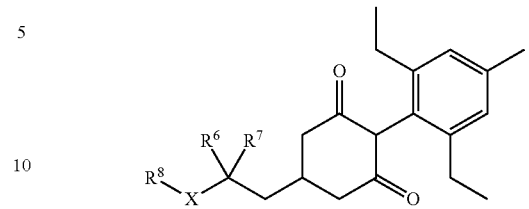

where X, $R^6$, $R^7$ and $R^8$ are as defined below:

| Compound number | $R^6$ | $R^7$ | X | $R^8$ |
|---|---|---|---|---|
| 26.190 | H | H | S | $C(CH_3)_2CH=CHCH_3$ |
| 26.191 | H | H | S | $C(CH_3)_2CH=C(CH_3)_2$ |
| 26.192 | H | H | S | $CH_2CH=CHCl$ |
| 26.193 | H | H | S | $CH_2CH=CCl_2$ |
| 26.194 | H | H | S | $CH_2CCl=CHCl$ |
| 26.195 | H | H | S | $CH_2CCl=CCl_2$ |
| 26.196 | H | H | S | $CH_2CH=CF_2$ |
| 26.197 | H | H | S | $CH_2CF=CF_2$ |
| 26.198 | H | H | S | $CH_2C\bullet CH$ |
| 26.199 | H | H | S | $CH_2C\bullet CCH_3$ |
| 26.200 | H | H | S | $CH_2C\bullet CCH_2CH_3$ |
| 26.201 | H | H | S | $CH(CH_3)C\bullet CH$ |
| 26.202 | H | H | S | $CH(CH_3)C\bullet CCH_3$ |
| 26.203 | H | H | S | $CH(CH_3)C\bullet CCH_2CH_3$ |
| 26.204 | H | H | S | $C(CH_3)_2C\bullet CH$ |
| 26.205 | H | H | S | $C(CH_3)_2C\bullet CCH_3$ |
| 26.206 | H | H | S | $C(CH_3)_2C\bullet CCH_2CH_3$ |
| 26.207 | H | H | S | Cyclopropyl |
| 26.208 | H | H | S | Cyclobutyl |
| 26.209 | H | H | S | Cyclopentyl |
| 26.210 | H | H | S | Cyclohexyl |
| 26.211 | H | H | S | $CH_2CF_3$ |
| 26.212 | H | H | S | $CH_2CH_2CF_3$ |
| 26.213 | H | H | S | $CH_2$-cyclopropyl |
| 26.214 | H | H | S | $CH_2$-cyclobutyl |
| 26.215 | H | H | S | $CH_2$-cyclopentyl |
| 26.216 | H | H | S | $CH_2$-cyclohexyl |
| 26.217 | $CH_3$ | H | S | $CH_3$ |
| 26.218 | $CH_3$ | H | S | $CH_2CH_3$ |
| 26.219 | $CH_3$ | H | S | $CH_2CH_2CH_3$ |
| 26.220 | $CH_3$ | H | S | $CH(CH_3)_2$ |
| 26.221 | $CH_3$ | H | S | $CH_2CH_2CH_2CH_3$ |
| 26.222 | $CH_3$ | H | S | $CH_2CH(CH_3)_2$ |
| 26.223 | $CH_3$ | H | S | $CH(CH_3)CH_2CH_3$ |
| 26.224 | $CH_3$ | H | S | $C(CH_3)_3$ |
| 26.225 | $CH_3$ | H | S | $CH_2CH_2CH_2CH_2CH_3$ |
| 26.226 | $CH_3$ | H | S | $CH_2CH_2CH(CH_3)_2$ |
| 26.227 | $CH_3$ | H | S | $CH_2C(CH_3)_3$ |
| 26.228 | $CH_3$ | H | S | $CH_2CH(CH_3)CH_2CH_3$ |
| 26.229 | $CH_3$ | H | S | $CH(CH_3)CH_2CH_2CH_3$ |
| 26.230 | $CH_3$ | H | S | $C(CH_3)_2CH_2CH_3$ |
| 26.231 | $CH_3$ | H | S | $CH_2CH=CH_2$ |
| 26.232 | $CH_3$ | H | S | $CH_2CH=CHCH_3$ |
| 26.233 | $CH_3$ | H | S | $CH_2CH=C(CH_3)_2$ |
| 26.234 | $CH_3$ | H | S | $CH_2C(CH_3)=CH_2$ |
| 26.235 | $CH_3$ | H | S | $CH_2C(CH_3)=CHCH_3$ |
| 26.236 | $CH_3$ | H | S | $CH_2C(CH_3)=C(CH_3)_2$ |
| 26.237 | $CH_3$ | H | S | $CH(CH_3)CH=CH_2$ |
| 26.238 | $CH_3$ | H | S | $CH(CH_3)CH=CHCH_3$ |
| 26.239 | $CH_3$ | H | S | $CH(CH_3)CH=C(CH_3)_2$ |
| 26.240 | $CH_3$ | H | S | $C(CH_3)_2CH=CH_2$ |
| 26.241 | $CH_3$ | H | S | $C(CH_3)_2CH=CHCH_3$ |
| 26.242 | $CH_3$ | H | S | $C(CH_3)_2CH=C(CH_3)_2$ |
| 26.243 | $CH_3$ | H | S | $CH_2CH=CHCl$ |
| 26.244 | $CH_3$ | H | S | $CH_2CH=CCl_2$ |
| 26.245 | $CH_3$ | H | S | $CH_2CCl=CHCl$ |
| 26.246 | $CH_3$ | H | S | $CH_2CCl=CCl_2$ |
| 26.247 | $CH_3$ | H | S | $CH_2CH=CF_2$ |
| 26.248 | $CH_3$ | H | S | $CH_2CF=CF_2$ |
| 26.249 | $CH_3$ | H | S | $CH_2C\bullet CH$ |
| 26.250 | $CH_3$ | H | S | $CH_2C\bullet CCH_3$ |
| 26.251 | $CH_3$ | H | S | $CH_2C\bullet CCH_2CH_3$ |
| 26.252 | $CH_3$ | H | S | $CH(CH_3)C\bullet CH$ |

TABLE 26-continued

This table contains 618 compounds of the following type,

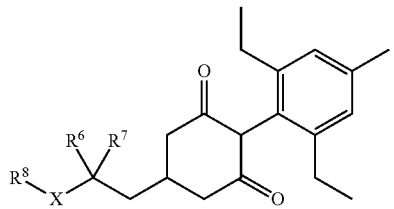

where X, $R^6$, $R^7$ and $R^8$ are as defined below:

| Compound number | $R^6$ | $R^7$ | X | $R^8$ |
|---|---|---|---|---|
| 26.253 | $CH_3$ | H | S | $CH(CH_3)C{\bullet}CCH_3$ |
| 26.254 | $CH_3$ | H | S | $CH(CH_3)C{\bullet}CCH_2CH_3$ |
| 26.255 | $CH_3$ | H | S | $C(CH_3)_2C{\bullet}CH$ |
| 26.256 | $CH_3$ | H | S | $C(CH_3)_2C{\bullet}CCH_3$ |
| 26.257 | $CH_3$ | H | S | $C(CH_3)_2C{\bullet}CCH_2CH_3$ |
| 26.258 | $CH_3$ | H | S | Cyclopropyl |
| 26.259 | $CH_3$ | H | S | Cyclobutyl |
| 26.260 | $CH_3$ | H | S | Cyclopentyl |
| 26.261 | $CH_3$ | H | S | Cyclohexyl |
| 26.262 | $CH_3$ | H | S | $CH_2CF_3$ |
| 26.263 | $CH_3$ | H | S | $CH_2CH_2CF_3$ |
| 26.264 | $CH_3$ | H | S | $CH_2$-cyclopropyl |
| 26.265 | $CH_3$ | H | S | $CH_2$-cyclobutyl |
| 26.266 | $CH_3$ | H | S | $CH_2$-cyclopentyl |
| 26.267 | $CH_3$ | H | S | $CH_2$-cyclohexyl |
| 26.268 | $CH_3$ | $CH_3$ | S | $CH_3$ |
| 26.269 | $CH_3$ | $CH_3$ | S | $CH_2CH_3$ |
| 26.270 | $CH_3$ | $CH_3$ | S | $CH_2CH_2CH_3$ |
| 26.271 | $CH_3$ | $CH_3$ | S | $CH(CH_3)_2$ |
| 26.272 | $CH_3$ | $CH_3$ | S | $CH_2CH_2CH_2CH_3$ |
| 26.273 | $CH_3$ | $CH_3$ | S | $CH_2CH(CH_3)_2$ |
| 26.274 | $CH_3$ | $CH_3$ | S | $CH(CH_3)CH_2CH_3$ |
| 26.275 | $CH_3$ | $CH_3$ | S | $C(CH_3)_3$ |
| 26.276 | $CH_3$ | $CH_3$ | S | $CH_2CH_2CH_2CH_2CH_3$ |
| 26.277 | $CH_3$ | $CH_3$ | S | $CH_2CH_2CH(CH_3)_2$ |
| 26.278 | $CH_3$ | $CH_3$ | S | $CH_2C(CH_3)_3$ |
| 26.279 | $CH_3$ | $CH_3$ | S | $CH_2CH(CH_3)CH_2CH_3$ |
| 26.280 | $CH_3$ | $CH_3$ | S | $CH(CH_3)CH_2CH_2CH_3$ |
| 26.281 | $CH_3$ | $CH_3$ | S | $C(CH_3)_2CH_2CH_3$ |
| 26.282 | $CH_3$ | $CH_3$ | S | $CH_2CH{=}CH_2$ |
| 26.283 | $CH_3$ | $CH_3$ | S | $CH_2CH{=}CHCH_3$ |
| 26.284 | $CH_3$ | $CH_3$ | S | $CH_2CH{=}C(CH_3)_2$ |
| 26.285 | $CH_3$ | $CH_3$ | S | $CH_2C(CH_3){=}CH_2$ |
| 26.286 | $CH_3$ | $CH_3$ | S | $CH_2C(CH_3){=}CHCH_3$ |
| 26.287 | $CH_3$ | $CH_3$ | S | $CH_2C(CH_3){=}C(CH_3)_2$ |
| 26.288 | $CH_3$ | $CH_3$ | S | $CH(CH_3)CH{=}CH_2$ |
| 26.289 | $CH_3$ | $CH_3$ | S | $CH(CH_3)CH{=}CHCH_3$ |
| 26.290 | $CH_3$ | $CH_3$ | S | $CH(CH_3)CH{=}C(CH_3)_2$ |
| 26.291 | $CH_3$ | $CH_3$ | S | $C(CH_3)_2CH{=}CH_2$ |
| 26.292 | $CH_3$ | $CH_3$ | S | $C(CH_3)_2CH{=}CHCH_3$ |
| 26.293 | $CH_3$ | $CH_3$ | S | $C(CH_3)_2CH{=}C(CH_3)_2$ |
| 26.294 | $CH_3$ | $CH_3$ | S | $CH_2CH{=}CHCl$ |
| 26.295 | $CH_3$ | $CH_3$ | S | $CH_2CH{=}CCl_2$ |
| 26.296 | $CH_3$ | $CH_3$ | S | $CH_2CCl{=}CHCl$ |
| 26.297 | $CH_3$ | $CH_3$ | S | $CH_2CCl{=}CCl_2$ |
| 26.298 | $CH_3$ | $CH_3$ | S | $CH_2CH{=}CF_2$ |
| 26.299 | $CH_3$ | $CH_3$ | S | $CH_2CF{=}CF_2$ |
| 26.300 | $CH_3$ | $CH_3$ | S | $CH_2C{\bullet}CH$ |
| 26.301 | $CH_3$ | $CH_3$ | S | $CH_2C{\bullet}CCH_3$ |
| 26.302 | $CH_3$ | $CH_3$ | S | $CH_2C{\bullet}CCH_2CH_3$ |
| 26.303 | $CH_3$ | $CH_3$ | S | $CH(CH_3)C{\bullet}CH$ |
| 26.304 | $CH_3$ | $CH_3$ | S | $CH(CH_3)C{\bullet}CCH_3$ |
| 26.305 | $CH_3$ | $CH_3$ | S | $CH(CH_3)C{\bullet}CCH_2CH_3$ |
| 26.306 | $CH_3$ | $CH_3$ | S | $C(CH_3)_2C{\bullet}CH$ |
| 26.307 | $CH_3$ | $CH_3$ | S | $C(CH_3)_2C{\bullet}CCH_3$ |
| 26.308 | $CH_3$ | $CH_3$ | S | $C(CH_3)_2C{\bullet}CCH_2CH_3$ |
| 26.309 | $CH_3$ | $CH_3$ | S | Cyclopropyl |
| 26.310 | $CH_3$ | $CH_3$ | S | Cyclobutyl |
| 26.311 | $CH_3$ | $CH_3$ | S | Cyclopentyl |
| 26.312 | $CH_3$ | $CH_3$ | S | Cyclohexyl |
| 26.313 | $CH_3$ | $CH_3$ | S | $CH_2CF_3$ |
| 26.314 | $CH_3$ | $CH_3$ | S | $CH_2CH_2CF_3$ |
| 26.315 | $CH_3$ | $CH_3$ | S | $CH_2$-cyclopropyl |

TABLE 26-continued

This table contains 618 compounds of the following type,

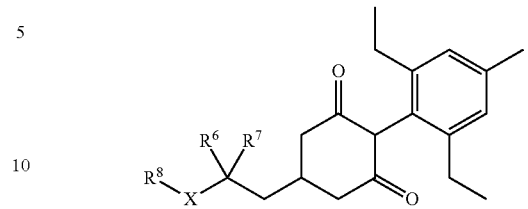

where X, $R^6$, $R^7$ and $R^8$ are as defined below:

| Compound number | $R^6$ | $R^7$ | X | $R^8$ |
|---|---|---|---|---|
| 26.316 | $CH_3$ | $CH_3$ | S | $CH_2$-cyclobutyl |
| 26.317 | $CH_3$ | $CH_3$ | S | $CH_2$-cyclopentyl |
| 26.318 | $CH_3$ | $CH_3$ | S | $CH_2$-cyclohexyl |
| 26.319 | H | H | S(O) | $CH_3$ |
| 26.320 | H | H | S(O) | $CH_2CH_3$ |
| 26.321 | H | H | S(O) | $CH_2CH_2CH_3$ |
| 26.322 | H | H | S(O) | $CH(CH_3)_2$ |
| 26.323 | H | H | S(O) | $CH_2CH_2CH_2CH_3$ |
| 26.324 | H | H | S(O) | $CH_2CH(CH_3)_2$ |
| 26.325 | H | H | S(O) | $CH(CH_3)CH_2CH_3$ |
| 26.326 | H | H | S(O) | $C(CH_3)_3$ |
| 26.327 | H | H | S(O) | $CH_2CH_2CH_2CH_2CH_3$ |
| 26.328 | H | H | S(O) | $CH_2CH_2CH(CH_3)_2$ |
| 26.329 | H | H | S(O) | $CH_2C(CH_3)_3$ |
| 26.330 | H | H | S(O) | $CH_2CH(CH_3)CH_2CH_3$ |
| 26.331 | H | H | S(O) | $CH(CH_3)CH_2CH_2CH_3$ |
| 26.332 | H | H | S(O) | $C(CH_3)_2CH_2CH_3$ |
| 26.333 | H | H | S(O) | $CH_2CH{=}CH_2$ |
| 26.334 | H | H | S(O) | $CH_2CH{=}CHCH_3$ |
| 26.335 | H | H | S(O) | $CH_2CH{=}C(CH_3)_2$ |
| 26.336 | H | H | S(O) | $CH_2C(CH_3){=}CH_2$ |
| 26.337 | H | H | S(O) | $CH_2C(CH_3){=}CHCH_3$ |
| 26.338 | H | H | S(O) | $CH_2C(CH_3){=}C(CH_3)_2$ |
| 26.339 | H | H | S(O) | $CH(CH_3)CH{=}CH_2$ |
| 26.340 | H | H | S(O) | $CH(CH_3)CH{=}CHCH_3$ |
| 26.341 | H | H | S(O) | $CH(CH_3)CH{=}C(CH_3)_2$ |
| 26.342 | H | H | S(O) | $C(CH_3)_2CH{=}CH_2$ |
| 26.343 | H | H | S(O) | $C(CH_3)_2CH{=}CHCH_3$ |
| 26.344 | H | H | S(O) | $C(CH_3)_2CH{=}C(CH_3)_2$ |
| 26.345 | H | H | S(O) | $CH_2CH{=}CHCl$ |
| 26.346 | H | H | S(O) | $CH_2CH{=}CCl_2$ |
| 26.347 | H | H | S(O) | $CH_2CCl{=}CHCl$ |
| 26.348 | H | H | S(O) | $CH_2CCl{=}CCl_2$ |
| 26.349 | H | H | S(O) | $CH_2CH{=}CF_2$ |
| 26.350 | H | H | S(O) | $CH_2CF{=}CF_2$ |
| 26.351 | H | H | S(O) | $CH_2C{\bullet}CH$ |
| 26.352 | H | H | S(O) | $CH_2C{\bullet}CCH_3$ |
| 26.353 | H | H | S(O) | $CH_2C{\bullet}CCH_2CH_3$ |
| 26.354 | H | H | S(O) | $CH(CH_3)C{\bullet}CH$ |
| 26.355 | H | H | S(O) | $CH(CH_3)C{\bullet}CCH_3$ |
| 26.356 | H | H | S(O) | $CH(CH_3)C{\bullet}CCH_2CH_3$ |
| 26.357 | H | H | S(O) | $C(CH_3)_2C{\bullet}CH$ |
| 26.358 | H | H | S(O) | $C(CH_3)_2C{\bullet}CCH_3$ |
| 26.359 | H | H | S(O) | $C(CH_3)_2C{\bullet}CCH_2CH_3$ |
| 26.360 | H | H | S(O) | Cyclopropyl |
| 26.361 | H | H | S(O) | Cyclobutyl |
| 26.362 | H | H | S(O) | Cyclopentyl |
| 26.363 | H | H | S(O) | Cyclohexyl |
| 26.364 | H | H | S(O) | $CH_2CF_3$ |
| 26.365 | H | H | S(O) | $CH_2CH_2CF_3$ |
| 26.366 | H | H | S(O) | $CH_2$-cyclopropyl |
| 26.357 | H | H | S(O) | $CH_2$-cyclobutyl |
| 26.358 | H | H | S(O) | $CH_2$-cyclopentyl |
| 26.359 | H | H | S(O) | $CH_2$-cyclohexyl |
| 26.360 | H | H | S(O) | $CH_2OCH_3$ |
| 26.361 | H | H | S(O) | $CH_2OCH_2CH_3$ |
| 26.362 | H | H | S(O) | $CH_2CH_2OCH_3$ |
| 26.363 | H | H | S(O) | $CH_2CH_2OCH_2CH_3$ |
| 26.364 | $CH_3$ | H | S(O) | $CH_3$ |
| 26.365 | $CH_3$ | H | S(O) | $CH_2CH_3$ |
| 26.366 | $CH_3$ | H | S(O) | $CH_2CH_2CH_3$ |
| 26.367 | $CH_3$ | H | S(O) | $CH(CH_3)_2$ |
| 26.368 | $CH_3$ | H | S(O) | $CH_2CH_2CH_2CH_3$ |

TABLE 26-continued

This table contains 618 compounds of the following type,

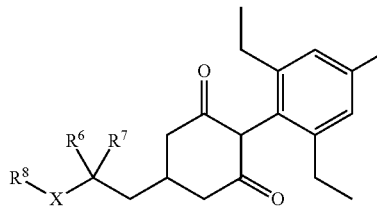

where X, R⁶, R⁷ and R⁸ are as defined below:

| Compound number | R⁶ | R⁷ | X | R⁸ |
|---|---|---|---|---|
| 26.369 | $CH_3$ | H | S(O) | $CH_2CH(CH_3)_2$ |
| 26.370 | $CH_3$ | H | S(O) | $CH(CH_3)CH_2CH_3$ |
| 26.371 | $CH_3$ | H | S(O) | $C(CH_3)_3$ |
| 26.372 | $CH_3$ | H | S(O) | $CH_2CH_2CH_2CH_2CH_3$ |
| 26.373 | $CH_3$ | H | S(O) | $CH_2CH_2CH(CH_3)_2$ |
| 26.374 | $CH_3$ | H | S(O) | $CH_2C(CH_3)_3$ |
| 26.375 | $CH_3$ | H | S(O) | $CH_2CH(CH_3)CH_2CH_3$ |
| 26.376 | $CH_3$ | H | S(O) | $CH(CH_3)CH_2CH_2CH_3$ |
| 26.377 | $CH_3$ | H | S(O) | $C(CH_3)_2CH_2CH_3$ |
| 26.378 | $CH_3$ | H | S(O) | $CH_2CH=CH_2$ |
| 26.379 | $CH_3$ | H | S(O) | $CH_2CH=CHCH_3$ |
| 26.380 | $CH_3$ | H | S(O) | $CH_2CH=C(CH_3)_2$ |
| 26.381 | $CH_3$ | H | S(O) | $CH_2C(CH_3)=CH_2$ |
| 26.382 | $CH_3$ | H | S(O) | $CH_2C(CH_3)=CHCH_3$ |
| 26.383 | $CH_3$ | H | S(O) | $CH_2C(CH_3)=C(CH_3)_2$ |
| 26.384 | $CH_3$ | H | S(O) | $CH(CH_3)CH=CH_2$ |
| 26.385 | $CH_3$ | H | S(O) | $CH(CH_3)CH=CHCH_3$ |
| 26.386 | $CH_3$ | H | S(O) | $CH(CH_3)CH=C(CH_3)_2$ |
| 26.387 | $CH_3$ | H | S(O) | $C(CH_3)_2CH=CH_2$ |
| 26.388 | $CH_3$ | H | S(O) | $C(CH_3)_2CH=CHCH_3$ |
| 26.389 | $CH_3$ | H | S(O) | $C(CH_3)_2CH=C(CH_3)_2$ |
| 26.390 | $CH_3$ | H | S(O) | $CH_2CH=CHCl$ |
| 26.391 | $CH_3$ | H | S(O) | $CH_2CH=CCl_2$ |
| 26.392 | $CH_3$ | H | S(O) | $CH_2CCl=CHCl$ |
| 26.393 | $CH_3$ | H | S(O) | $CH_2CCl=CCl_2$ |
| 26.394 | $CH_3$ | H | S(O) | $CH_2CH=CF_2$ |
| 26.395 | $CH_3$ | H | S(O) | $CH_2CF=CF_2$ |
| 26.396 | $CH_3$ | H | S(O) | $CH_2C•CH$ |
| 26.397 | $CH_3$ | H | S(O) | $CH_2C•CCH_3$ |
| 26.398 | $CH_3$ | H | S(O) | $CH_2C•CCH_2CH_3$ |
| 26.399 | $CH_3$ | H | S(O) | $CH(CH_3)C•CH$ |
| 26.400 | $CH_3$ | H | S(O) | $CH(CH_3)C•CCH_3$ |
| 26.401 | $CH_3$ | H | S(O) | $CH(CH_3)C•CCH_2CH_3$ |
| 26.402 | $CH_3$ | H | S(O) | $C(CH_3)_2C•CH$ |
| 26.403 | $CH_3$ | H | S(O) | $C(CH_3)_2C•CCH_3$ |
| 26.404 | $CH_3$ | H | S(O) | $C(CH_3)_2C•CCH_2CH_3$ |
| 26.405 | $CH_3$ | H | S(O) | Cyclopropyl |
| 26.406 | $CH_3$ | H | S(O) | Cyclobutyl |
| 26.407 | $CH_3$ | H | S(O) | Cyclopentyl |
| 26.408 | $CH_3$ | H | S(O) | Cyclohexyl |
| 26.409 | $CH_3$ | H | S(O) | $CH_2CF_3$ |
| 26.410 | $CH_3$ | H | S(O) | $CH_2CH_2CF_3$ |
| 26.411 | $CH_3$ | H | S(O) | $CH_2$-cyclopropyl |
| 26.412 | $CH_3$ | H | S(O) | $CH_2$-cyclobutyl |
| 26.413 | $CH_3$ | H | S(O) | $CH_2$-cyclopentyl |
| 26.414 | $CH_3$ | H | S(O) | $CH_2$-cyclohexyl |
| 26.415 | $CH_3$ | $CH_3$ | S(O) | $CH_3$ |
| 26.416 | $CH_3$ | $CH_3$ | S(O) | $CH_2CH_3$ |
| 26.417 | $CH_3$ | $CH_3$ | S(O) | $CH_2CH_2CH_3$ |
| 26.418 | $CH_3$ | $CH_3$ | S(O) | $CH(CH_3)_2$ |
| 26.419 | $CH_3$ | $CH_3$ | S(O) | $CH_2CH_2CH_2CH_3$ |
| 26.420 | $CH_3$ | $CH_3$ | S(O) | $CH_2CH(CH_3)_2$ |
| 26.421 | $CH_3$ | $CH_3$ | S(O) | $CH(CH_3)CH_2CH_3$ |
| 26.422 | $CH_3$ | $CH_3$ | S(O) | $C(CH_3)_3$ |
| 26.423 | $CH_3$ | $CH_3$ | S(O) | $CH_2CH_2CH_2CH_2CH_3$ |
| 26.424 | $CH_3$ | $CH_3$ | S(O) | $CH_2CH_2CH(CH_3)_2$ |
| 26.425 | $CH_3$ | $CH_3$ | S(O) | $CH_2C(CH_3)_3$ |
| 26.426 | $CH_3$ | $CH_3$ | S(O) | $CH_2CH(CH_3)CH_2CH_3$ |
| 26.427 | $CH_3$ | $CH_3$ | S(O) | $CH(CH_3)CH_2CH_2CH_3$ |
| 26.428 | $CH_3$ | $CH_3$ | S(O) | $C(CH_3)_2CH_2CH_3$ |
| 26.429 | $CH_3$ | $CH_3$ | S(O) | $CH_2CH=CH_2$ |
| 26.430 | $CH_3$ | $CH_3$ | S(O) | $CH_2CH=CHCH_3$ |
| 26.431 | $CH_3$ | $CH_3$ | S(O) | $CH_2CH=C(CH_3)_2$ |
| 26.432 | $CH_3$ | $CH_3$ | S(O) | $CH_2C(CH_3)=CH_2$ |
| 26.433 | $CH_3$ | $CH_3$ | S(O) | $CH_2C(CH_3)=CHCH_3$ |
| 26.434 | $CH_3$ | $CH_3$ | S(O) | $CH_2C(CH_3)=C(CH_3)_2$ |
| 26.435 | $CH_3$ | $CH_3$ | S(O) | $CH(CH_3)CH=CH_2$ |
| 26.436 | $CH_3$ | $CH_3$ | S(O) | $CH(CH_3)CH=CHCH_3$ |
| 26.437 | $CH_3$ | $CH_3$ | S(O) | $CH(CH_3)CH=C(CH_3)_2$ |
| 26.438 | $CH_3$ | $CH_3$ | S(O) | $C(CH_3)_2CH=CH_2$ |
| 26.439 | $CH_3$ | $CH_3$ | S(O) | $C(CH_3)_2CH=CHCH_3$ |
| 26.440 | $CH_3$ | $CH_3$ | S(O) | $C(CH_3)_2CH=C(CH_3)_2$ |
| 26.441 | $CH_3$ | $CH_3$ | S(O) | $CH_2CH=CHCl$ |
| 26.442 | $CH_3$ | $CH_3$ | S(O) | $CH_2CH=CCl_2$ |
| 26.443 | $CH_3$ | $CH_3$ | S(O) | $CH_2CCl=CHCl$ |
| 26.444 | $CH_3$ | $CH_3$ | S(O) | $CH_2CCl=CCl_2$ |
| 26.445 | $CH_3$ | $CH_3$ | S(O) | $CH_2CH=CF_2$ |
| 26.446 | $CH_3$ | $CH_3$ | S(O) | $CH_2CF=CF_2$ |
| 26.447 | $CH_3$ | $CH_3$ | S(O) | $CH_2C•CH$ |
| 26.448 | $CH_3$ | $CH_3$ | S(O) | $CH_2C•CCH_3$ |
| 26.449 | $CH_3$ | $CH_3$ | S(O) | $CH_2C•CCH_2CH_3$ |
| 26.450 | $CH_3$ | $CH_3$ | S(O) | $CH(CH_3)C•CH$ |
| 26.451 | $CH_3$ | $CH_3$ | S(O) | $CH(CH_3)C•CCH_3$ |
| 26.452 | $CH_3$ | $CH_3$ | S(O) | $CH(CH_3)C•CCH_2CH_3$ |
| 26.453 | $CH_3$ | $CH_3$ | S(O) | $C(CH_3)_2C•CH$ |
| 26.454 | $CH_3$ | $CH_3$ | S(O) | $C(CH_3)_2C•CCH_3$ |
| 26.455 | $CH_3$ | $CH_3$ | S(O) | $C(CH_3)_2C•CCH_2CH_3$ |
| 26.456 | $CH_3$ | $CH_3$ | S(O) | Cyclopropyl |
| 26.457 | $CH_3$ | $CH_3$ | S(O) | Cyclobutyl |
| 26.458 | $CH_3$ | $CH_3$ | S(O) | Cyclopentyl |
| 26.459 | $CH_3$ | $CH_3$ | S(O) | Cyclohexyl |
| 26.460 | $CH_3$ | $CH_3$ | S(O) | $CH_2CF_3$ |
| 26.461 | $CH_3$ | $CH_3$ | S(O) | $CH_2CH_2CF_3$ |
| 26.462 | $CH_3$ | $CH_3$ | S(O) | $CH_2$-cyclopropyl |
| 26.463 | $CH_3$ | $CH_3$ | S(O) | $CH_2$-cyclobutyl |
| 26.464 | $CH_3$ | $CH_3$ | S(O) | $CH_2$-cyclopentyl |
| 26.465 | $CH_3$ | $CH_3$ | S(O) | $CH_2$-cyclohexyl |
| 26.466 | H | H | $SO_2$ | $CH_3$ |
| 26.467 | H | H | $SO_2$ | $CH_2CH_3$ |
| 26.468 | H | H | $SO_2$ | $CH_2CH_2CH_3$ |
| 26.469 | H | H | $SO_2$ | $CH(CH_3)_2$ |
| 26.470 | H | H | $SO_2$ | $CH_2CH_2CH_2CH_3$ |
| 26.471 | H | H | $SO_2$ | $CH_2CH(CH_3)_2$ |
| 26.472 | H | H | $SO_2$ | $CH(CH_3)CH_2CH_3$ |
| 26.473 | H | H | $SO_2$ | $C(CH_3)_3$ |
| 26.474 | H | H | $SO_2$ | $CH_2CH_2CH_2CH_2CH_3$ |
| 26.475 | H | H | $SO_2$ | $CH_2CH_2CH(CH_3)_2$ |
| 26.476 | H | H | $SO_2$ | $CH_2C(CH_3)_3$ |
| 26.477 | H | H | $SO_2$ | $CH_2CH(CH_3)CH_2CH_3$ |
| 26.478 | H | H | $SO_2$ | $CH(CH_3)CH_2CH_2CH_3$ |
| 26.479 | H | H | $SO_2$ | $C(CH_3)_2CH_2CH_3$ |
| 26.480 | H | H | $SO_2$ | $CH_2CH=CH_2$ |
| 26.481 | H | H | $SO_2$ | $CH_2CH=CHCH_3$ |
| 26.482 | H | H | $SO_2$ | $CH_2CH=C(CH_3)_2$ |
| 26.483 | H | H | $SO_2$ | $CH_2C(CH_3)=CH_2$ |
| 26.484 | H | H | $SO_2$ | $CH_2C(CH_3)=CHCH_3$ |
| 26.485 | H | H | $SO_2$ | $CH_2C(CH_3)=C(CH_3)_2$ |
| 26.486 | H | H | $SO_2$ | $CH(CH_3)CH=CH_2$ |
| 26.487 | H | H | $SO_2$ | $CH(CH_3)CH=CHCH_3$ |
| 26.488 | H | H | $SO_2$ | $CH(CH_3)CH=C(CH_3)_2$ |
| 26.489 | H | H | $SO_2$ | $C(CH_3)_2CH=CH_2$ |
| 26.490 | H | H | $SO_2$ | $C(CH_3)_2CH=CHCH_3$ |
| 26.491 | H | H | $SO_2$ | $C(CH_3)_2CH=C(CH_3)_2$ |
| 26.492 | H | H | $SO_2$ | $CH_2CH=CHCl$ |
| 26.493 | H | H | $SO_2$ | $CH_2CH=CCl_2$ |
| 26.494 | H | H | $SO_2$ | $CH_2CCl=CHCl$ |

TABLE 26-continued

This table contains 618 compounds of the following type,

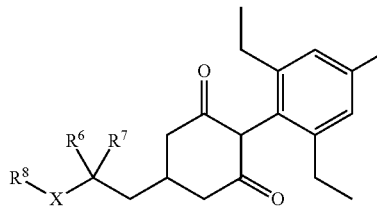

where X, $R^6$, $R^7$ and $R^8$ are as defined below:

| Compound number | $R^6$ | $R^7$ | X | $R^8$ |
|---|---|---|---|---|
| 26.495 | H | H | $SO_2$ | $CH_2CCl=CCl_2$ |
| 26.496 | H | H | $SO_2$ | $CH_2CH=CF_2$ |
| 26.497 | H | H | $SO_2$ | $CH_2CF=CF_2$ |
| 26.498 | H | H | $SO_2$ | $CH_2C\bullet CH$ |
| 26.499 | H | H | $SO_2$ | $CH_2C\bullet CCH_3$ |
| 26.500 | H | H | $SO_2$ | $CH_2C\bullet CCH_2CH_3$ |
| 26.501 | H | H | $SO_2$ | $CH(CH_3)C\bullet CH$ |
| 26.502 | H | H | $SO_2$ | $CH(CH_3)C\bullet CCH_3$ |
| 26.503 | H | H | $SO_2$ | $CH(CH_3)C\bullet CCH_2CH_3$ |
| 26.504 | H | H | $SO_2$ | $C(CH_3)_2C\bullet CH$ |
| 26.505 | H | H | $SO_2$ | $C(CH_3)_2C\bullet CCH_3$ |
| 26.506 | H | H | $SO_2$ | $C(CH_3)_2C\bullet CCH_2CH_3$ |
| 26.507 | H | H | $SO_2$ | Cyclopropyl |
| 26.508 | H | H | $SO_2$ | Cyclobutyl |
| 26.509 | H | H | $SO_2$ | Cyclopentyl |
| 26.510 | H | H | $SO_2$ | Cyclohexyl |
| 26.511 | H | H | $SO_2$ | $CH_2CF_3$ |
| 26.512 | H | H | $SO_2$ | $CH_2CH_2CF_3$ |
| 26.513 | H | H | $SO_2$ | $CH_2$-cyclopropyl |
| 26.514 | H | H | $SO_2$ | $CH_2$-cyclobutyl |
| 26.515 | H | H | $SO_2$ | $CH_2$-cyclopentyl |
| 26.516 | H | H | $SO_2$ | $CH_2$-cyclohexyl |
| 26.517 | $CH_3$ | H | $SO_2$ | $CH_3$ |
| 26.518 | $CH_3$ | H | $SO_2$ | $CH_2CH_3$ |
| 26.519 | $CH_3$ | H | $SO_2$ | $CH_2CH_2CH_3$ |
| 26.520 | $CH_3$ | H | $SO_2$ | $CH(CH_3)_2$ |
| 26.521 | $CH_3$ | H | $SO_2$ | $CH_2CH_2CH_2CH_3$ |
| 26.522 | $CH_3$ | H | $SO_2$ | $CH_2CH(CH_3)_2$ |
| 26.523 | $CH_3$ | H | $SO_2$ | $CH(CH_3)CH_2CH_3$ |
| 26.524 | $CH_3$ | H | $SO_2$ | $C(CH_3)_3$ |
| 26.525 | $CH_3$ | H | $SO_2$ | $CH_2CH_2CH_2CH_2CH_3$ |
| 26.526 | $CH_3$ | H | $SO_2$ | $CH_2CH_2CH(CH_3)_2$ |
| 26.527 | $CH_3$ | H | $SO_2$ | $CH_2C(CH_3)_3$ |
| 26.528 | $CH_3$ | H | $SO_2$ | $CH_2CH(CH_3)CH_2CH_3$ |
| 26.529 | $CH_3$ | H | $SO_2$ | $CH(CH_3)CH_2CH_2CH_3$ |
| 26.530 | $CH_3$ | H | $SO_2$ | $C(CH_3)_2CH_2CH_3$ |
| 26.531 | $CH_3$ | H | $SO_2$ | $CH_2CH=CH_2$ |
| 26.532 | $CH_3$ | H | $SO_2$ | $CH_2CH=CHCH_3$ |
| 26.533 | $CH_3$ | H | $SO_2$ | $CH_2CH=C(CH_3)_2$ |
| 26.534 | $CH_3$ | H | $SO_2$ | $CH_2C(CH_3)=CH_2$ |
| 26.535 | $CH_3$ | H | $SO_2$ | $CH_2C(CH_3)=CHCH_3$ |
| 26.536 | $CH_3$ | H | $SO_2$ | $CH_2C(CH_3)=C(CH_3)_2$ |
| 26.537 | $CH_3$ | H | $SO_2$ | $CH(CH_3)CH=CH_2$ |
| 26.538 | $CH_3$ | H | $SO_2$ | $CH(CH_3)CH=CHCH_3$ |
| 26.539 | $CH_3$ | H | $SO_2$ | $CH(CH_3)CH=C(CH_3)_2$ |
| 26.540 | $CH_3$ | H | $SO_2$ | $C(CH_3)_2CH=CH_2$ |
| 26.541 | $CH_3$ | H | $SO_2$ | $C(CH_3)_2CH=CHCH_3$ |
| 26.542 | $CH_3$ | H | $SO_2$ | $C(CH_3)_2CH=C(CH_3)_2$ |
| 26.543 | $CH_3$ | H | $SO_2$ | $CH_2CH=CHCl$ |
| 26.544 | $CH_3$ | H | $SO_2$ | $CH_2CH=CCl_2$ |
| 26.545 | $CH_3$ | H | $SO_2$ | $CH_2CCl=CHCl$ |
| 26.546 | $CH_3$ | H | $SO_2$ | $CH_2CCl=CCl_2$ |
| 26.547 | $CH_3$ | H | $SO_2$ | $CH_2CH=CF_2$ |
| 26.548 | $CH_3$ | H | $SO_2$ | $CH_2CF=CF_2$ |
| 26.549 | $CH_3$ | H | $SO_2$ | $CH_2C\bullet CH$ |
| 26.550 | $CH_3$ | H | $SO_2$ | $CH_2C\bullet CCH_3$ |
| 26.551 | $CH_3$ | H | $SO_2$ | $CH_2C\bullet CCH_2CH_3$ |
| 26.552 | $CH_3$ | H | $SO_2$ | $CH(CH_3)C\bullet CH$ |
| 26.553 | $CH_3$ | H | $SO_2$ | $CH(CH_3)C\bullet CCH_3$ |
| 26.554 | $CH_3$ | H | $SO_2$ | $CH(CH_3)C\bullet CCH_2CH_3$ |
| 26.555 | $CH_3$ | H | $SO_2$ | $C(CH_3)_2C\bullet CH$ |
| 26.556 | $CH_3$ | H | $SO_2$ | $C(CH_3)_2C\bullet CCH_3$ |
| 26.557 | $CH_3$ | H | $SO_2$ | $C(CH_3)_2C\bullet CCH_2CH_3$ |

TABLE 26-continued

This table contains 618 compounds of the following type,

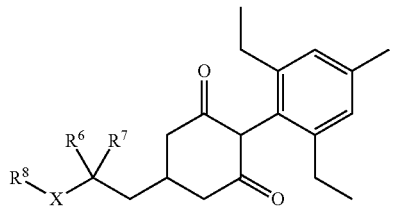

where X, $R^6$, $R^7$ and $R^8$ are as defined below:

| Compound number | $R^6$ | $R^7$ | X | $R^8$ |
|---|---|---|---|---|
| 26.558 | $CH_3$ | H | $SO_2$ | Cyclopropyl |
| 26.559 | $CH_3$ | H | $SO_2$ | Cyclobutyl |
| 26.560 | $CH_3$ | H | $SO_2$ | Cyclopentyl |
| 26.561 | $CH_3$ | H | $SO_2$ | Cyclohexyl |
| 26.562 | $CH_3$ | H | $SO_2$ | $CH_2CF_3$ |
| 26.563 | $CH_3$ | H | $SO_2$ | $CH_2CH_2CF_3$ |
| 26.564 | $CH_3$ | H | $SO_2$ | $CH_2$-cyclopropyl |
| 26.565 | $CH_3$ | H | $SO_2$ | $CH_2$-cyclobutyl |
| 26.566 | $CH_3$ | H | $SO_2$ | $CH_2$-cyclopentyl |
| 26.567 | $CH_3$ | H | $SO_2$ | $CH_2$-cyclohexyl |
| 26.568 | $CH_3$ | $CH_3$ | $SO_2$ | $CH_3$ |
| 26.569 | $CH_3$ | $CH_3$ | $SO_2$ | $CH_2CH_3$ |
| 26.570 | $CH_3$ | $CH_3$ | $SO_2$ | $CH_2CH_2CH_3$ |
| 26.571 | $CH_3$ | $CH_3$ | $SO_2$ | $CH(CH_3)_2$ |
| 26.572 | $CH_3$ | $CH_3$ | $SO_2$ | $CH_2CH_2CH_2CH_3$ |
| 26.573 | $CH_3$ | $CH_3$ | $SO_2$ | $CH_2CH(CH_3)_2$ |
| 26.574 | $CH_3$ | $CH_3$ | $SO_2$ | $CH(CH_3)CH_2CH_3$ |
| 26.575 | $CH_3$ | $CH_3$ | $SO_2$ | $C(CH_3)_3$ |
| 26.576 | $CH_3$ | $CH_3$ | $SO_2$ | $CH_2CH_2CH_2CH_2CH_3$ |
| 26.577 | $CH_3$ | $CH_3$ | $SO_2$ | $CH_2CH_2CH(CH_3)_2$ |
| 26.578 | $CH_3$ | $CH_3$ | $SO_2$ | $CH_2C(CH_3)_3$ |
| 26.579 | $CH_3$ | $CH_3$ | $SO_2$ | $CH_2CH(CH_3)CH_2CH_3$ |
| 26.580 | $CH_3$ | $CH_3$ | $SO_2$ | $CH(CH_3)CH_2CH_2CH_3$ |
| 26.581 | $CH_3$ | $CH_3$ | $SO_2$ | $C(CH_3)_2CH_2CH_3$ |
| 26.582 | $CH_3$ | $CH_3$ | $SO_2$ | $CH_2CH=CH_2$ |
| 26.583 | $CH_3$ | $CH_3$ | $SO_2$ | $CH_2CH=CHCH_3$ |
| 26.584 | $CH_3$ | $CH_3$ | $SO_2$ | $CH_2CH=C(CH_3)_2$ |
| 26.585 | $CH_3$ | $CH_3$ | $SO_2$ | $CH_2C(CH_3)=CH_2$ |
| 26.586 | $CH_3$ | $CH_3$ | $SO_2$ | $CH_2C(CH_3)=CHCH_3$ |
| 26.587 | $CH_3$ | $CH_3$ | $SO_2$ | $CH_2C(CH_3)=C(CH_3)_2$ |
| 26.588 | $CH_3$ | $CH_3$ | $SO_2$ | $CH(CH_3)CH=CH_2$ |
| 26.589 | $CH_3$ | $CH_3$ | $SO_2$ | $CH(CH_3)CH=CHCH_3$ |
| 26.590 | $CH_3$ | $CH_3$ | $SO_2$ | $CH(CH_3)CH=C(CH_3)_2$ |
| 26.591 | $CH_3$ | $CH_3$ | $SO_2$ | $C(CH_3)_2CH=CH_2$ |
| 26.592 | $CH_3$ | $CH_3$ | $SO_2$ | $C(CH_3)_2CH=CHCH_3$ |
| 26.593 | $CH_3$ | $CH_3$ | $SO_2$ | $C(CH_3)_2CH=C(CH_3)_2$ |
| 26.594 | $CH_3$ | $CH_3$ | $SO_2$ | $CH_2CH=CHCl$ |
| 26.595 | $CH_3$ | $CH_3$ | $SO_2$ | $CH_2CH=CCl_2$ |
| 26.596 | $CH_3$ | $CH_3$ | $SO_2$ | $CH_2CCl=CHCl$ |
| 26.597 | $CH_3$ | $CH_3$ | $SO_2$ | $CH_2CCl=CCl_2$ |
| 26.598 | $CH_3$ | $CH_3$ | $SO_2$ | $CH_2CH=CF_2$ |
| 26.599 | $CH_3$ | $CH_3$ | $SO_2$ | $CH_2CF=CF_2$ |
| 26.600 | $CH_3$ | $CH_3$ | $SO_2$ | $CH_2C\bullet CH$ |
| 26.601 | $CH_3$ | $CH_3$ | $SO_2$ | $CH_2C\bullet CCH_3$ |
| 26.602 | $CH_3$ | $CH_3$ | $SO_2$ | $CH_2C\bullet CCH_2CH_3$ |
| 26.603 | $CH_3$ | $CH_3$ | $SO_2$ | $CH(CH_3)C\bullet CH$ |
| 26.604 | $CH_3$ | $CH_3$ | $SO_2$ | $CH(CH_3)C\bullet CCH_3$ |
| 26.605 | $CH_3$ | $CH_3$ | $SO_2$ | $CH(CH_3)C\bullet CCH_2CH_3$ |
| 26.606 | $CH_3$ | $CH_3$ | $SO_2$ | $C(CH_3)_2C\bullet CH$ |
| 26.607 | $CH_3$ | $CH_3$ | $SO_2$ | $C(CH_3)_2C\bullet CCH_3$ |
| 26.608 | $CH_3$ | $CH_3$ | $SO_2$ | $C(CH_3)_2C\bullet CCH_2CH_3$ |
| 26.609 | $CH_3$ | $CH_3$ | $SO_2$ | Cyclopropyl |
| 26.610 | $CH_3$ | $CH_3$ | $SO_2$ | Cyclobutyl |
| 26.611 | $CH_3$ | $CH_3$ | $SO_2$ | Cyclopentyl |
| 26.612 | $CH_3$ | $CH_3$ | $SO_2$ | Cyclohexyl |
| 26.613 | $CH_3$ | $CH_3$ | $SO_2$ | $CH_2CF_3$ |
| 26.614 | $CH_3$ | $CH_3$ | $SO_2$ | $CH_2CH_2CF_3$ |
| 26.615 | $CH_3$ | $CH_3$ | $SO_2$ | $CH_2$-cyclopropyl |
| 26.616 | $CH_3$ | $CH_3$ | $SO_2$ | $CH_2$-cyclobutyl |
| 26.617 | $CH_3$ | $CH_3$ | $SO_2$ | $CH_2$-cyclopentyl |
| 26.618 | $CH_3$ | $CH_3$ | $SO_2$ | $CH_2$-cyclohexyl |

TABLE 27

This table contains 618 compounds of the following type,

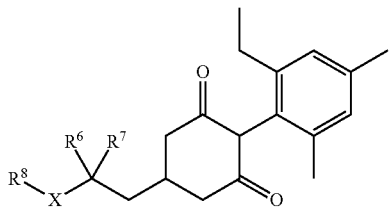

where X, $R^6$, $R^7$ and $R^8$ are as defined in Table 26.

TABLE 28

This table contains 618 compounds of the following type,

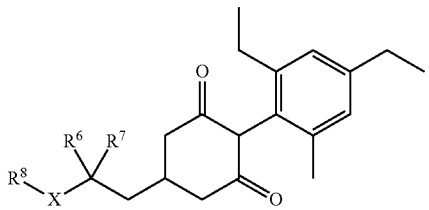

where X, $R^6$, $R^7$ and $R^8$ are as defined in Table 26.

TABLE 29

This table contains 618 compounds of the following type,

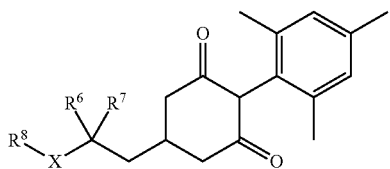

where X, $R^6$, $R^7$ and $R^8$ are as defined in Table 26.

TABLE 30

This table contains 618 compounds of the following type,

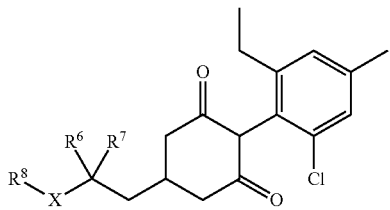

where X, $R^6$, $R^7$ and $R^8$ are as defined in Table 26.

TABLE 31

This table contains 618 compounds of the following type,

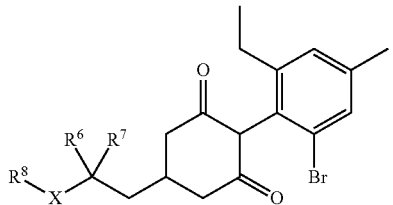

where X, $R^6$, $R^7$ and $R^8$ are as defined in Table 26.

TABLE 32

This table contains 618 compounds of the following type,

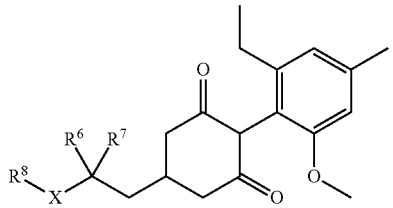

where X, $R^6$, $R^7$ and $R^8$ are as defined in Table 26.

TABLE 33

This table contains 618 compounds of the following type,

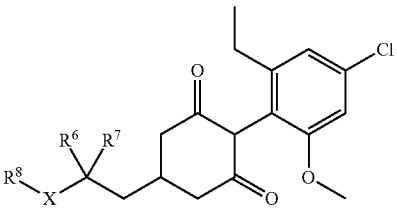

where X, $R^6$, $R^7$ and $R^8$ are as defined in Table 26.

TABLE 34

This table contains 618 compounds of the following type,

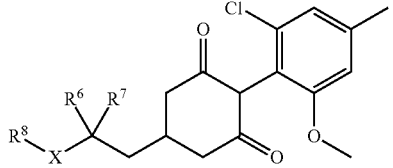

where X, $R^6$, $R^7$ and $R^8$ are as defined in Table 26.

TABLE 35

This table contains 618 compounds of the following type,

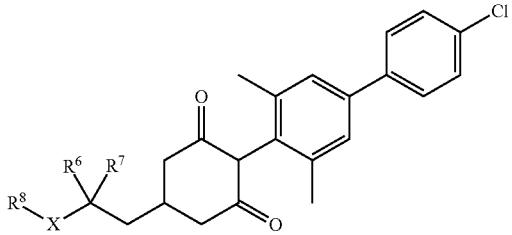

where X, $R^6$, $R^7$ and $R^8$ are as defined in Table 26.

TABLE 36

This table contains 618 compounds of the following type,

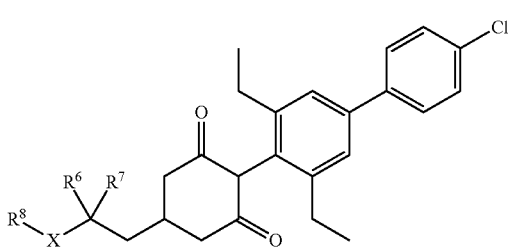

where X, $R^6$, $R^7$ and $R^8$ are as defined in Table 26.

TABLE 37

This table contains 618 compounds of the following type,

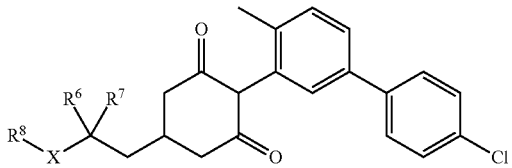

where X, $R^6$, $R^7$ and $R^8$ are as defined in Table 26.

TABLE 38

This table contains 618 compounds of the following type,

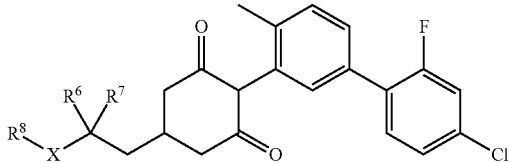

where X, $R^6$, $R^7$ and $R^8$ are as defined in Table 26.

TABLE 39

This table contains 618 compounds of the following type,

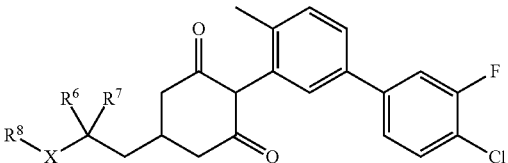

where X, $R^6$, $R^7$ and $R^8$ are as defined in Table 26.

TABLE 40

This table contains 618 compounds of the following type,

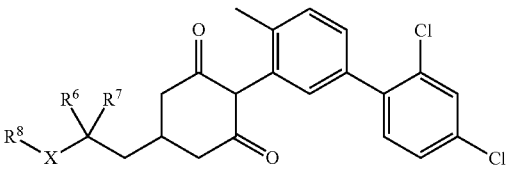

where X, $R^6$, $R^7$ and $R^8$ are as defined in Table 26.

TABLE 41

This table contains 618 compounds of the following type,

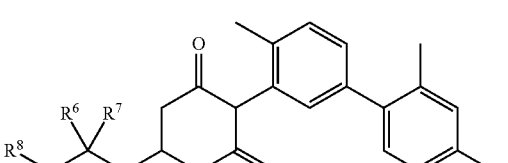

where X, $R^6$, $R^7$ and $R^8$ are as defined in Table 26.

TABLE 42

This table contains 618 compounds of the following type,

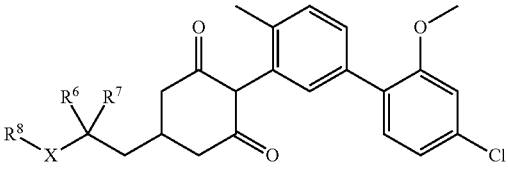

where X, $R^6$, $R^7$ and $R^8$ are as defined in Table 26.

TABLE 43

This table contains 618 compounds of the following type,

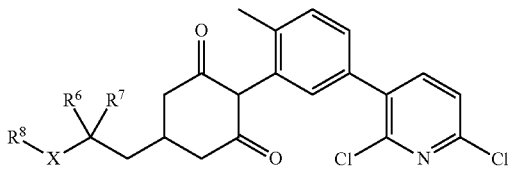

where X, $R^6$, $R^7$ and $R^8$ are as defined in Table 26.

TABLE 44

This table contains 618 compounds of the following type,

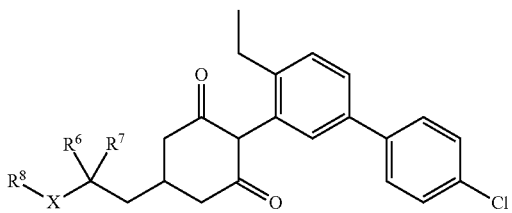

where X, $R^6$, $R^7$ and $R^8$ are as defined in Table 26.

TABLE 45

This table contains 618 compounds of the following type,

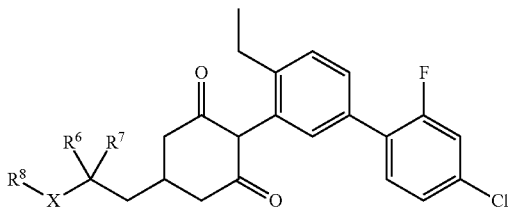

where X, $R^6$, $R^7$ and $R^8$ are as defined in Table 26.

TABLE 46

This table contains 618 compounds of the following type,

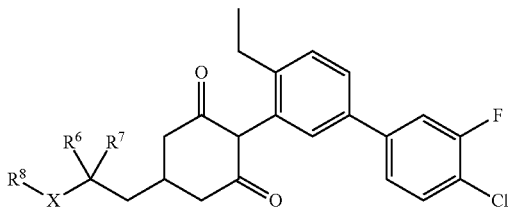

where X, $R^6$, $R^7$ and $R^8$ are as defined in Table 26.

TABLE 47

This table contains 618 compounds of the following type,

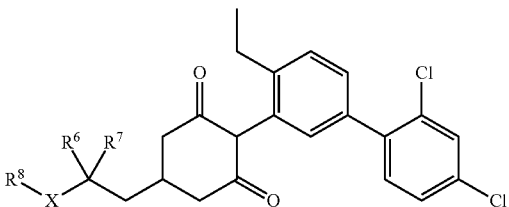

where X, $R^6$, $R^7$ and $R^8$ are as defined in Table 26.

TABLE 48

This table contains 618 compounds of the following type,

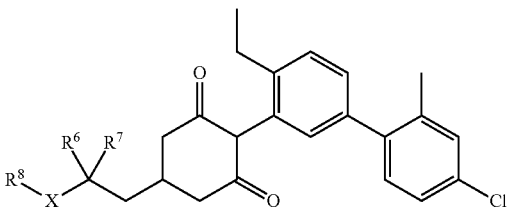

where X, $R^6$, $R^7$ and $R^8$ are as defined in Table 26.

TABLE 49

This table contains 618 compounds of the following type,

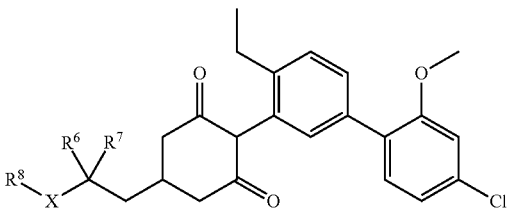

where X, $R^6$, $R^7$ and $R^8$ are as defined in Table 26.

TABLE 50

This table contains 618 compounds of the following type,

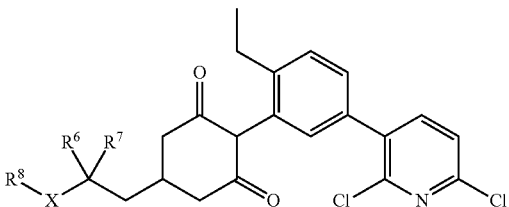

where X, $R^6$, $R^7$ and $R^8$ are as defined in Table 26.

TABLE 51

This table contains 220 compounds of the following type,

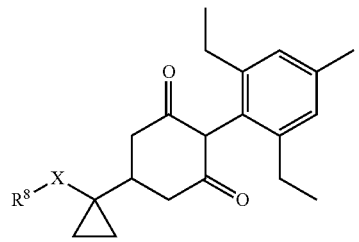

where X and R⁴ are as defined below:

| Compound number | X | R⁸ |
|---|---|---|
| 51.1 | O | $CH_3$ |
| 51.2 | O | $CH_2CH_3$ |
| 51.3 | O | $CH_2CH_2CH_3$ |
| 51.4 | O | $CH(CH_3)_2$ |
| 51.5 | O | $CH_2CH_2CH_2CH_3$ |
| 51.6 | O | $CH_2CH(CH_3)_2$ |
| 51.7 | O | $CH(CH_3)CH_2CH_3$ |
| 51.8 | O | $C(CH_3)_3$ |
| 51.9 | O | $CH_2CH_2CH_2CH_2CH_3$ |
| 51.10 | O | $CH_2CH_2CH(CH_3)_2$ |
| 51.11 | O | $CH_2C(CH_3)_3$ |
| 51.12 | O | $CH_2CH(CH_3)CH_2CH_3$ |
| 51.13 | O | $CH(CH_3)CH_2CH_2CH_3$ |
| 51.14 | O | $C(CH_3)_2CH_2CH_3$ |
| 51.15 | O | $CH_2CH=CH_2$ |
| 51.16 | O | $CH_2CH=CHCH_3$ |
| 51.17 | O | $CH_2CH=C(CH_3)_2$ |
| 51.18 | O | $CH_2C(CH_3)=CH_2$ |
| 51.19 | O | $CH_2C(CH_3)=CHCH_3$ |
| 51.20 | O | $CH_2C(CH_3)=C(CH_3)_2$ |
| 51.21 | O | $CH(CH_3)CH=CH_2$ |
| 51.22 | O | $CH(CH_3)CH=CHCH_3$ |
| 51.23 | O | $CH(CH_3)CH=C(CH_3)_2$ |
| 51.24 | O | $C(CH_3)_2CH=CH_2$ |
| 51.25 | O | $C(CH_3)_2CH=CHCH_3$ |
| 51.26 | O | $C(CH_3)_2CH=C(CH_3)_2$ |
| 51.27 | O | $CH_2CH=CHCl$ |
| 51.28 | O | $CH_2CH=CCl_2$ |
| 51.29 | O | $CH_2CCl=CHCl$ |
| 51.30 | O | $CH_2CCl=CCl_2$ |
| 51.31 | O | $CH_2CH=CF_2$ |
| 51.32 | O | $CH_2CF=CF_2$ |
| 51.33 | O | $CH_2C•CCH_3$ |
| 51.34 | O | $CH_2C•CCH_2CH_3$ |
| 51.35 | O | $CH_2C•CCH_2CH_3$ |
| 51.36 | O | $CH(CH_3)C•CH$ |
| 51.37 | O | $CH(CH_3)C•CCH_3$ |
| 51.38 | O | $CH(CH_3)C•CCH_2CH_3$ |
| 51.39 | O | $C(CH_3)_2C•CH$ |
| 51.40 | O | $C(CH_3)_2C•CCH_3$ |
| 51.41 | O | $C(CH_3)_2C•CCH_2CH_3$ |
| 51.42 | O | Cyclopropyl |
| 51.43 | O | Cyclobutyl |
| 51.44 | O | Cyclopentyl |
| 51.45 | O | Cyclohexyl |
| 51.46 | O | $CH_2CF_3$ |
| 51.47 | O | $CH_2CH_2CF_3$ |
| 51.48 | O | $CH_2$-cyclopropyl |
| 51.49 | O | $CH_2$-cyclobutyl |
| 51.50 | O | $CH_2$-cyclopentyl |
| 51.51 | O | $CH_2$-cyclohexyl |
| 51.52 | O | $CH_2OCH_3$ |
| 51.53 | O | $CH_2OCH_2CH_3$ |
| 51.54 | O | $CH_2CH_2OCH_3$ |
| 51.55 | O | $CH_2CH_2OCH_2CH_3$ |
| 51.56 | S | $CH_3$ |
| 51.57 | S | $CH_2CH_3$ |
| 51.58 | S | $CH_2CH_2CH_3$ |
| 51.59 | S | $CH(CH_3)_2$ |
| 51.60 | S | $CH_2CH_2CH_2CH_3$ |
| 51.61 | S | $CH_2CH(CH_3)_2$ |
| 51.62 | S | $CH(CH_3)CH_2CH_3$ |
| 51.63 | S | $C(CH_3)_3$ |
| 51.64 | S | $CH_2CH_2CH_2CH_2CH_3$ |
| 51.65 | S | $CH_2CH_2CH(CH_3)_2$ |
| 51.66 | S | $CH_2C(CH_3)_3$ |
| 51.67 | S | $CH_2CH(CH_3)CH_2CH_3$ |
| 51.68 | S | $CH(CH_3)CH_2CH_2CH_3$ |
| 51.69 | S | $C(CH_3)_2CH_2CH_3$ |
| 51.70 | S | $CH_2CH=CH_2$ |
| 51.71 | S | $CH_2CH=CHCH_3$ |
| 51.72 | S | $CH_2CH=C(CH_3)_2$ |
| 51.73 | S | $CH_2C(CH_3)=CH_2$ |
| 51.74 | S | $CH_2C(CH_3)=CHCH_3$ |
| 51.75 | S | $CH_2C(CH_3)=C(CH_3)_2$ |
| 51.76 | S | $CH(CH_3)CH=CH_2$ |
| 51.77 | S | $CH(CH_3)CH=CHCH_3$ |
| 51.78 | S | $CH(CH_3)CH=C(CH_3)_2$ |
| 51.79 | S | $C(CH_3)_2CH=CH_2$ |
| 51.80 | S | $C(CH_3)_2CH=CHCH_3$ |
| 51.81 | S | $C(CH_3)_2CH=C(CH_3)_2$ |
| 51.82 | S | $CH_2CH=CHCl$ |
| 51.83 | S | $CH_2CH=CCl_2$ |
| 51.84 | S | $CH_2CCl=CHCl$ |
| 51.85 | S | $CH_2CCl=CCl_2$ |
| 51.86 | S | $CH_2CH=CF_2$ |
| 51.87 | S | $CH_2CF=CF_2$ |
| 51.88 | S | $CH_2C•CH$ |
| 51.89 | S | $CH_2C•CCH_3$ |
| 51.90 | S | $CH_2C•CCH_2CH_3$ |
| 51.91 | S | $CH(CH_3)C•CH$ |
| 51.92 | S | $CH(CH_3)C•CCH_3$ |
| 51.93 | S | $CH(CH_3)C•CCH_2CH_3$ |
| 51.94 | S | $C(CH_3)_2C•CH$ |
| 51.95 | S | $C(CH_3)_2C•CCH_3$ |
| 51.96 | S | $C(CH_3)_2C•CCH_2CH_3$ |
| 51.97 | S | Cyclopropyl |
| 51.98 | S | Cyclobutyl |
| 51.99 | S | Cyclopentyl |
| 51.100 | S | Cyclohexyl |
| 51.101 | S | $CH_2CF_3$ |
| 51.102 | S | $CH_2CH_2CF_3$ |
| 51.103 | S | $CH_2$-cyclopropyl |
| 51.104 | S | $CH_2$-cyclobutyl |
| 51.105 | S | $CH_2$-cyclopentyl |
| 51.106 | S | $CH_2$-cyclohexyl |
| 51.107 | S | $CH_2OCH_3$ |
| 51.108 | S | $CH_2OCH_2CH_3$ |
| 51.109 | S | $CH_2CH_2OCH_3$ |
| 51.110 | S | $CH_2CH_2OCH_2CH_3$ |
| 51.111 | S(O) | $CH_3$ |
| 51.112 | S(O) | $CH_2CH_3$ |
| 51.113 | S(O) | $CH_2CH_2CH_3$ |
| 51.114 | S(O) | $CH(CH_3)_2$ |
| 51.115 | S(O) | $CH_2CH_2CH_2CH_3$ |
| 51.116 | S(O) | $CH_2CH(CH_3)_2$ |
| 51.117 | S(O) | $CH(CH_3)CH_2CH_3$ |
| 51.118 | S(O) | $C(CH_3)_3$ |
| 51.119 | S(O) | $CH_2CH_2CH_2CH_2CH_3$ |
| 51.120 | S(O) | $CH_2CH_2CH(CH_3)_2$ |
| 51.121 | S(O) | $CH_2C(CH_3)_3$ |
| 51.122 | S(O) | $CH_2CH(CH_3)CH_2CH_3$ |
| 51.123 | S(O) | $CH(CH_3)CH_2CH_2CH_3$ |
| 51.124 | S(O) | $C(CH_3)_2CH_2CH_3$ |

TABLE 51-continued

This table contains 220 compounds of the following type,

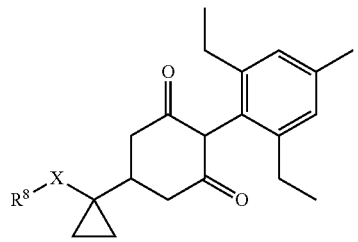

where X and R⁴ are as defined below:

| Compound number | X | R⁸ |
|---|---|---|
| 51.125 | S(O) | $CH_2CH=CH_2$ |
| 51.126 | S(O) | $CH_2CH=CHCH_3$ |
| 51.127 | S(O) | $CH_2CH=C(CH_3)_2$ |
| 51.128 | S(O) | $CH_2C(CH_3)=CH_2$ |
| 51.129 | S(O) | $CH_2C(CH_3)=CHCH_3$ |
| 51.130 | S(O) | $CH_2C(CH_3)=C(CH_3)_2$ |
| 51.131 | S(O) | $CH(CH_3)CH=CH_2$ |
| 51.132 | S(O) | $CH(CH_3)CH=CHCH_3$ |
| 51.133 | S(O) | $CH(CH_3)CH=C(CH_3)_2$ |
| 51.134 | S(O) | $C(CH_3)_2CH=CH_2$ |
| 51.135 | S(O) | $C(CH_3)_2CH=CHCH_3$ |
| 51.136 | S(O) | $C(CH_3)_2CH=C(CH_3)_2$ |
| 51.137 | S(O) | $CH_2CH=CHCl$ |
| 51.138 | S(O) | $CH_2CH=CCl_2$ |
| 51.139 | S(O) | $CH_2CCl=CHCl$ |
| 51.140 | S(O) | $CH_2CCl=CCl_2$ |
| 51.141 | S(O) | $CH_2CH=CF_2$ |
| 51.142 | S(O) | $CH_2CF=CF_2$ |
| 51.143 | S(O) | $CH_2C\bullet CH$ |
| 51.144 | S(O) | $CH_2C\bullet CCH_3$ |
| 51.145 | S(O) | $CH_2C\bullet CCH_2CH_3$ |
| 51.146 | S(O) | $CH(CH_3)C\bullet CH$ |
| 51.147 | S(O) | $CH(CH_3)C\bullet CCH_3$ |
| 51.148 | S(O) | $CH(CH_3)C\bullet CCH_2CH_3$ |
| 51.149 | S(O) | $C(CH_3)_2C\bullet CH$ |
| 51.150 | S(O) | $C(CH_3)_2C\bullet CCH_3$ |
| 51.151 | S(O) | $C(CH_3)_2C\bullet CCH_2CH_3$ |
| 51.152 | S(O) | Cyclopropyl |
| 51.153 | S(O) | Cyclobutyl |
| 51.154 | S(O) | Cyclopentyl |
| 51.155 | S(O) | Cyclohexyl |
| 51.156 | S(O) | $CHCF_3$ |
| 51.157 | S(O) | $CH_2CH_2CF_3$ |
| 51.158 | S(O) | $CH_2$-cyclopropyl |
| 51.159 | S(O) | $CH_2$-cyclobutyl |
| 51.160 | S(O) | $CH_2$-cyclopentyl |
| 51.161 | S(O) | $CH_2$-cyclohexyl |
| 51.162 | S(O) | $CH_2OCH_3$ |
| 51.163 | S(O) | $CH_2OCH_2CH_3$ |
| 51.164 | S(O) | $CH_2CH_2OCH_3$ |
| 51.165 | S(O) | $CH_2CH_2OCH_2CH_3$ |
| 51.166 | $SO_2$ | $CH_3$ |
| 51.167 | $SO_2$ | $CH_2CH_3$ |
| 51.168 | $SO_2$ | $CH_2CH_2CH_3$ |
| 51.169 | $SO_2$ | $CH(CH_3)_2$ |
| 51.170 | $SO_2$ | $CH_2CH_2CH_2CH_3$ |
| 51.171 | $SO_2$ | $CH_2CH(CH_3)_2$ |
| 51.172 | $SO_2$ | $CH(CH_3)CH_2CH_3$ |
| 51.173 | $SO_2$ | $C(CH_3)_3$ |
| 51.174 | $SO_2$ | $CH_2CH_2CH_2CH_2CH_3$ |
| 51.175 | $SO_2$ | $CH_2CH_2CH(CH_3)_2$ |
| 51.176 | $SO_2$ | $CH_2C(CH_3)_3$ |
| 51.177 | $SO_2$ | $CH_2CH(CH_3)CH_2CH_3$ |
| 51.178 | $SO_2$ | $CH(CH_3)CH_2CH_2CH_3$ |
| 51.179 | $SO_2$ | $C(CH_3)_2CH_2CH_3$ |
| 51.180 | $SO_2$ | $CH_2CH=CH_2$ |
| 51.181 | $SO_2$ | $CH_2CH=CHCH_3$ |
| 51.182 | $SO_2$ | $CH_2CH=C(CH_3)_2$ |
| 51.183 | $SO_2$ | $CH_2C(CH_3)=CH_2$ |
| 51.184 | $SO_2$ | $CH_2C(CH_3)=CHCH_3$ |
| 51.185 | $SO_2$ | $CH_2C(CH_3)=C(CH_3)_2$ |
| 51.186 | $SO_2$ | $CH(CH_3)CH=CH_2$ |
| 51.187 | $SO_2$ | $CH(CH_3)CH=CHCH_3$ |
| 51.188 | $SO_2$ | $CH(CH_3)CH=C(CH_3)_2$ |
| 51.189 | $SO_2$ | $C(CH_3)_2CH=CH_2$ |
| 51.190 | $SO_2$ | $C(CH_3)_2CH=CHCH_3$ |
| 51.191 | $SO_2$ | $C(CH_3)_2CHC(CH_3)_2$ |
| 51.192 | $SO_2$ | $CH_2CH=CHCl$ |
| 51.193 | $SO_2$ | $CH_2CH=CCl_2$ |
| 51.194 | $SO_2$ | $CH_2CCl=CHCl$ |
| 51.195 | $SO_2$ | $CH_2CCl=CCl_2$ |
| 51.196 | $SO_2$ | $CH_2CH=CF_2$ |
| 51.197 | $SO_2$ | $CH_2CF=CF_2$ |
| 51.198 | $SO_2$ | $CH_2C\bullet CH$ |
| 51.199 | $SO_2$ | $CH_2C\bullet CCH_3$ |
| 51.200 | $SO_2$ | $CH_2C\bullet CCH_2CH_3$ |
| 51.201 | $SO_2$ | $CH(CH_3)C\bullet CH$ |
| 51.202 | $SO_2$ | $CH(CH_3)C\bullet CCH_3$ |
| 51.203 | $SO_2$ | $CH(CH_3)C\bullet CCH_2CH_3$ |
| 51.204 | $SO_2$ | $C(CH_3)_2C\bullet CH$ |
| 51.205 | $SO_2$ | $C(CH_3)_2C\bullet CCH_3$ |
| 51.206 | $SO_2$ | $C(CH_3)_2C\bullet CCH_2CH_3$ |
| 51.207 | $SO_2$ | Cyclopropyl |
| 51.208 | $SO_2$ | Cyclobutyl |
| 51.209 | $SO_2$ | Cyclopentyl |
| 51.210 | $SO_2$ | Cyclohexyl |
| 51.211 | $SO_2$ | $CH_2CF_3$ |
| 51.212 | $SO_2$ | $CH_2CH_2CF_3$ |
| 51.213 | $SO_2$ | $CH_2$-cyclopropyl |
| 51.214 | $SO_2$ | $CH_2$-cyclobutyl |
| 51.215 | $SO_2$ | $CH_2$-cyclopentyl |
| 51.216 | $SO_2$ | $CH_2$-cyclohexyl |
| 51.217 | $SO_2$ | $CH_2OCH_3$ |
| 51.218 | $SO_2$ | $CH_2OCH_2CH_3$ |
| 51.219 | $SO_2$ | $CH_2CH_2OCH_3$ |
| 51.220 | $SO_2$ | $CH_2CH_2OCH_2CH_3$ |

TABLE 52

This table contains 220 compounds of the following type,

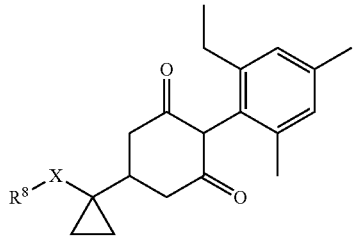

where X and R⁸ are as defined in Table 51.

TABLE 53

This table contains 220 compounds of the following type,

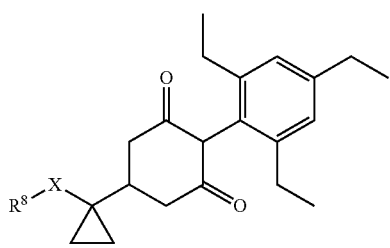

where X and R⁸ are as defined in Table 51.

TABLE 54

This table contains 220 compounds of the following type,

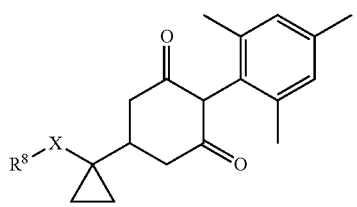

where X and R⁸ are as defined in Table 51.

TABLE 55

This table contains 220 compounds of the following type,

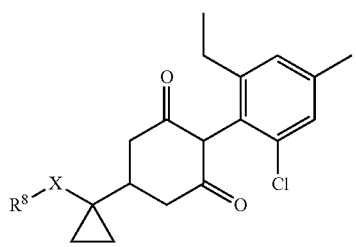

where X and R⁸ are as defined in Table 51.

TABLE 56

This table contains 220 compounds of the following type,

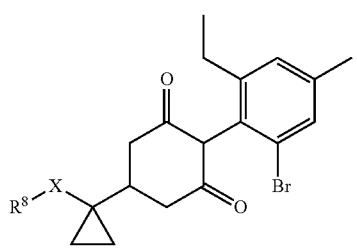

where X and R⁸ are as defined in Table 51.

TABLE 57

This table contains 220 compounds of the following type,

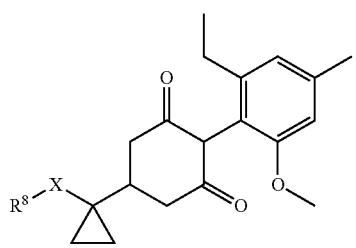

where X and R⁸ are as defined in Table 51.

TABLE 58

This table contains 220 compounds of the following type,

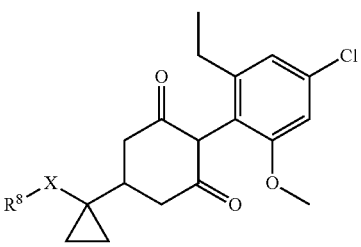

where X and R⁸ are as defined in Table 51.

TABLE 59

This table contains 220 compounds of the following type,

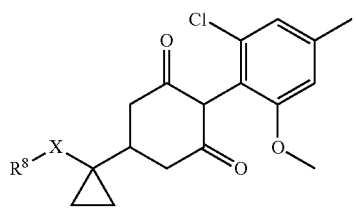

where X and R⁸ are as defined in Table 51.

TABLE 60

This table contains 220 compounds of the following type,

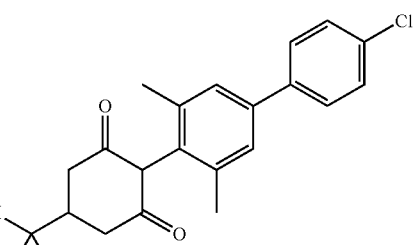

where X and R⁸ are as defined in Table 51.

TABLE 61

This table contains 220 compounds of the following type,

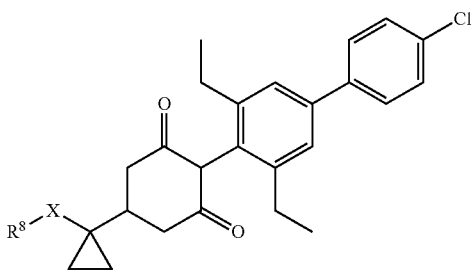

where X and R⁸ are as defined in Table 51.

TABLE 62

This table contains 220 compounds of the following type,

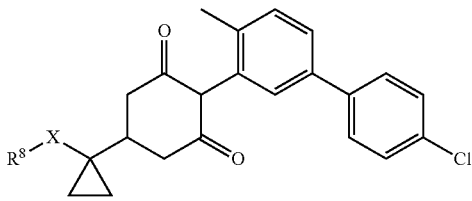

where X and R⁸ are as defined in Table 51.

TABLE 63

This table contains 220 compounds of the following type,

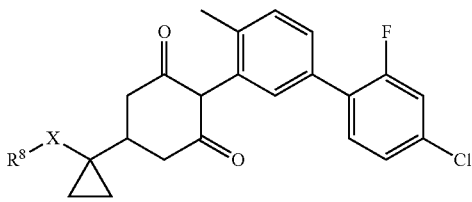

where X and R⁸ are as defined in Table 51.

TABLE 64

This table contains 220 compounds of the following type,

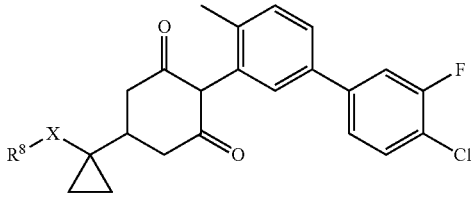

where X and R⁸ are as defined in Table 51.

TABLE 65

This table contains 220 compounds of the following type,

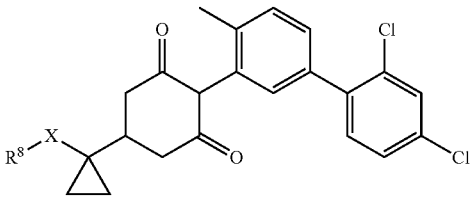

where X and R⁸ are as defined in Table 51.

TABLE 66

This table contains 220 compounds of the following type,

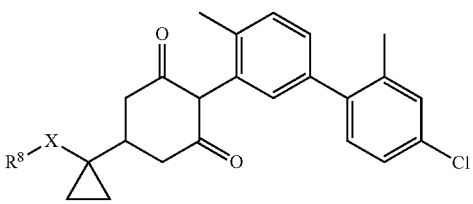

where X and R⁸ are as defined in Table 51.

TABLE 67

This table contains 220 compounds of the following type,

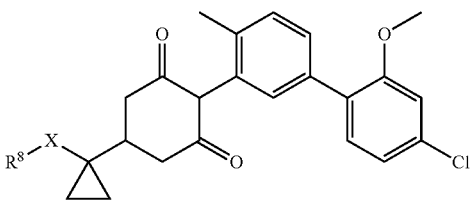

where X and R⁸ are as defined in Table 51.

TABLE 68

This table contains 220 compounds of the following type,

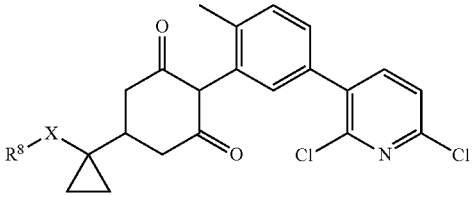

where X and R⁸ are as defined in Table 51.

TABLE 69

This table contains 220 compounds of the following type,

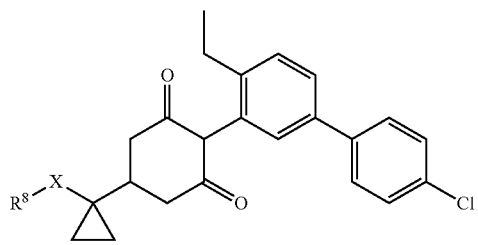

where X and R⁸ are as defined in Table 51.

TABLE 70

This table contains 220 compounds of the following type,

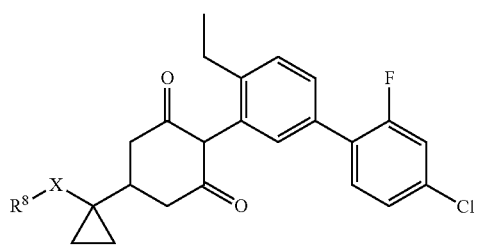

where X and R⁸ are as defined in Table 51.

TABLE 71

This table contains 220 compounds of the following type,

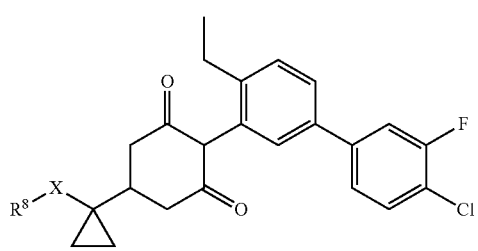

where X and R⁸ are as defined in Table 51.

TABLE 72

This table contains 220 compounds of the following type,

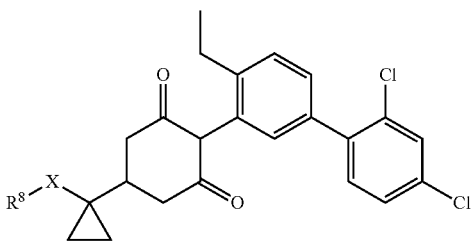

where X and R⁸ are as defined in Table 51.

TABLE 73

This table contains 220 compounds of the following type,

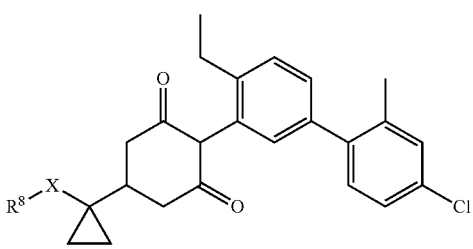

where X and R⁸ are as defined in Table 51.

TABLE 74

This table contains 220 compounds of the following type,

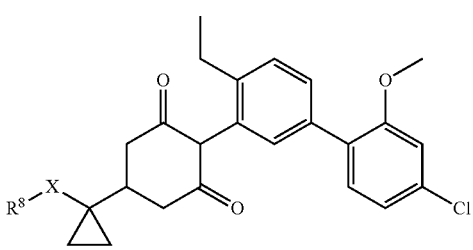

where X and R⁸ are as defined in Table 51.

TABLE 75

This table contains 220 compounds of the following type,

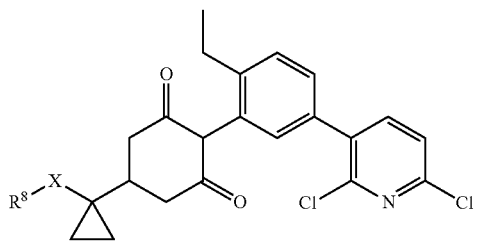

where X and R⁸ are as defined in Table 51.

TABLE 76

This table contains 12 compounds of the following type

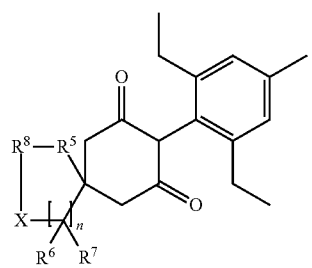

where n, X, $R^5$, $R^6$, $R^7$ and $R^8$ are as defined below:

| Compound No | n | X | $R^5$ | $R^6$ | $R^7$ | $R^8$ |
|---|---|---|---|---|---|---|
| 76.1 | 1 | O | $CH_2$ | H | H | $CH_2$ |
| 76.2 | 1 | O | $CH_2CH_2$ | H | H | $CH_2$ |
| 76.3 | 2 | O | $CH_2$ | H | H | $CH_2$ |
| 76.4 | 1 | S | $CH_2$ | H | H | $CH_2$ |
| 76.5 | 1 | S | $CH_2CH_2$ | H | H | $CH_2$ |
| 76.6 | 2 | S | $CH_2$ | H | H | $CH_2$ |
| 76.7 | 1 | S(O) | $CH_2$ | H | H | $CH_2$ |
| 76.8 | 1 | S(O) | $CH_2CH_2$ | H | H | $CH_2$ |
| 76.9 | 2 | S(O) | $CH_2$ | H | H | $CH_2$ |
| 76.10 | 1 | $SO_2$ | $CH_2$ | H | H | $CH_2$ |
| 76.11 | 1 | $SO_2$ | $CH_2CH_2$ | H | H | $CH_2$ |
| 76.12 | 2 | $SO_2$ | $CH_2$ | H | H | $CH_2$ |

TABLE 77

This table contains 12 compounds of the following type

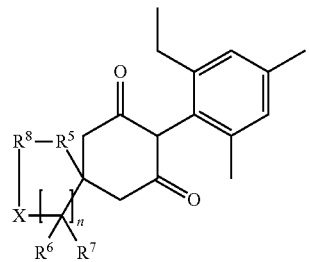

where n, X, $R^5$, $R^6$, $R^7$ and $R^8$ are as defined in Table 76.

TABLE 78

This table contains 12 compounds of the following type

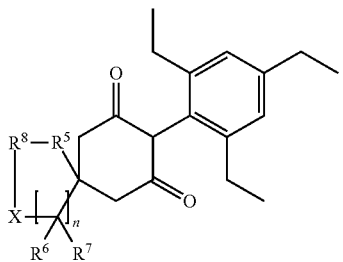

where n, X, $R^5$, $R^6$, $R^7$ and $R^8$ are as defined in Table 76.

TABLE 79

This table contains 12 compounds of the following type

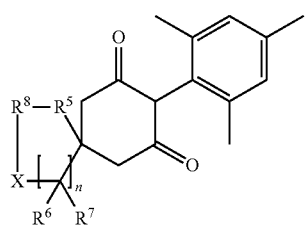

where n, X, $R^5$, $R^6$, $R^7$ and $R^8$ are as defined in Table 76.

TABLE 80

This table contains 12 compounds of the following type

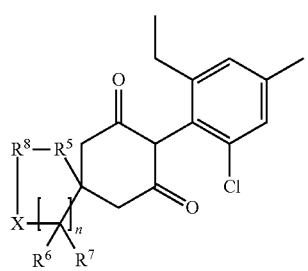

where n, X, $R^5$, $R^6$, $R^7$ and $R^8$ are as defined in Table 76.

TABLE 81

This table contains 12 compounds of the following type

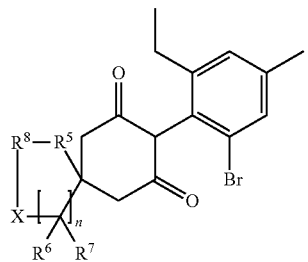

where n, X, $R^5$, $R^6$, $R^7$ and $R^8$ are as defined in Table 76.

TABLE 82

This table contains 12 compounds of the following type

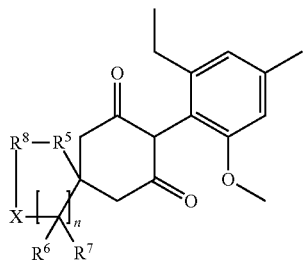

where n, X, $R^5$, $R^6$, $R^7$ and $R^8$ are as defined in Table 76.

TABLE 83

This table contains 12 compounds of the following type

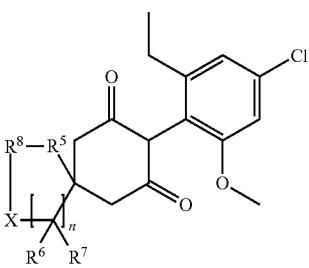

where n, X, $R^5$, $R^6$, $R^7$ and $R^8$ are as defined in Table 76.

TABLE 84

This table contains 12 compounds of the following type

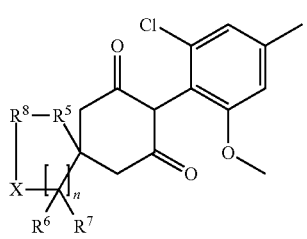

where n, X, $R^5$, $R^6$, $R^7$ and $R^8$ are as defined in Table 76.

TABLE 85

This table contains 12 compounds of the following type

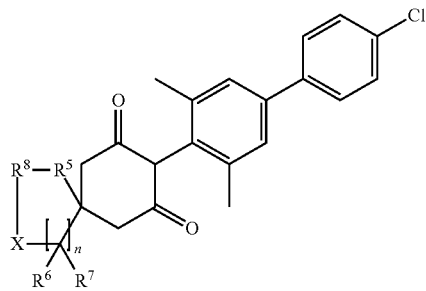

where n, X, $R^5$, $R^6$, $R^7$ and $R^8$ are as defined in Table 76.

TABLE 86

This table contains 12 compounds of the following type

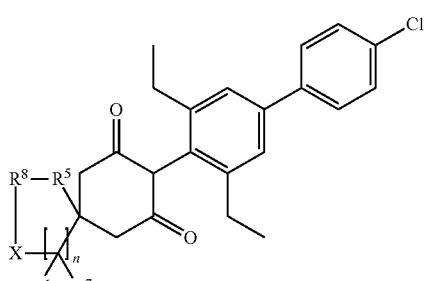

where n, X, $R^5$, $R^6$, $R^7$ and $R^8$ are as defined in Table 76.

TABLE 87

This table contains 12 compounds of the following type

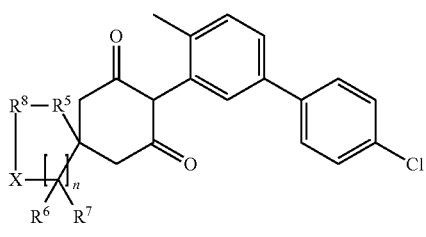

where n, X, $R^5$, $R^6$, $R^7$ and $R^8$ are as defined in Table 76.

TABLE 88

This table contains 12 compounds of the following type

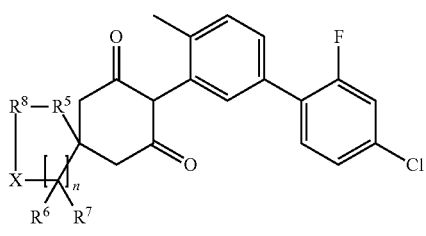

where n, X, $R^5$, $R^6$, $R^7$ and $R^8$ are as defined in Table 76.

TABLE 89

This table contains 12 compounds of the following type

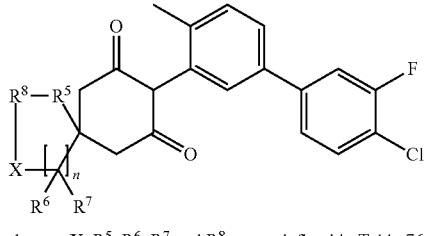

where n, X, $R^5$, $R^6$, $R^7$ and $R^8$ are as defined in Table 76.

TABLE 90

This table contains 12 compounds of the following type

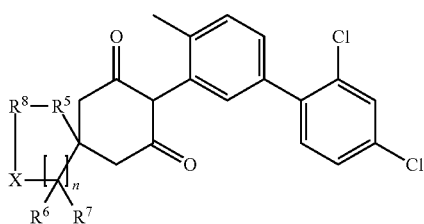

where n, X, $R^5$, $R^6$, $R^7$ and $R^8$ are as defined in Table 76.

TABLE 91

This table contains 12 compounds of the following type

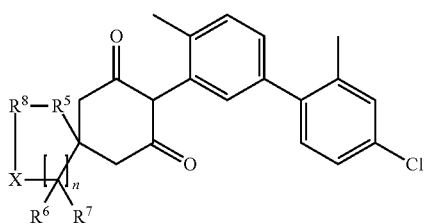

where n, X, $R^5$, $R^6$, $R^7$ and $R^8$ are as defined in Table 76.

TABLE 92

This table contains 12 compounds of the following type

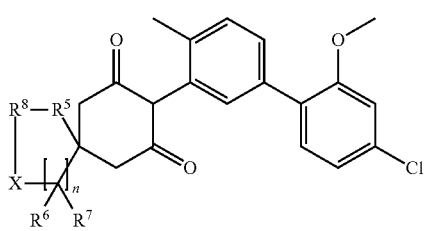

where n, X, $R^5$, $R^6$, $R^7$ and $R^8$ are as defined in Table 76.

TABLE 93

This table contains 12 compounds of the following type

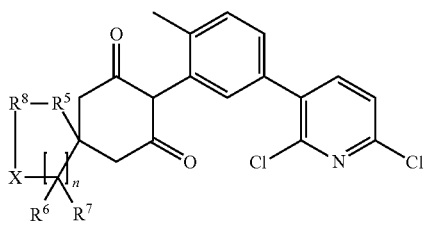

where n, X, $R^5$, $R^6$, $R^7$ and $R^8$ are as defined in Table 76.

TABLE 94

This table contains 12 compounds of the following type

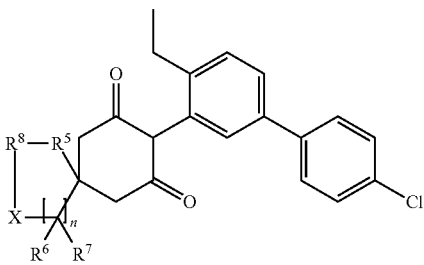

where n, X, $R^5$, $R^6$, $R^7$ and $R^8$ are as defined in Table 76.

TABLE 95

This table contains 12 compounds of the following type

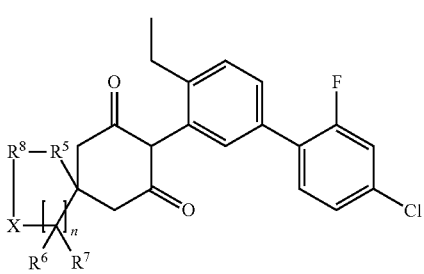

where n, X, $R^5$, $R^6$, $R^7$ and $R^8$ are as defined in Table 76.

TABLE 96

This table contains 12 compounds of the following type

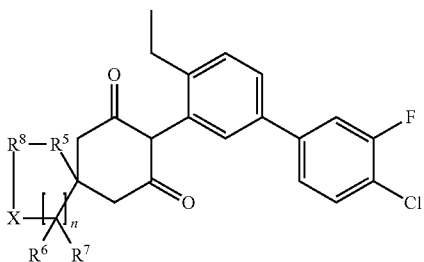

where n, X, $R^5$, $R^6$, $R^7$ and $R^8$ are as defined in Table 76.

TABLE 97

This table contains 12 compounds of the following type

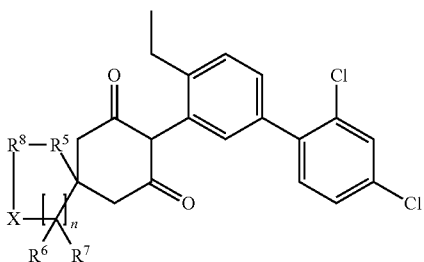

where n, X, $R^5$, $R^6$, $R^7$ and $R^8$ are as defined in Table 76.

TABLE 98

This table contains 12 compounds of the following type

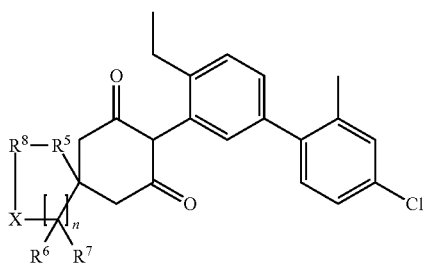

where n, X, $R^5$, $R^6$, $R^7$ and $R^8$ are as defined in Table 76.

TABLE 99

This table contains 12 compounds of the following type

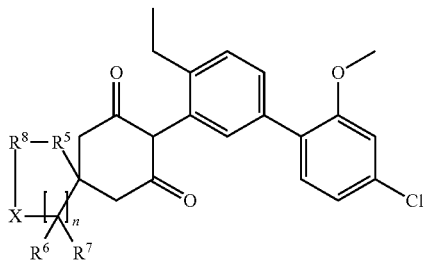

where n, X, $R^5$, $R^6$, $R^7$ and $R^8$ are as defined in Table 76.

TABLE 100

This table contains 12 compounds of the following type

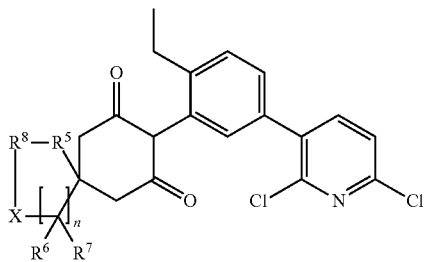

where n, X, $R^5$, $R^6$, $R^7$ and $R^8$ are as defined in Table 76.

TABLE 101

This table contains 12 compounds of the following type

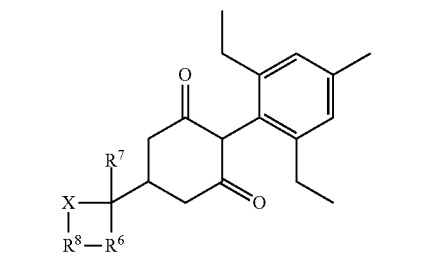

where X, $R^6$, $R^7$ and $R^8$ are as defined below:

| Compound Number | X | $R^6$ | $R^7$ | $R^8$ |
|---|---|---|---|---|
| 101.1 | O | $CH_2$ | H | $CH_2$ |
| 101.2 | O | $CH_2CH_2$ | H | $CH_2$ |

TABLE 101-continued

This table contains 12 compounds of the following type

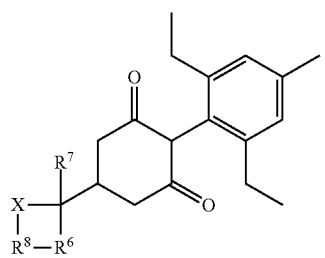

where X, $R^6$, $R^7$ and $R^8$ are as defined below:

| Compound Number | X | $R^6$ | $R^7$ | $R^8$ |
|---|---|---|---|---|
| 101.3 | O | $CH_2CH_2$ | H | $CH_2CH_2$ |
| 101.4 | S | $CH_2$ | H | $CH_2$ |
| 101.5 | S | $CH_2CH_2$ | H | $CH_2$ |
| 101.6 | S | $CH_2CH_2$ | H | $CH_2CH_2$ |
| 101.7 | S(O) | $CH_2$ | H | $CH_2$ |
| 101.8 | S(O) | $CH_2CH_2$ | H | $CH_2$ |
| 101.9 | S(O) | $CH_2CH_2$ | H | $CH_2CH_2$ |
| 101.10 | $SO_2$ | $CH_2$ | H | $CH_2$ |
| 101.11 | $SO_2$ | $CH_2CH_2$ | H | $CH_2$ |
| 101.12 | $SO_2$ | $CH_2CH_2$ | H | $CH_2CH_2$ |

TABLE 102

This table contains 12 compounds of the following type

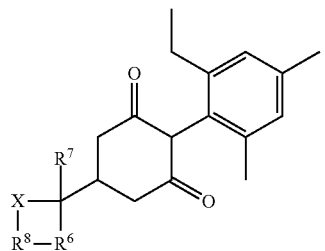

where X, $R^6$, $R^7$ and $R^8$ are as defined in Table 101.

TABLE 103

This table contains 12 compounds of the following type

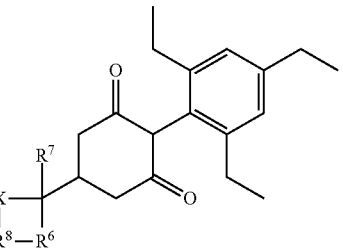

where X, $R^6$, $R^7$ and $R^8$ are as defined in Table 101.

TABLE 104

This table contains 12 compounds of the following type

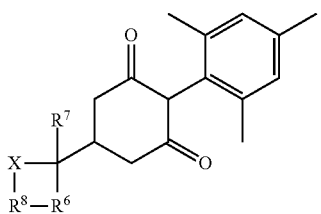

where X, $R^6$, $R^7$ and $R^8$ are as defined in Table 101.

TABLE 105

This table contains 12 compounds of the following type

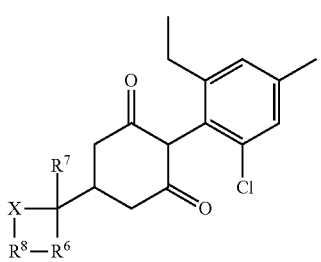

where X, $R^6$, $R^7$ and $R^8$ are as defined in Table 101.

TABLE 106

This table contains 12 compounds of the following type

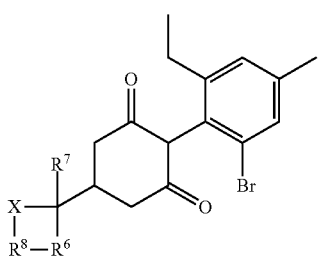

where X, $R^6$, $R^7$ and $R^8$ are as defined in Table 101.

TABLE 107

This table contains 12 compounds of the following type

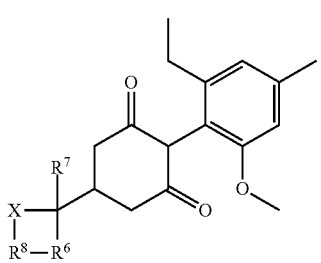

where X, $R^6$, $R^7$ and $R^8$ are as defined in Table 101.

TABLE 108

This table contains 12 compounds of the following type

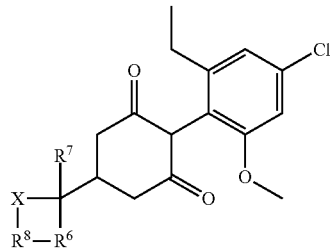

where X, $R^6$, $R^7$ and $R^8$ are as defined in Table 101.

TABLE 109

This table contains 12 compounds of the following type

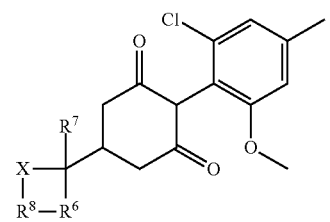

where X, $R^6$, $R^7$ and $R^8$ are as defined in Table 101.

TABLE 110

This table contains 12 compounds of the following type

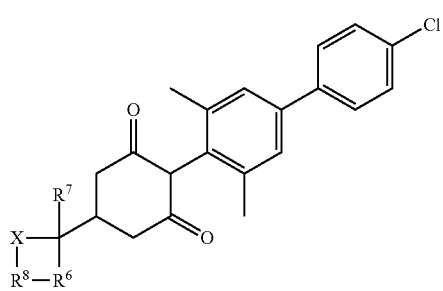

where X, $R^6$, $R^7$ and $R^8$ are as defined in Table 101.

TABLE 111

This table contains 12 compounds of the following type

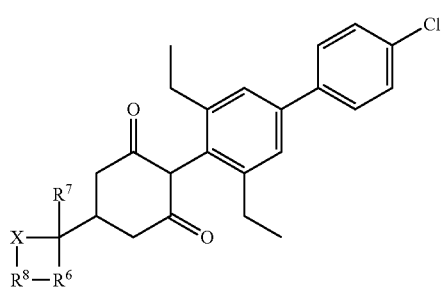

where X, $R^6$, $R^7$ and $R^8$ are as defined in Table 101.

TABLE 112

This table contains 12 compounds of the following type

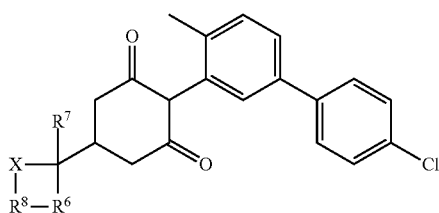

where X, $R^6$, $R^7$ and $R^8$ are as defined in Table 101.

TABLE 113

This table contains 12 compounds of the following type

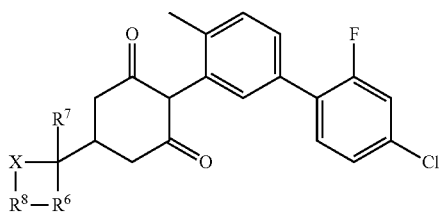

where X, $R^6$, $R^7$ and $R^8$ are as defined in Table 101.

TABLE 114

This table contains 12 compounds of the following type

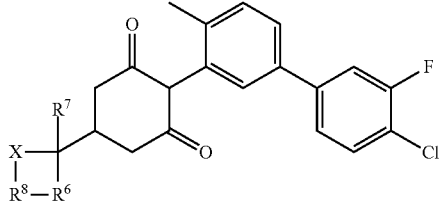

where X, $R^6$, $R^7$ and $R^8$ are as defined in Table 101.

TABLE 115

This table contains 12 compounds of the following type

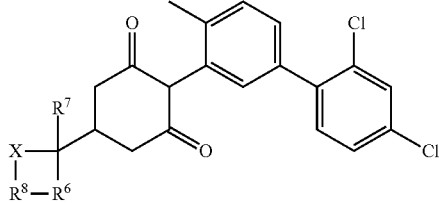

where X, $R^6$, $R^7$ and $R^8$ are as defined in Table 101.

TABLE 116

This table contains 12 compounds of the following type

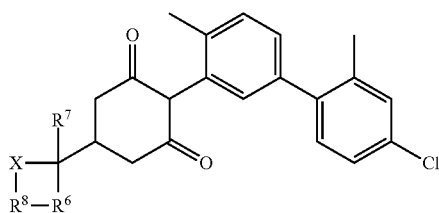

where X, $R^6$, $R^7$ and $R^8$ are as defined in Table 101.

TABLE 117

This table contains 12 compounds of the following type

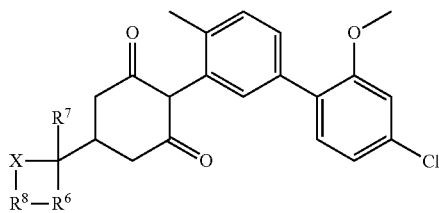

where X, $R^6$, $R^7$ and $R^8$ are as defined in Table 101.

TABLE 118

This table contains 12 compounds of the following type

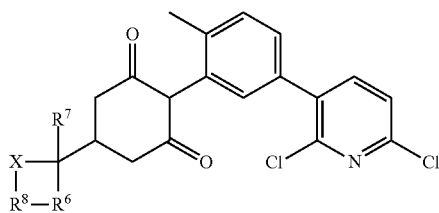

where X, $R^6$, $R^7$ and $R^8$ are as defined in Table 101.

TABLE 119

This table contains 12 compounds of the following type

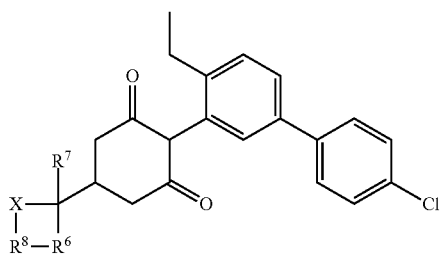

where X, $R^6$, $R^7$ and $R^8$ are as defined in Table 101.

TABLE 120

This table contains 12 compounds of the following type

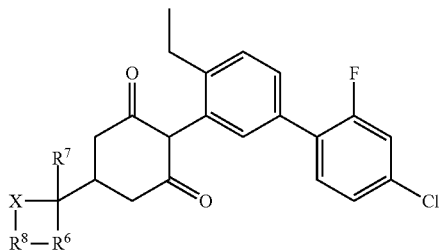

where X, $R^6$, $R^7$ and $R^8$ are as defined in Table 101.

TABLE 121

This table contains 12 compounds of the following type

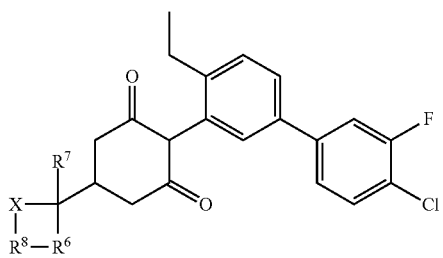

where X, $R^6$, $R^7$ and $R^8$ are as defined in Table 101.

TABLE 122

This table contains 12 compounds of the following type

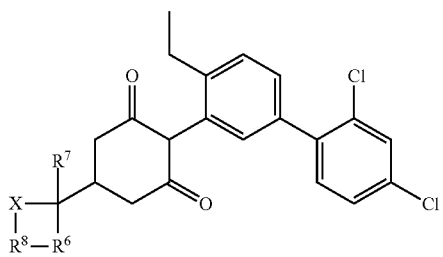

where X, $R^6$, $R^7$ and $R^8$ are as defined in Table 101.

TABLE 123

This table contains 12 compounds of the following type

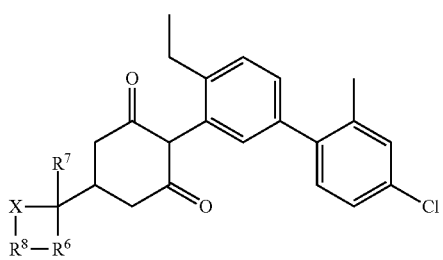

where X, $R^6$, $R^7$ and $R^8$ are as defined in Table 101.

TABLE 124

This table contains 12 compounds of the following type

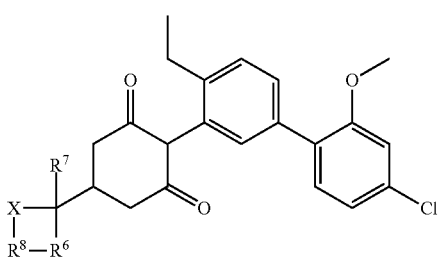

where X, $R^6$, $R^7$ and $R^8$ are as defined in Table 101.

TABLE 125

This table contains 12 compounds of the following type

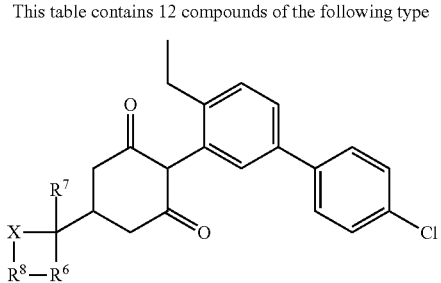

where X, $R^6$, $R^7$ and $R^8$ are as defined in Table 101.

TABLE 126

This table contains 16 compounds of the following type

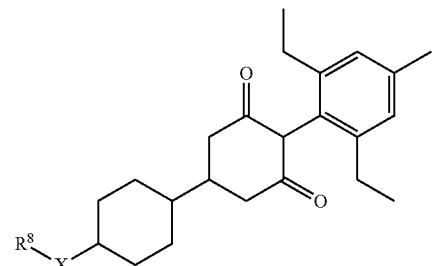

where X and $R^8$ are as defined below:

| Compound number | X | $R^8$ |
|---|---|---|
| 126.1 | O | $CH_3$ |
| 126.2 | O | $CH_2CH_3$ |
| 126.3 | O | $CH(CH_3)_2$ |
| 126.4 | O | $CF_3$ |
| 126.5 | S | $CH_3$ |
| 126.6 | S | $CH_2CH_3$ |
| 126.7 | S | $CH(CH_3)_2$ |
| 126.8 | S | $CF_3$ |
| 126.9 | S(O) | $CH_3$ |
| 126.10 | S(O) | $CH_2CH_3$ |
| 126.11 | S(O) | $CH(CH_3)_2$ |
| 126.12 | S(O) | $CF_3$ |
| 126.13 | $SO_2$ | $CH_3$ |
| 126.14 | $SO_2$ | $CH_2CH_3$ |
| 126.15 | $SO_2$ | $CH(CH_3)_2$ |
| 126.16 | $SO_2$ | $CF_3$ |

TABLE 127

This table contains 16 compounds of the following type

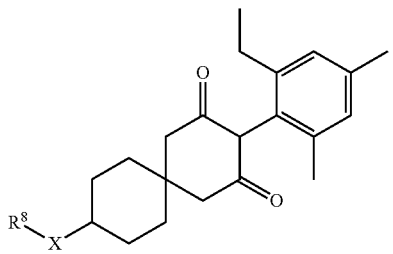

where n and R⁸ are as defined in Table 126.

TABLE 128

This table contains 16 compounds of the following type

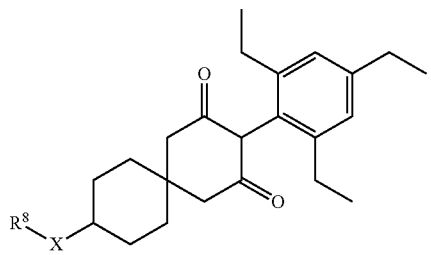

where n and R⁸ are as defined in Table 126.

TABLE 129

This table contains 16 compounds of the following type

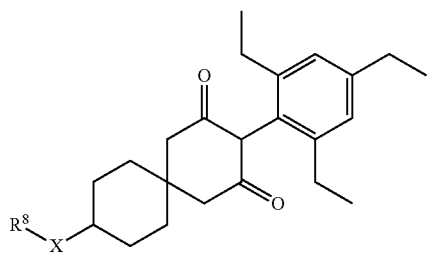

where n and R⁸ are as defined in Table 126.

TABLE 130

This table contains 16 compounds of the following type

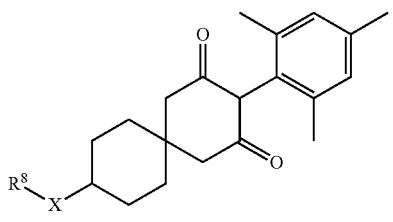

where n and R⁸ are as defined in Table 126.

TABLE 131

This table contains 16 compounds of the following type

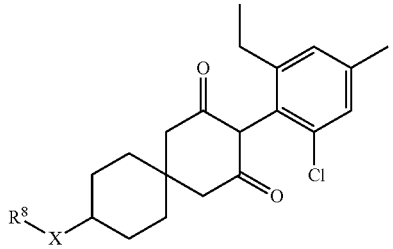

where n and R⁸ are as defined in Table 126.

TABLE 132

This table contains 16 compounds of the following type

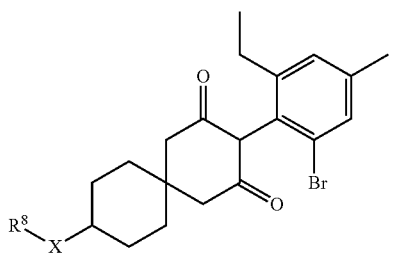

where n and R⁸ are as defined in Table 126.

TABLE 133

This table contains 16 compounds of the following type

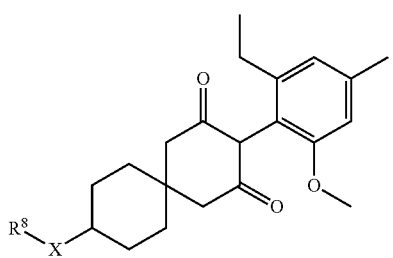

where n and R⁸ are as defined in Table 126.

TABLE 134

This table contains 16 compounds of the following type

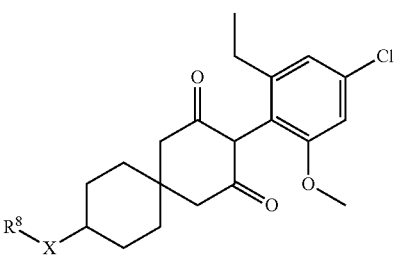

where n and R⁸ are as defined in Table 126.

TABLE 135

This table contains 16 compounds of the following type

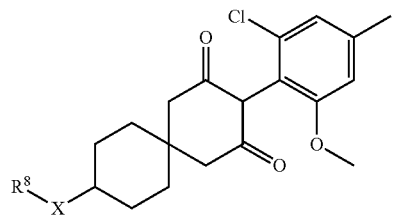

where n and R⁸ are as defined in Table 126.

TABLE 136

This table contains 16 compounds of the following type

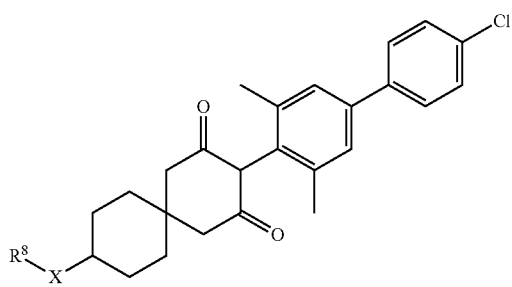

where n and R⁸ are as defined in Table 126.

TABLE 137

This table contains 16 compounds of the following type

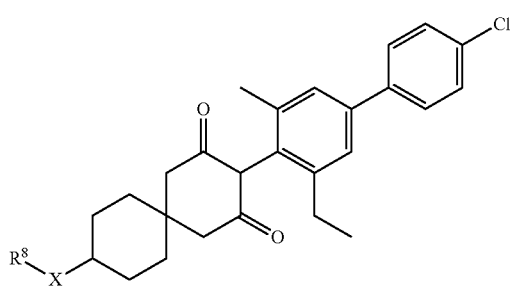

where n and R⁸ are as defined in Table 126.

TABLE 138

This table contains 16 compounds of the following type

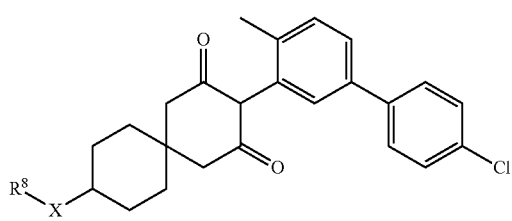

where n and R⁸ are as defined in Table 126.

TABLE 139

This table contains 16 compounds of the following type

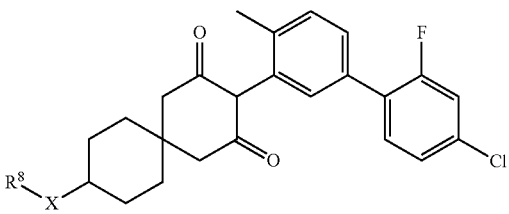

where n and R⁸ are as defined in Table 126.

TABLE 140

This table contains 16 compounds of the following type

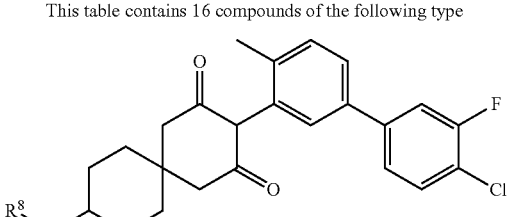

where n and R⁸ are as defined in Table 126.

TABLE 141

This table contains 16 compounds of the following type

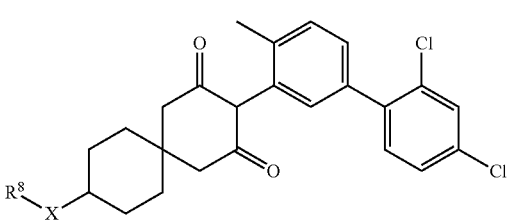

where n and R⁸ are as defined in Table 126.

TABLE 142

This table contains 16 compounds of the following type

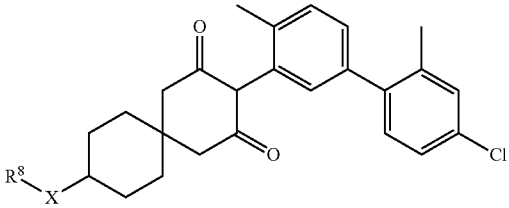

where n and R⁸ are as defined in Table 126.

TABLE 143

This table contains 16 compounds of the following type

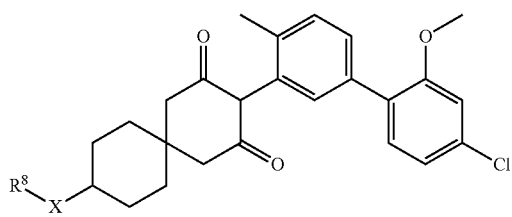

where n and R[8] are as defined in Table 126.

TABLE 144

This table contains 16 compounds of the following type

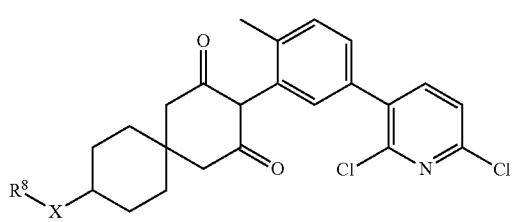

where n and R[8] are as defined in Table 126.

TABLE 145

This table contains 16 compounds of the following type

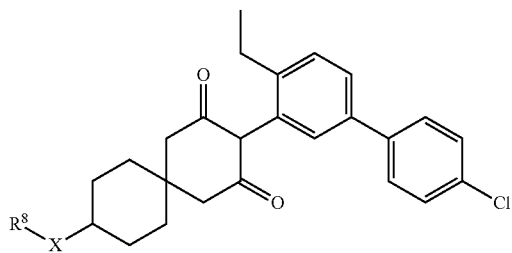

where n and R[8] are as defined in Table 126.

TABLE 146

This table contains 16 compounds of the following type

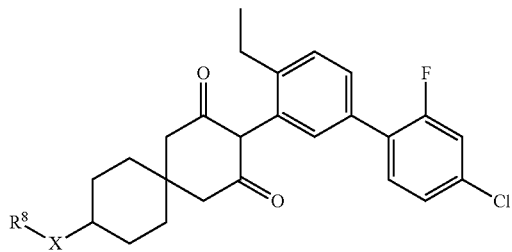

where n and R[8] are as defined in Table 126.

TABLE 147

This table contains 16 compounds of the following type

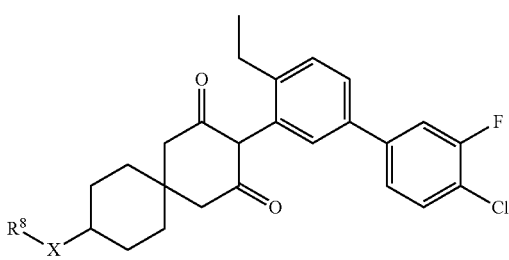

where n and R[8] are as defined in Table 126.

TABLE 148

This table contains 16 compounds of the following type

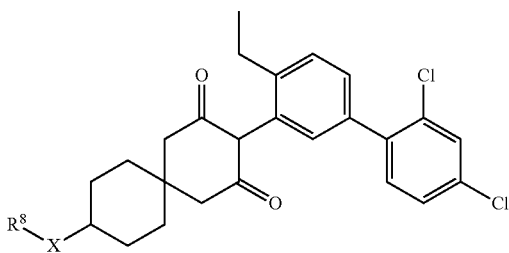

where n and R[8] are as defined in Table 126.

TABLE 149

This table contains 16 compounds of the following type

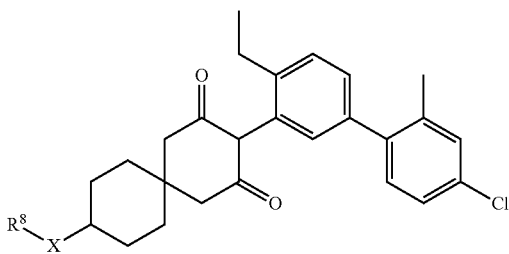

where n and R[8] are as defined in Table 126.

TABLE 150

This table contains 16 compounds of the following type

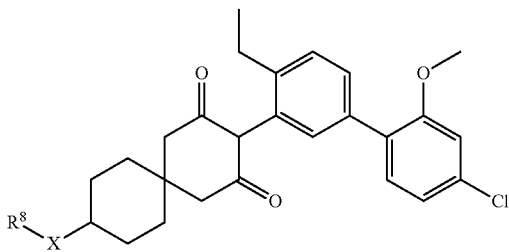

where n and R[8] are as defined in Table 126.

TABLE 151

This table contains 16 compounds of the following type

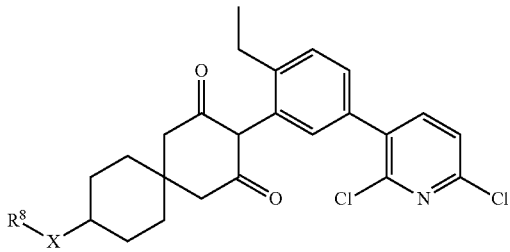

where n and R⁸ are as defined in Table 126.

TABLE 152

This table contains 646 compounds of the following type,

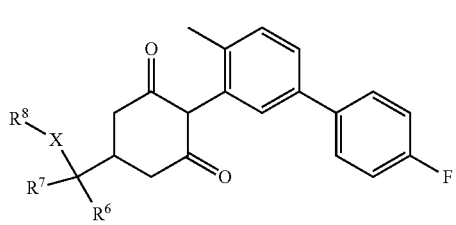

where X, R⁶, R⁷ and R⁸ are as defined in Table 1.

TABLE 153

This table contains 646 compounds of the following type.

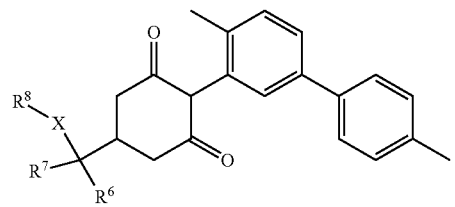

where X, R⁶, R⁷ and R⁸ are as defined in Table 1.

TABLE 154

This table contains 646 compounds of the following type,

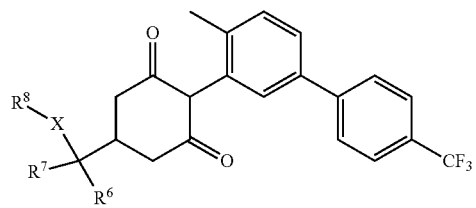

where X, R⁶, R⁷ and R⁸ are as defined in Table 1.

TABLE 155

This table contains 646 compounds of the following type,

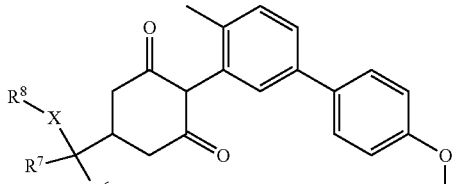

where X, R⁶, R⁷ and R⁸ are as defined in Table 1.

TABLE 156

This table contains 646 compounds of the following type,

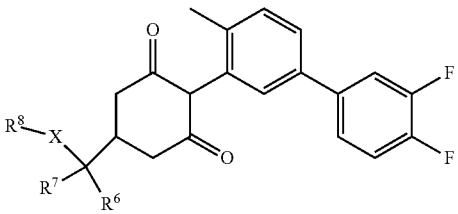

where X, R⁶, R⁷ and R⁸ are as defined in Table 1.

TABLE 157

This table contains 646 compounds of the following type,

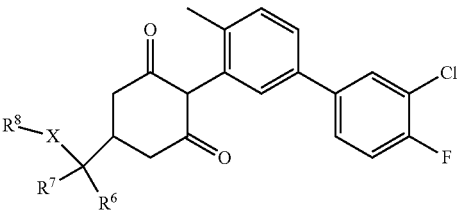

where X, R⁶, R⁷ and R⁸ are as defined in Table 1.

TABLE 158

This table contains 646 compounds of the following type,

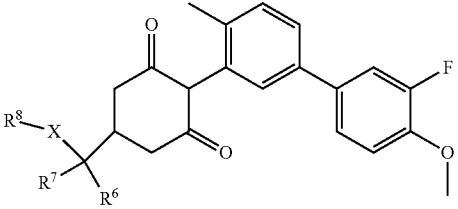

where X, R⁶, R⁷ and R⁸ are as defined in Table 1.

TABLE 159

This table contains 646 compounds of the following type,

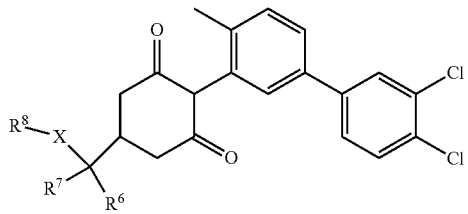

where X, $R^6$, $R^7$ and $R^8$ are as defined in Table 1.

TABLE 160

This table contains 646 compounds of the following type,

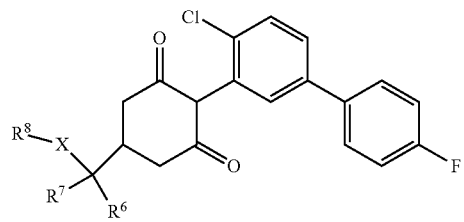

where X, $R^6$, $R^7$ and $R^8$ are as defined in Table 1.

TABLE 161

This table contains 646 compounds of the following type,

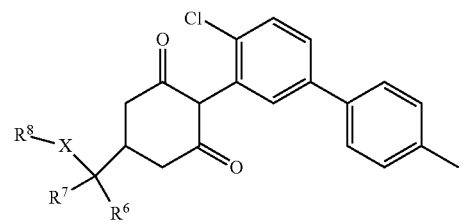

where X, $R^6$, $R^7$ and $R^8$ are as defined in Table 1.

TABLE 162

This table contains 646 compounds of the following type,

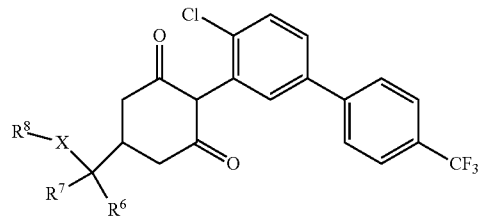

where X, $R^6$, $R^7$ and $R^8$ are as defined in Table 1.

TABLE 163

This table contains 646 compounds of the following type,

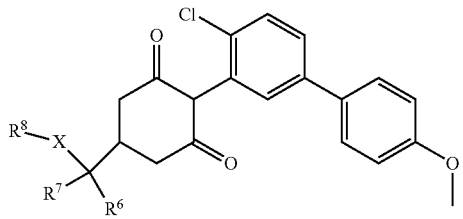

where X, $R^6$, $R^7$ and $R^8$ are as defined in Table 1.

TABLE 164

This table contains 646 compounds of the following type,

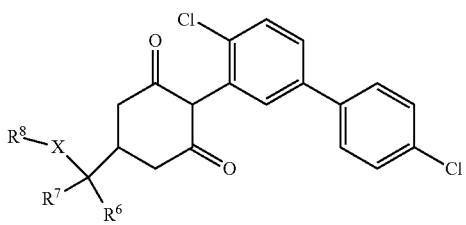

where X, $R^6$, $R^7$ and $R^8$ are as defined in Table 1.

TABLE 165

This table contains 646 compounds of the following type,

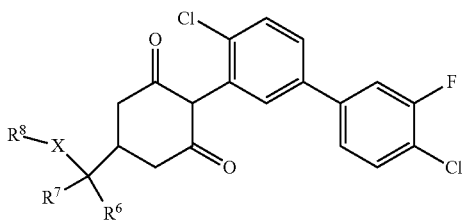

where X, $R^6$, $R^7$ and $R^8$ are as defined in Table 1.

TABLE 166

This table contains 646 compounds of the following type,

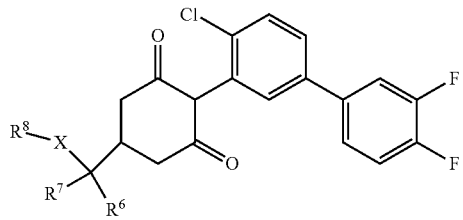

where X, $R^6$, $R^7$ and $R^8$ are as defined in Table 1.

TABLE 167

This table contains 646 compounds of the following type,

where X, $R^6$, $R^7$ and $R^8$ are as defined in Table 1.

TABLE 168

This table contains 646 compounds of the following type,

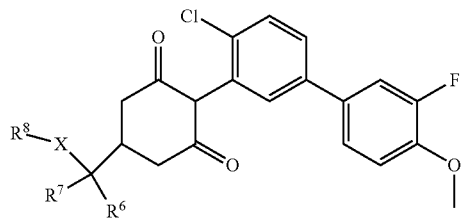

where X, $R^6$, $R^7$ and $R^8$ are as defined in Table 1.

TABLE 169

This table contains 646 compounds of the following type,

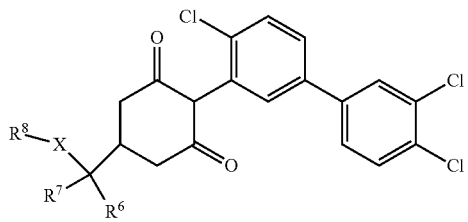

where X, $R^6$, $R^7$ and $R^8$ are as defined in Table 1.

TABLE 170

This table contains 646 compounds of the following type,

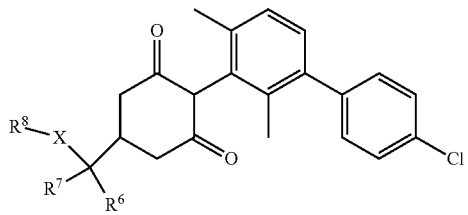

where X, $R^6$, $R^7$ and $R^8$ are as defined in Table 1.

TABLE 171

This table contains 646 compounds of the following type,

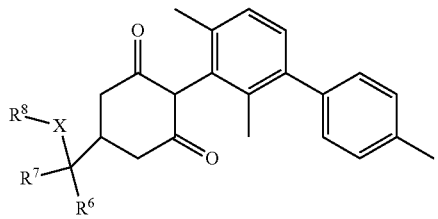

where X, $R^6$, $R^7$ and $R^8$ are as defined in Table 1.

TABLE 172

This table contains 646 compounds of the following type,

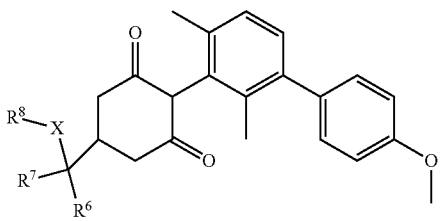

where X, $R^6$, $R^7$ and $R^8$ are as defined in Table 1.

TABLE 173

This table contains 646 compounds of the following type,

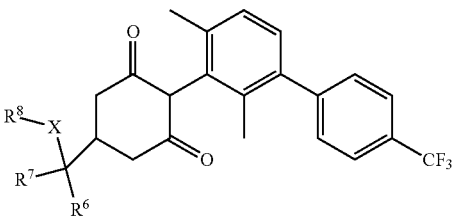

where X, $R^6$, $R^7$ and $R^8$ are as defined in Table 1.

TABLE 174

This table contains 646 compounds of the following type,

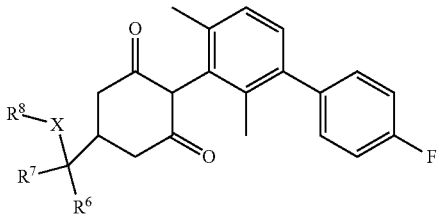

where X, $R^6$, $R^7$ and $R^8$ are as defined in Table 1.

TABLE 175

This table contains 646 compounds of the following type,

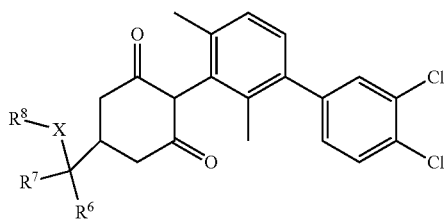

where X, $R^6$, $R^7$ and $R^8$ are as defined in Table 1.

TABLE 176

This table contains 646 compounds of the following type,

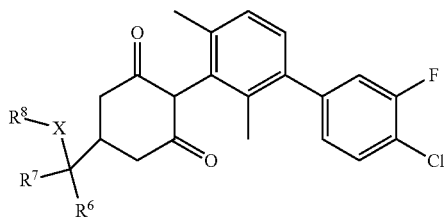

where X, $R^6$, $R^7$ and $R^8$ are as defined in Table 1.

TABLE 177

This table contains 646 compounds of the following type,

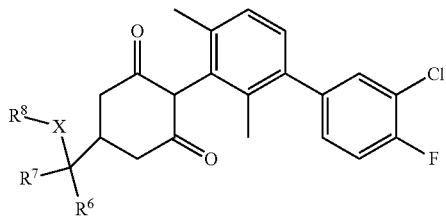

where X, $R^6$, $R^7$ and $R^8$ are as defined in Table 1

TABLE 178

This table contains 646 compounds of the following type,

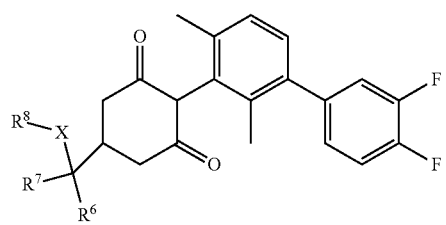

where X, $R^6$, $R^7$ and $R^8$ are as defined in Table 1.

TABLE 179

This table contains 646 compounds of the following type,

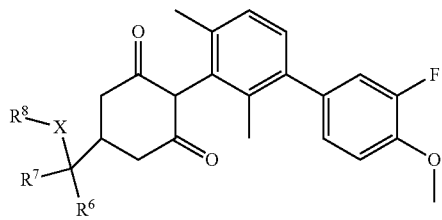

where X, $R^6$, $R^7$ and $R^8$ are as defined in Table 1.

TABLE 180

This table contains 646 compounds of the following type.

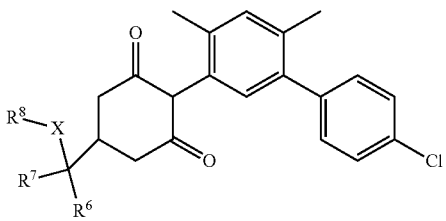

where X, $R^6$, $R^7$ and $R^8$ are as defined in Table 1.

TABLE 181

This table contains 646 compounds of the following type,

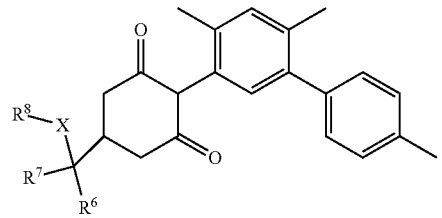

where X, $R^6$, $R^7$ and $R^8$ are as defined in Table 1.

TABLE 182

This table contains 646 compounds of the following type,

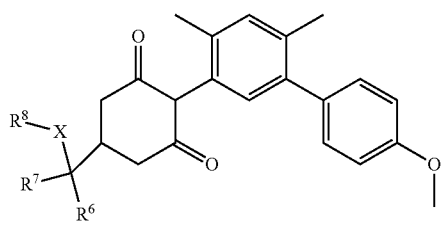

where X, $R^6$, $R^7$ and $R^8$ are as defined in Table 1.

TABLE 183

This table contains 646 compounds of the following type,

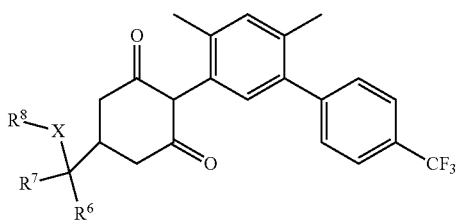

where X, $R^6$, $R^7$ and $R^8$ are as defined in Table 1.

TABLE 184

This table contains 646 compounds of the following type,

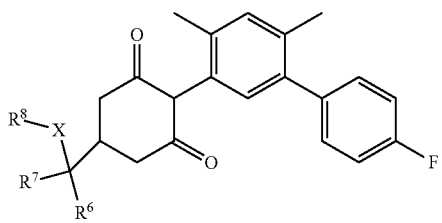

where X, $R^6$, $R^7$ and $R^8$ are as defined in Table 1.

TABLE 185

This table contains 646 compounds of the following type,

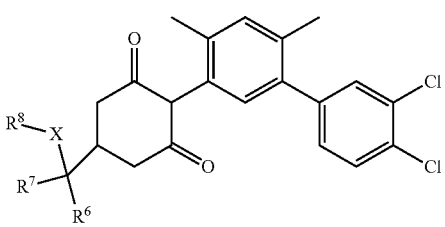

where X, $R^6$, $R^7$ and $R^8$ are as defined in Table 1.

TABLE 186

This table contains 646 compounds of the following type,

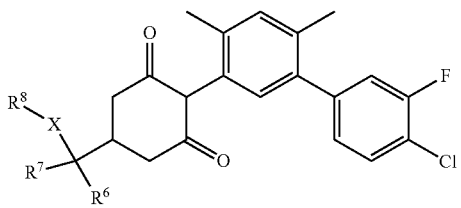

where X, $R^6$, $R^7$ and $R^8$ are as defined in Table 1.

TABLE 187

This table contains 646 compounds of the following type,

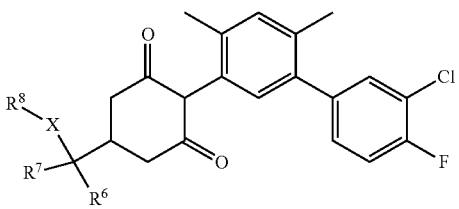

where X, $R^6$, $R^7$ and $R^8$ are as defined in Table 1.

TABLE 188

This table contains 646 compounds of the following type,

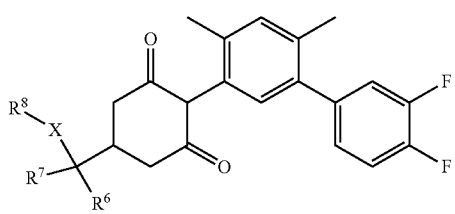

where X, $R^6$, $R^7$ and $R^8$ are as defined in Table 1.

TABLE 189

This table contains 646 compounds of the following type,

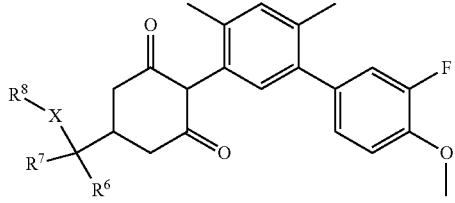

where X, $R^6$, $R^7$ and $R^8$ are as defined in Table 1.

TABLE 190

This table contains 646 compounds of the following type,

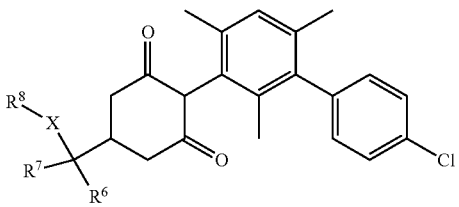

where X, $R^6$, $R^7$ and $R^8$ are as defined in Table 1.

TABLE 191

This table contains 646 compounds of the following type,

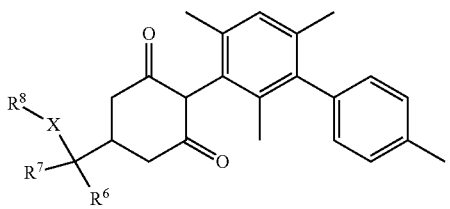

where X, R⁶, R⁷ and R⁸ are as defined in Table 1.

TABLE 192

This table contains 646 compounds of the following type,

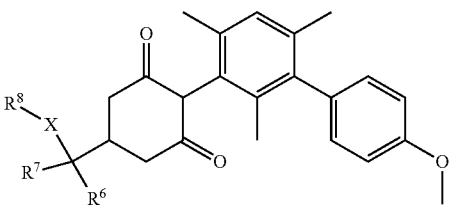

where X, R⁶, R⁷ and R⁸ are as defined in Table 1.

TABLE 193

This table contains 646 compounds of the following type,

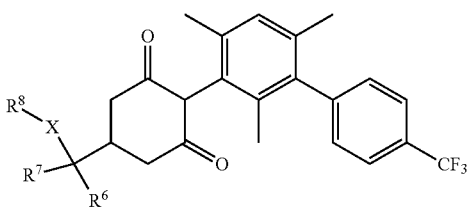

where X, R⁶, R⁷ and R⁸ are as defined in Table 1.

TABLE 194

This table contains 646 compounds of the following type,

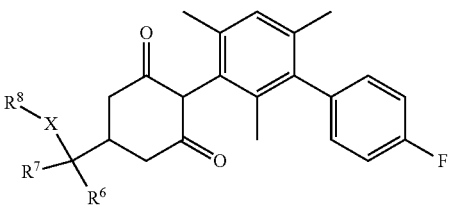

where X, R⁶, R⁷ and R⁶ are as defined in Table 1.

TABLE 195

This table contains 646 compounds of the following type,

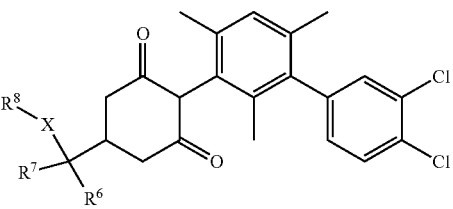

where X, R⁶, R⁷ and R⁸ are as defined in Table 1.

TABLE 196

This table contains 646 compounds of the following type,

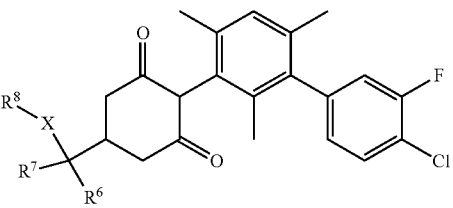

where X, R⁶, R⁷ and R⁸ are as defined in Table 1.

TABLE 197

This table contains 646 compounds of the following type,

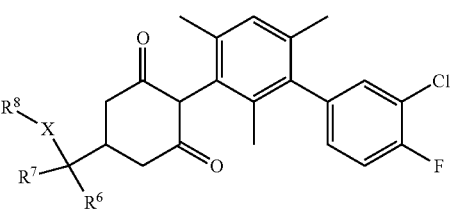

where X, R⁶, R⁷ and R⁸ are as defined in Table 1.

TABLE 198

This table contains 646 compounds of the following type,

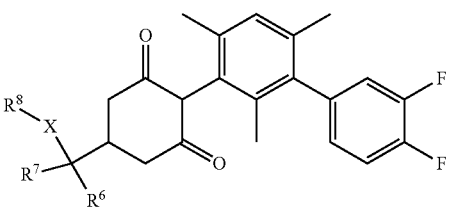

where X, R⁶, R⁷ and R⁸ are as defined in Table 1.

TABLE 199

This table contains 646 compounds of the following type,

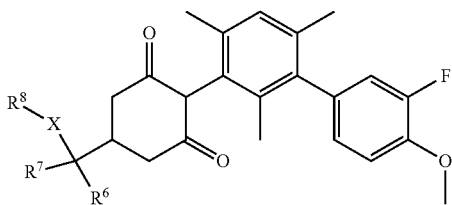

where X, $R^6$, $R^7$ and $R^8$ are as defined in Table 1.

TABLE 200

This table contains 618 compounds of the following type,

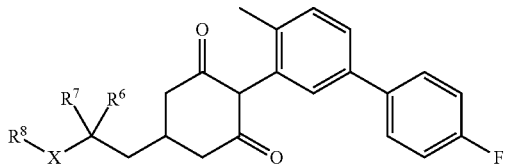

where X, $R^6$, $R^7$ and $R^8$ are as defined in Table 26.

TABLE 201

This table contains 618 compounds of the following type,

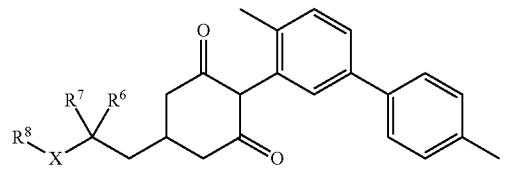

where X, $R^6$, $R^7$ and $R^8$ are as defined in Table 26.

TABLE 202

This table contains 618 compounds of the following type,

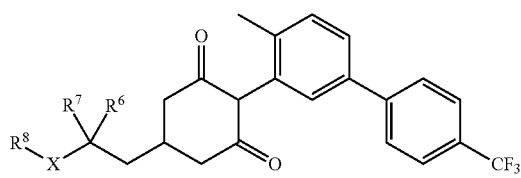

where X, $R^6$, $R^7$ and $R^8$ are as defined in Table 26.

TABLE 203

This table contains 618 compounds of the following type,

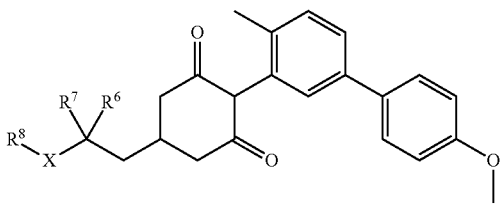

where X, $R^6$, $R^7$ and $R^8$ are as defined in Table 26.

TABLE 204

This table contains 618 compounds of the following type,

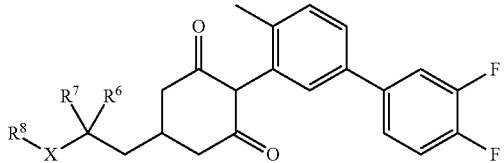

where X, $R^6$, $R^7$ and $R^8$ are as defined in Table 26.

TABLE 205

This table contains 618 compounds of the following type,

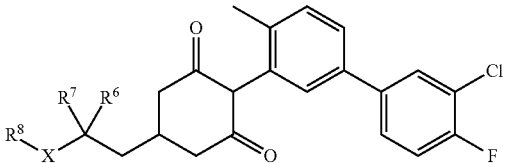

where X, $R^6$, $R^7$ and $R^8$ are as defined in Table 26.

TABLE 206

This table contains 618 compounds of the following type,

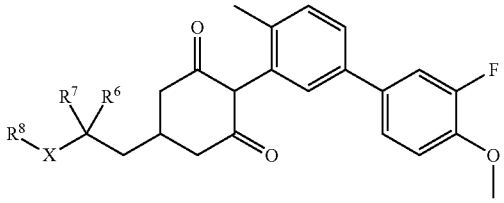

where X, $R^6$, $R^7$ and $R^8$ are as defined in Table 26.

TABLE 207

This table contains 618 compounds of the following type,

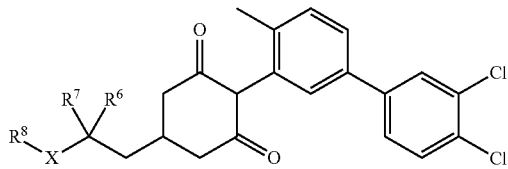

where X, $R^6$, $R^7$ and $R^8$ are as defined in Table 26.

TABLE 208

This table contains 618 compounds of the following type,

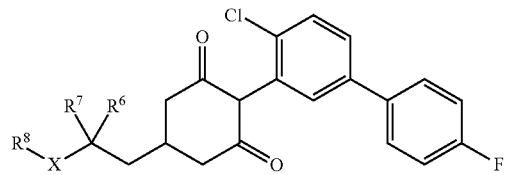

where X, $R^6$, $R^7$ and $R^8$ are as defined in Table 26.

TABLE 209

This table contains 618 compounds of the following type,

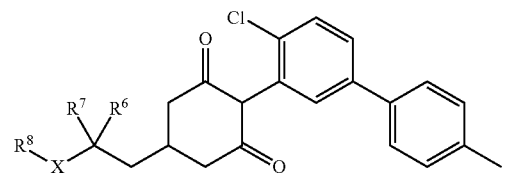

where X, $R^6$, $R^7$ and $R^8$ are as defined in Table 26.

TABLE 210

This table contains 618 compounds of the following type,

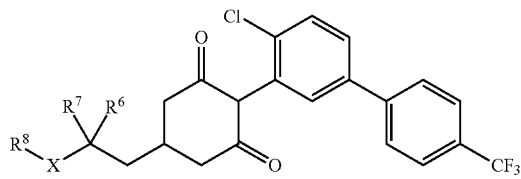

where X, $R^6$, $R^7$ and $R^8$ are as defined in Table 26.

TABLE 211

This table contains 618 compounds of the following type,

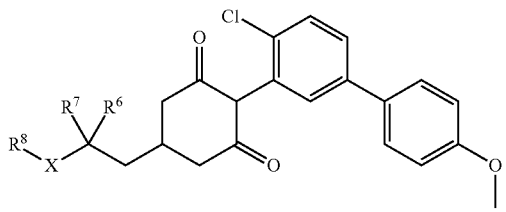

where X, $R^6$, $R^7$ and $R^8$ are as defined in Table 26.

TABLE 212

This table contains 618 compounds of the following type,

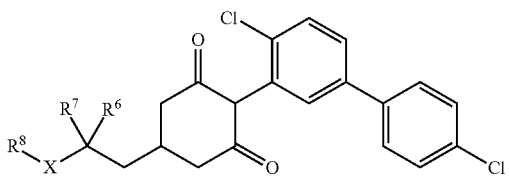

where X, $R^6$, $R^7$ and $R^8$ are as defined in Table 26.

TABLE 213

This table contains 618 compounds of the following type,

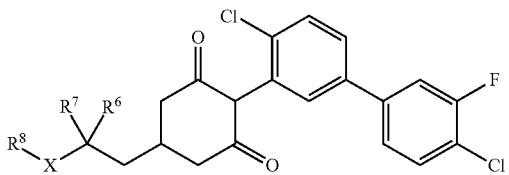

where X, $R^6$, $R^7$ and $R^8$ are as defined in Table 26.

TABLE 214

This table contains 618 compounds of the following type,

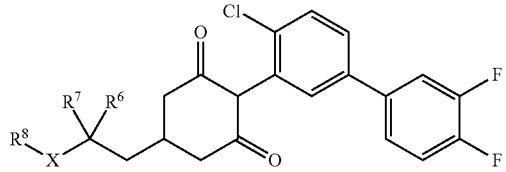

where X, $R^6$, $R^7$ and $R^8$ are as defined in Table 26.

TABLE 215

This table contains 618 compounds of the following type,

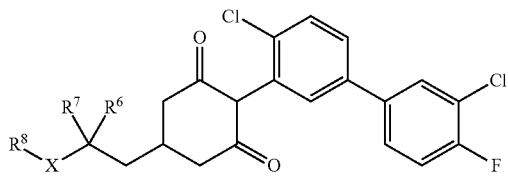

where X, $R^6$, $R^7$ and $R^8$ are as defined in Table 26.

TABLE 216

This table contains 618 compounds of the following type,

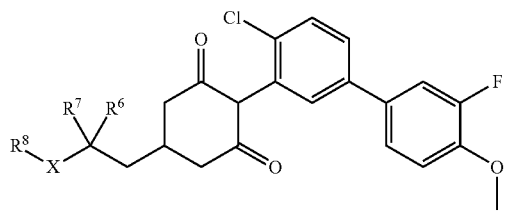

where X, $R^6$, $R^7$ and $R^8$ are as defined in Table 26.

TABLE 217

This table contains 618 compounds of the following type,

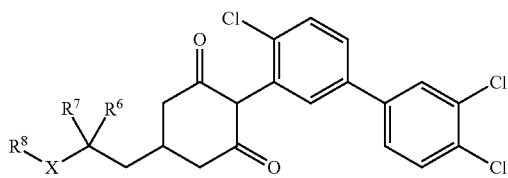

where X, $R^6$, $R^7$ and $R^8$ are as defined in Table 26.

TABLE 218

This table contains 618 compounds of the following type,

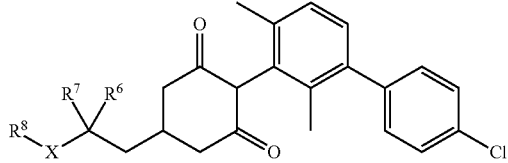

where X, $R^6$, $R^7$ and $R^8$ are as defined in Table 26.

TABLE 219

This table contains 618 compounds of the following type,

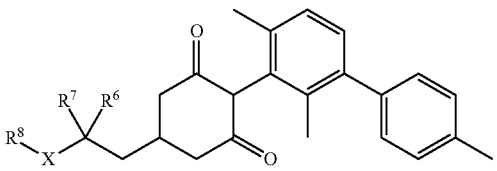

where X, $R^6$, $R^7$ and $R^8$ are as defined in Table 26.

TABLE 220

This table contains 618 compounds of the following type,

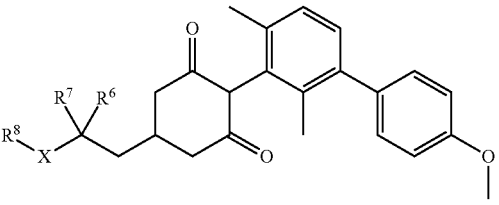

where X, $R^6$, $R^7$ and $R^8$ are as defined in Table 26.

TABLE 221

This table contains 618 compounds of the following type,

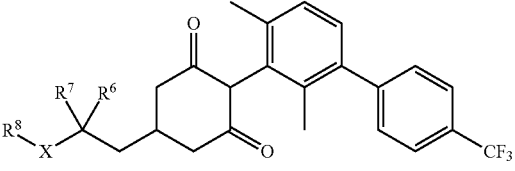

where X, $R^6$, $R^7$ and $R^8$ are as defined in Table 26.

TABLE 222

This table contains 618 compounds of the following type,

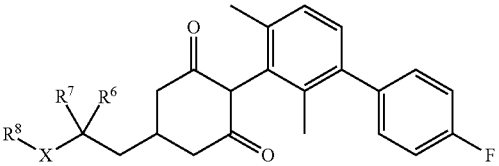

where X, $R^6$, $R^7$ and $R^8$ are as defined in Table 26.

TABLE 223

This table contains 618 compounds of the following type,

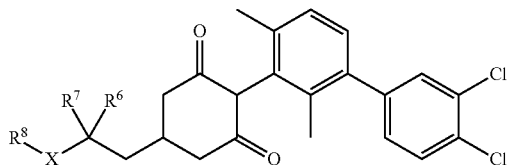

where X, $R^6$, $R^7$ and $R^8$ are as defined in Table 26.

TABLE 224

This table contains 618 compounds of the following type,

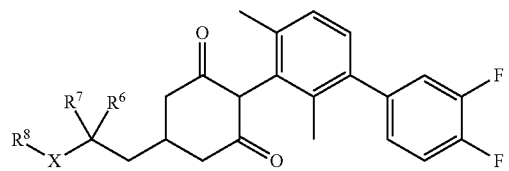

where X, $R^6$, $R^7$ and $R^8$ are as defined in Table 26.

TABLE 225

This table contains 618 compounds of the following type,

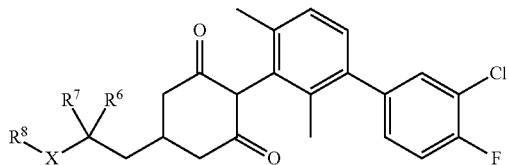

where X, $R^6$, $R^7$ and $R^8$ are as defined in Table 26.

TABLE 226

This table contains 618 compounds of the following type,

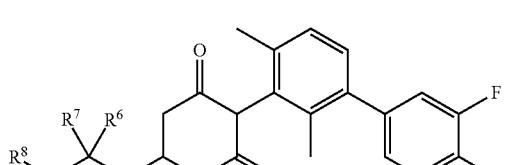

where X, $R^6$, $R^7$ and $R^8$ are as defined in Table 26.

TABLE 227

This table contains 618 compounds of the following type,

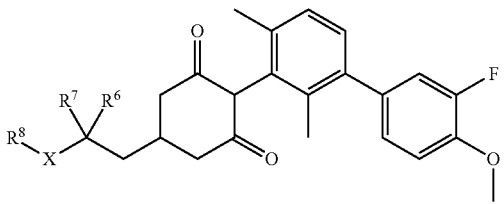

where X, $R^6$, $R^7$ and $R^8$ are as defined in Table 26.

TABLE 228

This table contains 618 compounds of the following type,

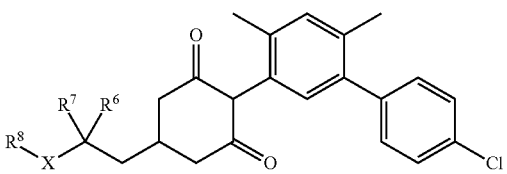

where X, $R^6$, $R^7$ and $R^8$ are as defined in Table 26.

TABLE 229

This table contains 618 compounds of the following type,

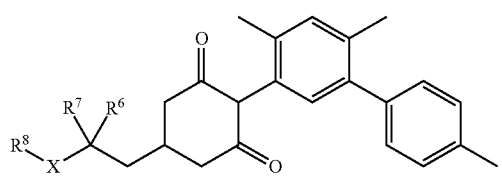

where X, $R^6$, $R^7$ and $R^8$ are as defined in Table 26.

TABLE 230

This table contains 618 compounds of the following type,

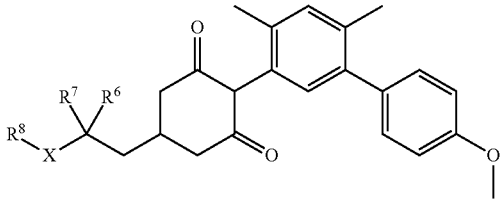

where X, $R^6$, $R^7$ and $R^8$ are as defined in Table 26.

TABLE 231

This table contains 618 compounds of the following type,

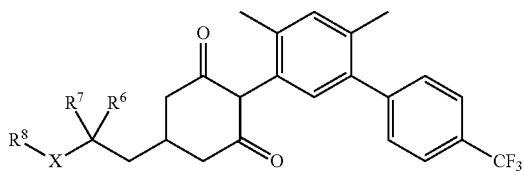

where X, $R^6$, $R^7$ and $R^8$ are as defined in Table 26.

TABLE 232

This table contains 618 compounds of the following type,

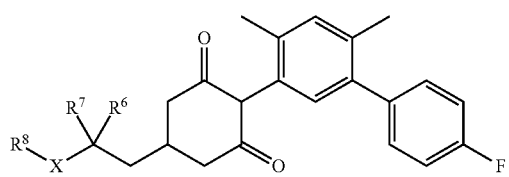

where X, $R^6$, $R^7$ and $R^8$ are as defined in Table 26.

TABLE 233

This table contains 618 compounds of the following type,

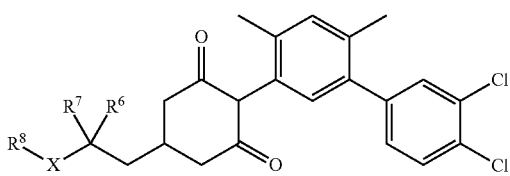

where X, $R^6$, $R^7$ and $R^8$ are as defined in Table 26.

TABLE 234

This table contains 618 compounds of the following type,

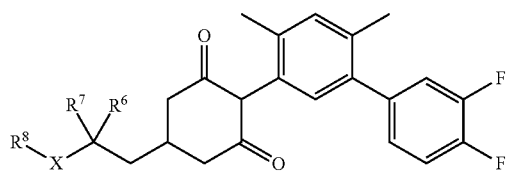

where X, $R^6$, $R^7$ and $R^8$ are as defined in Table 26.

TABLE 235

This table contains 618 compounds of the following type,

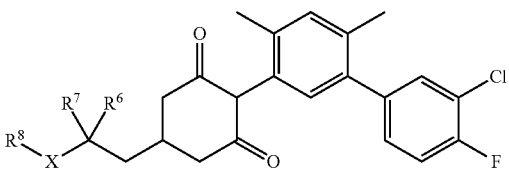

where X, $R^6$, $R^7$ and $R^8$ are as defined in Table 26.

TABLE 236

This table contains 618 compounds of the following type,

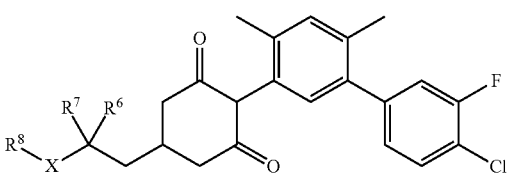

where X, $R^6$, $R^7$ and $R^8$ are as defined in Table 26.

TABLE 237

This table contains 618 compounds of the following type,

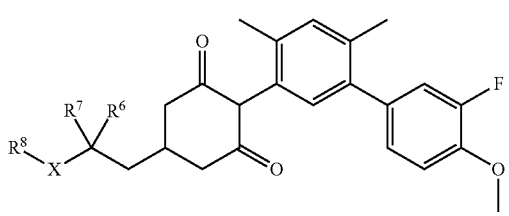

where X, $R^6$, $R^7$ and $R^8$ are as defined in Table 26.

TABLE 238

This table contains 618 compounds of the following type,

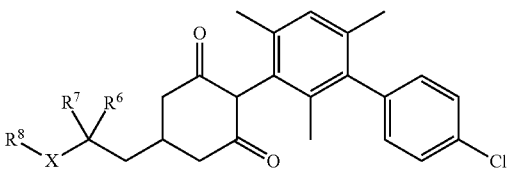

where X, $R^6$, $R^7$ and $R^8$ are as defined in Table 26.

TABLE 239

This table contains 618 compounds of the following type, where X, $R^6$, $R^7$ and $R^8$ are as defined in Table 26.

TABLE 240

This table contains 618 compounds of the following type, where X, $R^6$, $R^7$ and $R^8$ are as defined in Table 26.

TABLE 241

This table contains 618 compounds of the following type, where X, $R^6$, $R^7$ and $R^8$ are as defined in Table 26.

TABLE 242

This table contains 618 compounds of the following type, where X, $R^6$, $R^7$ and $R^8$ are as defined in Table 26.

TABLE 243

This table contains 618 compounds of the following type, where X, $R^6$, $R^7$ and $R^8$ are as defined in Table 26.

TABLE 244

This table contains 618 compounds of the following type, where X, $R^6$, $R^7$ and $R^8$ are as defined in Table 26.

TABLE 245

This table contains 618 compounds of the following type, where X, $R^6$, $R^7$ and $R^8$ are as defined in Table 26.

TABLE 246

This table contains 618 compounds of the following type, where X, $R^6$, $R^7$ and $R^8$ are as defined in Table 26.

TABLE 247

This table contains 618 compounds of the following type,

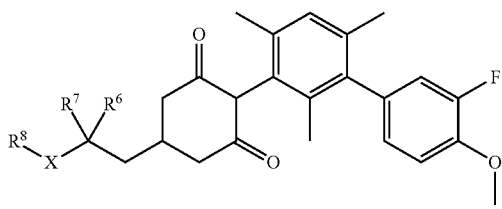

where X, $R^6$, $R^7$ and $R^8$ are as defined in Table 26.

TABLE 248

This table contains 220 compounds of the following type,

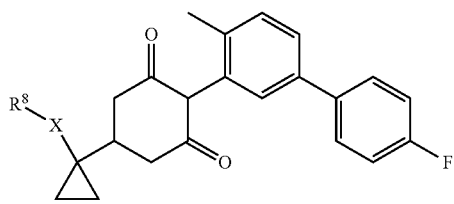

where X and $R^8$ are as defined in Table 51.

TABLE 249

This table contains 220 compounds of the following type,

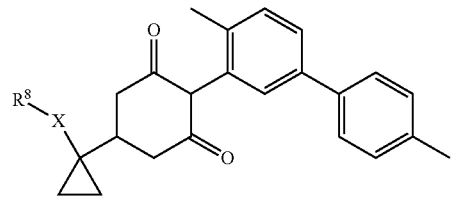

where X and $R^8$ are as defined in Table 51.

TABLE 250

This table contains 220 compounds of the following type,

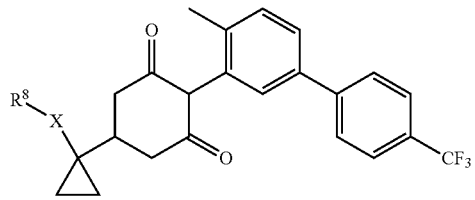

where X and $R^8$ are as defined in Table 51.

TABLE 251

This table contains 220 compounds of the following type,

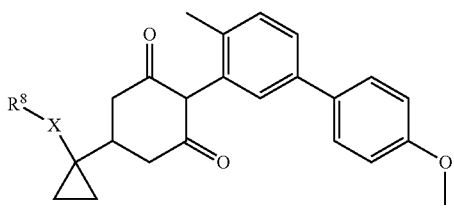

where X and $R^8$ are as defined in Table 51.

TABLE 252

This table contains 220 compounds of the following type,

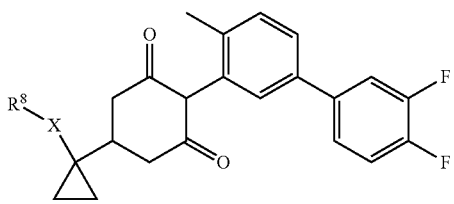

where X and $R^8$ are as defined in Table 51.

TABLE 253

This table contains 220 compounds of the following type,

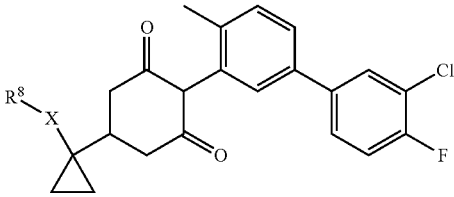

where X and $R^8$ are as defined in Table 51.

TABLE 254

This table contains 220 compounds of the following type,

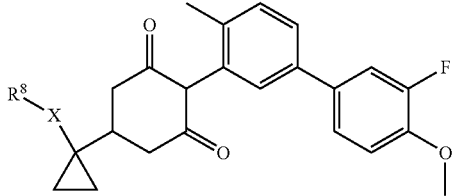

where X and $R^8$ are as defined in Table 51.

TABLE 255

This table contains 220 compounds of the following type,

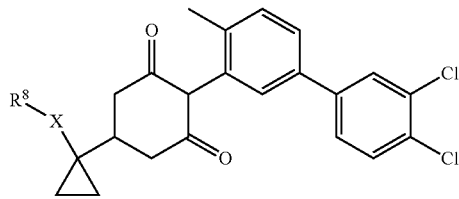

where X and R⁸ are as defined in Table 51.

TABLE 256

This table contains 220 compounds of the following type,

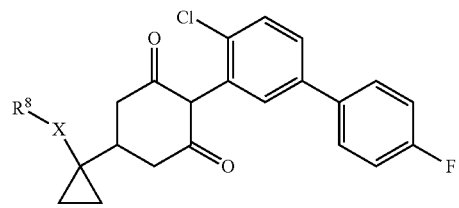

where X and R⁸ are as defined in Table 51.

TABLE 257

This table contains 220 compounds of the following type,

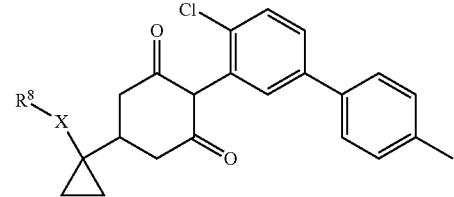

where X and R⁸ are as defined in Table 51.

TABLE 258

This table contains 220 compounds of the following type,

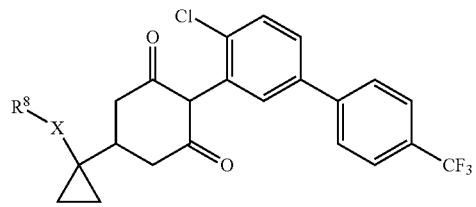

where X and R⁸ are as defined in Table 51.

TABLE 259

This table contains 220 compounds of the following type,

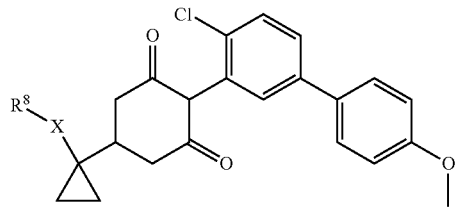

where X and R⁸ are as defined in Table 51.

TABLE 260

This table contains 220 compounds of the following type,

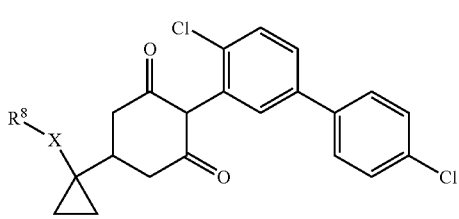

where X and R⁸ are as defined in Table 51.

TABLE 261

This table contains 220 compounds of the following type,

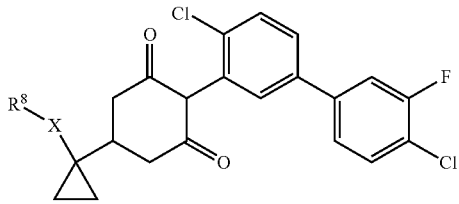

where X and R⁸ are as defined in Table 51.

TABLE 262

This table contains 220 compounds of the following type,

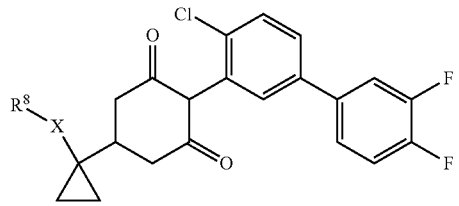

where X and R⁸ are as defined in Table 51.

TABLE 263

This table contains 220 compounds of the following type,

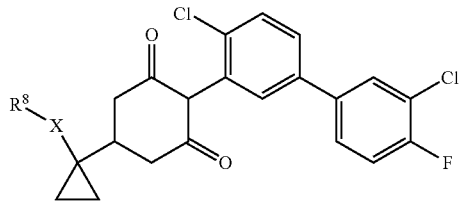

where X and R⁸ are as defined in Table 51.

TABLE 264

This table contains 220 compounds of the following type,

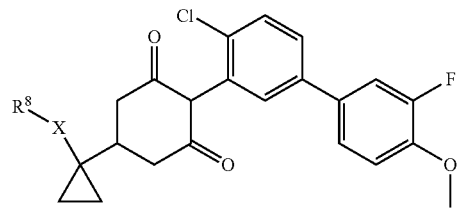

where X and R⁸ are as defined in Table 51.

TABLE 265

This table contains 220 compounds of the following type,

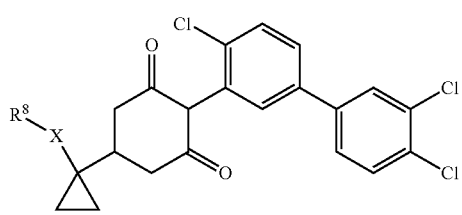

where X and R⁸ are as defined in Table 51.

TABLE 266

This table contains 220 compounds of the following type,

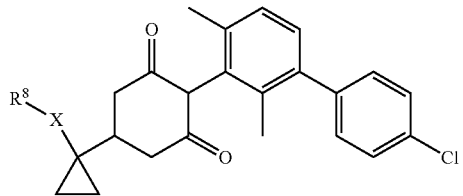

where X and R⁸ are as defined in Table 51.

TABLE 267

This table contains 220 compounds of the following type,

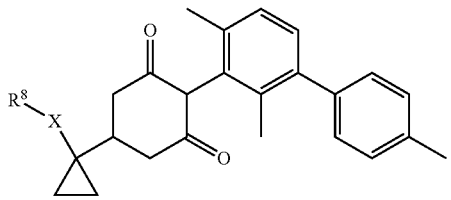

where X and R⁸ are as defined in Table 51.

TABLE 268

This table contains 220 compounds of the following type,

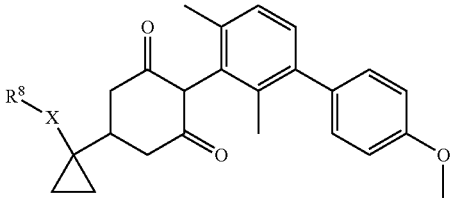

where X and R⁸ are as defined in Table 51.

TABLE 269

This table contains 220 compounds of the following type,

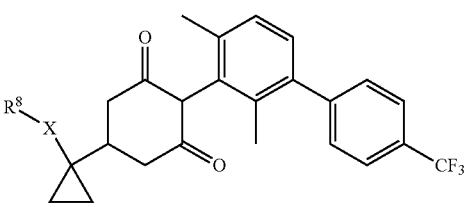

where X and R⁸ are as defined in Table 51.

TABLE 270

This table contains 220 compounds of the following type,

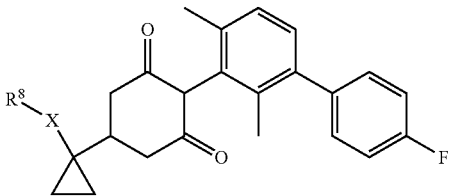

where X and R⁸ are as defined in Table 51.

TABLE 271

This table contains 220 compounds of the following type,

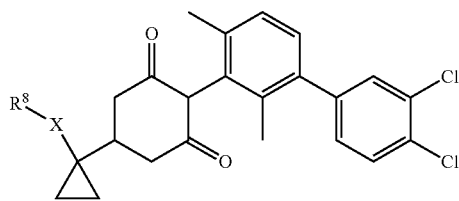

where X and R⁸ are as defined in Table 51.

TABLE 272

This table contains 220 compounds of the following type,

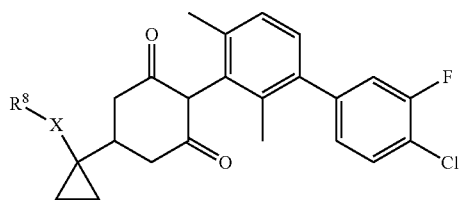

where X and R⁸ are as defined in Table 51.

TABLE 273

This table contains 220 compounds of the following type,

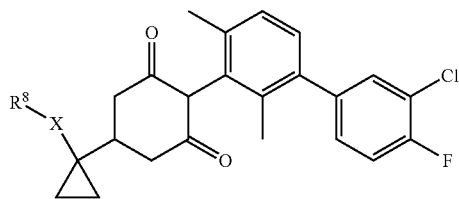

where X and R⁸ are as defined in Table 51.

TABLE 274

This table contains 220 compounds of the following type,

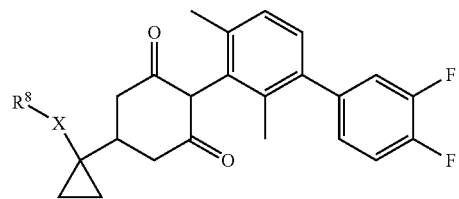

where X and R⁸ are as defined in Table 51.

TABLE 275

This table contains 220 compounds of the following type,

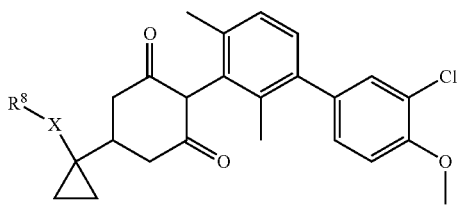

where X and R⁸ are as defined in Table 51.

TABLE 276

This table contains 220 compounds of the following type,

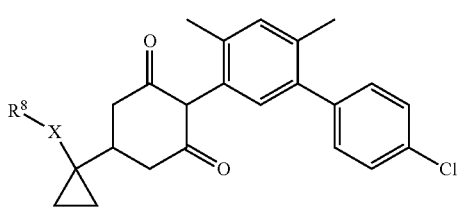

where X and R⁸ are as defined in Table 51.

TABLE 277

This table contains 220 compounds of the following type,

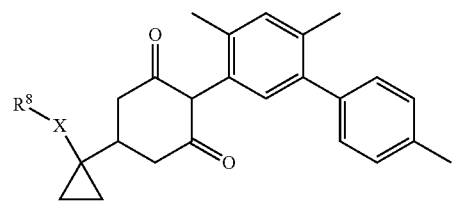

where X and R⁸ are as defined in Table 51.

TABLE 278

This table contains 220 compounds of the following type,

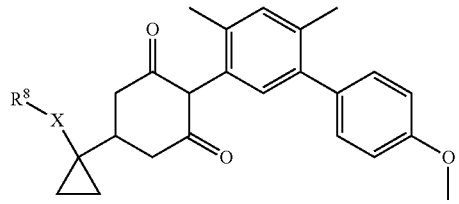

where X and R⁸ are as defined in Table 51.

TABLE 279

This table contains 220 compounds of the following type,

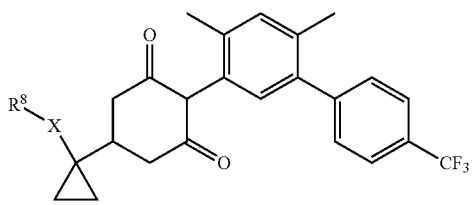

where X and R⁸ are as defined in Table 51.

TABLE 280

This table contains 220 compounds of the following type,

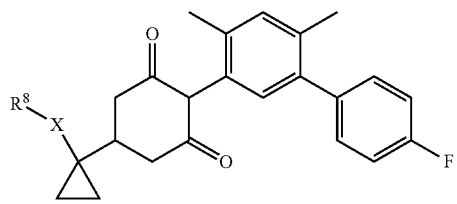

where X and R⁸ are as defined in Table 51.

TABLE 281

This table contains 220 compounds of the following type,

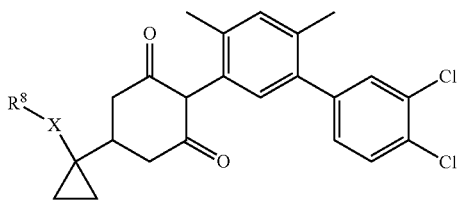

where X and R⁸ are as defined in Table 51.

TABLE 282

This table contains 220 compounds of the following type,

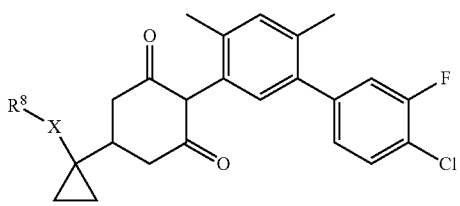

where X and R⁸ are as defined in Table 51.

TABLE 283

This table contains 220 compounds of the following type,

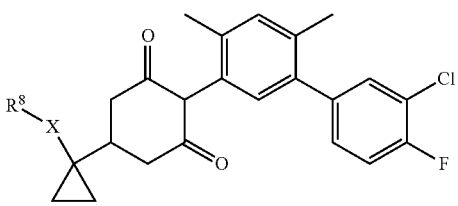

where X and R⁸ are as defined in Table 51.

TABLE 284

This table contains 220 compounds of the following type,

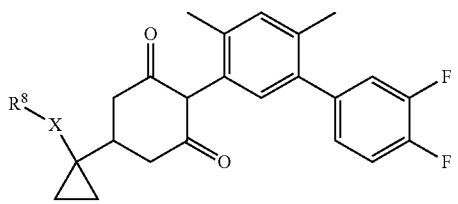

where X and R⁸ are as defined in Table 51.

TABLE 285

This table contains 220 compounds of the following type,

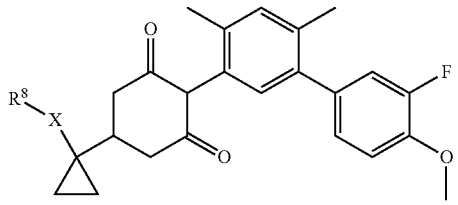

where X and R⁸ are as defined in Table 51.

TABLE 286

This table contains 220 compounds of the following type,

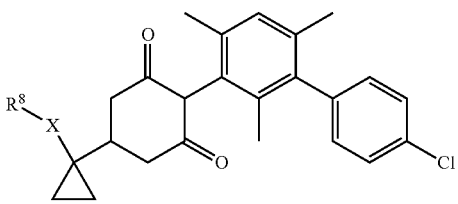

where X and R⁸ are as defined in Table 51.

TABLE 287

This table contains 220 compounds of the following type,

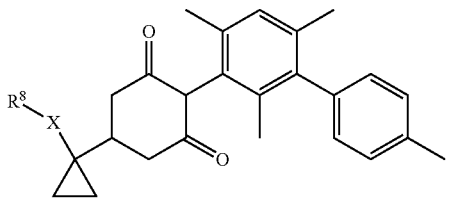

where X and R⁸ are as defined in Table 51.

TABLE 288

This table contains 220 compounds of the following type,

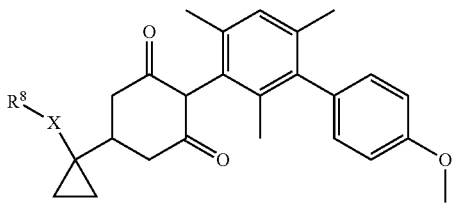

where X and R⁸ are as defined in Table 51.

TABLE 289

This table contains 220 compounds of the following type,

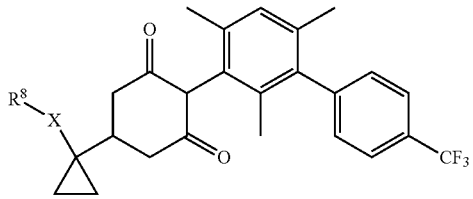

where X and R⁸ are as defined in Table 51.

TABLE 290

This table contains 220 compounds of the following type,

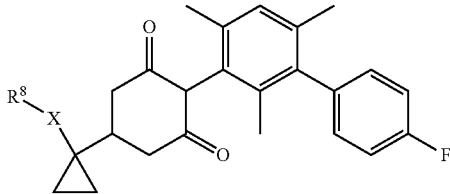

where X and R⁸ are as defined in Table 51.

TABLE 291

This table contains 220 compounds of the following type,

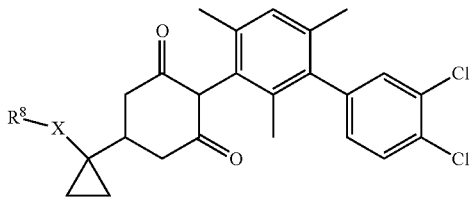

where X and R⁸ are as defined in Table 51.

TABLE 292

This table contains 220 compounds of the following type,

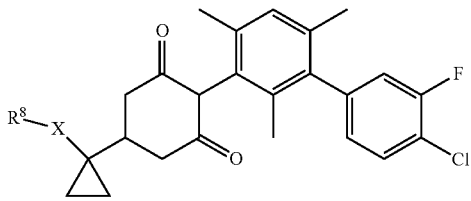

where X and R⁸ are as defined in Table 51.

TABLE 293

This table contains 220 compounds of the following type,

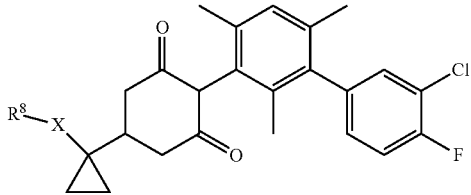

where X and R⁸ are as defined in Table 51.

TABLE 294

This table contains 220 compounds of the following type,

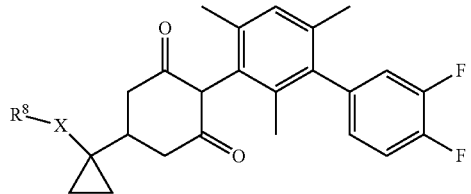

where X and R⁸ are as defined in Table 51.

TABLE 295

This table contains 220 compounds of the following type,

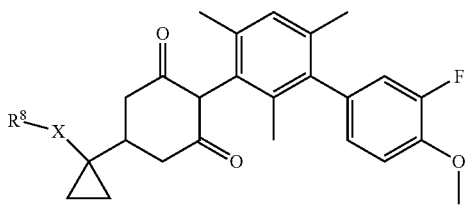

where X and R⁸ are as defined in Table 51.

TABLE 296

This table contains 12 compounds of the following type,

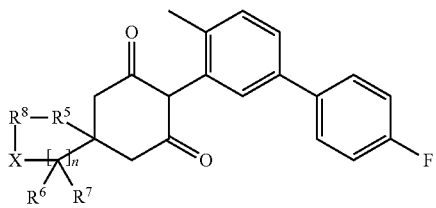

where n, X, R⁵, R⁶, R⁷ and R⁸ are as defined in Table 76.

TABLE 297

This table contains 12 compounds of the following type,

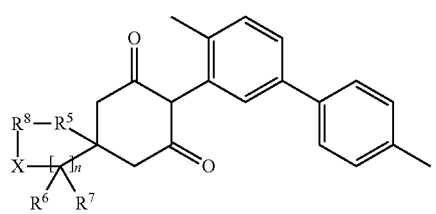

where n, X, R⁵, R⁶, R⁷ and R⁸ are as defined in Table 76.

TABLE 298

This table contains 12 compounds of the following type,

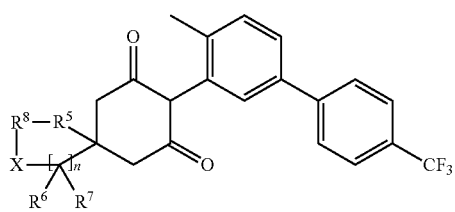

where n, X, R⁵, R⁶, R⁷ and R⁸ are as defined in Table 76.

TABLE 299

This table contains 12 compounds of the following type,

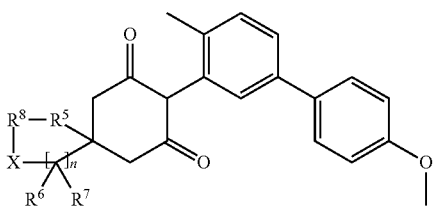

where n, X, R⁵, R⁶, R⁷ and R⁸ are as defined in Table 76.

TABLE 300

This table contains 12 compounds of the following type,

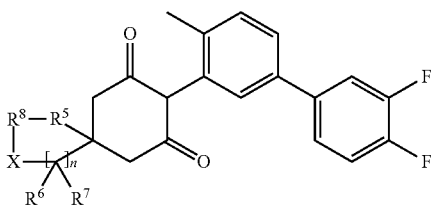

where n, X, R⁵, R⁶, R⁷ and R⁸ are as defined in Table 76.

TABLE 301

This table contains 12 compounds of the following type,

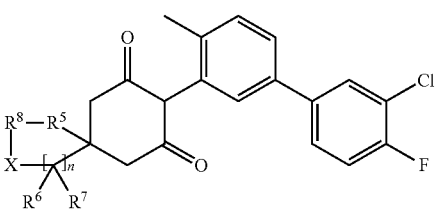

where n, X, R⁵, R⁶, R⁷ and R⁸ are as defined in Table 76.

TABLE 302

This table contains 12 compounds of the following type,

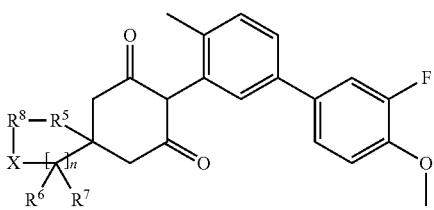

where n, X, R⁵, R⁶, R⁷ and R⁸ are as defined in Table 76.

TABLE 303

This table contains 12 compounds of the following type,

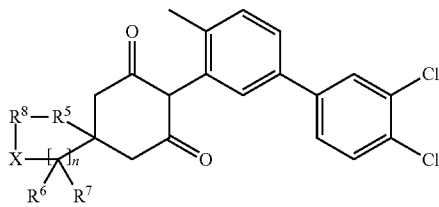

where n, X, $R^5$, $R^6$, $R^7$ and $R^8$ are as defined in Table 76.

TABLE 304

This table contains 12 compounds of the following type,

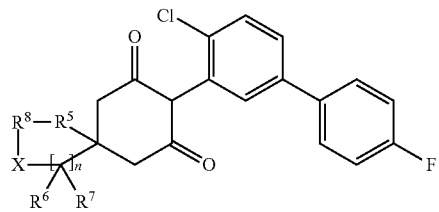

where n, X, $R^5$, $R^6$, $R^7$ and $R^8$ are as defined in Table 76.

TABLE 305

This table contains 12 compounds of the following type,

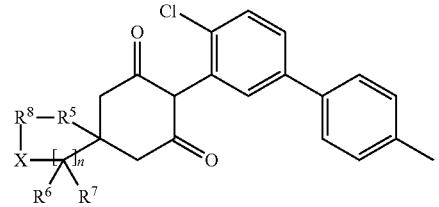

where n, X, $R^5$, $R^6$, $R^7$ and $R^8$ are as defined in Table 76.

TABLE 306

This table contains 12 compounds of the following type,

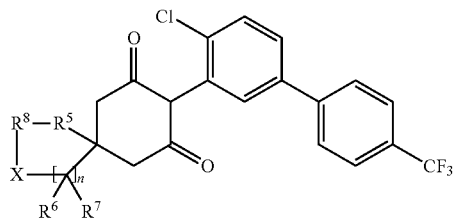

where n, X, $R^5$, $R^6$, $R^7$ and $R^8$ are as defined in Table 76.

TABLE 307

This table contains 12 compounds of the following type,

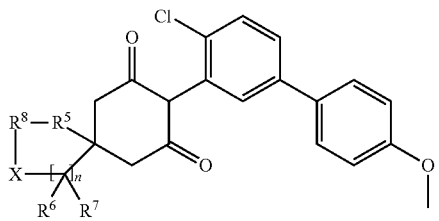

where n, X, $R^5$, $R^6$, $R^7$ and $R^8$ are as defined in Table 76.

TABLE 308

This table contains 12 compounds of the following type,

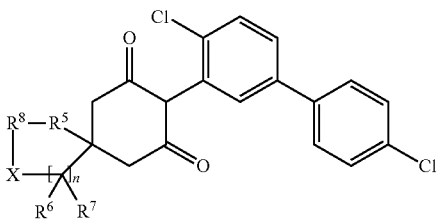

where n, X, $R^5$, $R^6$, $R^7$ and $R^8$ are as defined in Table 76.

TABLE 309

This table contains 12 compounds of the following type,

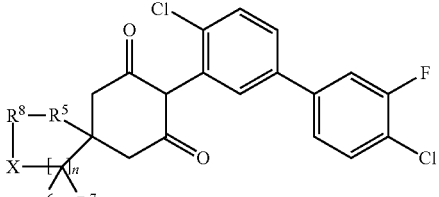

where n, X, $R^5$, $R^6$, $R^7$ and $R^8$ are as defined in Table 76.

TABLE 310

This table contains 12 compounds of the following type,

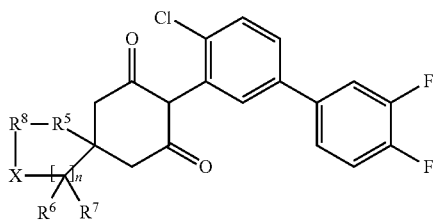

where n, X, $R^5$, $R^6$, $R^7$ and $R^8$ are as defined in Table 76.

TABLE 311

This table contains 12 compounds of the following type,

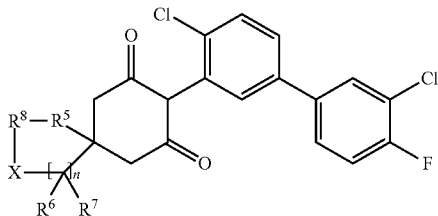

where n, X, $R^5$, $R^6$, $R^7$ and $R^8$ are as defined in Table 76.

TABLE 312

This table contains 12 compounds of the following type,

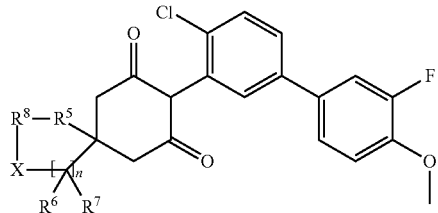

where n, X, $R^5$, $R^6$, $R^7$ and $R^8$ are as defined in Table 76.

TABLE 313

This table contains 12 compounds of the following type,

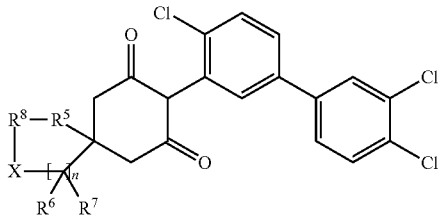

where n, X, $R^5$, $R^6$, $R^7$ and $R^8$ are as defined in Table 76.

TABLE 314

This table contains 12 compounds of the following type,

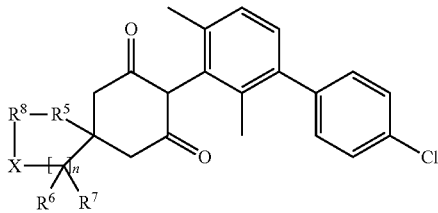

where n, X, $R^5$, $R^6$, $R^7$ and $R^8$ are as defined in Table 76.

TABLE 315

This table contains 12 compounds of the following type,

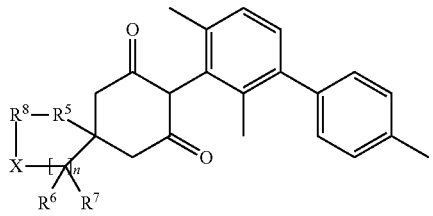

where n, X, $R^5$, $R^6$, $R^7$ and $R^8$ are as defined in Table 76.

TABLE 316

This table contains 12 compounds of the following type,

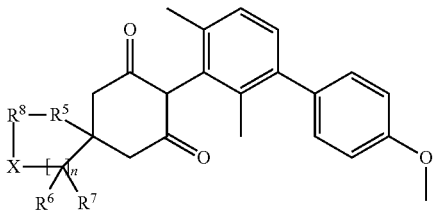

where n, X, $R^5$, $R^6$, $R^7$ and $R^8$ are as defined in Table 76.

TABLE 317

This table contains 12 compounds of the following type,

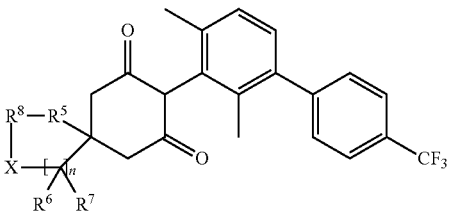

where n, X, $R^5$, $R^6$, $R^7$ and $R^8$ are as defined in Table 76.

TABLE 318

This table contains 12 compounds of the following type,

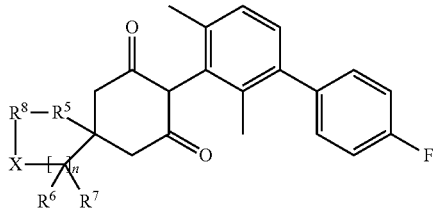

where n, X, $R^5$, $R^6$, $R^7$ and $R^8$ are as defined in Table 76.

TABLE 319

This table contains 12 compounds of the following type, where n, X, $R^5$, $R^6$, $R^7$ and $R^8$ are as defined in Table 76.

TABLE 320

This table contains 12 compounds of the following type, where n, X, $R^5$, $R^6$, $R^7$ and $R^8$ are as defined in Table 76.

TABLE 321

This table contains 12 compounds of the following type, where n, X, $R^5$, $R^6$, $R^7$ and $R^8$ are as defined in Table 76.

TABLE 322

This table contains 12 compounds of the following type, where n, X, $R^5$, $R^6$, $R^7$ and $R^8$ are as defined in Table 76.

TABLE 323

This table contains 12 compounds of the following type, where n, X, $R^5$, $R^6$, $R^7$ and $R^8$ are as defined in Table 76.

TABLE 324

This table contains 12 compounds of the following type, where n, X, $R^5$, $R^6$, $R^7$ and $R^8$ are as defined in Table 76.

TABLE 325

This table contains 12 compounds of the following type, where n, X, $R^5$, $R^6$, $R^7$ and $R^8$ are as defined in Table 76.

TABLE 326

This table contains 12 compounds of the following type, where n, X, $R^5$, $R^6$, $R^7$ and $R^8$ are as defined in Table 76.

TABLE 327

This table contains 12 compounds of the following type,

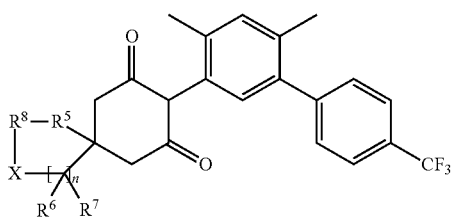

where n, X, $R^5$, $R^6$, $R^7$ and $R^8$ are as defined in Table 76.

TABLE 328

This table contains 12 compounds of the following type,

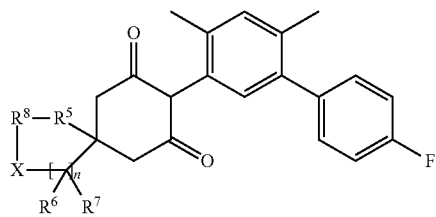

where n, X, $R^5$, $R^6$, $R^7$ and $R^8$ are as defined in Table 76.

TABLE 329

This table contains 12 compounds of the following type,

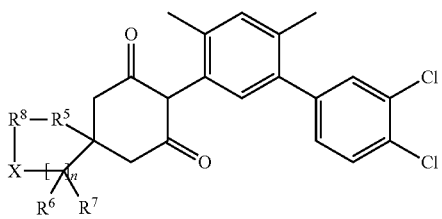

where n, X, $R^5$, $R^6$, $R^7$ and $R^8$ are as defined in Table 76.

TABLE 330

This table contains 12 compounds of the following type,

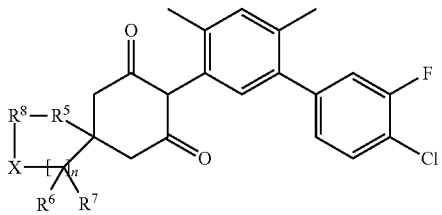

where n, X, $R^5$, $R^6$, $R^7$ and $R^8$ are as defined in Table 76.

TABLE 331

This table contains 12 compounds of the following type,

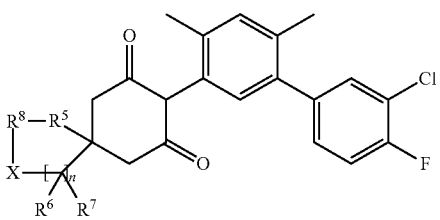

where n, X, $R^5$, $R^6$, $R^7$ and $R^8$ are as defined in Table 76.

TABLE 332

This table contains 12 compounds of the following type,

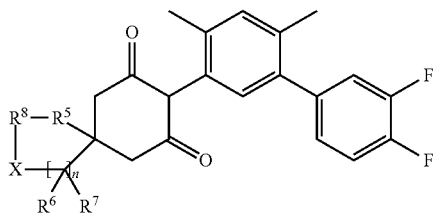

where n, X, $R^5$, $R^6$, $R^7$ and $R^8$ are as defined in Table 76.

TABLE 333

This table contains 12 compounds of the following type,

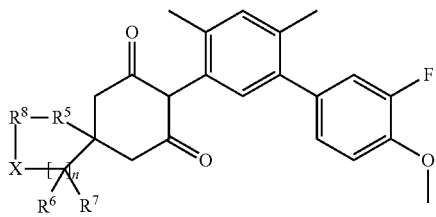

where n, X, $R^5$, $R^6$, $R^7$ and $R^8$ are as defined in Table 76.

TABLE 334

This table contains 12 compounds of the following type,

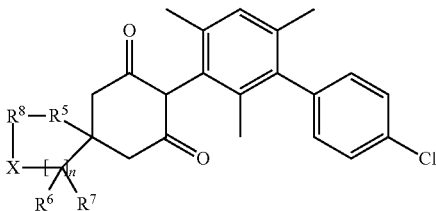

where n, X, $R^5$, $R^6$, $R^7$ and $R^8$ are as defined in Table 76.

TABLE 335

This table contains 12 compounds of the following type,

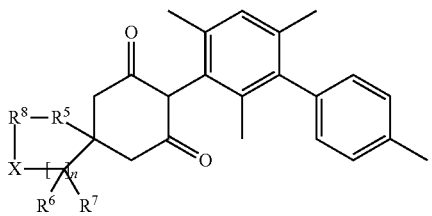

where n, X, $R^5$, $R^6$, $R^7$ and $R^8$ are as defined in Table 76.

TABLE 336

This table contains 12 compounds of the following type,

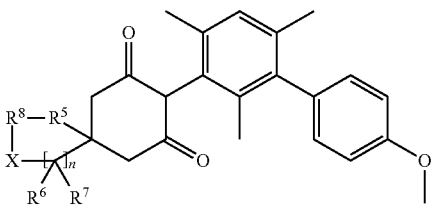

where n, X, $R^5$, $R^6$, $R^7$ and $R^8$ are as defined in Table 76.

TABLE 337

This table contains 12 compounds of the following type,

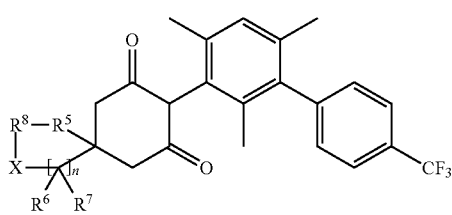

where n, X, $R^5$, $R^6$, $R^7$ and $R^8$ are as defined in Table 76.

TABLE 338

This table contains 12 compounds of the following type,

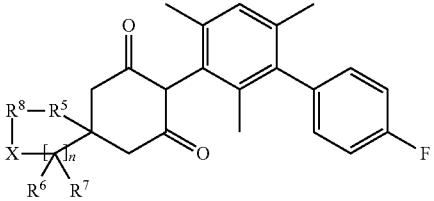

where n, X, $R^5$, $R^6$, $R^7$ and $R^8$ are as defined in Table 76.

TABLE 339

This table contains 12 compounds of the following type,

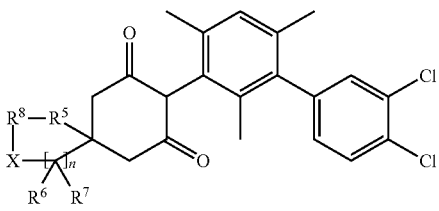

where n, X, $R^5$, $R^6$, $R^7$ and $R^8$ are as defined in Table 76.

TABLE 340

This table contains 12 compounds of the following type,

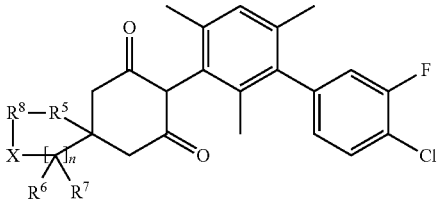

where n, X, $R^5$, $R^6$, $R^7$ and $R^8$ are as defined in Table 76.

TABLE 341

This table contains 12 compounds of the following type,

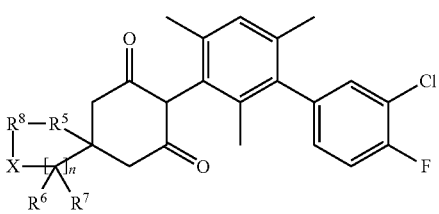

where n, X, $R^5$, $R^6$, $R^7$ and $R^8$ are as defined in Table 76.

TABLE 342

This table contains 12 compounds of the following type,

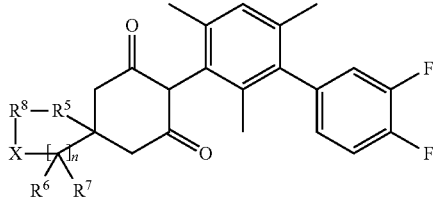

where n, X, $R^5$, $R^6$, $R^7$ and $R^8$ are as defined in Table 76.

TABLE 343

This table contains 12 compounds of the following type,

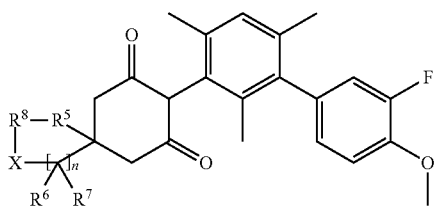

where n, X, $R^5$, $R^6$, $R^7$ and $R^8$ are as defined in Table 76.

TABLE 344

This table contains 12 compounds of the following type,

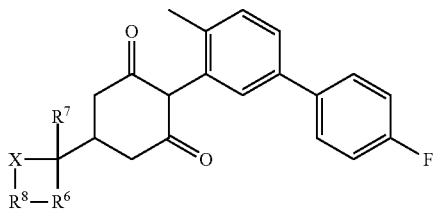

where X, $R^6$, $R^7$ and $R^8$ are as defined in Table 101.

TABLE 345

This table contains 12 compounds of the following type,

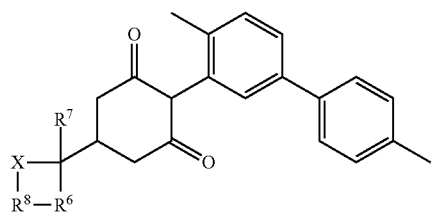

where X, $R^6$, $R^7$ and $R^8$ are as defined in Table 101.

TABLE 346

This table contains 12 compounds of the following type,

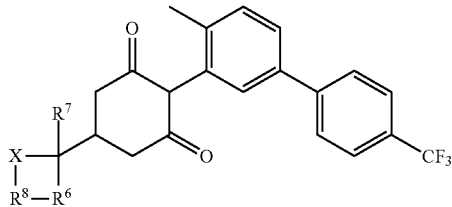

where X, $R^6$, $R^7$ and $R^8$ are as defined in Table 101.

TABLE 347

This table contains 12 compounds of the following type,

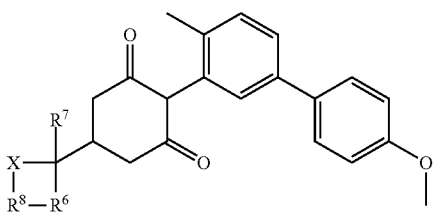

where X, $R^6$, $R^7$ and $R^8$ are as defined in Table 101.

TABLE 348

This table contains 12 compounds of the following type,

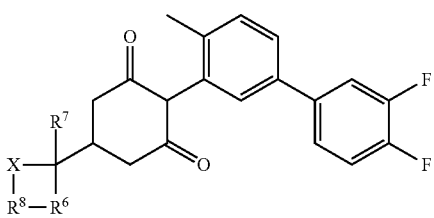

where X, $R^6$, $R^7$ and $R^8$ are as defined in Table 101.

TABLE 349

This table contains 12 compounds of the following type,

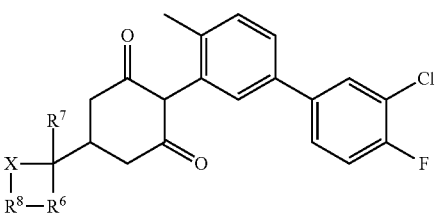

where X, $R^6$, $R^7$ and $R^8$ are as defined in Table 101.

TABLE 350

This table contains 12 compounds of the following type,

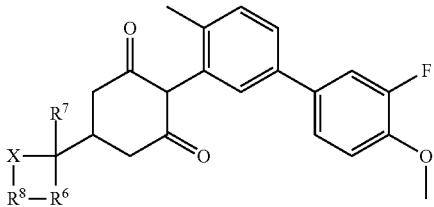

where X, $R^6$, $R^7$ and $R^8$ are as defined in Table 101.

TABLE 351

This table contains 12 compounds of the following type,

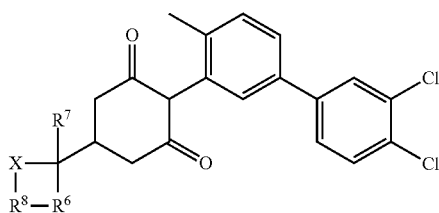

where X, $R^6$, $R^7$ and $R^8$ are as defined in Table 101.

TABLE 352

This table contains 12 compounds of the following type,

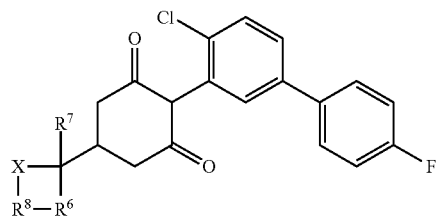

where X, $R^6$, $R^7$ and $R^8$ are as defined in Table 101.

TABLE 353

This table contains 12 compounds of the following type,

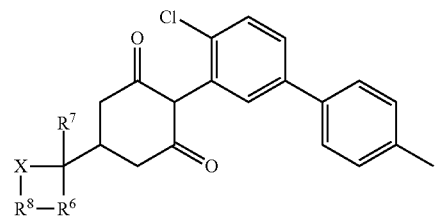

where X, $R^6$, $R^7$ and $R^8$ are as defined in Table 101.

TABLE 354

This table contains 12 compounds of the following type,

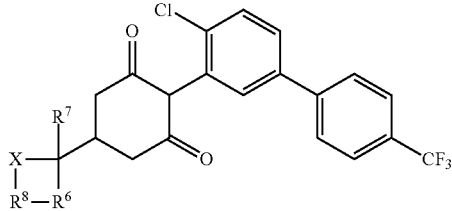

where X, $R^6$, $R^7$ and $R^8$ are as defined in Table 101.

TABLE 355

This table contains 12 compounds of the following type,

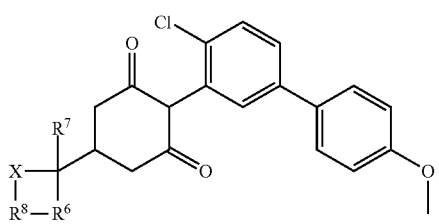

where X, $R^6$, $R^7$ and $R^8$ are as defined in Table 101.

TABLE 356

This table contains 12 compounds of the following type,

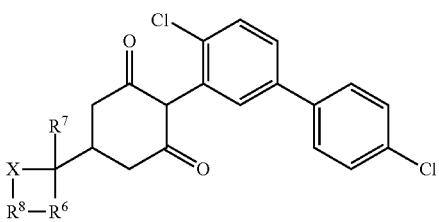

where X, $R^6$, $R^7$ and $R^8$ are as defined in Table 101.

TABLE 357

This table contains 12 compounds of the following type,

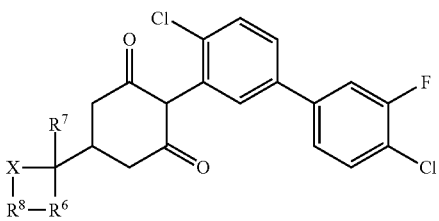

where X, $R^6$, $R^7$ and $R^8$ are as defined in Table 101.

TABLE 358

This table contains 12 compounds of the following type,

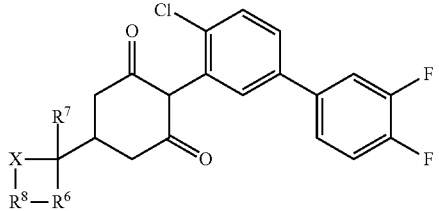

where X, $R^6$, $R^7$ and $R^8$ are as defined in Table 101.

TABLE 359

This table contains 12 compounds of the following type,

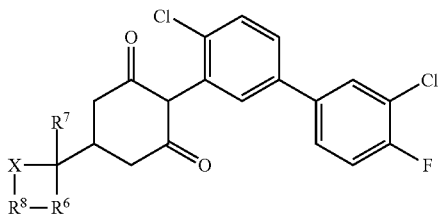

where X, $R^6$, $R^7$ and $R^8$ are as defined in Table 101.

TABLE 360

This table contains 12 compounds of the following type,

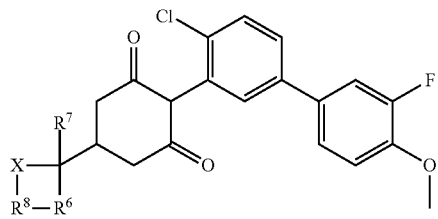

where X, $R^6$, $R^7$ and $R^8$ are as defined in Table 101.

TABLE 361

This table contains 12 compounds of the following type,

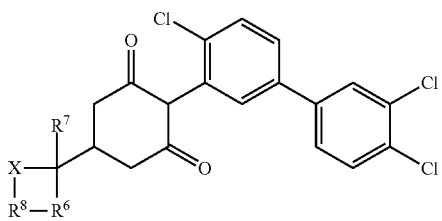

where X, $R^6$, $R^7$ and $R^8$ are as defined in Table 101.

TABLE 362

This table contains 12 compounds of the following type,

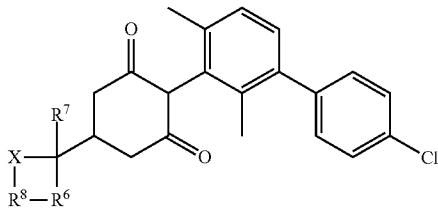

where X, $R^6$, $R^7$ and $R^8$ are as defined in Table 101.

TABLE 363

This table contains 12 compounds of the following type,

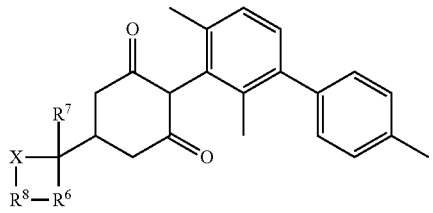

where X, $R^6$, $R^7$ and $R^8$ are as defined in Table 101.

TABLE 364

This table contains 12 compounds of the following type,

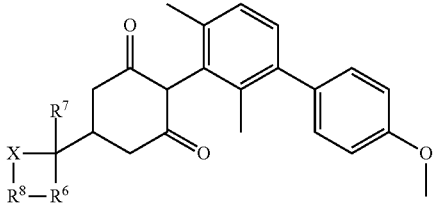

where X, $R^6$, $R^7$ and $R^8$ are as defined in Table 101.

TABLE 365

This table contains 12 compounds of the following type,

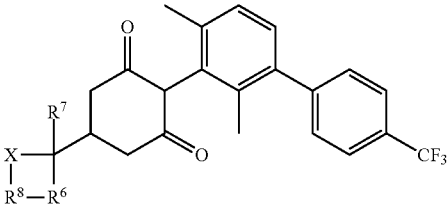

where X, $R^6$, $R^7$ and $R^8$ are as defined in Table 101.

TABLE 366

This table contains 12 compounds of the following type,

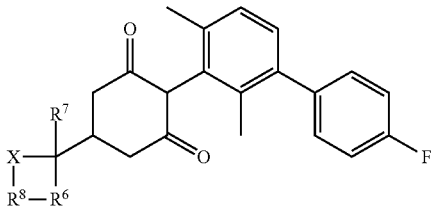

where X, $R^6$, $R^7$ and $R^8$ are as defined in Table 101.

TABLE 367

This table contains 12 compounds of the following type,

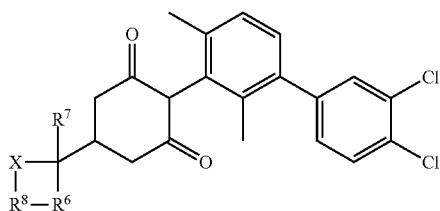

where X, $R^6$, $R^7$ and $R^8$ are as defined in Table 101.

TABLE 368

This table contains 12 compounds of the following type,

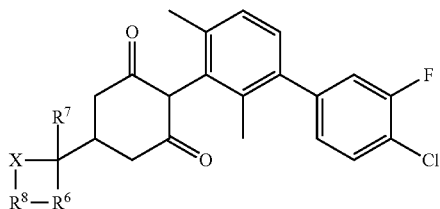

where X, $R^6$, $R^7$ and $R^8$ are as defined in Table 101.

TABLE 369

This table contains 12 compounds of the following type,

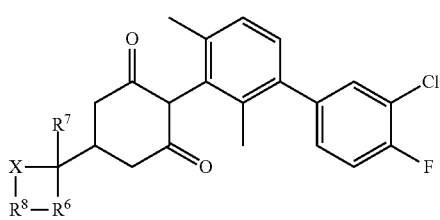

where X, $R^6$, $R^7$ and $R^8$ are as defined in Table 101.

TABLE 370

This table contains 12 compounds of the following type,

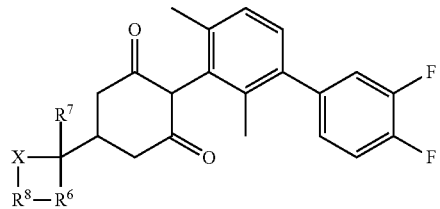

where X, $R^6$, $R^7$ and $R^8$ are as defined in Table 101.

TABLE 371

This table contains 12 compounds of the following type,

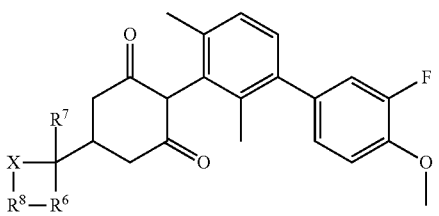

where X, $R^6$, $R^7$ and $R^8$ are as defined in Table 101.

TABLE 372

This table contains 12 compounds of the following type,

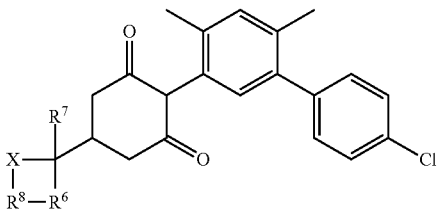

where X, $R^6$, $R^7$ and $R^8$ are as defined in Table 101.

TABLE 373

This table contains 12 compounds of the following type,

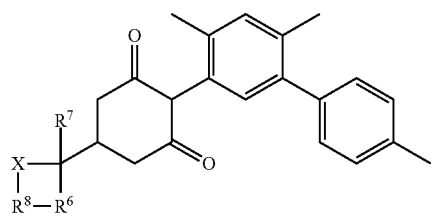

where X, $R^6$, $R^7$ and $R^8$ are as defined in Table 101.

TABLE 374

This table contains 12 compounds of the following type,

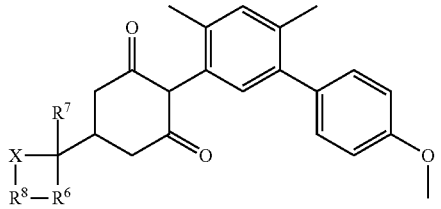

where X, $R^6$, $R^7$ and $R^8$ are as defined in Table 101.

TABLE 375

This table contains 12 compounds of the following type,

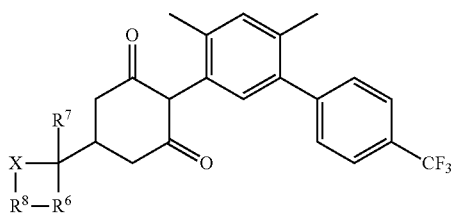

where X, $R^6$, $R^7$ and $R^8$ are as defined in Table 101.

TABLE 376

This table contains 12 compounds of the following type,

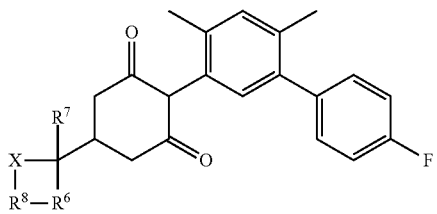

where X, $R^6$, $R^7$ and $R^8$ are as defined in Table 101.

TABLE 377

This table contains 12 compounds of the following type,

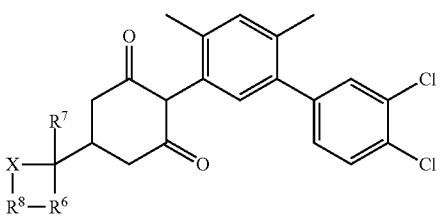

where X, $R^6$, $R^7$ and $R^8$ are as defined in Table 101.

TABLE 378

This table contains 12 compounds of the following type,

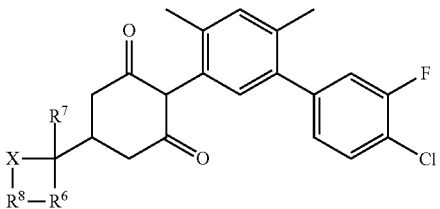

where X, $R^6$, $R^7$ and $R^8$ are as defined in Table 101.

TABLE 379

This table contains 12 compounds of the following type,

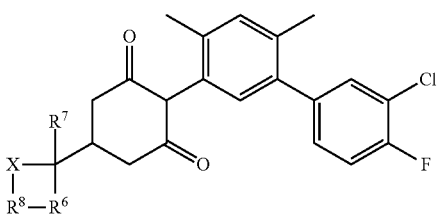

where X, $R^6$, $R^7$ and $R^8$ are as defined in Table 101.

TABLE 380

This table contains 12 compounds of the following type,

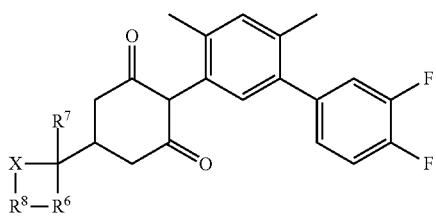

where X, $R^6$, $R^7$ and $R^8$ are as defined in Table 101.

TABLE 381

This table contains 12 compounds of the following type,

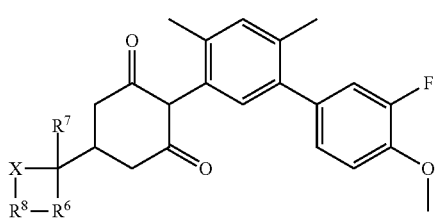

where X, $R^6$, $R^7$ and $R^8$ are as defined in Table 101.

TABLE 382

This table contains 12 compounds of the following type,

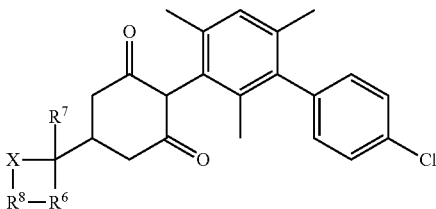

where X, $R^6$, $R^7$ and $R^8$ are as defined in Table 101.

TABLE 383

This table contains 12 compounds of the following type,

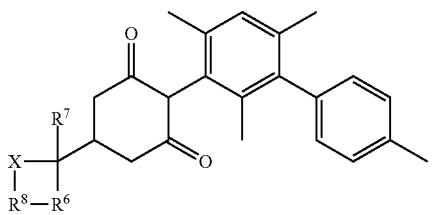

where X, $R^6$, $R^7$ and $R^8$ are as defined in Table 101.

TABLE 384

This table contains 12 compounds of the following type,

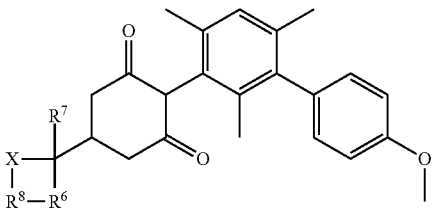

where X, $R^6$, $R^7$ and $R^8$ are as defined in Table 101.

TABLE 385

This table contains 12 compounds of the following type,

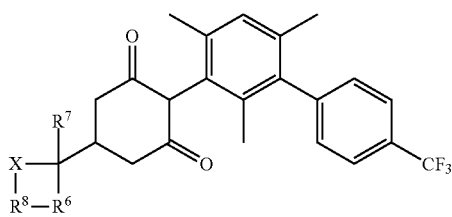

where X, $R^6$, $R^7$ and $R^8$ are as defined in Table 101.

TABLE 386

This table contains 12 compounds of the following type,

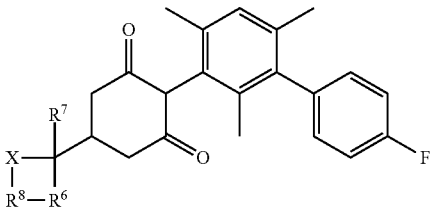

where X, $R^6$, $R^7$ and $R^8$ are as defined in Table 101.

TABLE 387

This table contains 12 compounds of the following type,

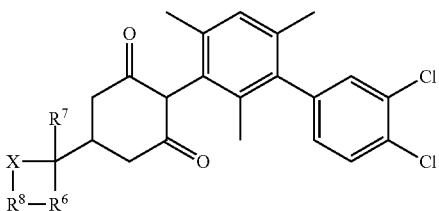

where X, $R^6$, $R^7$ and $R^8$ are as defined in Table 101.

TABLE 388

This table contains 12 compounds of the following type,

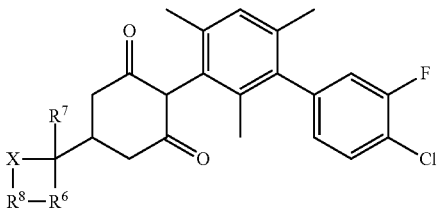

where X, $R^6$, $R^7$ and $R^8$ are as defined in Table 101.

TABLE 389

This table contains 12 compounds of the following type,

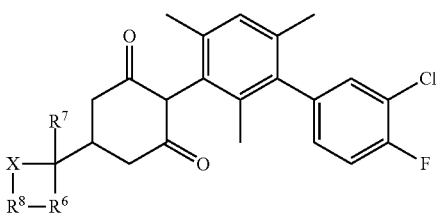

where X, $R^6$, $R^7$ and $R^8$ are as defined in Table 101.

TABLE 390

This table contains 12 compounds of the following type,

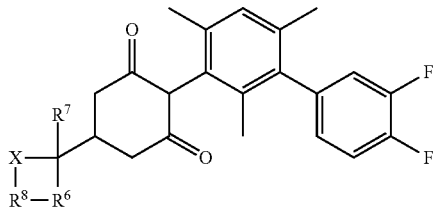

where X, $R^6$, $R^7$ and $R^8$ are as defined in Table 101.

TABLE 391

This table contains 12 compounds of the following type,

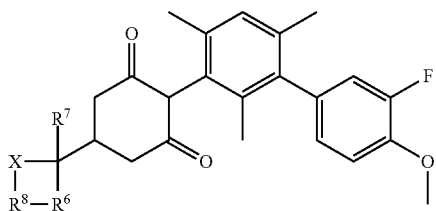

where X, $R^6$, $R^7$ and $R^8$ are as defined in Table 101.

TABLE 392

This table contains 16 compounds of the following type,

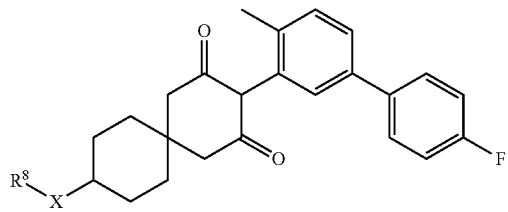

where n and $R^8$ are as defined in Table 126.

TABLE 393

This table contains 16 compounds of the following type,

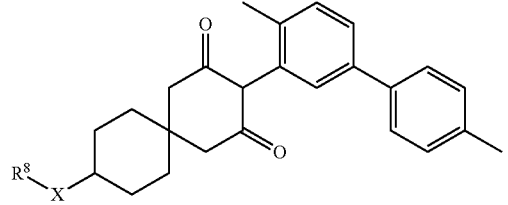

where n and $R^8$ are as defined in Table 126.

TABLE 394

This table contains 16 compounds of the following type,

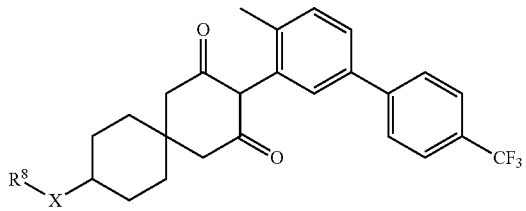

where n and $R^8$ are as defined in Table 126.

TABLE 395

This table contains 16 compounds of the following type,

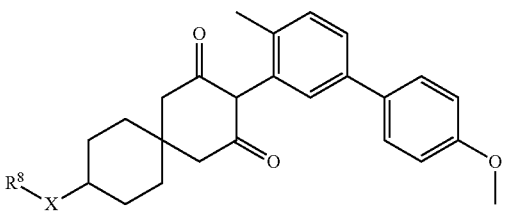

where n and $R^8$ are as defined in Table 126.

TABLE 396

This table contains 16 compounds of the following type,

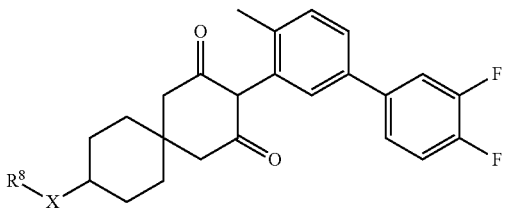

where n and $R^8$ are as defined in Table 126.

TABLE 397

This table contains 16 compounds of the following type,

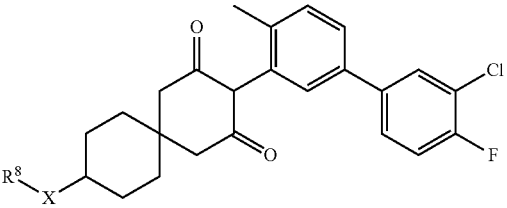

where n and $R^8$ are as defined in Table 126.

TABLE 398

This table contains 16 compounds of the following type,

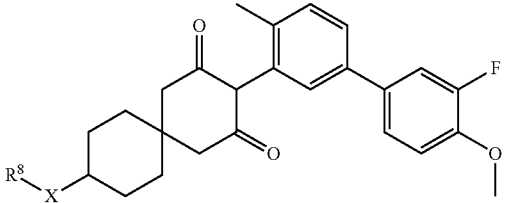

where n and $R^8$ are as defined in Table 126.

TABLE 399

This table contains 16 compounds of the following type,

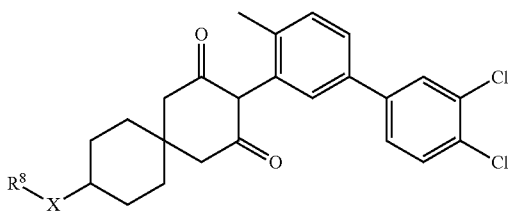

where n and $R^8$ are as defined in Table 126.

TABLE 400

This table contains 16 compounds of the following type,

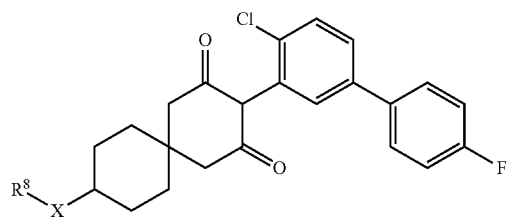

where n and $R^8$ are as defined in Table 126.

TABLE 401

This table contains 16 compounds of the following type,

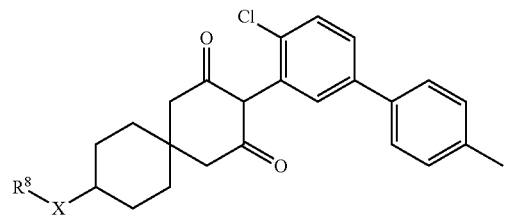

where n and $R^8$ are as defined in Table 126.

TABLE 402

This table contains 16 compounds of the following type,

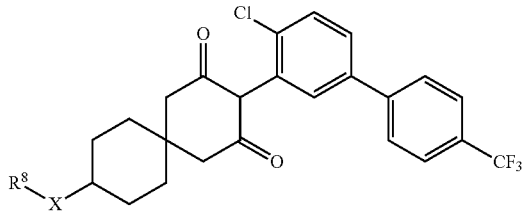

where n and $R^8$ are as defined in Table 126.

TABLE 403

This table contains 16 compounds of the following type,

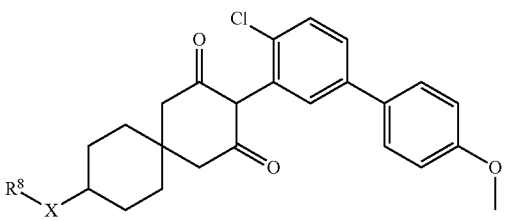

where n and $R^8$ are as defined in Table 126.

TABLE 404

This table contains 16 compounds of the following type,

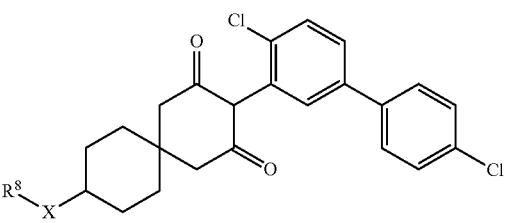

where n and $R^8$ are as defined in Table 126.

TABLE 405

This table contains 16 compounds of the following type,

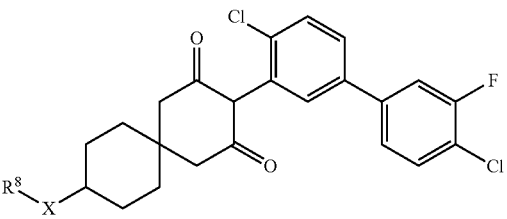

where n and $R^8$ are as defined in Table 126.

TABLE 406

This table contains 16 compounds of the following type,

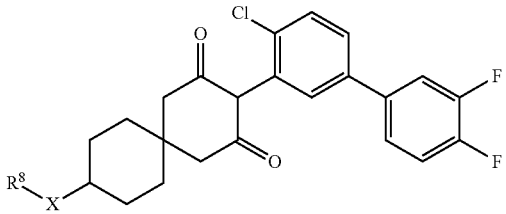

where n and $R^8$ are as defined in Table 126.

TABLE 407

This table contains 16 compounds of the following type,

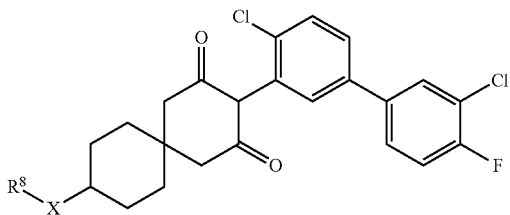

where n and R$^8$ are as defined in Table 126.

TABLE 408

This table contains 16 compounds of the following type,

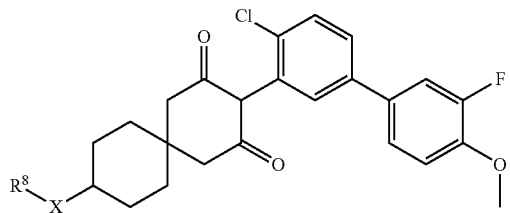

where n and R$^8$ are as defined in Table 126.

TABLE 409

This table contains 16 compounds of the following type,

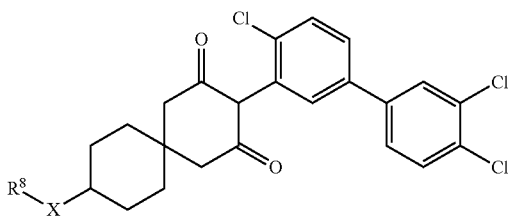

where n and R$^8$ are as defined in Table 126.

TABLE 410

This table contains 16 compounds of the following type,

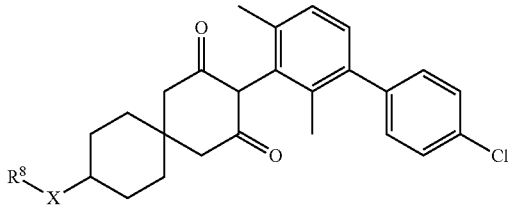

where n and R$^8$ are as defined in Table 126.

TABLE 411

This table contains 16 compounds of the following type,

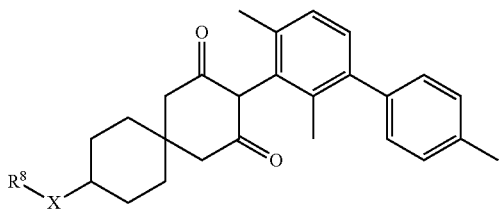

where n and R$^8$ are as defined in Table 126.

TABLE 412

This table contains 16 compounds of the following type,

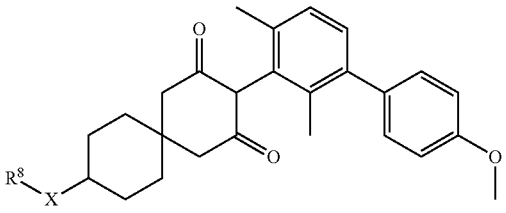

where n and R$^8$ are as defined in Table 126.

TABLE 413

This table contains 16 compounds of the following type,

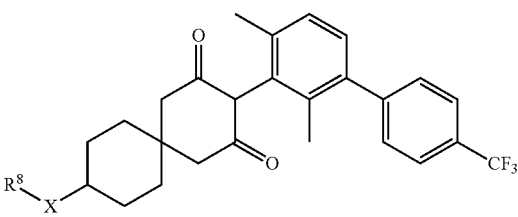

where n and R$^8$ are as defined in Table 126.

TABLE 414

This table contains 16 compounds of the following type,

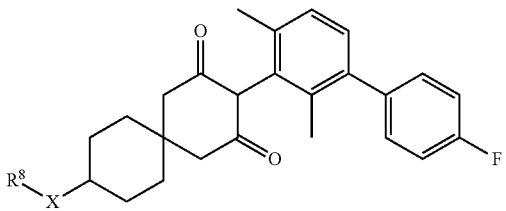

where n and R$^8$ are as defined in Table 126.

TABLE 415

This table contains 16 compounds of the following type,

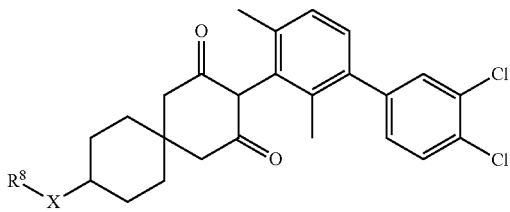

where n and R⁸ are as defined in Table 126.

TABLE 416

This table contains 16 compounds of the following type,

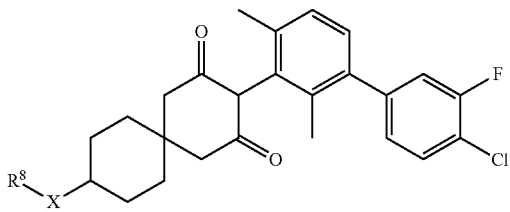

where n and R⁸ are as defined in Table 126.

TABLE 417

This table contains 16 compounds of the following type,

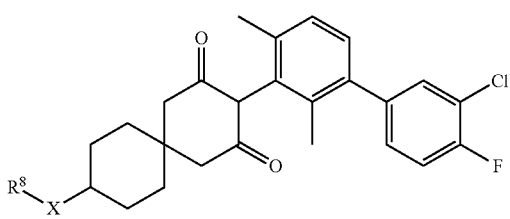

where n and R⁸ are as defined in Table 126.

TABLE 418

This table contains 16 compounds of the following type,

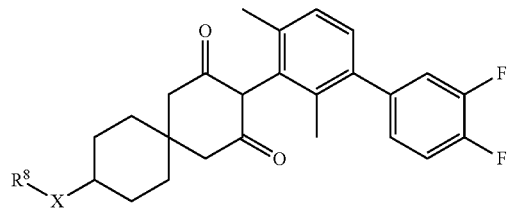

where n and R⁸ are as defined in Table 126.

TABLE 419

This table contains 16 compounds of the following type,

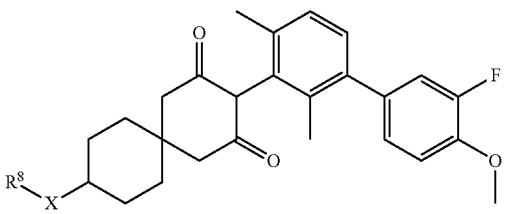

where n and R⁸ are as defined in Table 126.

TABLE 420

This table contains 16 compounds of the following type,

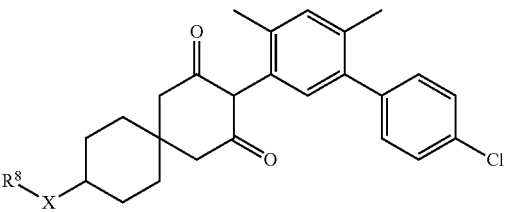

where n and R⁸ are as defined in Table 126.

TABLE 421

This table contains 16 compounds of the following type,

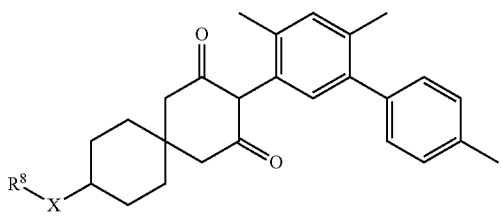

where n and R⁸ are as defined in Table 126.

TABLE 422

This table contains 16 compounds of the following type,

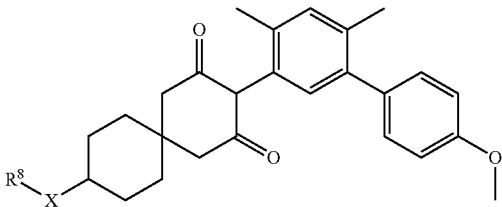

where n and R⁸ are as defined in Table 126.

TABLE 423

This table contains 16 compounds of the following type,

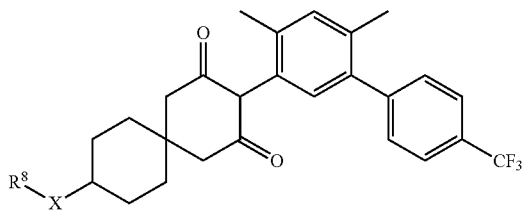

where n and R⁸ are as defined in Table 126.

TABLE 424

This table contains 16 compounds of the following type,

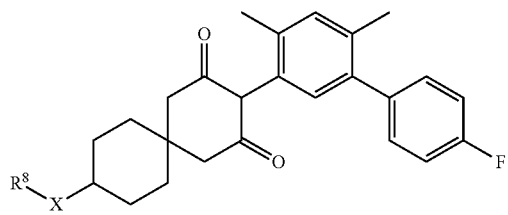

where n and R⁸ are as defined in Table 126.

TABLE 425

This table contains 16 compounds of the following type,

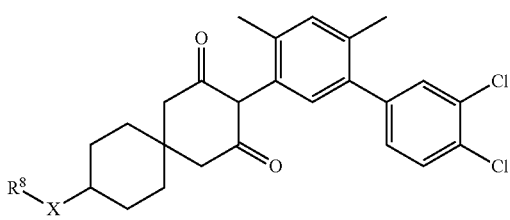

where n and R⁸ are as defined in Table 126.

TABLE 426

This table contains 16 compounds of the following type,

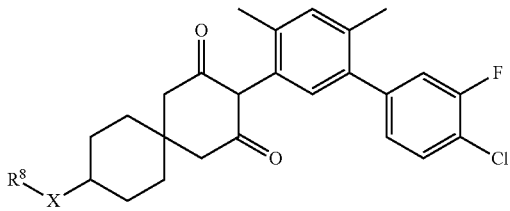

where n and R⁸ are as defined in Table 126.

TABLE 427

This table contains 16 compounds of the following type,

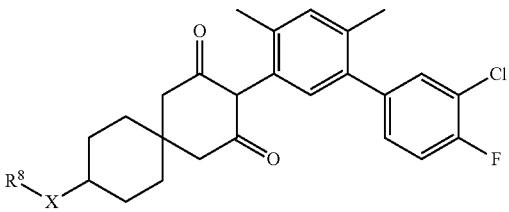

where n and R⁸ are as defined in Table 126.

TABLE 428

This table contains 16 compounds of the following type,

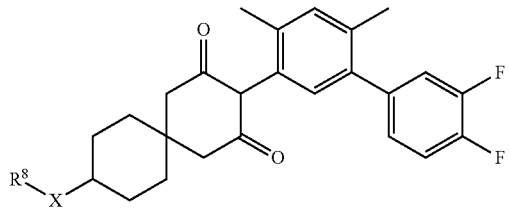

where n and R⁸ are as defined in Table 126.

TABLE 429

This table contains 16 compounds of the following type,

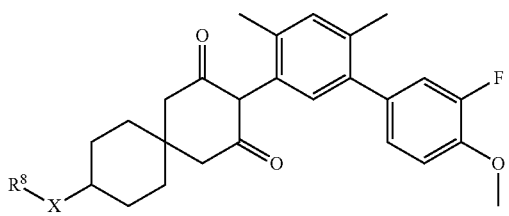

where n and R⁸ are as defined in Table 126.

TABLE 430

This table contains 16 compounds of the following type,

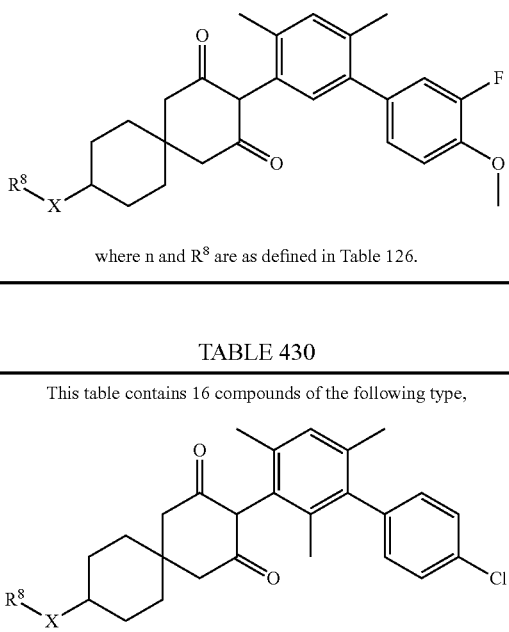

where n and R⁸ are as defined in Table 126.

TABLE 431

This table contains 16 compounds of the following type,

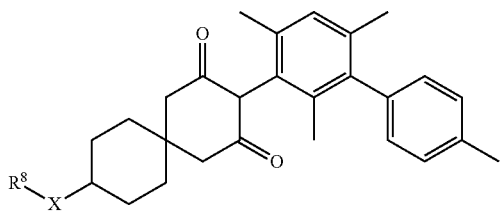

where n and R⁸ are as defined in Table 126.

TABLE 432

This table contains 16 compounds of the following type,

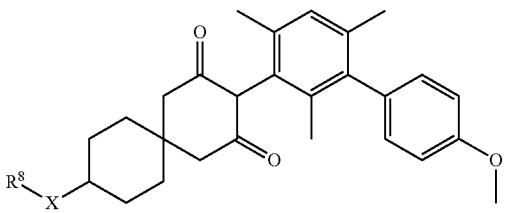

where n and R⁸ are as defined in Table 126.

TABLE 433

This table contains 16 compounds of the following type,

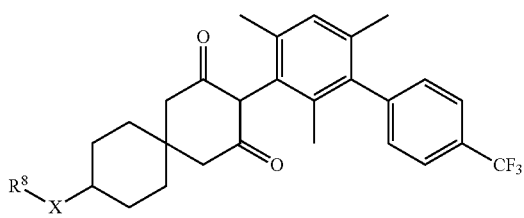

where n and R⁸ are as defined in Table 126.

TABLE 434

This table contains 16 compounds of the following type,

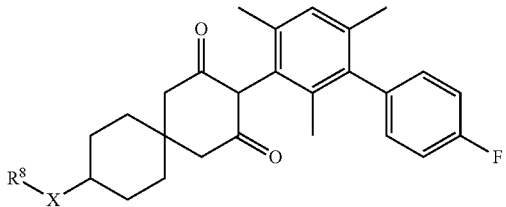

where n and R⁸ are as defined in Table 126.

TABLE 435

This table contains 16 compounds of the following type,

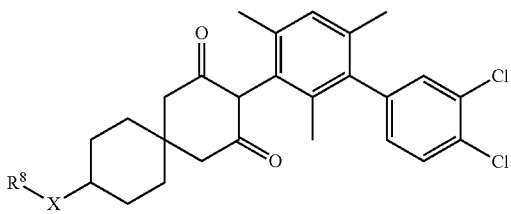

where n and R⁸ are as defined in Table 126.

TABLE 436

This table contains 16 compounds of the following type,

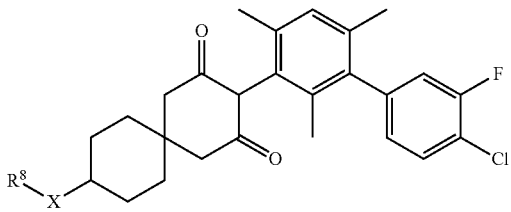

where n and R⁸ are as defined in Table 126.

TABLE 437

This table contains 16 compounds of the following type,

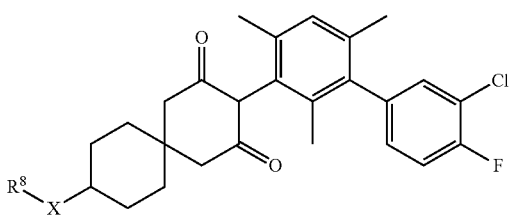

where n and R⁸ are as defined in Table 126.

TABLE 438

This table contains 16 compounds of the following type,

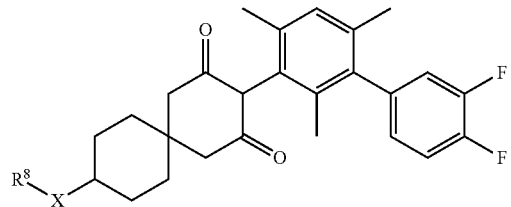

where n and R⁸ are as defined in Table 126.

TABLE 439
This table contains 16 compounds of the following type,
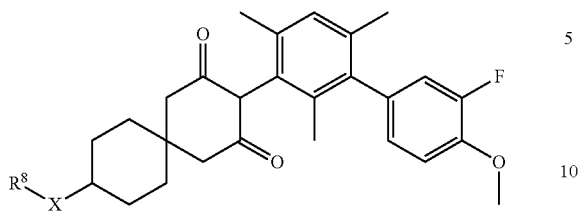
where n and R⁸ are as defined in Table 126.
TABLE T2
| Compound Number | Structure | ¹H nmr (CDCl₃ unless stated) or other physical data |
|---|---|---|
| P1 | 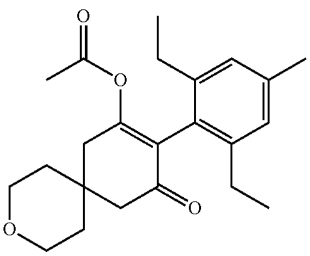 [SMILES: CCc1cc(C)cc(CC)c1C1=C(OC(C)=O)CC2(CCOCC2)CC1=O] | δ 6.99 (s, 2H), 3.75 (m, 4H), 2.80 (s, 2H), 2.64 (s, 2H), 2.35-2.28 (m, 7H), 1.89 (s, 3H), 1.74 (m, 4H), 1.07 (t, 6H) |
| P2 | 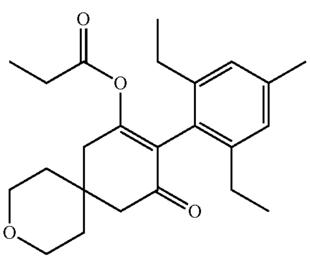 [SMILES: CCC(=O)OC1=C(c2c(CC)cc(C)cc2CC)C(=O)CC2(CCOCC2)C1] | δ 6.88 (s, 2H), 3.75 (m, 4H), 2.80 (s, 2H), 2.64 (s, 2H), 2.35-2.29 (m, 7H), 2.14 (q, 2H), 1.75 (m, 4H), 1.06 (t, 6H), 0.84 (t, 3H) |
| P3 | 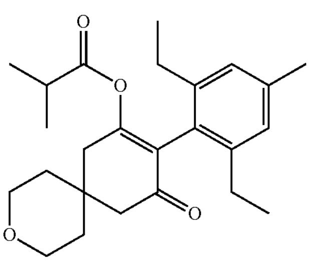 [SMILES: CCc1cc(C)cc(CC)c1C1=C(OC(=O)C(C)C)CC2(CCOCC2)CC1=O] | δ 6.88 (s, 2H), 3.75 (m, 4H), 2.79 (s, 2H), 2.65 (s, 2H), 2.40-2.26 (m, 8H), 1.75 (m, 4H), 1.06 (t, 6H), 0.82 (d, 6H) |
| P4 | 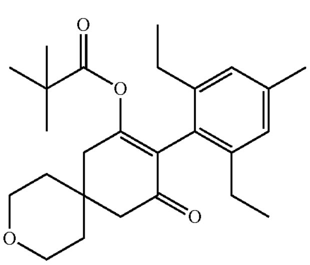 [SMILES: CCc1cc(C)cc(CC)c1C1=C(OC(=O)C(C)(C)C)CC2(CCOCC2)CC1=O] | δ 6.87 (s, 2H), 3.76 (t, 4H), 2.78 (s, 2H), 2.65 (s, 2H), 2.39-2.25 (m, 4H), 2.28 (s, 3H), 1.83-1.67 (m, 4H), 1.07 (t, 6H), 0.88 (s, 9H) |

TABLE T2-continued

| Compound Number | Structure | ¹H nmr (CDCl₃ unless stated) or other physical data |
| --- | --- | --- |
| P5 | 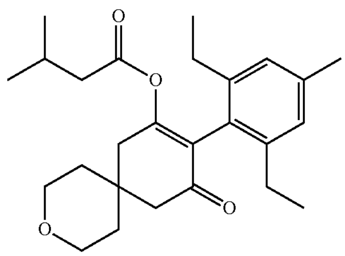 [SMILES: CCc1cc(C)cc(CC)c1C1=C(OC(=O)CC(C)C)CC2(CCOCC2)CC1=O] | δ 6.87 (s, 2H), 3.75 (m, 4H), 2.78 (s 2H), 2.64 (s, 2H), 2.37-2.27 (m, 7H), 2.03 (d, 2H), 1.75 (m, 5H), 1.07 (t, 6H), 0.67 (d, 6H) |
| P6 | 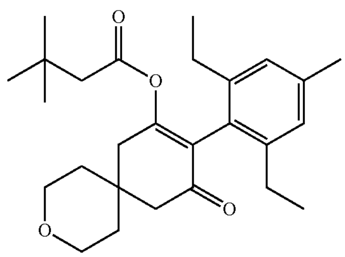 [SMILES: CCc1cc(C)cc(CC)c1C1=C(OC(=O)CC(C)(C)C)CC2(CCOCC2)CC1=O] | δ 6.87 (s, 2H), 3.75 (m, 4H), 2.78 (s 2H), 2.64 (s, 2H), 2.33 (m, 4H), 2.28 (s, 3H), 1.74 (m, 4H), 1.07 (t, 6H), 0.79 (s, 9H) |
| P7 | 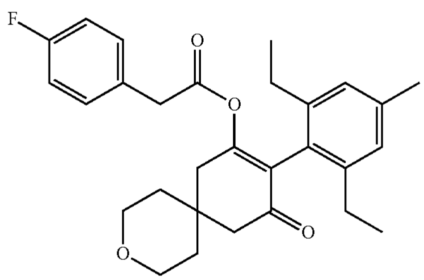 [SMILES: CCc1cc(C)cc(CC)c1C1=C(OC(=O)Cc2ccc(F)cc2)CC2(CCOCC2)CC1=O] | δ 6.84-6.74 (m, 6H), 3.74 (m, 4H), 3.41 (s, 2H), 2.79 (s, 2H), 2.62 (s, 2H), 2.34 (s, 3H), 2.31-2.13 (m, 4H), 1.73 (m, 4H), 0.98 (t, 3H) |
| P8 | 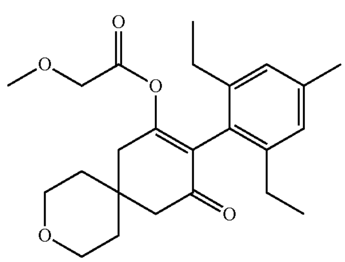 | δ 6.89 (s, 2H), 3.79 (s, 2H), 3.76 (m, 4H), 3.13 (s, 3H), 2.82 (s, 2H), 2.66 (s, 2H), 2.37-2.27 (m, 7H), 1.76 (m, 4H), 1.07 (t, 6H) |
| P9 | 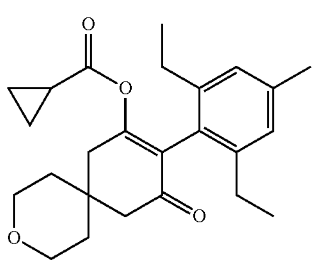 [SMILES: CCc1cc(C)cc(CC)c1C1=C(OC(=O)C2CC2)CC2(CCOCC2)CC1=O] | δ 6.90 (s, 2H), 3.75 (m, 4H), 2.82 (s, 2H), 2.63 (s, 2H), 2.38-2.23 (m, 7H), 1.74 (m, 4H), 1.42 (m, 1 H), 1.06 (t, 6H), 0.78-0.65 (m, 4H) |
| P10 | 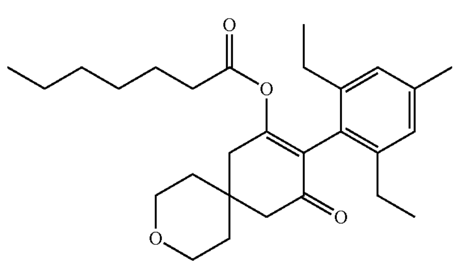 [SMILES: CCCCCCC(=O)OC1=C(c2c(CC)cc(C)cc2CC)C(=O)CC2(CCOCC2)C1] | δ 6.88 (s, 2H), 3.76 (m, 4H), 2.79 (s, 2H), 2.64 (s, 2H), 2.37-2.27 (m, 7H), 1.75 (m, 4H), 1.40-1.15 and 1.07 (m and t, 10H), 0.85 (t, 3H) |

TABLE T2-continued

| Compound Number | Structure | ¹H nmr (CDCl₃ unless stated) or other physical data |
|---|---|---|
| P11 | 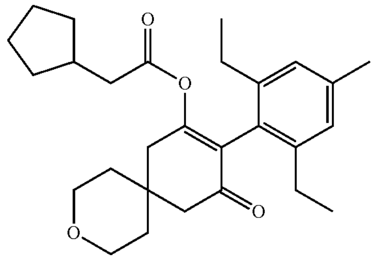 [SMILES: CCc1cc(C)cc(CC)c1C1=C(OC(=O)CC2CCCC2)CC2(CCOCC2)CC1=O] | δ 6.88 (s, 2H), 3.76 (m, 4H), 2.79 (s, 2H), 2.64 (s, 2H), 2.38-2.25 (m, 7H), 2.15 (d, 2H), 1.75 (m, 6H), 1.44 (m, 6H), 1.07 (t, 6H), 0.84 (m, 2H) |
| P12 | 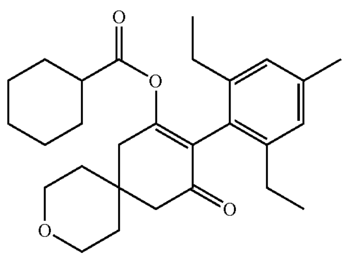 [SMILES: CCc1cc(C)cc(CC)c1C1=C(OC(=O)C2CCCCC2)CC2(CCOCC2)CC1=O] | δ 6.88 (s, 2H), 3.75 (m, 4H), 2.78 (s, 2H), 2.64 (s, 2H), 2.38-2.24 (m, 7H), 2.15 (m, 1H), 1.75 (m, 4H), 1.53-1.41 (br m, 6H), 1.15-1.03 (m and t, 10H) |
| P13 | 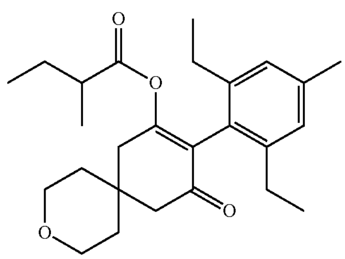 [SMILES: CCc1cc(C)cc(CC)c1C1=C(OC(=O)C(C)CC)CC2(CCOCC2)CC1=O] | δ 6.87 (s, 2H), 3.75 (m, 4H), 2.75 (s, 2H), 2.65 (s, 2H), 2.32 (m, 4H), 2.29 (s, 3H), 2.20 (m, 1H), 1.75 (m, 4H), 1.30 (m, 1H), 1.18 (m, 1H), 1.07 (t, 6H), 0.82 (d, 3H), 0.62 (t, 3H) |
| P14 | 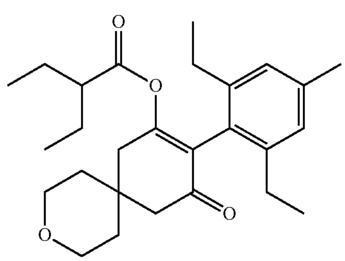 [SMILES: CCc1cc(C)cc(CC)c1C1=C(OC(=O)C(CC)CC)CC2(CCOCC2)CC1=O] | δ 6.86 (s, 2H), 3.76 (m, 4H), 2.77 (s, 2H), 2.65 (s, 2H), 2.33 (m, 4H), 2.28 (s, 3H), 2.05 (m, 1H), 1.75 (m, 4H), 1.30 (m, 4H), 1.07 (t, 6H), 0.60 (t, 6H) |
| P15 | 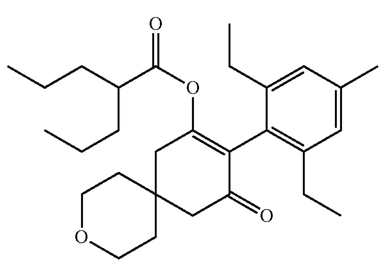 [SMILES: CCCC(CCC)C(=O)OC1=C(c2c(CC)cc(C)cc2CC)C(=O)CC2(CCOCC2)C1] | δ 6.87 (s, 2H), 3.76 (m, 4H), 2.76 (s, 2H), 2.65 (s, 2H), 2.60-2.15 (m, 8H), 1.85-0.70 (m, 24H) |
| P16 | 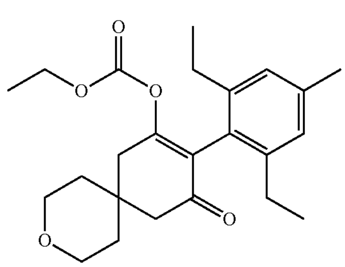 [SMILES: CCOC(=O)OC1=C(c2c(CC)cc(C)cc2CC)C(=O)CC2(CCOCC2)C1] | δ 6.90 (s, 2H), 4.11 (q, 2H), 3.76 (m, 4H), 2.84 (s, 2H), 2.65 (s, 2H), 2.32 (m, 7H), 1.75 (m, 4H), 1.20 (t, 3H), 1.07 (t, 6H) |

TABLE T2-continued

| Compound Number | Structure | ¹H nmr (CDCl₃ unless stated) or other physical data |
|---|---|---|
| P17 | 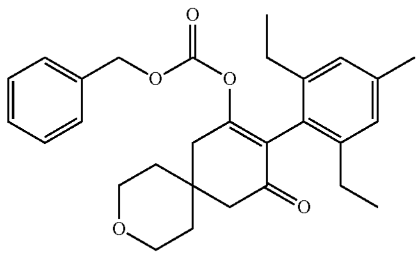 [SMILES: CCc1cc(C)cc(CC)c1C1=C(OC(=O)OCc2ccccc2)CC2(CCOCC2)CC1=O] | δ 7.34 (m, 3H), 7.19 (m, 2H), 6.88 (s, 2H), 5.06 (s, 2H), 3.74 (m, 4H), 2.82 (s, 2H), 2.64 (s, 2H), 2.34-2.24 (m, 7H), 1.74 (m, 4H), 1.04 (t, 6H) |
| P18 | 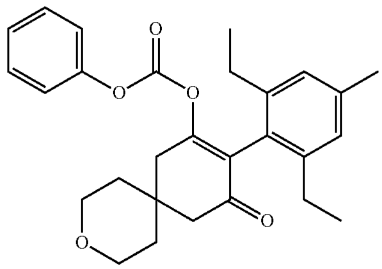 [SMILES: CCc1cc(C)cc(CC)c1C1=C(OC(=O)Oc2ccccc2)CC2(CCOCC2)CC1=O] | δ 7.30-7.20 (m, 3H), 6.95 (s, 2H), 6.85 (m, 2H), 3.76 (m, 4H), 2.91 (s, 2H), 2.67 (s, 2H), 2.37-2.31 (m, 7H), 1.76 (m, 4H), 1.07 (t, 6H) |
| P19 | 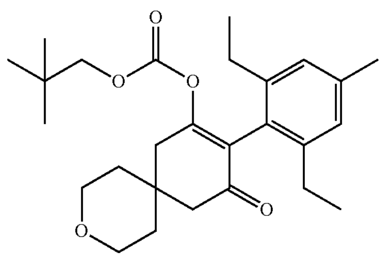 [SMILES: CCc1cc(C)cc(CC)c1C1=C(OC(=O)OCC(C)(C)C)CC2(CCOCC2)CC1=O] | δ 6.89 (s, 2H), 3.75 (m, 4H), 3.72 (s, 2H), 2.82 (s, 2H), 2.62 (s, 2H), 2.33 (m, 4H), 2.30 (s, 3H), 1.75 (m, 4H), 1.08 (s, 6H), 0.79 (9H) |
| P20 | 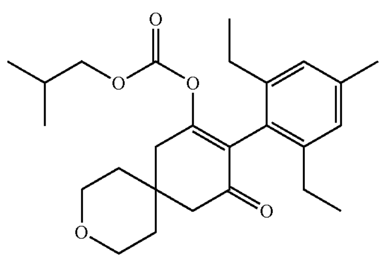 [SMILES: CCc1cc(C)cc(CC)c1C1=C(OC(=O)OCC(C)C)CC2(CCOCC2)CC1=O] | δ 6.90 (s, 2H), 3.81 (d, 2H), 3.76 (m, 4H), 2.83 (s, 2H), 2.65 (s, 2H), 2.38-2.30 (m, 7H), 1.90-1.70 (m, 5H), 1.07 (t, 6H), 0.80 (d, 6H) |
| P21 | 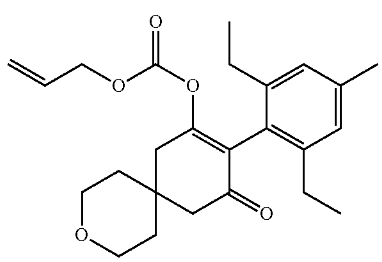 [SMILES: C=CCOC(=O)OC1=C(c2c(CC)cc(C)cc2CC)C(=O)CC2(CCOCC2)C1] | δ 6.90 (s, 2H), 5.81-5.72 (m, 1H), 5.22-5.16 (m, 2H), 4.53 (d, 2H), 3.76 (m, 4H), 2.84 (s, 2H), 2.65 (s, 2H), 2.35-2.29 (m, 7H), 1.75 (m, 4H), 1.07 (t, 6H) |
| P22 | 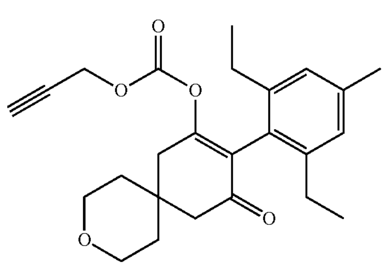 [SMILES: C#CCOC(=O)OC1=C(c2c(CC)cc(C)cc2CC)C(=O)CC2(CCOCC2)C1] | δ 6.90 (s, 2H), 4.62 (s, 2H), 3.76 (m, 4H), 2.86 (s, 2H), 2.65 (s, 2H), 2.52 (m, 1H), 2.35-2.29 (m, 7H), 1.75 (m, 4H), 1.07 (t, 6H) |

TABLE T2-continued

| Compound Number | Structure | ¹H nmr (CDCl₃ unless stated) or other physical data |
|---|---|---|
| P23 | 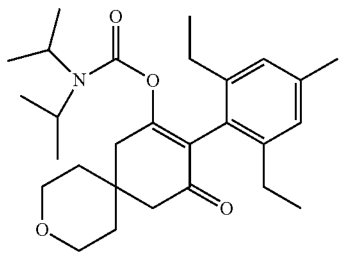 [SMILES: CCc1cc(C)cc(CC)c1C1=C(OC(=O)N(C(C)C)C(C)C)CC2(CCOCC2)CC1=O] | δ 6.86 (s, 2H), 3.76 (m, 5H), 3.49 (m, 1H), 2.91 (s, 2H), 2.64 (s, 2H), 2.36 (m, 4H), 2.27 (s, 3H), 1.75 (m, 4H), 1.14 (d, 6H), 1.06 (t, 6H), 0.77 (d, 6H) |
| P24 | 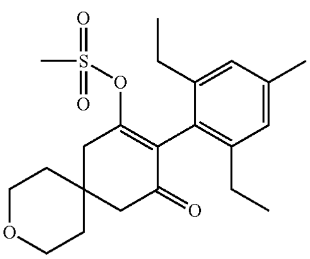 [SMILES: CCc1cc(C)cc(CC)c1C1=C(OS(C)(=O)=O)CC2(CCOCC2)CC1=O] | δ 6.94 (s, 2H), 3.76 (m, 4H), 2.96 (s, 2H), 2.65 (s, 2H), 2.44 (s, 3H), 2.36 (m, 4H), 2 31 (s, 3H), 1.73 (m, 4H), 1.11 (t, 6H) |
| P25 | 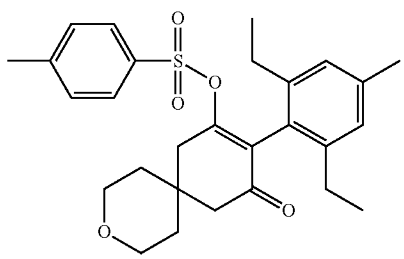 | δ 7.10 (ABq, 4H), 6.79 (s, 2H), 3.77 (m, 4H), 2.76 (s, 2H), 3.06 (s, 2H), 2.65 (s, 2H), 2.39 (s, 3H), 2.31 (s, 3H), 2.25 (q, 4H), 1.75 (m, 4H), 1.02 (t, 6H) |
| P26 | 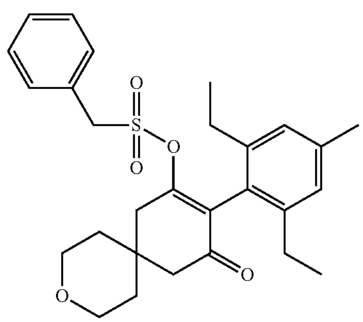 [SMILES: CCc1cc(C)cc(CC)c1C1=C(OS(=O)(=O)Cc2ccccc2)CC2(CCOCC2)CC1=O] | δ 7.35-7.23 (m, 2H), 7.00 (s, 2H), 6.82 (d, 2H), 3.86 (s, 2H), 3.72 (m, 4H), 2.93 (s, 2H), 2.62 (s, 2H), 2.38-2.31 (m, 7H), 1.69 (m, 4H), 1.08 (t, 6H) |
| P27 | 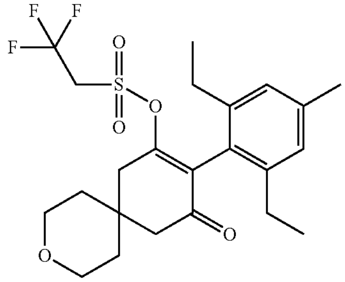 [SMILES: CCc1cc(C)cc(CC)c1C1=C(OS(=O)(=O)CC(F)(F)F)CC2(CCOCC2)CC1=O] | δ 6.98 (s, 2H), 3.76 (m, 4H), 2.92 (s, 2H), 2.88 (q, 2H), 2.67 (s, 2H), 2.45-2.27 (m and s, 7H), 1.74 (m, 4H), 1.11 (t, 6H) |

TABLE T2-continued

| Compound Number | Structure | ¹H nmr (CDCl₃ unless stated) or other physical data |
|---|---|---|
| P28 | 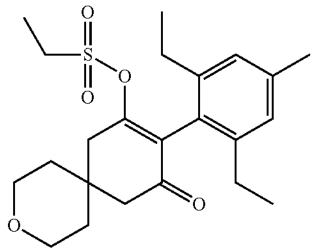 [SMILES: CCc1cc(C)cc(CC)c1C1=C(OS(=O)(=O)CC)CC2(CCOCC2)CC1=O] | δ 6.92 (s, 2H), 3.76 (m, 4H), 3.02 (s, 2H), 2.65 (m, 4H), 2.34 (m, 4H), 2.31 (s, 3H), 1.74 (m, 4H), 1.10 (t, 6H), 0.89 (t, 3H) |
| P29 | 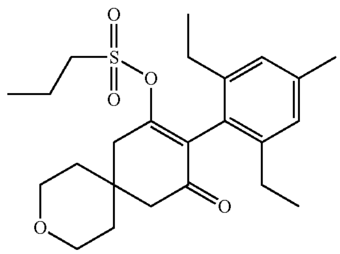 [SMILES: CCCS(=O)(=O)OC1=C(c2c(CC)cc(C)cc2CC)C(=O)CC2(CCOCC2)C1] | δ 6.93 (s, 2H), 3.76 (t, 4H), 2.99 (s, 2H), 2.64 (s, 2H), 2.49 (m, 2H), 2.36 (m, 4H), 2.32 (s, 3H), 1.73 (m, 4H), 1.33 (m, 2H), 1.10 (t, 6H), 0.71 (t, 3H) |
| P30 | 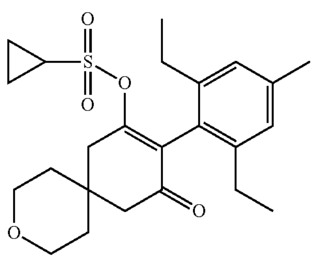 [SMILES: CCc1cc(C)cc(CC)c1C1=C(OS(=O)(=O)C2CC2)CC2(CCOCC2)CC1=O] | δ 6.92 (s, 2H), 3.76 (t, 4H), 2.99 (s, 2H), 2.65 (s, 2H), 2.38 (m, 4H), 2.30 (s, 3H), 1.83-1.72 (m, 5H), 1.11 (t, 6H), 0.96 (m, 2H), 0.71 (m, 2H) |
| P31 | 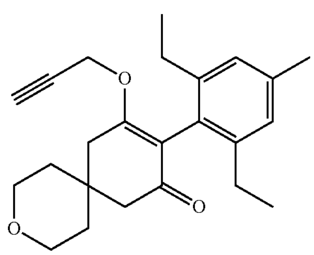 [SMILES: C#CCOC1=C(c2c(CC)cc(C)cc2CC)C(=O)CC2(CCOCC2)C1] | δ 6.92 (s, 2H), 4.50 (s, 2H), 3.76 (t, 4H), 2.85 (s, 2H), 2.60 (s, 2H), 2.56 (t, 1H), 2.32 (m, 7H), 1.74 (t, 4H), 1.07 (t, 6H) |
| P32 | 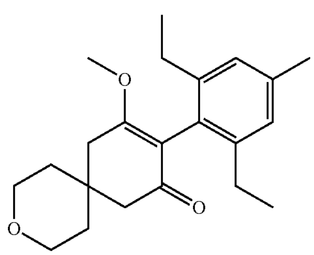 [SMILES: CCc1cc(C)cc(CC)c1C1=C(OC)CC2(CCOCC2)CC1=O] | δ 6.91 (s, 2H), 3.76 (m, 4H), 3.64 (s, 3H), 2.66 (s, 2H), 2.60 (s, 2H), 2.31 (m, 7H), 1.73 (m, 4H), 1.07 (t, 6H) |
| P33 | 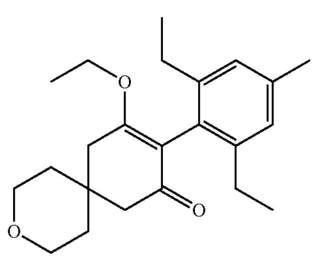 [SMILES: CCOC1=C(c2c(CC)cc(C)cc2CC)C(=O)CC2(CCOCC2)C1] | δ 6.89 (s, 2H), 3.87 (q, 2H), 3.76 (m, 4H), 2.65 (s, 2H), 2.59 (s, 2H), 2.31 (m, 7H0, 1.72 (m, 4H), 1.14 (t, 3H), 1.06 (t, 6H) |

TABLE T2-continued

| Compound Number | Structure | ¹H nmr (CDCl₃ unless stated) or other physical data |
|---|---|---|
| P34 | 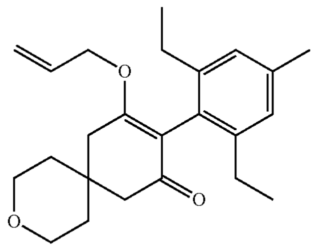 [SMILES: C=CCOC1=C(c2c(CC)cc(C)cc2CC)C(=O)CC2(CCOCC2)C1] | δ 6.90 (s, 2H), 5.83-5.73 (m, 1H), 5.20-5.13 (m, 2H), 4.39 (d, 2H), 3.74 (m, 4H), 2.69 (s, 2H), 2.58 (s, 2H), 2.31 (m, 7H), 1.71 (m, 4H), 1.07 (t, 6H) |
| P35 | 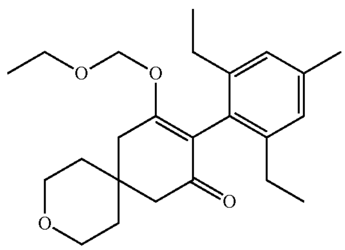 [SMILES: CCOCOC1=C(c2c(CC)cc(C)cc2CC)C(=O)CC2(CCOCC2)C1] | δ 6.91 (s, 2H), 5.02 (s, 2H), 3.76 (m, 4H), 3.55 (q, 2H), 2.83 (s, 2H), 2.59 (s, 2H), 2.32 (s, 7H), 1.73 (t, 4H), 1.16 (t, 3H), 1.06 (t, 6H) |
| P36 | 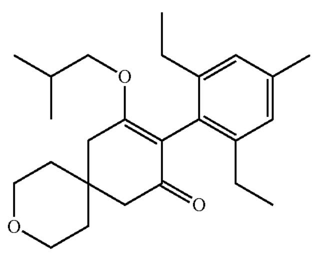 [SMILES: CCc1cc(C)cc(CC)c1C1=C(OCC(C)C)CC2(CCOCC2)CC1=O] | δ 6.87 (s, 2H), 3.76 (m, 4H), 3.56 (d, 2H), 2.64 (s, 2H), 2.59 (s, 2H), 2.30 (m, 7H), 1.72 (m, 4H), 1.05 (m and t, 7H), 0.73 (d, 6H) |
| P37 | 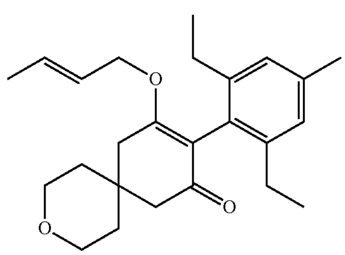 [SMILES: C/C=C/COC1=C(c2c(CC)cc(C)cc2CC)C(=O)CC2(CCOCC2)C1] | δ 6.90 (s, 2H), 5.67-5.39 (2 × m, 2H), 4.43 (d, 1H), 4.29 (d, 1H), 3.74 (m, 4H), 2.68 (s, 2H), 2.57 (s, 2H), 2.31 (m, 7H), 1.69 (m, 6H), 1.60 (m, 1H), 1.07 (t, 6H) |
| P38 | 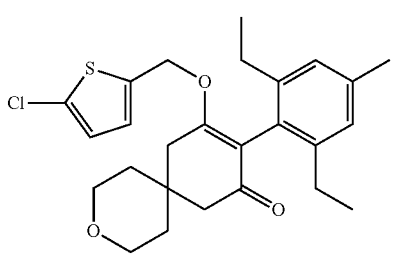 [SMILES: CCc1cc(C)cc(CC)c1C1=C(OCc2ccc(Cl)s2)CC2(CCOCC2)CC1=O] | δ 6.92 (s, 2H), 6.68 (ABq 2H), 4.80 (s, 2H), 3.71 (m, 4H), 2.69 (s, 2H), 2.58 (s, 2H), 2.33 (m, 7H), 1.69 (m, 4H), 1.08 (t, 6H) |
| P41 | 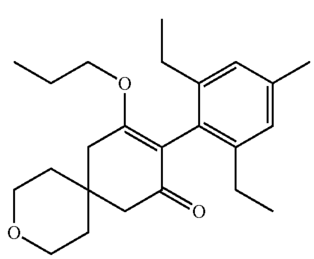 [SMILES: CCCOC1=C(c2c(CC)cc(C)cc2CC)C(=O)CC2(CCOCC2)C1] | δ 6.87 (s, 2H), 3.75 (m, 4H), 2.64 (s, 2H), 2.59 (s, 2H), 2.30 (m, 7H), 1.71 (m, 4H), 1.50 (m, 2H), 1.05 (t, 6H), 0.76 (t, 3H) |

TABLE T2-continued
| Compound Number | Structure | $^1$H nmr (CDCl$_3$ unless stated) or other physical data |
|---|---|---|
| P42 | 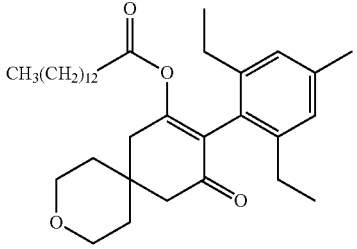 | δ 6.88 (s, 2H), 3.76 (m, 4H), 2.79 (s, 2H), 2.64 (s, 2H), 2.30 (m, 7H), 2.12 (t, 2H), 1.74 (m, 4H), 1.40-1.05 (br m, 22H); 1.07 (t, 6H), 0.88 (t, 3H) |
| P43 | 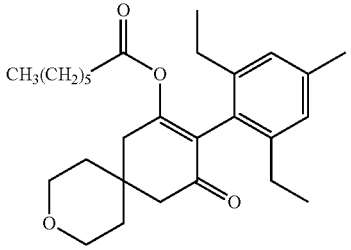 | δ 6.88 (s, 2H), 3.76 (m, 4H), 2.79 (s, 2H), 2.64 (s, 2H), 2.30 (m, 7H), 2.12 (t, 2H), 1.75 (m, 4H), 1.35-095 (br m, 14 H); 1.07 (t, 6H), 0.89 (t, 3H) |
| P44 | 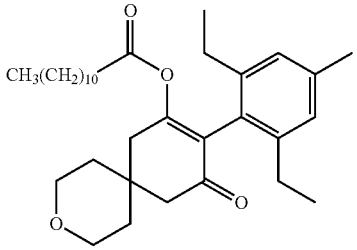 | δ 6.88 (s, 2H), 3.76 (m, 4H), 2.79 (s, 2H), 2.64 (s, 2H), 2.30 (m, 7H), 2.12 (t, 2H), 1.75 (m, 4H), 1.35-0.95 (br m, 18H); 1.07 (t, 6H), 0.89 (t, 3H) |
| P45 | 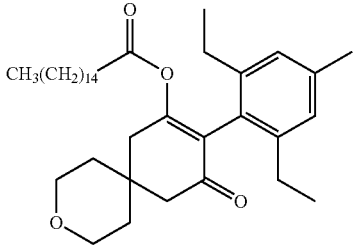 | δ 6.88 (s, 2H), 3.75 (m, 4H), 2.79 (s, 2H), 2.64 (s, 2H), 2.30 (m, 7H), 2.12 (t, 2H), 1.75 (m, 4H), 1.35-0.95 (br m, 26H); 1.07 (t, 6H), 0.89 (t, 3H) |
| P46 | 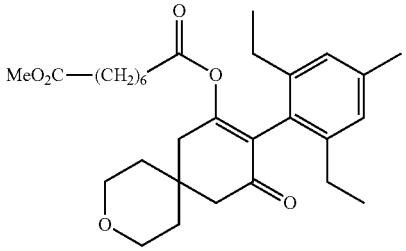 | δ 6.88 (s, 2H), 3.76 (m, 4H), 3.67 (s, 3H), 2.79 (s, 2H), 2.64 (s, 2H), 2.35-2.24 (m, 9H), 2.13 (t, 2H), 1.74 (m, 4H), 1.56-1.51 (m, 2H), 1.25 (m, 2H), 1.16-0.98 (t and m, 10H) |
| P47 | 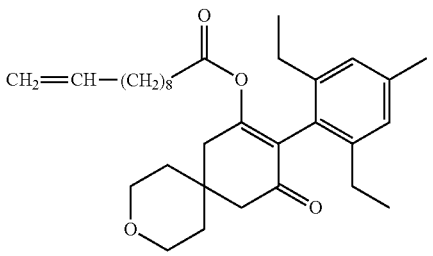 | δ 6.88 (s, 2H), 5.84-5.76 (m, 1H), 5.02-4.92 (m, 2H), 3.76 (m, 4H), 2.79 (s, 2H), 2.29 (s, 2H), 2.29 (m, 7H), 2.12 (t, 2H), 2.05 (m, 2H), 1.76 (m, 4H), 1.40-0.96 (t and m, 18H) |

TABLE T2-continued

| Compound Number | Structure | ¹H nmr (CDCl₃ unless stated) or other physical data |
|---|---|---|
| P48 | 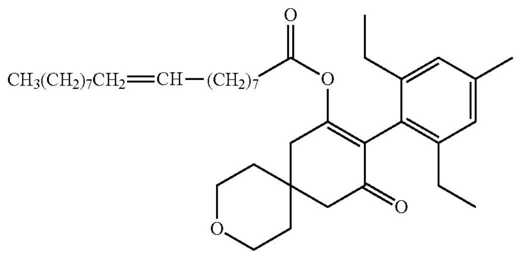 | δ 6.88 (s, 2H), 5.34 (m, 2H), 3.76 (m, 4H), 2.79 (s, 2H), 2.64 (s, 2H), 2.35-2.24 (m, 9H), 2.01 (br m, 4H), 1.75 (m, 4H), 1.4-0.95 (t and m, 28H), 0.88 (t, 3H) |
| P49 | 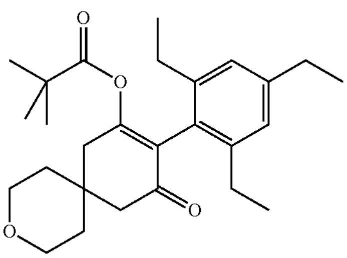 [SMILES: CCc1cc(CC)c(C2=C(OC(=O)C(C)(C)C)CC3(CCOCC3)CC2=O)c(CC)c1] | δ 6.88 (s, 2H), 3.76 (m, 4H), 2.78 (s, 2H), 2.65 (s, 2H), 2.58 (q, 2H), 2.33 (m, 4H), 1.76 (m, 4H), 1.18 (t, 3H), 1.07 (t, 6H), 0.85 (s, 9H) |
| P50 | 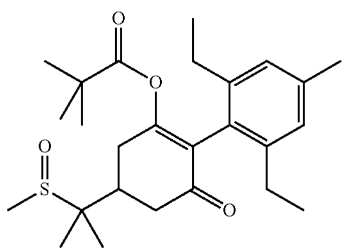 | δ 6.88 (s, 2H), 3.11-2.49 (m, 5H), 2.47 (s, 3H), 2.40-2.21 (m, 4H), 2.28 (s, 3H), 1.37 (s, 3H), 1.21 and 1.19 (s, 3H), 1.14-1.02 (m, 6H), 0.87 (s, 9H) |
| P51 | 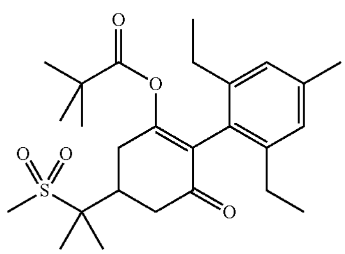 | δ 6.88 (s, 2H), 3.08-2.80 (m, 4H), 2.90 (s, 3H), 2.64-2.52 (m, 1H), 2.40-2.24 (m, 4H), 2.28 (s, 3H), 1.51 (s, 3H), 1.50 (s, 3H), 1.15-1.02 (m, 6H), 0.86 (s, 9H) |
| P52 | 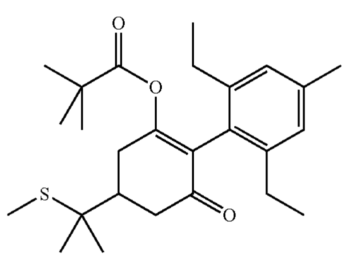 | δ 6.87 (s, 2H), 2.94-2.71 (m, 3H), 2.56-2.25 (m, 6H), 2.28 (s, 3H), 2.07 (s, 3H), 1.38 (s, 3H), 1.35 (s, 3H), 1.14-1.02 (m, 6H), 0.87 (s, 9H) |
| P53 | 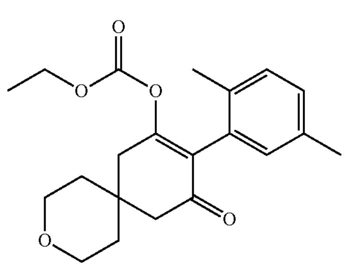 [SMILES: CCOC(=O)OC1=C(c2cc(C)ccc2C)C(=O)CC2(CCOCC2)C1] | δ 7.08 (d, 1H), 7.03 (d, 1H), 6.76 (s, 1H), 4.18-4.02 (m, 2H), 3.74 (t, 4H), 2.77 (d, 1H), 2.75 (d, 1H), 2.63 (s, 2H), 2.27 (s, 3H), 2.04 (s, 3H), 1.82-1.63 (m, 4H), 1.17 (t, 3H) |

TABLE T2-continued

| Compound Number | Structure | ¹H nmr (CDCl₃ unless stated) or other physical data |
|---|---|---|
| P54 | 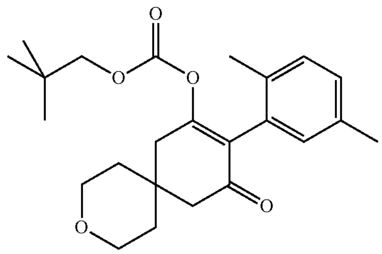 [SMILES: Cc1ccc(C)c(C2=C(OC(=O)OCC(C)(C)C)CC3(CCOCC3)CC2=O)c1] | δ 7.05 (d; 1H), 6.99 (d, 1H), 6.73 (s, 1H), 3.74 (m, 4H), 2.76 (d, 1H), 2.67 (d, 1H), 2.62 (m, 2H), 2.24 (s, 3H), 2.07 (s, 2H), 2.04 (s, 3H), 1.83-1.64 (m, 4H), 0.76 (s, 9H) |
| P55 | 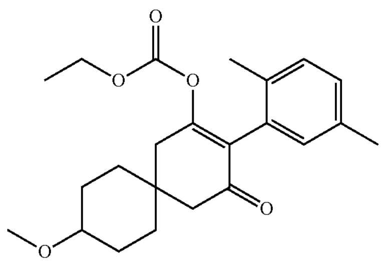 | δ 7.07 (d, 1H), 7.02 (d, 1H), 6.77 (s, 1H), 4.17-4.01 (m, 2H), 3.35 and 3.33 (2 × s, 3H), 3.26 (m, 1H), 2.75-2.50 (m, 4H), 2.26 (s, 3H), 2.05 (s, 3H), 1.97-1.70 (m, 4H), 1.70-1.34 (m, 4H), 1.17 (t, 3H) |
| P56 | 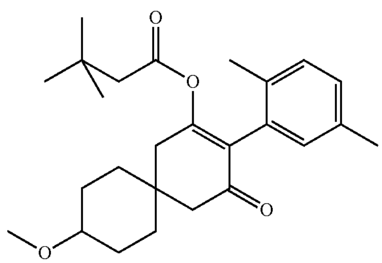 | δ 7.04 (d, 1H), 6.97 (d, 1H), 6.74 (s, 1H), 3.35 and 3.33 (2 × s, 3H), 3.26 (m, 1H), 2.69-2.48 (m, 4H), 2.24 (s, 3H), 2.05 (s, 2H), 2.04 (s, 3H), 1.98-1.73 (m, 4H), 1.69-1.36 (m, 4H), 0.75 (s, 9H) |
| P57 | 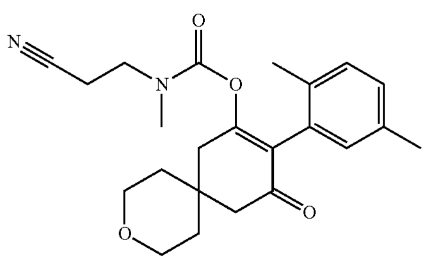 [SMILES: Cc1ccc(C)c(C2=C(OC(=O)N(C)CCC#N)CC3(CCOCC3)CC2=O)c1] | M.p. 108-114° C.<br>MS (electrospray ES+): 397 (M + H)⁺ |
| P58 | 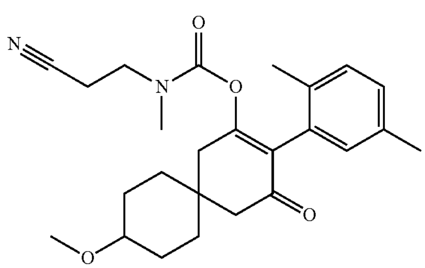 [SMILES: COC1CCC2(CC1)CC(=O)C(c1cc(C)ccc1C)=C(OC(=O)N(C)CCC#N)C2] | Oil<br>MS (electrospray ES+): 425 (M + H)⁺ |
| P59 | 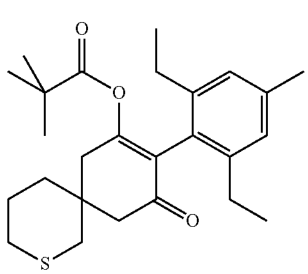 [SMILES: CCc1cc(C)cc(CC)c1C1=C(OC(=O)C(C)(C)C)CC2(CCCSC2)CC1=O] | δ 6.87 (s, 2H), 2.98 (m, 2H), 2.71 (m, 4H), 2.58 (m, 2H), 2.31 (m, 7H), 1.93 (m, 2H), 1.81 (m, 1H), 1.56 (m, 1H), 1.08 (t, 6H), 0.80 (s, 9H) |

| Compound Number | Structure | ¹H nmr (CDCl₃ unless stated) or other physical data |
|---|---|---|
| P60 | 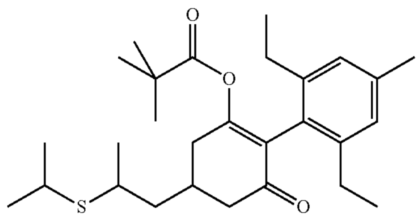 [SMILES: CCc1cc(C)cc(CC)c1C1=C(OC(=O)C(C)(C)C)CC(CC(C)SC(C)C)CC1=O] | δ 6.87 (d, 2H), 3.02 (m, 1H), 2.91 (m, 1H), 2.55-2.79 (m, 4H), 2.23-2.45 (m, 5H), 2.28 (s, 3H), 1.61-1.77 (m, 2H), 1.33 (dd, 3H), 1.28 (m, 6H), 1.08 (m, 6H), 0.88 (s, 9H) |

The active compounds of the invention, in combination with good plant tolerance and favourable toxicity to warm-blooded animals and being tolerated well by the environment, are suitable for protecting plants and plant organs, for increasing harvest yields, for improving the quality of the harvested material and for controlling animal pests, in particular insects, arachnids, helminths, nematodes and mollusks, which are encountered in agriculture, in horticulture, in animal husbandry, in forests, in gardens and leisure facilities, in the protection of stored products and of materials, and in the hygiene sector. They can be preferably employed as plant protection agents. They are active against normally sensitive and resistant species and against all or some stages of development. The abovementioned pests include:

From the phylum of Mollusca e.g. from the class of the Lamellibranchiata e.g. *Dreissena* spp.

From the class of the Gastropoda e.g. *Arion* spp., *Biomphalaria* spp., *Bulinus* spp., *Deroceras* spp., *Galba* spp., *Lymnaea* spp., *Oncomelania* spp. *Pomacea* spp., *Succinea* spp.

From the phylum: Arthropoda e.g. from the order of Isopoda e.g. *Annadillidium vulgare, Oniscus asellus, Porcellio scaber.*

From the class of the Arachnida e.g. *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Centruroides* spp., *Chorioptes* spp. *Dermanyssus gallinae, Dermatophagoides pteronyssius, Dermatophagoides farinae. Dermacentor* spp., *Eotetranychus* spp., *Epitrimerus pyri, Eutetranychus* spp., *Eriophyes* spp., *Halotydeus destructor, Hemitarsonemus* spp. *Hyalomma* spp., *Ixodes* spp. *Latrodectus* spp., *Loxosceles* spp. *Metatetranychus* spp., *Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vaejovis* spp., *Vasates lycopersici.*

From the order of Symphyla e.g. *Scutigerella* spp.

From the order of Chilopoda e.g. *Geophilus* spp., *Scutigera* spp.

From the order of Collembola e.g. *Onychiurus armatus.*

From the order of Diplopoda e.g. *Blaniulus guttulatus.*

From the order of Zygentoma e.g. *Lepisma saccharina, Thermobia domestica.*

From the order of Orthoptera e.g. *Acheta domesticus, Blatta orientalis, Blattella germanica, Dichroplus* spp., *Gryllotalpa* spp., *Leucophaea maderae, Locusta* spp., *Melanoplus* spp., *Periplaneta* spp., *Pulex irritans, Schistocerca gregaria, Supella longipalpa.*

From the order of Isoptera e.g. *Coptotermes* spp., *Cornitermes cumulans. Cryptotermes* spp., *Incisitermes* spp., *Microtermes obesi, Odontotermes* spp., *Reticulitermes* spp.

From the order of Heteroptera e.g. *Anasa tristis, Antestiopsis* spp., *Boisea* spp., *Blissus* spp., *Calocoris* spp., *Campylomma livida. Cavelerius* spp., *Cimex lectularius, Collaria* spp., *Creontiades dilutus, Dasynus piperis. Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of Anoplura (Phthiraptera) e.g. *Damalinia* spp., *Haematopinus* spp. *Linognathus* spp., *Pediculus* spp., *Ptirus pubis, Trichodectes* spp.

From the order of Homoptera e.g. *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Cameocephala fulgida, Ceratovacuna lanigera, Cercopidae, Ceroplastes* spp., *Chaetosiphon fragaefolii, Chionaspis tegalensis, Chlorita omikii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nepho-tettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagons, Pseudococcus* spp. *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of Coleoptera e.g. *Acalymma vittatum, Acanthoscelides obtectus, Adoretus* spp., *Agelastica alni, Agriotes* spp., *Alphitobius diaperinus, Amphimailon solstitialis, Anobium punctatum, Anoplophora* spp., *Anthonomus* spp., *Anthrenus* spp., *Apion* spp. *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lena* spp., *Leptinotarsa decemlineata, Leucoptera* spp., *Lisso-rhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Prostephanus truncatus, Psylliodes* spp., *Ptinus* spp., *Rhizobius ventralis, Rhizopertha dominica, Sitophilus* spp., *Sphenophorus* spp., *Stegobium paniceum, Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of Hymenoptera e.g. *Acromyrmex* spp., *Athalia* spp., *Atta* spp., *Diprion* spp., *Hoplocampa* spp., *Lasius* spp., *Monomorium pharaonis, Solenopsis invicta, Tapinoma* spp., *Vespa* spp.

From the order of Lepidoptera e.g. *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalo-cerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis. Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis. Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp. *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichophaga tapetzella, Trichoplusia* spp., *Tuta absoluta, Virachola* spp.

From the order of Diptera e.g. *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Chrysops* spp., *Cochliomyia* spp., *Contarinia* spp., *Cordylobia anthropophaga, Culex* spp., *Culicoides* spp., *Culiseta* spp., *Cuterebra* spp. *Dacus oleae, Dasyneura* spp., *Delia* spp., *Dermatobia hominis. Drosophila* spp., *Echinocnemus* spp. *Fannia* spp., *Gasterophilus* spp., *Glossina* spp., *Haematopota* spp. *Hydrellia* spp., *Hylemyia* spp., *Hyppobosca* spp., *Hypoderma* spp., *Liriomyza* spp. *Lucilia* spp., *Lutzomia* spp., *Mansonia* spp., *Musca* spp., *Nezara* spp., *Oestrus* spp., *Oscinella frit, Pegomyia* spp., *Phlebotomus* spp., *Phorbia* spp., *Phormia* spp., *Prodiplosis* spp., *Psila rosae, Rhagoletis* spp., *Sarcophaga* spp., *Simulium* spp. *Stomoxys* spp., *Tabanus* spp., *Tannia* spp., *Tetanops* spp., *Tipula* spp.

From the order of Thysanoptera e.g. *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp. *Taeniothrips cardamoni, Thrips* spp.

From the order of Siphonaptera e.g. *Ceratophyllus* spp., *Ctenocephalides* spp., *Tunga penetrans, Xenopsylla cheopis.*

From the phylums Plathelminthes and Nematoda as animal parasites e.g. from the class of the Helminths e.g. *Ancylostoma duodenale, Ancylostoma ceylanicum, Acylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa. Nematodirus* spp., *Oesophagostomum* spp., *Opisthorchis* spp., *Onchocerca volvulus, Ostertagia* spp., *Paragonimus* spp., *Schistosomen* spp, *Strongyloides fuellebomi, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

From the phylum Nematoda as plant pests e e.g. *Aphelenchoides* spp., *Bursaphelenchus* spp. *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans. Xiphinema* spp.

From the subphylum of protozoa e.g. *Eimeria*.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:

for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or lattices, such as guts arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example. *Haematopinus* spp., *Linognathus* spp *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp. *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* app. *Morellia* spp., *Fannia* spp. *Glossina* spp., *Calliphora* spp., *Lucilia* spp., *Chrysomyia* spp. *Wohlfahrtia* spp., *Sarcophaga* spp. *Oestrus* spp., *Hypoderma* spp., *Gasterophilus* spp., *Hippobosca* spp., *Lipoptena* spp., *Melophagus* spp.

From the order of the Siphonapterida, for example. *Pulex* spp., *Ctenocephalides* spp. *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example. *Blatta orientalis, Periplaneta americana, Blattela germanica, Supella* spp.

From the subclass of the Acari (Acarina) and the orders of the Meta- and Mesostigmata, for example, *Argas* spp., *Ornithodoros* spp., *Otobius* spp., *Ixodes* spp., *Amblyomma* spp., *Boophilus* spp., *Dermacentor* spp., *Haemophysalis* spp., *Hyalomma* spp. *Rhipicephalus* spp., *Dermanyssus* spp., *Raillietia* spp., *Pneumonyssus* spp., *Stemostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rafovillosum, Ptilinus pecticornis, Dendrobium pertinex, Ernobius moths, Priobium carpini, Lyctus brunneus, Lyctus africanus, Lyctus planicollis, Lyctus linearis, Lyctus pubescens, Trogoxylon aequale, Minthes rugicollis, Xylebonis* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis. Cryptotermes brevis, Heterotermes indicola, Reticulitermes flavipes, Reticulitermes santonensis, Reticulitermes lucifugus, Mastotennes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, such as hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, Avicularidae, Araneidae.

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example. *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestics, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example. *Pediculus humanus capitis, Pediculus humanus corporis. Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The compounds according to the invention exhibit a strong microbicidal action and can be used for combating undesirable microorganisms, such as fungi and bacteria, in plant protection and in material protection.

Fungicides can be used in plant protection for combating Plasmodiophoromycetes, Oomycetes, Chytridiomycetes, Zygomycetes, Ascomycetes, Basidiomycetes and Deuteromycetes.

Bactericides can be used in plant protection for combating Pseudomonadaceae, Rhizobaceae, Enterobacteriaceae, Corynebacteriaceae and Streptomycetaceae.

Mention may be made, by way of example but without limitation, of some pathogens of fungal and bacterial diseases which come under the generic terms listed above:

diseases caused by pathogens of powdery mildew, such as, for example,

*Blumeria* species, such as, for example, *Blumeria graminis;*

*Podosphaera* species, such as, for example, *Podosphaera leucotricha;*

*Sphaerotheca* species, such as, for example, *Sphaerotheca fuliginea;*

*Uncinula* species, such as, for example, *Uncinula necator;* diseases caused by rust pathogens, such as, e.g.,

*Gymnosporangium* species, such as, for example, *Gymnosporangium sabinae;*

*Hemileia* species, such as, for example, *Hemileia vastatrix;*

*Phakopsora* species, such as, for example, *Phakopsora pachyrhizi* and *Phakopsora meibomiae;*

*Puccinia* species, such as, for example, *Puccinia recondita;*

*Uromyces* species, such as, for example, *Uromyces appendiculatus;* diseases caused by pathogens of the Oomycetes group, such as, e.g.,

*Bremia* species, such as, for example, *Bremia lactucae;*

*Peronospora* species, such as, for example, *Peronospora pisi* or *P. brassicae;*

*Phytophthora* species, such as, for example, *Phytophthora infestans;*

*Plasmopara* species, such as, for example, *Plasmopara viticola;*

*Pseudoperonospora* species, such as, for example, *Pseudoperonospora humuli* or *Pseudoperonospora cubensis;*

*Pythium* species, such as, for example, *Pythium ultimum;* leaf spot diseases and leaf wilts caused by, e.g.,

*Alternaria* species, such as, for example. *Alternaria solani;*

*Cercospora* species, such as, for example, *Cercospora beticola;*

*Cladosporium* species, such as, for example, *Cladosporium cucumerinum;*

*Cochliobolus* species, such as, for example, *Cochliobolus sativus*

(conidial form: *Drechslera*, syn: *Helminthosporium*);

*Colletotrichum* species, such as, for example, *Colletotrichum lindemuthanium;*

*Cycloconium* species, such as, for example, *Cycloconium oleaginum;*

*Diaporthe* species, such as, for example, *Diaporthe citri;*

*Elsinoe* species, such as, for example, *Elsinoe fawcettii;*

*Gloeosporium* species, such as, for example, *Gloeosporium laeticolor;*

*Glomerella* species, such as, for example, *Glomerella cingulata;*

*Guignardia* species, such as, for example, *Guignardia bidwelli;*

*Leptosphaeria* species, such as, for example, *Leptosphaeria maculans;*

*Magnaporthe* species, such as, for example, *Magnaporthe grisea;*

*Mycosphaerella* species, such as, for example, *Mycosphaerella graminicola* and *Mycosphaerella fijiensis;*

*Phaeosphaeria* species, such as, for example, *Phaeosphaeria nodorum,*

*Pyrenophora* species, such as, for example, *Pyrenophora teres;*

*Ramularia* species, such as, for example, *Ramularia collocygni;*

*Rhynchosporium* species, such as, for example, *Rhynchosporium secalis;*

*Septoria* species, such as, for example, *Septoria apii;*

*Typhula* species, such as, for example, *Typhula incarnata;*

*Venturia* species, such as, for example, *Venturia inaequalis;* root and stalk diseases caused by, e.g.,

*Corticium* species, such as, for example, *Corticium graminearum;*

*Fusarium* species, such as, for example, *Fusarium oxysporum;*

*Gaeumannomyces* species, such as, for example, *Gaeumannomyces graminis;*

*Rhizoctonia* species, such as, for example, *Rhizoctonia solani;*

*Tapesia* species, such as, for example, *Tapesia acuformis;*

*Thielaviopsis* species, such as, for example, *Thielaviopsis basicola;* ear and panicle diseases (including maize cobs) caused by, e.g.,

*Alternaria* species, such as, for example, *Alternaria* spp.;

*Aspergillus* species, such as, for example, *Aspergillus flavus;*

*Cladosporium* species, such as, for example, *Cladosporium cladosporioides;*

*Claviceps* species, such as, for example, *Claviceps purpurea;*

*Fusarium* species, such as, for example, *Fusarium culmorum;*

*Gibberella* species, such as, for example, *Gibberella zeae;*

*Monographella* species, such as, for example, *Monographella nivalis;* diseases caused by smuts, such as, e.g.,

*Sphacelotheca* species, such as, for example, *Sphacelotheca reiliana;*

*Tilletia* species, such as, for example, *Tilletia caries;*

*Urocystis* species, such as, for example, *Urocystis occulta;*

*Ustilago* species, such as, for example, *Ustilago nuda;* fruit rot caused by, e.g.,

*Aspergillus* species, such as, for example, *Aspergillus flavus;*

*Botrytis* species, such as, for example, *Botrytis cinerea;*

*Penicillium* species, such as, for example, *Penicillium expansum* and *Penicillium purpurogenum;*

*Sclerotinia* species, such as, for example, *Sclerotinia sclerotiorum;*

*Verticilium* species, such as, for example, *Verticilium alboatrum;* seed- and soil-borne rots and wilts, and seedling diseases, caused by, e.g.,

*Alternaria* species, such as, for example, *Alternaria brassicicola;*

*Aphanomyces* species, such as, for example, *Aphanomyces euteiches;*

*Ascochyta* species, such as, for example, *Ascochyta lentis;*

*Aspergillus* species, such as, for example, *Aspergillus flavus;*

*Cladosporium* species, such as, for example, *Cladosporium herbarum;*

*Cochliobolus* species, such as, for example, *Cochliobolus sativus*

(conidial form: *Drechslera*, *Bipolaris* syn: *Helminthosporium*);

*Colletotrichum* species, such as, for example, *Colletotrichum coccodes:*

*Fusarium* species, such as, for example, *Fusarium culmorum;*

*Gibberella* species, such as, for example, *Gibberella zeae;*

*Macrophomina* species, such as, for example, *Macrophomina phaseolina;*

*Monographella* species, such as, for example, *Monographella nivalis;*

*Penicillium* species, such as, for example, *Penicillium expansum;*

*Phoma* species, such as, for example, *Phoma lingam;*

*Phomopsis* species, such as, for example, *Phomopsis sojae;*

*Phytophthora* species, such as, for example, *Phytophthora cactorum;*

*Pyrenophora* species, such as, for example, *Pyrenophora graminea;*

*Pyricularia* species, such as, for example, *Pyricularia oryzae;*

*Pythium* species, such as, for example, *Pythium ultimum;*

*Rhizoctonia* species, such as, for example, *Rhizoctonia solani;*

*Rhizopus* species, such as, for example, *Rhizopus oryzae;*

*Sclerotium* species, such as, for example, *Sclerotium rolfsii;*

*Septoria* species, such as, for example, *Septoria nodorum;*

*Typhula* species, such as, for example, *Typhula incarnata;*

*Verticillium* species, such as, for example, *Verticillium dahliae;* cankers, galls and witches' broom disease caused by, e.g.,

*Nectria* species, such as, for example, *Nectria galligena;* wilts caused by, e.g.,

*Monilinia* species, such as, for example, *Monilinia laxa;* deformations of leaves, flowers and fruits caused by, e.g.,

*Taphrina* species, such as, for example, *Taphrina deformans;* degenerative diseases of woody plants caused by, e.g.,

*Esca* species, such as, for example, *Phaeomoniella chlamydospora, Phaeoacremonium aleophilum* and *Fomitiporia mediterranea;* flower and seed diseases caused by, e.g.,

*Botrytis* species, such as, for example, *Botrytis cinerea;* diseases of plant tubers caused by, e.g.,

*Rhizoctonia* species, such as, for example, *Rhizoctonia solani;*

*Helminthosporium* species, such as, for example, *Helminthosporium solani*:

diseases caused by bacterial pathogens, such as, e.g.,

*Xanthomonas* species, such as, for example, *Xanthomonas campestris* pv. *oryzae*;

*Pseudomonas* species, such as, for example, *Pseudomonas syringae* pv. *lachrymans*;

*Erwinia* species, such as, for example, *Erwinia amylovora*.

Preferably, the following diseases of soybeans can be combated:

fungal diseases on leaves, stalks, pods and seeds caused by, e.g., alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*)

fungal diseases on roots and the stem base caused by, e.g., black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active substances according to the invention also exhibit a strong strengthening activity in plants. They are accordingly suitable for mobilizing intrinsic defences of plants against attack by undesirable microorganisms.

In the present context, plant-strengthening (resistance-inducing) substances are to be understood as meaning those materials which are capable of stimulating the defence system of plants such that the treated plants, on subsequent inoculation with undesirable microorganisms, exhibit extensive resistance to these microorganisms.

In the present case, undesirable microorganisms are to be understood as meaning phytopathogenic fungi, bacteria and viruses. The substances according to the invention can thus be used to protect plants from attack by the harmful pathogens mentioned for a certain period of time after the treatment. The period of time for which protection is brought about generally ranges from 1 to 10 days, preferably 1 to 7 days, after the treatment of the plants with the active substances.

The fact that the active substances are well tolerated by plants in the concentrations necessary for combating plant diseases makes possible treatment of aboveground plant parts, of plant propagation material and seed, and of the soil.

In this connection, the active substances according to the invention can be used particularly successfully in combating cereal diseases, such as, e.g., *Puccinia* species, and diseases in viticulture and in the cultivation of fruit and vegetables, such as, e.g., *Botrytis, Venturia* or *Alternaria* species.

The active substances according to the invention are also suitable for increasing the crop yield. In addition, they are of lower toxicity and are well tolerated by plants.

The active substances according to the invention can also optionally be used, in specific concentrations and application amounts, as herbicides, for affecting plant growth and for combating animal pests. They can optionally also be used as intermediates and precursors for the synthesis of additional active substances.

All plants and plant parts can be treated according to the invention. In this connection, plants are to be understood as meaning all plants and plant populations, such as desirable and undesirable wild plants or cultivated plants (including naturally occurring cultivated plants). Cultivated plants can be plants which can be obtained by conventional breeding and optimization methods or by biotechnological and genetic engineering methods or combinations of these methods, including transgenic plants and including plant varieties which may or may not be protected by laws on variety certification. Plant parts should be understood as meaning all aboveground and subsoil parts and organs of plants, such as shoot, leaf, flower and root, examples which are listed being leaves, needles, stalks, stems, flowers, fruiting bodies, fruits and seeds, and also roots, tubers and rhizomes. Plant parts also include harvested crops, and also vegetative and generative propagation material, for example cuttings, tubers, rhizomes, layers and seeds.

The treatment according to the invention of the plants and plant parts with the active substances is carried out directly or by acting on the environment, habitat or storage area thereof using conventional treatment methods, e.g. by dipping, spraying, evaporating, atomizing, scattering, spreading and, with propagation material, in particular with seeds, furthermore by coating with one or more layers.

In addition, it is possible, by the treatment according to the invention, to reduce the mycotoxin content in harvested crops and the foodstuffs and feedstuffs prepared therefrom. In this connection, mention may in particular but not exclusively be made of the following mycotoxins: deoxynivalenol (DON), nivalenol, 15-Ac-DON, 3-Ac-DON, T2 and HT2 toxin, fumonisins, zearalenone, moniliformin, fusarin, diacetoxyscirpenol (DAS), beauvericin, enniatin, fusaroproliferin, fusarenol, ochratoxins, patulin, ergot alkaloids and aflatoxins, which can be caused, for example, by the following fungi: *Fusarium* spec., such as *Fusarium acuminatum, F. avenaceum, F. crookwellense, F. culmorum, F. graminearum* (*Gibberella zeae*), *F. equiseti, F. fujikoroi, F. musanim, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, and others, and also by *Aspergillus* spec., *Penicillium* spec., *Claviceps purpurea, Stachybotrys* spec., and others.

In material protection, the substances according to the invention can be used for the protection of industrial materials from attack and destruction by undesirable microorganisms.

Industrial materials are to be understood in the present context as meaning nonliving materials which have been prepared for use in industry. For example, industrial materials which are to be protected by active substances according to the invention from microbial change or destruction can be adhesives, sizes, paper and board, textiles, leather, wood, paints and plastic articles, cooling lubricants and other materials which can be attacked or destroyed by microorganisms. In the context of the materials to be protected, mention may also be made of parts of production plants, for example cooling water circuits, which can be detrimentally affected by proliferation of microorganisms. In the context of the present invention, mention may preferably be made, as industrial materials, of adhesives, sizes, papers and boards, leather, wood, paints, cooling lubricants and heat-transfer liquids, particularly preferably of wood.

Examples which may be mentioned of microorganisms which can decompose or modify industrial materials are bacteria, fungi, yeasts, algae and slime organisms. The active substances according to the invention are preferably active against fungi, in particular moulds, wood-discolouring and wood-destroying fungi (Basidiomycetes), and against slime organisms and algae.

Mention may be made, by way of example, of microorganisms of the following genera:
- *Alternaria*, such as *Alternaria tennis*,
- *Aspergillus*, such as *Aspergillus niger*,
- *Chaetomium*, such as *Chaetomium globosum*,
- *Coniophora*, such as *Coniophora puetana*,
- *Lentinus*, such as *Lentinus tigrinus*,
- *Penicillium*, such as *Penicillium glaucum*,
- *Polyporus*, such as *Polyporus versicolor*,
- *Aureobasidium*, such as *Aureobasidium pullulans*.
- *Sclerophoma*, such as *Sclerophoma pityophila*,
- *Trichoderma*, such as *Trichoderma viride*,
- *Escherichia*, such as *Escherichia coli*,
- *Pseudomonas*, such as *Pseudomonas aeruginosa*,
- *Staphylococcus*, such as *Staphylococcus aureus*.

The present invention relates to a composition for combating undesirable microorganisms, comprising at least one of the compounds according to the invention.

The compounds according to the invention can for this, depending on their respective physical and/or chemical properties, be converted into the standard formulations, such as solutions, emulsions, suspensions, powders, foams, pastes, granules, aerosols, very fine encapsulations in polymeric substances and in coating materials for seed, and also ULV cold- and hot-fogging formulations.

These formulations are prepared in a known way, e.g. by mixing the active substances with extenders, that is liquid solvents, liquefied gases under pressure and/or solid carriers, optionally with the use of surface-active agents, that is emulsifiers and/or dispersants and/or foaming agents. In the case of the use of water as extender, use may also be made, e.g., of organic solvents as cosolvents. Possible liquid solvents are essentially: aromatic hydrocarbons, such as xylene, toluene or alkylnaphthalenes, chlorinated aromatic hydrocarbons or chlorinated aliphatic hydrocarbons, such as chlorobenzenes, chloroethylenes or methylene chloride, aliphatic hydrocarbons, such as cyclohexane or paraffins, e.g. petroleum fractions, alcohols, such as butanol or glycol, and the ethers and esters thereof, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are to be understood as meaning those liquids which are in the gas form at standard temperature and at standard pressure, e.g. aerosol propellants, such as halogenated hydrocarbons and also butane, propane, nitrogen and carbon dioxide. Possible solid carriers are, e.g., ground natural minerals, such as kaolins, argillaceous earths, talc, chalk, quartz, attapulgite, montmorillonite or diatomaceous earth, and ground synthetic minerals, such as highly dispersed silica, aluminium oxide and silicates. Possible solid carriers for granules are, e.g., broken and fractionated natural rocks, such as calcite, pumice, marble, sepiolite or dolomite, and also synthetic granules formed from inorganic and organic dusts, and also granules formed from organic material, such as sawdust, coconut shells, maize cobs and tobacco stalks. Possible emulsifiers and/or foaming agents are, e.g., nonionic and anionic emulsifiers, such as polyoxyethylene fatty acid esters, polyoxyethylene fatty alcohol ethers, e.g. alkylaryl polyglycol ethers, alkylsulphonates, alkyl sulphates, arylsulphonates, and also protein hydrolysates. Possible dispersants are, e.g., lignosulphite waste liquors and methylcellulose.

Use may be made, in the formulations, of stickers, such as carboxymethylcellulose, natural and synthetic polymers in the powder, granule or latex form, such as gum arabic, polyvinyl alcohol, polyvinyl acetate, and also natural phospholipids, such as cephalins and lecithins, and synthetic phospholipids. Other possible additives are mineral and vegetable oils.

Use may also be made of colorants, such as inorganic pigments, e.g. iron oxide, titanium oxide, Prussian blue, and organic colorants, such as alizarin dyes, azo dyes and metal phthalocyanine dyes, and trace elements, such as salts of iron, manganese, boron, copper, cobalt, molybdenum and zinc.

The formulations generally comprise between 0.1 and 95% by weight of active substance, preferably between 0.5 and 90%.

The formulations described above can be used in a method according to the invention for combating undesirable microorganisms, in which the compounds according to the invention are applied to the microorganisms and/or to the habitat thereof.

The combating of phytopathogenic fungi by the treatment of the seed of plants has been known for a long time and is the subject-matter of continuous improvements. Nevertheless, a series of problems arises in the treatment of seed, which problems may not always be satisfactorily solved. Thus, it is desirable to develop methods for protecting the seed and the germinating plant which render superfluous or at least markedly reduce the additional application of plant protection compositions after sowing or after emergence of the plants. It is furthermore desirable to optimize the amount of the active substance used, so that the seed and the germinating plant are given the best possible protection against attack by phytopathogenic fungi but without the plant itself being damaged by the active substance used. In particular, methods for the treatment of seed should also include the intrinsic fungicidal properties of transgenic plants in order to achieve optimum protection of the seed and the germinating plant with a minimum expenditure of plant protection compositions.

The present invention therefore also relates in particular to a method for the protection of seed and germinating plants from attack by phytopathogenic fungi, by treating the seed with a composition according to the invention.

The invention likewise relates to the use of the compositions according to the invention for the treatment of seed to protect the seed and the germinating plant from phytopathogenic fungi.

Furthermore, the invention relates to seed which has been treated with a composition according to the invention in order to protect from phytopathogenic fungi.

One of the advantages of the present invention is that, because of the particular systemic properties of the compositions according to the invention, the treatment of the seed with these compositions not only protects the seed itself from phytopathogenic fungi but also protects the plants resulting therefrom after emergence from phytopathogenic fungi. In this way, the immediate treatment of the crop at the time of sowing or shortly thereafter can be dispensed with.

It is likewise to be regarded as advantageous that the mixtures according to the invention can in particular also be used with transgenic seed.

The compositions according to the invention are suitable for the protection of seed of any plant variety used in agriculture, in the greenhouse, in forests or in horticulture. The seed concerned in this connection is in particular seed of cereals (such as wheat, barley, rye, millet and oats), maize, cotton, soya, rice, potatoes, sunflowers, beans, coffee, beet (e.g., sugarbeet and forage beet), peanuts, vegetables (such as tomatoes, cucumbers, onions and lettuce), lawns and ornamental plants. The treatment of the seed of cereals (such as wheat, barley, rye and oats), maize and rice is of particular importance.

In the context of the present invention, the composition according to the invention is applied to the seed alone or in a suitable formulation. Preferably, the seed is treated in a condition sufficiently stable for no damage to occur during the treatment. In general, the treatment of the seed can be carried out at any point in time between harvesting and sowing. Use is usually made of seed which has been separated from the plant and freed from pods, shells, stalks, skins, hairs or fruit flesh. Thus, it is possible, for example, to use seed which has been harvested, cleaned and dried up to a moisture content of less than 15% by weight. Alternatively, it is also possible to use seed which, after drying, has been treated, e.g. with water, and then dried again.

In general, care must be taken, in the treatment of the seed, that the amount of the composition according to the invention and/or of additional additives applied to the seed is chosen so that the germination of the seed is not impaired or that the plant resulting therefrom is not damaged. This is to be taken into consideration in particular with active substances which may show phytotoxic effects at certain application rates.

The compositions according to the invention can be applied immediately, thus without comprising additional components and without having been diluted. It is generally preferable to apply the compositions to the seed in the form of a suitable formulation. Suitable formulations and methods for seed treatment are known to a person skilled in the art and are described, e.g., in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active substance combinations which can be used according to the invention can be converted into the usual seed dressing formulations, such as solutions, emulsions, suspensions, powders, foams, slurries or other coating materials for seed, and also ULV formulations.

These formulations are prepared in a known way by mixing the active substances or active substance combinations with conventional additives, such as, for example, conventional extenders and also solvents or diluents, colorants, wetting agents, dispersants, emulsifiers, antifoaming agents, preservatives, secondary thickeners, adhesives, gibberellins and also water.

Suitable colorants which may be present in the seed dressing formulations which can be used according to the invention comprise all colorants conventional for such purposes. In this connection, use may be made both of pigments, which are sparingly soluble in water, and dyes, which are soluble in water. Mention may be made, as examples, of the colorants known under the descriptions Rhodamine B, C.I. Pigment Red 112 and C.I. Solvent Red 1.

Possible wetting agents which can be present in the seed dressing formulations which can be used according to the invention comprise all substances which promote wetting and are conventional in the formulation of agrochemical active substances. Use may preferably be made of alkylnaphthalenesulphonates, such as diisopropyl- or diisobutylnaphthalenesulphonates.

Suitable dispersants and/or emulsifiers which may be present in the seed dressing formulations which can be used according to the invention comprise all nonionic, anionic and cationic dispersants conventional in the formulation of agrochemical active substances. Use may preferably be made of nonionic or anionic dispersants or mixtures of nonionic or anionic dispersants. Mention may in particular be made, as suitable nonionic dispersants, of ethylene oxide/propylene oxide block polymers, alkylphenol polyglycol ethers and also tristyrylphenol polyglycol ethers, and the phosphated or sulphated derivatives thereof. Suitable anionic dispersants are in particular lignosulphonates, polyacrylic acid salts and arylsulphonate/formaldehyde condensates.

Antifoaming agents which may be present in the seed dressing formulations which can be used according to the invention comprise all foam-inhibiting substances conventional in the formulation of agrochemical active substances. Use may preferably be made of silicone defoaming agents and magnesium stearate.

Preservatives which may be present in the seed dressing formulations which can be used according to the invention comprise all substances which can be used in agrochemical compositions for such purposes. Mention may be made, by way of example, of dichlorophen and benzyl alcohol hemiformal.

Possible secondary thickeners which may be present in the seed dressing formulations which can be used according to the invention comprise all substances which can be used in agrochemical compositions for such purposes. Preferably suitable are cellulose derivatives, acrylic acid derivatives, xanthan, modified clays and highly dispersed silica.

Possible adhesives which may be present in the seed dressing formulations which can be used according to the invention comprise all conventional binders which can be used in seed dressings. Mention may preferably be made of polyvinylpyrrolidone, polyvinyl acetate, polyvinyl alcohol and tylose.

Possible gibberellins which may be present in the seed dressing formulations which can be used according to the invention preferably comprise gibberellins A1, A3 (=gibberellic acid), A4 and A7; use is particularly preferably made of gibberellic acid. Gibberellins are known (cf. R. Wegler, "Chemie der Pflanzenschutz- and Schädlingsbekämpfungsmittel" [Chemistry of Plant Protection and Pest Control Agents], Vol. 2, Springer Verlag, 1970, pp. 401-412).

The seed dressing formulations which can be used according to the invention can be used, either directly or after prior diluting with water, for the treatment of seed of the most varied species. Thus, the concentrates or the compositions which can be obtained therefrom by diluting with water can be used for the dressing of the seed of cereals, such as wheat, barley, rye, oats and triticale, and also the seed of maize, rice, rape, peas, beans, cotton, sunflowers and beet, or also of vegetable seed of the most varied natures. The seed dressing formulations which can be used according to the invention or the diluted compositions thereof can also be used for the dressing of seed of transgenic plants. In this connection, additional synergistic effects may also occur in interaction with the substances formed by expression.

All mixing devices which can be conventionally used for dressing are suitable for the treatment of seed with the seed dressing formulations which can be used according to the invention or the compositions prepared therefrom by addition of water. Specifically, the dressing procedure is such that the seed is introduced into a mixer, the amount of seed dressing formulation desired each time is added, either as such or after prior dilution with water, and mixing is carried out until the formulation is uniformly distributed over the seed. If appropriate, a drying operation follows.

The application rate of the seed dressing formulations which can be used according to the invention can be varied within a relatively wide range. It depends on the respective content of the active substances in the formulations and on the seed. The application rates of active substance combination are generally between 0.001 and 50 g per kilogram of seed, preferably between 0.01 and 15 g per kilogram of seed.

The compounds according to the invention can be used, as such or in their formulations, also in a mixture with known fungicides, bactericides, acaricides, nematicides or insecticides, in order thus, e.g., to broaden the spectrum of activity or to prevent the development of resistance.

A mixture with other known active substances, such as herbicides, or with fertilizers and growth regulators, safeners or semiochemicals is also possible.

In addition, the compounds of the formula (I) according to the invention also exhibit very good antimycotic activities. They have a very broad spectrum of antimycotic activity, in particular against dermatophytes and budding fungi, moulds and diphasic fungi (e.g. against *Candida* species, such as *Candida albicans, Candida glabrata*), and also *Epidermophyton floccosum, Aspergillus* species, such as *Aspergillus niger* and *Aspergillus fumigatus, Trichophyton* species, such as *Trichophyton mentagrophytes, Microsporon* species, such as *Microsporon canis* and *audouinii*. The enumeration of these fungi does not represent in any way a limitation on the mycotic spectrum which can be included but has only an illustrative nature.

The compounds according to the invention can accordingly be used both in medicinal and in nonmedicinal applications.

The active substances can be applied as such, in the form of their formulations or in the form of the application forms prepared therefrom, such as ready-to-use solutions, suspensions, wettable powders, pastes, soluble powders, dusts and granules. Application takes place in standard fashion, e.g. by pouring, spraying, atomizing, scattering, dusting, foaming, spreading, and the like. It is furthermore possible to apply the active substances by the ultra-low-volume method or to inject the active substance composition or the active substance itself into the soil.

The seed of the plant can also be treated.

When the compound according to the invention are used as fungicides, the application rates can be varied within a relatively wide range depending on the type of application. In the treatment of plant parts, the application rates of active substance are generally between 0.1 and 10 000 g/ha, preferably between 10 and 1000 g/ha. In seed treatment, the application rates of active substance are generally between 0.001 and 50 g per kilogram of seed, preferably between 0.01 and 10 g per kilogram of seed. In soil treatment, the application rates of active substance are generally between 0.1 and 10 000 g/ha, preferably between 1 and 5000 g/ha.

As already mentioned above, all plants and the parts thereof can be treated according to the invention. In a preferred embodiment, plant species and plant varieties occurring in the wild or obtained by conventional biological breeding methods, such as crossing or protoplast fusion, and the parts thereof are treated. In an additional preferred embodiment, transgenic plants and plant varieties obtained by genetic engineering methods, optionally in combination with conventional methods, (genetically modified organisms) and the parts thereof are treated. The term "parts" or "parts of plants" or "plant parts" was explained above.

The method of treatment according to the invention can be used in the treatment of genetically modified organisms (GMOs), e.g. plants or seeds. Genetically modified plants (or transgenic plants) are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using, for example, antisense technology, cosuppression technology or RNA interference—RNAi technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active substances and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active substance combinations according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active substances.

Plants and plant cultivars which are preferably treated according to the invention include all plants which have genetic material which imparts particularly advantageous, useful traits to these plants (whether obtained by breeding and/or biotechnological means).

Plants and plant cultivars which are also preferably treated according to the invention are resistant against one or more biotic stresses, i.e. the said plants show a better defence against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention are those plants characterized by enhanced yield characteristics. Increased yield in the said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pot dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis or hybrid vigour which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in maize) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants that contain the genetic determinants responsible for male sterility is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described in *Brassica* species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Male sterile plants can also be obtained by plant biotechnology methods, such as genetic engineering. A particularly useful means of obtaining male-sterile plants is described in WO 89/10396 in which, for example, a ribonuclease, such as barnase, is selectively expressed in the tapetum cells in the stamens. Fertility can then be restored by expression in the tapetum cells of a ribonuclease inhibitor, such as barstar (e.g. WO 1991/002069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289) or an eleusine EPSPS (WO 2001/66704). It can also be a mutated EPSPS as described in for example EP-A 0837944, WO 2000/066746, WO 2000/066747 or WO 2002/026995. Glyphosate-tolerant plants can also be obtained by expressing a gene that encodes a glyphosate oxidoreductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described in for example WO 2002/036782, WO 2003/092360, WO 2005/012515 and WO 2007/024782. Glyphosate-tolerant plants can also be obtained by selecting plants containing naturally-occurring mutations of the abovementioned genes, as described in for example WO 2001/024615 or WO 2003/013226.

Other herbicide-resistant plants are for example plants that are made tolerant to herbicides inhibiting the enzyme glutamine synthase, such as bialaphos, phosphinotricin or glufosinate. Such plants can be obtained by expressing an enzyme detoxifying the herbicide or a mutant of the glutamine synthase enzyme that is resistant to inhibition. One such efficient detoxifying enzyme is an enzyme encoding a phosphinotricin acetyltransferase (such as the bar or pat protein from *Streptomyces* species). Plants expressing an exogenous phosphinotricin acetyltransferase are for example described in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme as described in WO 1996/038567, WO 1999/024585 and WO 1999/024586. Tolerance to HPPD inhibitors can also be obtained by transforming plants with genes encoding certain enzymes enabling the formation of homogentisate despite the inhibition of the native HPPD enzyme by the HPPD inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Further herbicide-resistant plants are plants that are made tolerant to acetolactate synthase (ALS) inhibitors. Known ALS inhibitors include, for example, sulphonylurea, imidazolinone, triazolopyrimidines, pyrimidinyloxy(thio)benzoates and/or sulphonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed Science (2002), 50, 700-712, but also in U.S. Pat. No. 5,605,011, U.S. Pat. No. 5,378,824, U.S. Pat. No. 5,141,870 and U.S. Pat. No. 5,013,659. The production of sulphonylurea-tolerant plants and imidazolinone-tolerant plants is described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and international publication WO 1996/033270. Other imidazolinone-tolerant plants are also described in, for example, WO 2004/040012, WO 2004/106529, WO 2005/020673, WO 2005/093093, WO 2006/007373, WO 2006/015376, WO 2006/024351 and WO 2006/060634. Further sulphonylurea- and imidazolinone-tolerant plants are also described in, for example, WO 2007/024782.

Other plants tolerant to imidazolinone and/or sulphonylurea can be obtained by induced mutagenesis, selection in cell cultures in the presence of herbicide or mutation breeding as described for example for soybeans in U.S. Pat. No. 5,084,082, for rice in WO 1997/41218, for sugarbeet in U.S. Pat. No. 5,773,702 and WO 1999/057965, for lettuce in U.S. Pat. No. 5,198,599, or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g. proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or 3) a hybrid insecticidal protein comprising parts of two different insecticidal crystal proteins from *Bacillus thuringiensis*, such as a hybrid of the proteins of 1) above or a hybrid of the proteins of 2) above, e.g. the Cry1A.105 protein produced by maize event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in maize events MON863 or MON88017, or the Cry3A protein in maize event MIR 604;

5) an insecticidal secreted protein from *Bacillus thuringiensis* or *Bacillus cereus*, or an insecticidal portion thereof, such as the vegetative insecticidal (VIP) proteins listed at http://www.lifesci.sussex.ac.uk/Home/Neil_Crickmore/Bt/vip.html, e.g., proteins from VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795);

7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT 102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of the poly(ADP-ribose) polymerase (PARP) gene in the plant cells or plants as described in WO 2000/004173 or EP 04077984.5 or EP 06009836.5;

b. plants which contain a stress tolerance enhancing transgene capable of reducing the expression and/or activity of the PARG encoding genes of the plants or plant cells, as described e.g. in WO 2004/090140;

c. plants which contain a stress tolerance enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase, as described, e.g., in EP 04077624.7 or WO 2006/133827 or PCT/EP07/002,433.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesized starch in wild type plant cells or plants, so that this modified starch is better suited for special applications. The said transgenic plants synthesizing a modified starch are disclosed, for example, in EP 0 571 427, WO 1995/004826, EP 0 719 338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO 99/58688, WO 1999/58690, WO 1999/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192. WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026 or WO 1997/20936.

2) transgenic plants which synthesize nonstarch carbohydrate polymers or which synthesize nonstarch carbohydrate polymers with altered properties in comparison to wild type plants without genetic modification. Examples are plants producing polyfructose, especially of the inulin and levan type, as disclosed in EP 0 663 956, WO 1996/001904, WO 1996/021023, WO 1998/039460 and WO 1999/024593, plants producing alpha-1,4-glucans as disclosed in WO 1995/031553, US 2002/031826, U.S. Pat. No. 6,284,479, U.S. Pat. No. 5,712,107, WO 1997/047806, WO 1997/047807, WO 1997/047808 and WO 2000/14249, plants producing alpha-1,6 branched alpha-1,4-glucans, as disclosed in WO 2000/73422, and plants producing alternan, as disclosed in WO 2000/047727, EP 06077301.7, U.S. Pat. No. 5,908,975 and EP 0 728 213.

3) transgenic plants which produce hyaluronan, as for example disclosed in WO 2006/032538, WO 2007/039314, WO 2007/039315, WO 2007/039316, JP 2006/304779 and WO 2005/012529.

Plants or plant cultivars (obtained by plant biotechnology methods, such as genetic engineering) which may also be treated according to the invention are plants, such as cotton plants, with altered fibre characteristics. Such plants can be obtained by genetic transformation, or by selection of plants containing a mutation imparting such altered fibre characteristics and include:

a) plants, such as cotton plants, containing an altered form of cellulose synthase genes as described in WO 1998/000549, b) plants, such as cotton plants, containing an altered form of rsw2 or rsw3 homologous nucleic acids as described in WO 2004/053219;

c) plants, such as cotton plants, with increased expression of sucrose phosphate synthase as described in WO 2001/017333;

d) plants, such as cotton plants, with increased expression of sucrose synthase as described in WO 02/45485;

e) plants, such as cotton plants, wherein the timing of the plasmodesmatal gating at the basis of the fibre cell is altered, e.g. through downregulation of fibre selective β-1,3-glucanase as described in WO 2005/017157;

f) plants, such as cotton plants, having fibres with altered reactivity, e.g. through the expression of N-acetylglucosamine transferase gene including nodC and chitin synthase genes as described in WO 2006/136351.

Plants or plant cultivars (obtained by plant biotechnology methods, such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, producing oil having a high oleic acid content as described, e.g., in U.S. Pat. No. 5,969,169, U.S. Pat. No. 5,840,946, U.S. Pat. No. 6,323,392 or U.S. Pat. No. 6,063,947;

b) plants such as oilseed rape plants, producing oil having a low linolenic acid content as described in U.S. Pat. No. 6,270,828, U.S. Pat. No. 6,169,190 or U.S. Pat. No. 5,965,755;

c) plants such as oilseed rape plants, producing oil having a low level of saturated fatty acids as described, e.g. in U.S. Pat. No. 5,434,283.

Particularly useful transgenic plants which may be treated according to the invention are plants which comprise one or more genes which encode one or more toxins are the transgenic plants which are sold under the following trade names: YIELD GARD® (for example maize, cotton, soybeans), KnockOut® (for example maize), BiteGard® (for example maize), BT-Xtra® (for example maize), StarLink® (for example maize), Bollgard® (cotton), Nucotn® (cotton). Nucotn 33B® (cotton), NatureGard® (for example maize), Protects® and NewLeaf® (potato). Examples of herbicide-tolerant plants which may be mentioned are maize varieties, cotton varieties and soybean varieties which are sold under the following trade names: Roundup Ready® (tolerance to glyphosate, for example maize, cotton, soybean), Liberty Link® (tolerance to phosphinotricin, for example oilseed rape), IMI® (tolerance to imidazolinone) and SCS® (tolerance to sulphonylurea), for example maize. Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, that are listed for example in the databases from various national or regional regulatory agencies (see for example http://gmoinfo.jrc.it/gmp_browse.aspx and http://www.agbios.com/dbase.php).

EXAMPLE 1

*Phaedon cochleariae*-Test; (PHAECO Spray Application)

Solvent: 78.0 parts by weight of acetone
1.5 parts by weight of dimethylformamide
Emulsifier: 0.5 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration. Chinese cabbage (*Brassica pekinesis*) leaf-disks are sprayed with a preparation of the active ingredient of the desired concentration. Once dry, the leaf disks are infested with mustard beetle larvae (*Phaedon cochleariae*). After 7 days mortality in % is determined. 100% means that all beetle larvae have been killed and 0% means that none of the beetle larvae have been killed.

In this test for example, the following compounds from the preparation examples showed good activity of ≧80% at application rate of 500 g/ha:
Ex No: T74, T76

EXAMPLE 2

*Spodoptera frugiperda*-Test (SPODFR Spray Application)

Solvent: 78.0 parts by weight acetone
1.5 parts by weight dimethylformamide
Emulsifier: 0.5 parts by weight alkylarylpolyglcolether To produce a suitable preparation of the active compound, 1 part by weight of active compound is mixed with the stated amount of solvent and emulsifier, and the concentrate is dilutes with emulsifier-containing water to the desired concentration. Maize (*Zea mais*) leaf sections are sprayed with a preparation of the active ingredient of the desired concentration. Once dry, the leaf sections are infested with fall armyworm larvae (*Spodoptera frugiperda*). After 7 days mortality in % is determined. 100% means that all caterpillars have been killed and 0% means that none of the caterpillars have been killed.

In this test for example, the following compounds from the preparation examples showed good activity of ≧80% at application rate of 500 g/ha:
Ex No: T3, T74, T76

EXAMPLE 3

*Myzus persicae*-Test; (MYZUPE Spray Application)

Solvent: 78.0 parts by weight acetone
1.5 parts by weight dimethylformamide
Emulsifier: 0.5 parts by weight alkylarylpolyglcolether To produce a suitable preparation of active compound, 1 part by weight of active compound is mixed with the stated amount of solvent and emulsifier, and the concentrate is diluted with emulsifier-containing water to the desired concentration. Chinese cabbage (*Brassica pekinesis*) leaf-disks infected with all instars of the green peach aphid (*Myzus persicae*), are sprayed with a preparation of the active ingredient at the desired concentration. After 6 days mortality in % is determined 100% means that all aphids have been killed; 0% means that none of the aphids have been killed.

In this test for example, the following compounds from the preparation examples showed good activity of ≧80% at application rate of 500 g/ha:
Ex No: T22, T75, T76

EXAMPLE 4

*Tetranychus urticae*-Test; (OP-Resistant (TETRUR Spray Application)

Solvent: 78.0 parts by weight acetone
1.5 parts by weight dimethylformamide
Emulsifier: 0.5 parts by weight alkylarylpolyglcolether To produce a suitable preparation of active compound, 1 part by weight of active compound is mixed with the stated amount of solvent and emulsifier, and the concentrate is diluted with emulsifier-containing water to the desired concentration. French beans (*Phaseolus vulgaris*) which are heavily infested with all stages of the two spotted spidermite (*Tetranychus urticae*), are sprayed with a preparation of the active ingredient at the desired concentration. After 6 days mortality in % is determined. 100% means that all spider mites have been killed and 0% means that none of the spider mites have been killed.

In this test for example, the following compounds from the preparation examples showed good activity of ≧80% at application rate of 500 g/ha:
Ex No: T3, T75, T76

EXAMPLE 5

*Phaedon cochleariae* Larvae-Test

Solvent: 7 parts by weight of dimethylformamide
Emulsifier: 1 parts by weight of alkylaryl polyglycolether To produce a suitable preparation of active compound, 1 parts by weight of active compound is mixed with the stated amount of solvent and emulsifier, and the concentrate is diluted with emulsifier-containing water to the desired concentration. Cabbage leaves (*Brassica oleracea*) are treated by being sprayed with a preparation of the active compound of the desired concentration and are infested with mustard beetle larvae (*Phaedon cochleariae*) as long as the leaves are still moist. After 7 days mortality in % is determined. 100% means that all the beetle larvae have been killed; 0% means that none of the beetle larvae have been killed.

In this test for example, the following compounds from the preparation examples showed good activity of ≧80% at application rate of 100 ppm:
Ex No: T3

EXAMPLE 6

*Plutella xylostella*-Test (PLUTMA)

Solvent: 7 parts by weight of dimethylformamide
Emulsifier: 1 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration. Cabbage leaves (*Brassica oleracea*) are treated by being sprayed with a preparation of the active compound of the desired concentration and are infested with larvae of the diamondback moth (*Plutella xylostella*/sensible strain) as long as the leaves are still moist. After 7 days mortality in % is determined. 100% means that all the caterpillars have been killed; 0% means that none of the caterpillars have been killed.

In this test for example, the following compounds from the preparation examples showed good activity of ≧80% at application rate of 100 ppm:
Ex No: T3

EXAMPLE 7

*Myzus persicae*-Test (MYZUPE)

Solvent: 7 parts by weight of dimethylformamide
Emulsifier: 1 part by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration. Cabbage leaves (*Brassica oleracea*) which are heavily infested by the green peach aphid (*Myzus persicae*) are treated by being sprayed with a preparation of the active compound of the desired concentration. After 6 days mortality in % is determined. 100% means that all the aphids have been killed; 0% means that none of the aphids have been killed.

In this test for example, the following compounds from the preparation examples showed good activity of ≧80% at application rate of 100 ppm:
Ex No: T3

EXAMPLE 8

*Aphis gossypii* Test (APHIGO)

Solvent: 7 parts by weight of dimethylformamide
Emulsifier: 1 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration. Cotton leaves (*Gossypium hirsutum*) which are heavily infested by the cotton aphid (*Aphis gossypii*) are treated by being sprayed with a preparation of the active compound of the desired concentration. After 6 days mortality in % is determined. 100% means that all the aphids have been killed; 0% means that none of the aphids have been killed.

In this test for example, the following compounds from the preparation examples showed good activity of ≧80% at application rate of 100 ppm:
Ex No: T3

EXAMPLE 9

*Bemisia tabaci*-Test (BEMITA)

Solvent: 7 parts by weight of dimethylformamide
Emulsifier: 1 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration. Cotton plants (*Gossypium hirsutum*) infested with eggs, larvae and pupae of the white fly (*Bemisia tabaci*) are sprayed with a test solution containing the desired concentration of the active ingredient. After 7 days mortality in % is determined. 100% means that all the white flies have been killed; 0% means that none of the white flies have been killed.

In this test for example, the following compounds from the preparation examples showed good activity of ≧80% at application rate of 20 ppm:
Ex No: T3, T 74. T 75

EXAMPLE 10

*Liriomyza trifolii*-Test (LIRITR Spray Application)

Solvent: 78.0 parts by weight of acetone
1.5 parts by weight of dimethylformamide
Emulsifier: 0.5 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration. French bean (*Phaseolus vulgaris*) leaf-disks infested with larvaes of the am. serpentine leaf miner (*Liriomyza trifolii*) are sprayed with a test solution containing the desired concentration of the active ingredient. After 7 days mortality in % is determined. 100% means that all the leaf miners have been killed; 0% means that none of the leaf miners have been killed.

In this test for example, the following compounds from the preparation examples showed good activity of ≧80% at application rate of 500 g/ha:
Ex No: T3, T 74, T 75

EXAMPLE 11

*Nilaparvata lugens*-Test; (NILALU Hydroponic Application)

Solvent: 78.0 parts by weight of acetone
1.5 parts by weight of dimethylformamide
Emulsifier: 0.5 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration. The compound solution of the desired concentration is pipeted in water. The desired concentration is referring to the amount of compound per volume indicator. The plants are infested with the braun planthopper (*Nilaparvata lugens*). After the specified period of time mortality in % is determined. 100% means that all planthopper have been killed and 0% means that none of the planthopper have been killed.

In this test for example, the following compounds from the preparation examples showed good activity of ≧80% at application rate of 500 g/ha:
Ex No: T3, T 74

EXAMPLE 12

*Tetranychus*-Test (OP-Resistant)

Solvent: 7 parts by weight of dimethylformamide
Emulsifier: 1 part by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration. Bean plants (*Phaseolus vulgaris*) which are heavily infested with all stages of the two-spotted spider mite (*Tetranychus urticae*) are treated by sprayed with a preparation of the active compound of the desired concentration. After the specified period of time, mortality in % is determined 100% means that all the spider mites have been killed; 0% means that none of the spider mites have been killed.

In this test for example, the following compounds from the preparation examples showed good activity of ≧80% at application rate of 20 ppm:
Ex No: T 74

EXAMPLE 13

*Phytophthora* Test (Tomato)/Preventive

Solvent: 49 parts by weight of N,N-Dimethylformamide
Emulsifier: 1 part by weight of Alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Phytophthora infestans*. The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the control, while an efficacy of 100% means that no disease is observed.

TABLE

*Phytophthora* test (tomato)/preventive

| | Rate of application of active compound in ppm | Efficacy in % |
|---|---|---|
| T 3 | 500 | 75 |

What is claimed is:

1. A method of controlling an animal pest or unwanted fungi of a plant comprising contacting the plant or its environment with a compound of Formula (I)

(I)

wherein
$R^1$ is methyl, ethyl, n-propyl, iso-propyl, cyclopropyl, halomethyl, haloethyl, halogen, vinyl, ethynyl, methoxy, ethoxy, halomethoxy or haloethoxy,
$R^2$ and $R^3$ are, independently of each other hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkylsulfonyloxy, $C_1$-$C_6$haloalkylsulfonyloxy, cyano, nitro, phenyl, phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl, heteroaryl or heteroaryl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio, $C_1$-$C_3$alkylsulfinyl or $C_1$-$C_3$alkylsulfonyl,
$R^4$ is hydrogen, methyl, ethyl, n-propyl, iso-propyl, halomethyl, haloethyl, halogen, vinyl, ethynyl, methoxy, ethoxy, halomethoxy or haloethoxy,
n is 2,
X is O,
$R^6$ and $R^7$ are each hydrogen,
$R^5$ and $R^8$ together form an ethylene chain, and
G represents hydrogen (a).

2. The method according to claim 1, wherein $R^2$ is hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_1$-$C_6$alkylthio, $C_1$-$C_6$alkylsulfinyl, $C_1$-$C_6$alkylsulfonyl, $C_1$-$C_6$alkylsulfonyloxy, $C_1$-$C_6$haloalkylsulfonyloxy, cyano or nitro.

3. The method according to claim 1, wherein $R^3$ is phenyl substituted by $C_1$-$C_4$alkyl, $C_1$-$C_3$haloalkyl, $C_1$-$C_3$alkoxy, $C_1$-$C_3$haloalkoxy, cyano, nitro, halogen, $C_1$-$C_3$alkylthio $C_1$-$C_3$alkylsulfinyl or $C_1$-$C_3$alkylsulfonyl.

4. The method according to claim 3, wherein $R^3$ is phenyl substituted by halogen.

5. The method according to claim 1, wherein the compound of Formula (I) is (T3)

6. The method according to claim 1, wherein the compound of Formula (I) is (T22)

7. The method according to claim 1, wherein the compound of Formula (I) is (T74)

8. The method according to claim 1, wherein the compound of Formula (I) is
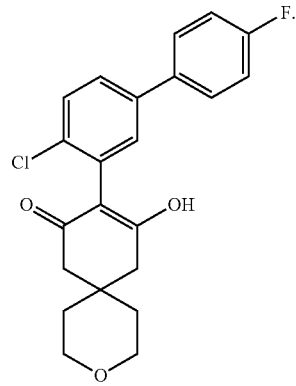
(T75)
9. The method according to claim 1, wherein the compound of Formula (I) is
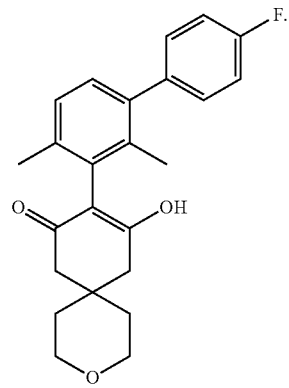
(T76)
10. The method according to claim 1, wherein the animal pest is an insect, an arachnid, a helminth, a nematode or a mollusc.
* * * * *